US007550607B2

(12) United States Patent
Hong et al.

(10) Patent No.: US 7,550,607 B2
(45) Date of Patent: Jun. 23, 2009

(54) METHOD OF PREPARATION OF HETEROCYCLIC MOLECULES WITH PHARMACEUTICAL, PHARMACEUTICAL EXCIPIENT, COSMECEUTICAL, AGROCHEMICAL AND INDUSTRIAL USES

(75) Inventors: Borcherng Hong, Vista, CA (US); Zhong-Yi Chen, Vista, CA (US); Arumugam Nagarajan, Vista, CA (US); Kottani Rudresha, Vista, CA (US); Vishal P. Chavan, Vista, CA (US); Sepehr Sarshar, Cardiff by the Sea, CA (US)

(73) Assignee: Auspex Pharmaceutical, Inc., Vista, CA (US)

(*) Notice: Subject to any disclaimer, the term of this patent is extended or adjusted under 35 U.S.C. 154(b) by 64 days.

(21) Appl. No.: 10/542,176

(22) PCT Filed: Jan. 16, 2004

(86) PCT No.: PCT/US2004/001344

§ 371 (c)(1),
(2), (4) Date: Jan. 6, 2006

(87) PCT Pub. No.: WO2004/064745

PCT Pub. Date: Aug. 5, 2004

(65) Prior Publication Data

US 2006/0173199 A1  Aug. 3, 2006

Related U.S. Application Data

(60) Provisional application No. 60/440,982, filed on Jan. 17, 2003.

(51) Int. Cl.
*C07D 309/30* (2006.01)
(52) U.S. Cl. .................................................. 549/420
(58) Field of Classification Search ................. 549/420
See application file for complete search history.

(56) References Cited

U.S. PATENT DOCUMENTS 5,916,975 A  6/1999 Bell et al. ................... 525/270

OTHER PUBLICATIONS

Adam et al. "Benzyl Enol Ethers via Decarboxylation of α-Benzyloxy-β-lactones Derived from the Lithium α-Benzyloxy-α-lithioacetate Synthon," *Synthesis*. 388-390 (1979).
Agami et al. "Cyclization of a Chiral Oxazolidine as a Key-Step for the Synthesis of Functionalized Piperidines," *Tetrahedron Letters*. 37(23), 4001-4002 (1996).
Allart et al., "1,5-Anhydro-2-Deoxy-D-Altritol Oligonucleotides as Conformationally Restricted Analogues of RNA," *Nucleosides Nucleotide.s* 1523 (1998).
Allart et al, "D-Altritol Nucleic Acids (ANA): Hybridisation Properties, Stability, and Initial Structural Analysis," *Chem. Eur. J.* 5(8) 2424-2431 (1999).
Allart et al. "Synthesis of Protected D-Altritol Nucleosides as Building Blocks for Oligonucleotide Synthesis," *Tetrahedron Letters*. 55, 6527-6546 (1999).
Alvarez, et al, "A Concise Synthesis of *Ortho*-Condensed Oxane-Oxene, Oxepene, Oxocene and Oxonene Ring Systems," 37(16), 2865-2868 (1996).
Araki et al, "Synthetic Studies of Carbohydrate Derivatives with Photochemical Reaction. Photochemical Addition of Ethanethiol and 1-Propanethiol to Enoses," *Chemistry Letters*, pp. 383-386 (1973).
Aspinall, H.C., "Chiral Lanthanide Complexes: Coordination Chemistry and Applications," *Chemical Reviews*. (Washington D.C., United States), 102(6), 1807-1850 (2002).
Asano, et al, "New entry for asymmetric deoxyazasugar synthesis: syntheses of deoxymannojirimycin, deoxyaltrojirimycin and deoxygalactostatin," *Chem. Commun.*, 41-42 (1999).
Auge et al. "Synthesis with an Immobilized Enzyme of N-Acetyl-9-O-Acetyl-Neuraminic Acid, A Sugar Reported as a Component of Embryonic and Tumor Antigens," *Tetrahedron Letters*. 26(20), 2439-2440 (1985).
Bandgar et al., "Synthesis of 4-epi-2-deoxy-2-$H_{eq}$-N-acetylneuraminic acid and 2,4-dideoxy-2-$H_{eq}$-N-acetylneuraminic acid," *Carbohydrate Research*. 270920, 201-210 (1995).
Beau et al., "Total Synthesis of (+)-Methyl Pseudomonate C from Carbohydrates," *Journal of the American Chemical Society*. 105(3), 621-622 (1983).
Beckwith et al., "Kinetics of the Coupling Reactions of the Nitroxyl Radical 1,1,3,3-Tetramethylisoindoline-2-oxyl with Carton-Centered Radicals," *Journal of Organic Chemistry*. 53, 1632-1641 (1988).
Bedjeguelal, et al, "Aglycon Directed Palladium β-Alcoxyelimination on Carbohydrate Templates," 40, 87-90 (1999).
Bedjeguelal, et al, "Intramolecular Heck Cyclisation-β-Alkoxy Elimination in Carbohydrate Chemistry. A Simple Route to Enantiopure Annelated Dioxatricyclic Compounds," 6, 762-764 (1999).
Bedjeguelal, et al, "Palladium-Mediated Cyclization on Carbohydrate Templates. 3. Extension of the Cyclization to the Threo Series," *J. Carbohydrate Chemistry* 19(2), 221-232 (2000).
Benko, Zoltan and Fraser-Reid, Bert "Conjugate Addition of Methanol to α-Enones: Photochemistry and Stereochemical Details," *J. Org. Chem*. 53, 2066-2072 (1988).
Bhattacharjee, S.S., and Gorin P.A.J., "Identification of di-*O*-, tri-*O*-methylmannoses by gas-liquid chromatography," *Canadian Journal of Chemistry* 47 1207-1215 (1969).

(Continued)

*Primary Examiner*—Bernard Dentz
(74) *Attorney, Agent, or Firm*—Dennis A. Bennett

(57) ABSTRACT

Processes for preparing racemic and optically pure 3,6-dihydro-2H-pyrans of formulae H, I, N and O are described. These compounds may be further transformed into compounds of formulae J, K, L, M, P, Q, S, T, U, V, Y and Z with potential pharmaceutical, pharmaceutical excipient, cosmeceutical, agrochemical and industrial applications.

11 Claims, 11 Drawing Sheets

OTHER PUBLICATIONS

Blades, et al, "A *syn* selective dihydroxylation of cyclic allylic trichloroacetamides using catalytic osmium tetroxide," *Tetrahedron Letters* 41, 4701-4704 (2000).

Blaser, H.U., "Enantioselective catalysis in fine chemicals production," *Applied Catalysis, A General*. 221(1-2), 119-143 (2001).

Brockway et al, "Unusual Stereochemistry in the Copper-catalysed Ring Opening of a Carbohydrate Oxirane with Vinylmagnesium Bromide," *Journal of the Chemical Society Perkin Transactions 1*. 5, 875-878 (1984).

Broxterman et al, "Synthesis of 2-Acetamido-2-Deoxy-D-Mannose Analogues as Potential Inhibitors of Sialic Acid Biosynthesis," *Journal of Carbohydrate Chemistry*. 10(2), 215-237 (1991).

Burke et al, "Tandem Glycolate Claisen Rearrangement/Ring-Closing Metathesis: A Stereochemically General Synthesis Substituted Dihydropyran-2-carboxylates," *Journal of Organic Chemistry*. 63(10), 3160-3161 (1998).

Cai et al, "Polyphenol-Anthocyanin Copigmentation," *Journal of Chemical Society Chemical Communications*. 5, 380-383 (1990).

Cardillo et al, "A new, convenient improvement of a selective silylation-desilylation sequence in polyhydroxylated compounds by means of polymeric reagents," *Chemistry and Industry (London)*. 16, 643-644 (1983).

Cassel et al, "Original Synthesis of Linear, Branched and Cyclic Oligoglycerol Standards," *European Journal of Organic Chemistry*. 5, 875-896 (2001).

Chapleur et al, "On the Reaction of 4,6-0-Benzylidene-2-deoxypyranosides with Sodium Cyanoborohydride: Formation of 1,5-Anhydroalditols," *Journal of the Chemical Society Perkin Transactions 1*. 703-705 (1989).

Cho et al, "LiOH-mediated *N*-monoalkylation of α-amino acid esters and a dipeptide ester using activated alkyl bromides," *Tetrahedron Letters*. 43, 1273-1276 (2002).

Cocker et al, "Hydroxyalkylamino-Acids. Part I.," *Journal of Chemical Society*. 373 (1943).

Colonna et al, "Nucleophilic Substitution at Sulphur With Retention of Configuration in Alkyl-p-Toluenesulphinamides," *Gazzetta Chimica Italiana*. 67 (1987).

Corey, E. J., "Catalytic Enantioselective Diels—Alder Reactions: Methods, Mechanistic Fundamentals, Pathways, and Applications," *Angewandte Chemie*. International Ed. 41(10), 1650-1667 (2002).

Crimmins et al, "Asymmetric Aldol-Ring-Closing Metathesis Strategy for the Enantioselective Construction of Six- to Nine-Membered Oxygen Heterocycles," *Journal of Organic Chemistry*. 62(22), 7548-7549 (1997).

Crimmins et al, "An Efficient, General Asymmetric Synthesis of Carbocyclic Nucleosides: Application of an Asymmetric Aldol/Ring-Closing Metathesis Strategy," *Journal of Organic Chemistry*. 65(25), 8499-8509 (2000).

Csuk et al, "Synthesis and Structure of a New 1,5-Anhydro-hex-2-enitol," *Zeitschrift für Naturforschung B*. 42(11), 1461-1464 (1987).

Cui et al, "Stereocontrolled allylation of 2-amino-2-deoxy sugar derivatives by a free-radical procedure[1]," *Carbohydrate Research*. 309(4), 319-330 (1998).

Davoille et al, "Homologation of allylic alcohols. An approach to cyclic and acyclic polyoxygenated compounds," *Tetrahedron Letters*. 41(8), 1255-1259 (2000).

Dawe et al, "The Synthesis and Reactions of Some 3-C-Methyl Glycals," *Journal of Carbohydrate Chemistry* 1(1), 21-35 (1982).

Dias et al, "Chiral Lewis Acid Catalyzed Ene-Reactions," *Current Organic Chemistry*. 4(3), 305-342 (2000).

Donohoe et al, "The Directed Dihydroxylation of Allytic Alcohols," *Tetrahedron Letters*. 38(28), 5027-5030 (1997).

Dromowicz et al, "Syntheses of 2,6-anhydroaldonic acids from the corresponding anhydrodeoxynitroalditols (glycopyranosylnitromethanes) and their conversion into methyl esters, amides, and alditols," *Carbohydrate Research*. 311(3), 103-119 (1998).

Dupuis et al, "Conformation of Glycosyl Radicals: Radical Stabilization by β-CO Bonds**," *Angewandte Chemie (International edition in English)*. 23(11), 896-897 (1984).

Durette et al., "Synthesis and immunoadjuvant activity of 2-acetamido-1,5-anhydro-2-deoxy-3-O-[®-2-propanoyl-L-alanyl-D-isoglutamine]-D-glucitol ("1-deoxymuramoyl dipeptide") and its 6-(2-behenoyloxyisobutyrate)," *Carbohydrate Research*. 108(1), 139-147 (1982).

Engelbrecht et al, "Stereoselective Palladium Catalyzed Cyclization on Carbohudrate Templates-A Route to Chiral Cyclopentanes and Some Heterocyclic Analogs," *Tetrahedron Letters*. 32(19), 2161-2164 (1991).

Estevez et al, "Synthesis of tetrahydropyrans from sugar lactones," *Tetrahedron*. 13591 (1998).

Estevez et al, "Tetrahydropyran Derivatives from γ-and δ-Hexonolactones," *Tetrahedron Letters*. 35(20), 3361-3364 (1994).

Evans et al, "Stereoselective Aldol Condensations via Boron Enolates," *Journal of the American Chemical Society*. 103(11), 3099-3111 (1981).

Ferey et al, "Aldol Reactions of Ethyl N-Benzyl-N-methylglycinate and of its Borane Adduct: Selective Access to Syn or Anti α-Amino-β-hydroxyesters," *Journal of Chemical Society Chemical Communications*. 487 (1995).

Fernandez-Mayoralas et al, "Preparation of Pyranoid Glycal Derivatives from Phenyl Thioglycosides and Glycosyl Phenyl Sulphones," *Carbohydrate Reseach*. 188, 81-95 (1989).

Fernandez-Mayoralas et al, "Convenient Synthesis of Substituted Pyranoid Glycals from Thiophenyl Glycosides and Glycosyl Phenylsulfones," *Tetrahedron Letters*. 30(19), 2537-2540 (1989).

Fuchs et al, "Synthese von 7-Amino-2.6-anhydro-7-desoxy-D-glycero-1-manno-heptonsaure und 7-Amino-2,6-anhydro-7-desoxy-D-glycero-D-gulo-heptonsaure," *Chemische Berichte*. 2254 (1975).

Furneaux et al, "The Chemistry of Castanospermine, Part I: Synthetic Modifications at C-6," *Tetrahedron*. 50(7) 2131-2160 (1994).

Garner et al, "An Asymmetric Synthesis of 5-O-Carbamoylpolyoxamic Acid from D-Serine," *Journal of Organic Chemistry*. 53, 2979 (1988).

Ghelfi et al, "Easy approach to 3-benzylimino-2-pyrrolidinones from 3-chloro-4-chloromethyl-2-pyrrolidinones," *Tetrahedron Letters*, 40, 8595-8597 (1999).

Gil et al, "An Enantioselective Entry to Substituted 6-Membered Nitrogen Heterocycles from Chiral Pyridinium Salts via Selective Epoxidation of Tetrahydropyridine Intermediates," *Synthesis*. 2117-2126 (2000).

Gilchrist et al, "Formation of Pyridazino [6,1-c][1-4]oxazin-8(7H)-ones by Intramolecular Cycloaddition of Azoalkenes," *Journal of the Chemical Society Perkin Transactions 1*. 2517-2522 (1987).

Giuliano et al, "Diastereofacial Selectivity of Diels-Alder Reactions of Carbohydrate-Derived Dienes and Their Carbocyclic Analogs," *Journal of Organic Chemistry*. 58(18), 4979-4988 (1993).

Gribble et al, "Synthesis and Reactions of 9,10-Diazatetracyclo-," *Journal of Heterocyclic Chemistry*. 719 (1996).

Gridley, et al, "Regioselective Lipase-catalysed acylation of 4,6-O-benzylidene-β-D-pyranoside derivatives displaying a range of anomeric substituents," *Synlett* 1397-1399 (1997).

Griffin et al, "2-Keta Sugars as Preformed Heterocyclic Building Blocks. Synthetic Studies," *Heterocycles*. 35(2), 1247-1258 (1993).

Grigg et al, "Sequential 1,3-Dipolar Cycloaddition-Palladium Catalysed cyclisation. A Powerful New Tactical Combination," *Tetrahedron Letters*. 32, 1359-1363 (1991).

Groaning et al, "New Homochiral Cyclic Diol Ligands for Titanium Alkoxide Catalyzed Phosphonylation of Aldehydes," *Tetrahedron Letters*. 39(31), 5485-5488 (1998).

Groger et al, "the Development of New Monometallic Bifunctional Catalysts with Lewis acid and Lewis Base Properties, and their Application in Asymmetric Cyanation Reactions," *Chemistry—A European Journal*. 7(24), 5246-5251 (2001).

Grubbs et al, "Recent Advances in Olefin Metathesis and Its Application in Organic Synthesis," *Tetrahedron*. 54(18), 4413-4450 (1998).

Guo et al, "A New Strategy for the Stereoselective Syntheses of C-Glycosyl Compounds of β-Pentapyranoses," *Synthetic Communications*, 26(11), 2067-2073 (1996).

Hall et al, "Reaction of Chlorosulphonyl Isocyanate with Unsaturated Sugars," *Journal of the Chemical Society Perkin Transactions 1*. 1, 38-44 (1973).

Haque et al, "Rapid Communication," *Indian Journal of Chemistry, Section B*. 38B(1), 8-9 (1999).

Heiker et al, "Synthesis of D-*galacto*-1-deoxynojirimycin (1,5-dideoxy-1,5-imino-D-galactitol) starting from 1-deoxynojirimycin*," *Carbohydrate Research*. 314 (1990).

Helterich et al, "Notiz zum Ubergang von Kohlenhydraten in Derivate mit stabilem Pyranring," *Chemische Berichte*. 1701 (1971).

Hermann et al, "64. Herstellung von Dihydro-, Tetrahydro- and Hexahydro-chelidamsaure-Derivaten[1])," *Helvetica Chimica Acta*. 626 (1976).

Herold et al, "39. Synthesis of D-erythro- and D-threo-Sphingosine Derivatives from L-Serine," *Helvetica Chimica Acta*. 354 (1988).

Hiersemann et al, "Synthesis of α-Allyloxy-Substituted α,β-Unsaturated Esters via Aldol Condensation. Convenient Access to Highly Substituted Allyl Vinyl Ethers," *Synthesis*. 9, 1279-1290 (2000).

Hiersemann et al, "The Ester Dienolate [2,3]-Wittig Rearrangement. Diastereoselective Synthesis of 2,3-Dialkenyl-Substituted 2-Hydroxy-γ-Lactones," *Tetrahedron* 55, 2625-2638 (1999).

Horton et al, "Reaction of Butyllithium with Benzylidene Acetals of Aldopyranosides and 1,5-Anhydroalditols," *Carbohydrate Research*. 174, 305-312 (1988).

Hossain et al, "Facile Synthesis of 3'-C-Branched 1,5-Anhydrohexitol Nucleosides," *Nucleosides Nucleotides*. 17(9-11), 1781-1786 (1998).

Hossain et al, "Oligonucleotides Composed of 2'-Deoxy-1',5'-anhydro-D-mannitol Nucleosides with a Purine Base Moiety," *J. Org. Chem*. 63, 1574-1582 (1998).

Hossain et al, "Synthesis of 3'-*C*-branched 1',5'-anhydromannitol Nucleosides as new Antiherpes Agents," *Tetrahedron*. 54(10), 2209-2226 (1998).

Hu et al, "Cross-Metathesis of N-Alkenyl Peptoids with O- or C-Allyl Glycosides," *Tetrahedron Letters*. 40, 3305-3308 (1999).

Igarashi, Y. et al., "A Concise Synthesis of α-Glycolyl Cyanides," *Bioorg. Med. Chem. Lett*. 7(5), 613-616 (1997).

Ikeya et al, "Four New Phenolic Glycosides from Polygala tenuifolia," *Chemical and Pharmaceutical Bulletin*. 39(10), 2600-2605 (1991).

Jacobsen et al, "Enantioselective Catalytic Ring Opening of Epoxides with Carboxylic Acids," *Tetrahedron Letters*. 38(5), 773-776 (1997).

Jendrzejewski et al, "Total Synthesis of Restricticin," *Tetrahedron Letters*. 34(4), 615-618 (1993).

Jorgensen, K.A. (2000) "Catalytic Asymmetric Hetero-Diels-alder Reactions of Barbonyl Compounds and Imines," *Angewandte Chemie*, International Ed. 39(20), 3558-3588.

Jung et al, "Conversion of D-Mannose into 1,5-Anhydro-D-Allitol-4,6-Acetonide; Unusual Intramolecular Epoxy Alcohol Opening in Base," *Tetrahedron Letters*. 32(43), 6089-6092 (1991).

Kanai et al, "Design of a new bifunctional asymmetric catalyst from carbohydrates: application to catalytic asymmetric cyanosilylation of aldehydes and acetophenone," *Tetrahedron Letters*. 41, 2405-2409 (2000).

Kelly et al, "Synthesis of 9-Deoxy-8,9-oxaprostaglandins," *Journal of the Chemical Society Perkin Transactions* 1. 8, 2352-2353 (1990).

Kelly et al, "Preparation of Some Novel Prostanoids Based on a Tetrahydropyran Ring," *Journal of the Chemical Society Perkin Transactions* 1. 4, 787-797 (1991).

Khanna et al, *Journal of Carbohydrate Chemistry*. "Nucleophilic Opening of N-Carboalkoxy-2,3-Anhydro-1-Deoxymannojirimycin. A Useful Method for the Syntheses of 2-, 3- and 2,3-Disunstituted 1-Deoxynojirimycin Analogs," (1995).

Kier et al, "Synthesis of Sydnones as Potential Therapeutic Agents," *Journal of Pharmaceutical Sciences*. 1058 (1962).

Kim, Y.H. "Dual Enantioselective Control in Asymmetric Synthesis," *Accounts of Chemical Research*, 34(12), 955-962 (2001).

Kiso et al, "Synthesis of 1,5-Anhydro-2-Deoxy-4-O-Phosphono-3-)-Tetradecanoyl-2-[)3R)- and (3S)-3-tetradecanoyloxytetradecanamido]-," *Journal of Carbohydrate Chemistry*. 5(4), 621-630 (1986).

Kiso et al, "Studies on Selectin Binding Inhibitors: Synthesis of Sialyl-Lewis X and Sialyl-Lewis X and Sialyl-Lewis A Epitope Analogs Containing 2-Acetamido Derivative of N-Methyl-1-Deoxynojirimycin," *Journal of Carbohydrate Chemistry*. 1 (1996).

Klein et al, Kettenverlangerung von Kohlenhydraten: Synthese von Pyrazolen aus optisch aktiven Carbonsauren, *Liebs. Ann. Chem*. 6, 485-489 (1987).

Knapp et al, "Assignment of the Liposidomycin Diazepanone Stereochemistry," *Journal of Organic Chemistry*. 66, 5822 (2001).

Kohrt et al, "Highly Functionalized Cyclohexenyl Systems: Enzymatic Resolution and Selective Oxirane Opening Reactionsof p-Benzoquinone Derivatives," *Journal of Organic Chemistry*. 63(15), 5088-5093 (1998).

Koll et al, "Ein Neuer Effizienter Weg Zur Darstellung von Glyco-Pyranosylcyaniden (2,6-Anhydroaldononitrilen) Ohne Nachbargruppenbeteiligung. Reduktion von 2,6-Anhydro-1-Desoxy-1-Nitroalditolen mit Phosphortrichlorid," *Carbohydrate Research*. 301 (1987).

Kondo et al, "Partial Benzoylation of Methyl 4,6-0-Benzylidene-α- and 3-D-Glucopyrano-sides, and 1,5-Anhydro-4-6-O-benzyl-idene-D-glucitol with Benzoic Anhydride in Chloroform," *Agricultural and Biological Chemistry*. 41(10), 2089-2090 (1977).

Kondo et al, "Partial tosylation of 1,5-anhydro-D-glucitol," *Canadian Journal of Chemistry*. 55(22), 3820-3824 (1977).

Kondo et al, "Selective esterification of 1,5-anhydro-4,6-O-benzylidene-o-galactitol," *Carbohydrate Research*. 193, 279-282 (1989).

Korth et al, "Electron Spin Resonance Spectroscopic Investigation of Carbohydrate Radicals," *Journal of the Chemical Society Perkin Transactions* 2. 9, 1453-1459 (1986).

Kusano et al, "A New Amino Acide, (2S,3R)-(-)-Hydroxybaikiain from Russula subnigricans HONGO," *Chemical and Pharmaceutical Bulletin*. 3482 (1987).

Leeuwenburgh et al, "A Novel Approach Towards *cis*- and *trans*-Fused Pyranopyrans Based on Ring-Closing Metathesis Reaction of Carbohydrate Derivatives," *Synlett*. 11, 1263-1264 (1997).

Leeuwenburgh et al, "Synthesis of a *trans*-Fused Tricyclic Ether Using a Novel Differentially Protected Glucal," *Synlett*. 12, 1945-1947 (1999).

Lehmann et al, "Reaktionen Enolischer Zuckerderivate," *Carbohydrate Research*. 2(6), 486-499 (1966).

Lopez et al, "Serial Radical Reactions of Enol Ethers: Ready Routes to Highly Functionalized C-Glycosyl Derivatives," *Journal of the American Chemical Society*. 111(9), 3450-3452 (1989).

Luengo, Juan and Koreeda, Masato, "Stereospecific Synthesis of *z*- and *E*-1-Alkoxy-1,3-Butadienes," *Tetrahedron Letters*. 25(43), 4881-4884 (1984).

Luyten et al, "Synthesis and Conformational Behavior of Purine and Pyrimidine β-D-*threo*-Hex-3'-enopyranosyl Nucleosides," *Tetrahedron*. 52(27), 9249-9262 (1996).

Maeda et al, "Synthetic Studies on Sialogylcoconjugates 71: Synthesis of Sulfo- and Sialyl-Lewis X Epitope Analogs Containing the 1-Deoxy-N-Acetylglucosamine in Place of N-Acetylglucosamine Residue," *Journal of*", 14(3), 369-385 (1995).

Mallet et al, "The Use of Selenophenly Galactopyranosides for the Synthesis of α and β-(1→4)-*C*-Disaccharides," *Tetrahedron Asymmetry*. 5(12), 2593-2608 (1994).

Martin et al, A Concise Enantioselective Entry to the Synthesis of Deoxy-azasugars, *Organic Letters*. 2(1) 93-95 (2000).

Martin, J. et al. "Efficient Synthesis of α-Aldopyranosyl Cyanides via Radical Cyanation Reactions," *Tetrahedron Lett*. 39, 5927-5930 (1998).

Meyer et al, "Photochemical rearrangement of 2-( N-allyl-N-alkylamino) cyclohex-2-enones," *Receuil des Travaux Chimiques des Pays-Bas*.114, 492-497 (1995).

Miller et al, "Synthesis of Conformationally Restricted Amino Acids and Peptides Employing Olefin Metathesis," *Journal of the American Chemical Society*. 117, 5855 (1995).

Molander et al, "Sequenced Reactions with Samarium(II) Iodide," *Journal of Organic Chemistry*. 62(9), 2944-2956 (1997).

Nakai et al, "The [2,3] Wittig Rearrangement of 2-Alkenyloxyacetic Acids and its applications to the stereocontrolled synthesis of β, γ-Unsaturated Aldehydes and Conjugated Dienoic Acids," *Tetrahedron Letters*. 22, 69-72 (1981).

Newth, F.H., "The O-Toluene-p-sulphonyl Derivatives of 1,5-Anhydro-4,6-Obenzylidene-D-glucitol," pp. 2717-2720 (1959).

Nguefack et al, "Palladium-Mediated Cyclization on Barbohydrate Templates," *Journal of Organic Chemistry*. 62(5), 1341-1347 (1997).

Nicolaou et al, "Novel Strategies for the Construction of Complex Polycyclic Ether Frameworks," *Angewandte Chemie (International edition in English)*. 30(3), 299-303 (1991).

Nicolaou et al, "Novel IBX-Mediated Processes for the Synthesis of Amino Sugars and Libraries Thereof," *Angewandte Chemie (International edition in English)*. 39(14), 2526-2529 (2000).

Nicolaou et al, "Total Synthesis of Brevetoxin A: Part 1: First Generation Strategy and Construction of BCD Ring System," *Chemistry : a European Journal*. 5(2), 599-617 (1999).

Nicolaou et al, "Bridging of Macrodithionolactones to Bicyclic Systems," *Journal of the American Chemical Society*. 112(8), 3040-3054 (1990).

Nicolaou et al, "Iodine(V) Reagents in Organic Synthesis.," *Journal of the American Chemical Society*. 124(10), 2233-2244 (2002).

Nikitskaya et al, "The Synthesis of 7-Hydroxy-3, 9-Diazabicyclo[3.3.3]Nonane," *Chemistry of Heterocyclic Compounds*. 196 (1965).

Nikitskaya et al, "The Synthesis of 7-Hydroxy-3, 9-Methyl-3, 9-Diazabicyclo[3.3.1]Nonane and Some of it Derivatives," *Journal of Organic Chemistry USSR*. 170 (1965).

Nishikawa et al, "Improved Conditions for Facile Overman Rearrangement," *Journal of Organic Chemistry*. 63, 188-192 (1998).

Oishi et al, "Convergent Synthesis of a *Trans*-fused 6-7-6 Tricyclic Ether System Based on a Ring-closing Metathesis Reaction," *Synlett*. 8, 980-982 (1997).

Palacios et al, "Easy and Efficient Generation of Reactive Anions with Free and Supported Ylides as Neutral Bronsted Bases," *Tetrahedron*. 56, 663-669 (2000).

Parsons et al, "Synthesis of hydroxyl pyrrolidines and piperidines via free-radical cyclisations," *Journal of the Chemical Society* Perkin Trans. 2 651 (1998).

Pelzer et al, "Isoselektivitat bei der asymmetrischen Paterno-Buchi-Reaktion unter Verwendung von Kohlenhydraten als chorale Auxiliare," *Chemische Berichte*. 122(3), 487-491 (1989).

Perez-Perez et al, "Synthesis and Antiviral Activity of 2-Deoxy-1,5-Anhydro-D-Mannitol Nucleosides Containing a Pyrimidine Base Moiety," *Bioorganic and Medicinal Chemistry Letters*. 1457 (1996).

Phillips et al, "Ring-Closing Metathesis of Nitrogen-Containing Compounds: Applications to Heterocycles, Alkaloids, and Peptidomimetics," *Aldrichimica Acta*. 32(3), 75-89 (1999).

Rajanbabu, T.V. et al. "Carbohydrate Phosphinites as Practical Ligands in Asymmetric Catalysis: Electronic Effects and Dependence of Backbone Chirality in Rh-Catalyzed Asymmetric Hydrogenations. Synthesis of R- or S—Amino Acids Using Natural Sugars as Ligand Precursors," (1997) *J. Org. Chem.* 62, 6012-6028.

Reichwein et al, "Synthesis of Cyclic Dipeptides by Ring-Closing Metathesis," *European Journal of Organic Chemistry*. 4, 2335 (2000).

Rolf, D. et al., "Reductive Cleavage of Glycosides," *J. Amer. Chem. Soc.* 104, 3539-3541 (1982).

Rutjes et al, "Ruthenium-Catalyzed Ring Closing Olefin Metathesis of Non-Natural α-Amino Acids," *Tetrahedron Letters*. 38(4), 677-680 (1997).

Sakai et al, "Isolation, Structure Determination, and Synthesis of Neodysiherbaine A, a New Excitatory Amino Acid from a Marine Sponge," *Organic Letters*. 3(10), 1479-1482 (2001).

Sakaibara et al, "Anomeric Effect on Kinetic Acidity: Examples for the Oxygen Atom of Ethers to Accelerate Abstraction of an α-Hydrogen Atom," *Tetrahedron Letters*. 34(21), 3429-3432 (1993).

Sakata et al, "Synthesis and Reactions of Glycosyl Methyl- and Benzyl- Xanthates: A Facile Synthesis of 1-Thioglycosides," *Carbohydrate Research*. 13(3), 379-386 (1970).

Sano et al, "A Novel Method for the Deoxygenation of Acetylated Sugars," *Synthesis*. 5, 402-403 (1988).

Sasaki et al, "Intramolecular Radical Cyclization—Ring Closing Metathesis Approach to Fused Polycyclic Ethers, Convergent Synthesis and Conformational Analysis of the (E)FGH Ring System of Ciguatoxin," *Journal of Organic Chemistry*. 67(10), 3301-3310 (2002).

Schleich et al, "Pd-Catalyzed Asymmetric Allylic Alkylation of 3-Acetoxy-N-(tert-butyloxycarbonyl)-1,2,3,6-tetrahydropyridine—Preparation of Key Intermediates for Natural Product Synthesis," *European Journal of Organic Chemistry*. 3, 2515 (1999).

Schmidt et al, "A Synthesis of Densely Functionalized 2,3-Dihydropyrans Using Ring-Closing Metathesis and Base-Induced Rearrangements of Dihydropyran Oxides," *European Journal of Organic Chemistry*. 4, 3145 (2000).

Schmidt et al, "Synthesis of Functionalized 2,3- and 3,4-Dihydropyrans Starting from a-Hydroxycarboxylic Esters via RCM," *Synlett*. 1591-1593 (1999).

Seebach, D. (2001) "TADDOLs, Their Derivatives, and TADDOL Analogues: Versatile Chiral Auxiliaries," *Angewandte Chemie*, International Ed.m 40(1), 92-138.

Shen et al, "Enantioselective Synthesis of Ethyl 4,5,7,8,9-Penta-O-acetyl-2,6-anhydro-3-deoxy-D-erythro-L-gluca-nononate: a 2-Monodeoxygenated Derivative of '2-Keto-3-deoxy-D-glycero-D-galacto-nononic Acid'," *Helvetica Chimica Acta*. 83(5), 943-953 (2000).

Sherman et al, "Studies of model compounds for the analysis of ester-containing polysaccharides by the reductive-cleavage method," *Carbohydrate Research*. 231, 221-235 (1992).

Sinou et al, "Palladium-Mediated Cyclization on Carbohydrate Templates Synthesis of Enantiopure Annelated Tricyclic Compounds," *European Journal of Organic Chemistry*. 4, 4071-4077 (2000).

Snider et al, "Intramolecular [2+2] Cycloadditions of Alkoxyketenes and Alkoxyketeniminium Salts," *Journal of Organic Chemistry*. 50, 5167-5176 (1985).

Speziale et al, "N-Substituted Glycinate and Alaninate Esters," *Journal of Organic Chemistry*. 25, 728-732 (1960).

Spohr et al, "Inhibitors of *endo*-α-mannosidase. Part I.[1] Derivatives of 3-O-(α-D-glucopyranosyl)-D-mannopyronose," *Canadian Journal of Chemistry*. 71(11), 1919-1927 (1993).

Stähle, Wolfgang and Kunz, Horst "Carbohydrates as Chiral Templates: Stereoselective Diels-Alder Synthesis with Dienes of Differing Reactivity," *Synlett*. 4, 260-262 (1991).

Still et al, "A Convergent Synthesis of the O-Benzyl Derivative of Enantio-Ineupatoriol from a Carbohydrate Precursor," *Synthetic Communications*. 18(13), 1461-1474 (1988).

Sugai et al, "A Chemo-Enzymatic Synthesis of D-Allosamine Derivatives from Tri-O-acetyl-D-glucal," *Bulletin of the Chemical Society of Japan*. 70(10), 2535-2540 (1997).

Sustmann et al, "Selective Formation and Conformational Analysis of Carbohydrate-derived Radicals," *Journal of the Chemical Society* Faraday Trans. 1 1987, 83(1), 95-105 (1987).

Tanaka et al,"Synthesis and evaluation of a bicyclic deoxymannojirimycin derivative as a potential glycosidase inhibitor," *Canadian Journal of Chemistry*. 431 (1998).

Thoma et al, "Preorganization of the Bioactive Conformation of Sialyl Lewis[X] Analogues Correlates with Their Affinity to E-Selection," *Angewandte Chemie (International edition in English)*. 40(10), 1941-1945 (2001).

Tian et al, "myo-Inositol 1-Phosphate Synthase: Dose a Single Active-Site Amino Acid Catalyze Multiple Proton Transfers?," *Journal of the American Chemical Society*. 121, 5795-5796 (1999).

Togo et al, "Radical Decarboxylative Alkylation onto Heteroaromatic Bases with Trivalent Iodine Compounds," *Journal of the Chemical Society Perkin Transactions 1*. 2417-2427 (1993).

Tsukuda et al, "Synthesis of Restrictinol and 9,10,11,12-Tetrahydro-7-Desmethylrestricticin," *Chemical and Pharmaceutical Bulletin* . 41(6), 1191-1193 (1993).

Tulshian et al, "Out-of-Ring Claisen Rearrangements are Highly Stereoselective in Pyranoses: Routes to gem-Dialkylated Sugars," *Journal of Organic Chemistry* 1984, 49(13), 2347-2355.

Van Aerschot et al, "Synthesis of nucleoside analogues with a 1,5-anhydrohexitol moiety," *Bioorganic and Medicinal Chemistry Letters* 1993, 3(6), 1013-1018.

Van Aerschot et al, "Increased RNA Affinity of HNA Analogues by Introducing Alkoxy Substituents at the C-1 or C-3 Position," *Nucleosides Nucleotides*. 781 (2001).

Vassilev et al, "L-Threonine Aldolase in Organic Synthesis: Preparation of Novel β-Hydroxy-β-Amino Acids," *Tetrahedron Letters*. 36(23), 4081-4084 (1995).

Vega-Perez et al, "Conformationally restricted analogues of the muramyldipeptide MDP," *Carbohydrate Research*. 248, 95-106 (1993).

Verheggen et al, "Synthesis and Antiherpes Virus Activity of 1,5-Anhydrohexitol Nucleosides," *Journal of Medicinal Chemistry*. 36(14), 2033-2040 (1993).

Verheggen et al, "Synthesis of 1,5-Andydro-2-($N^6$-Cyclopentyladenin-9-YL)-2-Deoxy-D-Altrohexitol," *Nucleosides Nucleotides*. 321 (1995).

Viaud et al, "Zinc Azide Mediated Mitsunobu Substitution. An Expedient Method for the One-Pot Azidation of Alcohols," *Synthesis*. 2, 130-132 (1990).

Wang et al, "Cyclohexene Nucleic Acids (CeNA) Form Stable Duplexes With RNA and Induce RNASE H Activity," *Nucleosides Nucleotides*. 785 (2001).

Wotiz et al, "D-Glucopyranosiduronates. I. Steroidyl-β-D-glucopyranuronosides," *Journal of the American Chemical Society*. 81, 1704-1706 (1959).

Yamagishi et al, "Total Synthesis of Trehalase Inhibitor Salbostatin," *Bioorganic and Medicinal Chemistry Letters*. 5(5), 487-490 (1995).

Ye et al, "Anomerica Reactivity-Based One-Pot Oligosaccharide Synthesis: A Rapid Route to Oligosaccharide Libraries," *Journal of Organic Chemistry*. 65(8), 2410-2431 (2000).

Yet et al, "Recent Developments in Catalytic Asymmetric strecker-Type Reactions," *Angewandte Chemie, International Edition*. 40(5), 875-877 (2001).

Zeller et al, "Synthesis and mass spectra of 4-*O*-acetyl-1,5-anhydro-2,3,6-tri-*O*-acetyl-1,5-anhydro-di-*O*-(methoxycarbo-nylmethyl)-*O*-methyl-D-glucitol and 4-*O*-(methoxycarbo-nylmethyl)-*O*-acetyl-1,5-anhydro-*O*-(methoxycarbonylmethyl)-di-*O*-methyl-D-glucitol*," *Carbohydrate Research*. 211(1), 47-57 (1991).

Zeller et al, "Analysis of Macrocystitis *pyrifera* and *Pseudomonas aeruginosa* alginic acids by the redcuctive-cleavage method*," *Carbohydrate Research*. 226, 313-326 (1992).

Zissis et al, "1,5-Anhydro-D-altritol," *Journal of the American Chemical Society*. 77, 5154 (1955).

Zumpe et al, "A Mild Palladium Catalyzed *N*-Allylation of Amino Acids and Peptides," Synlett. 1199-1200 (1998).

Zumpe et al, "Application of the Palladium Catalyzed *N*-Allylation to the Modification of Amino Acids and Peptides," *Synthesis*. 1785-1791(1999).

Ferrier et al., "A New Route to L-Ascorbic Acid (Vitamin C)," *Journal of The Chemical Society*, vol. 10, pp. 332-333 (1997).

Vodonik and Gray, "Analysis of Linkage Positions in a Polysaccharide Containing Nonreducing, Terminal α-D-Gluco-Pyranosyluronic Groups by the Reductive-Cleavage Method," *Carbohydrate Research*, 172:255-266 (1988).

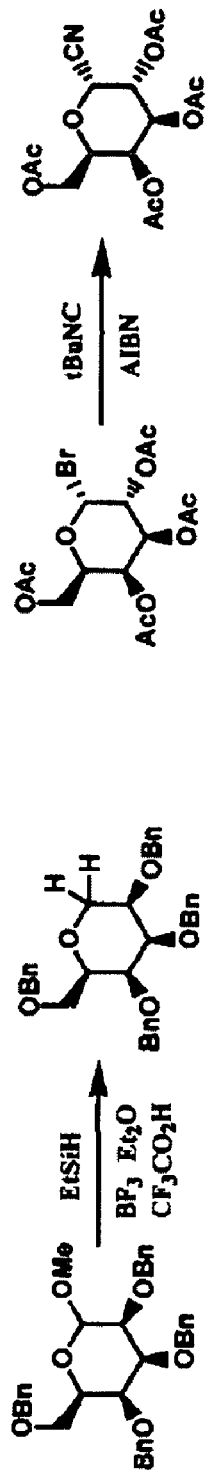
FIGURE 1 – Prior Art
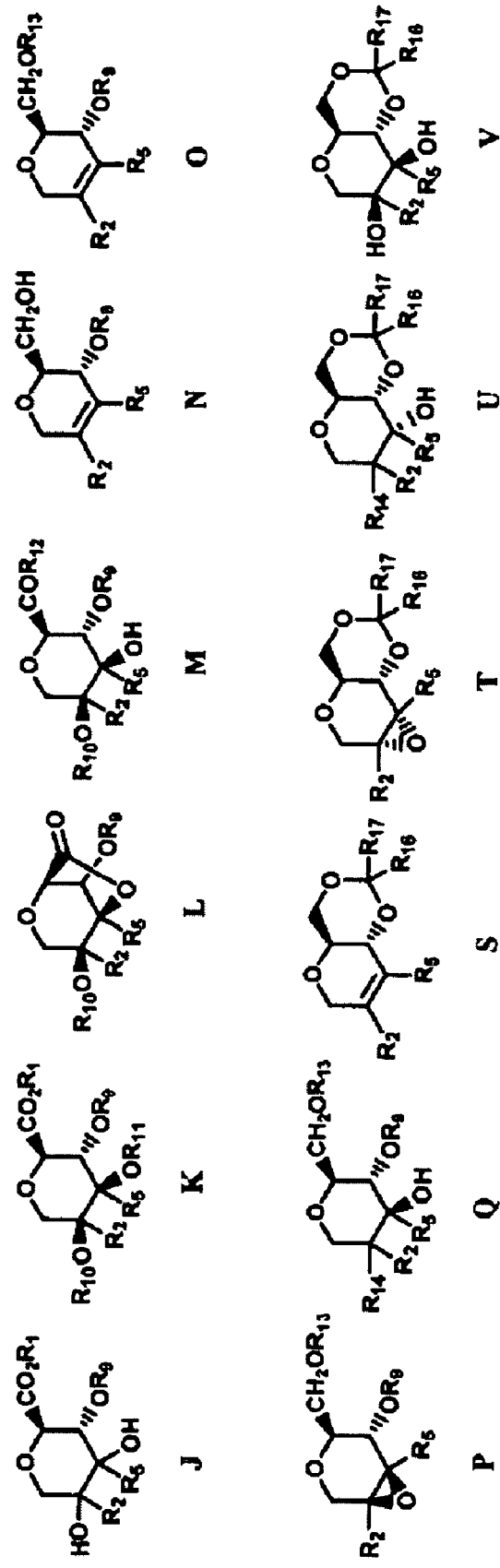
FIGURE 2
If $R_9$ = H then Y
If $R_{13}$ = H then Z

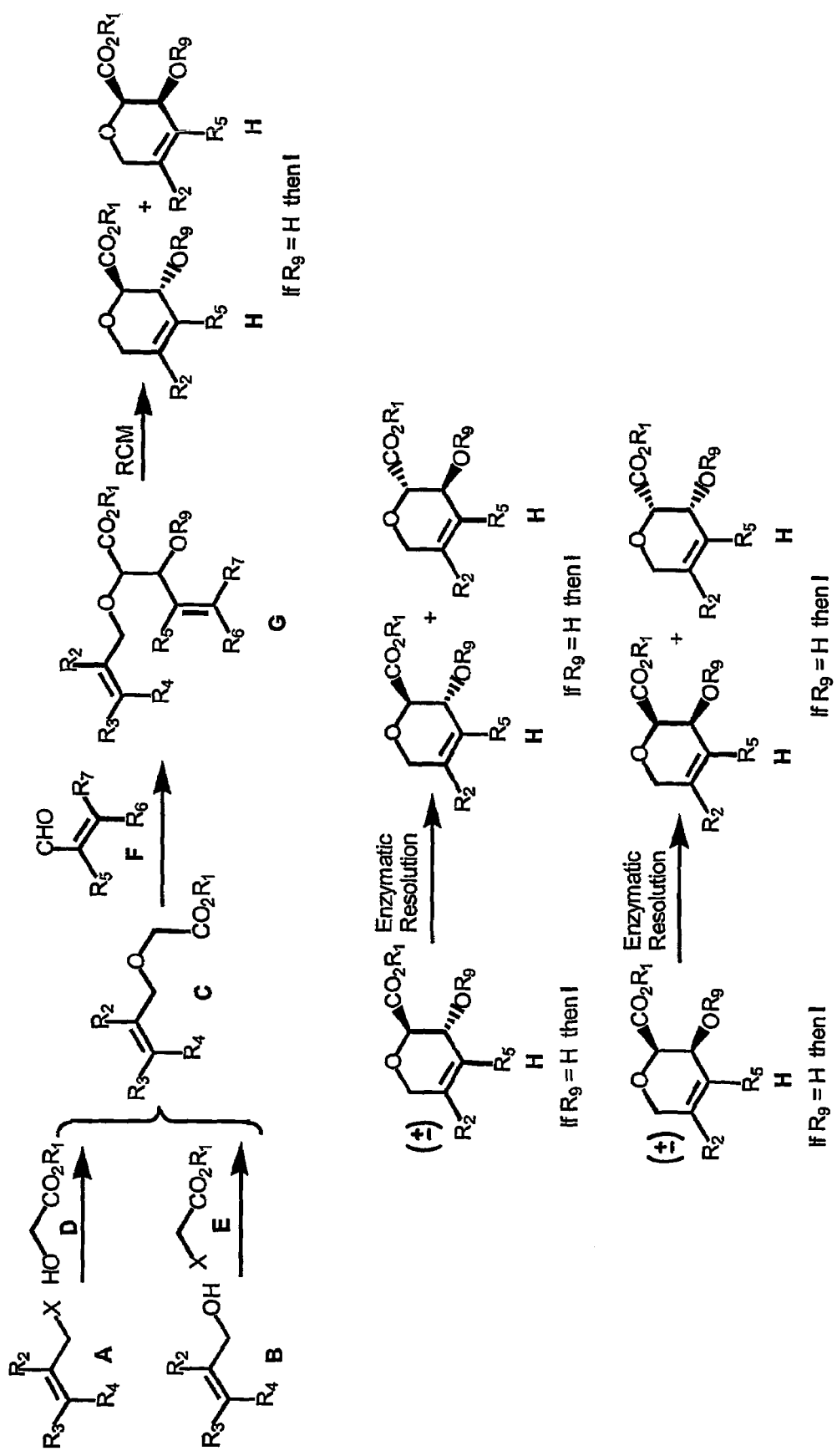
SCHEME 1

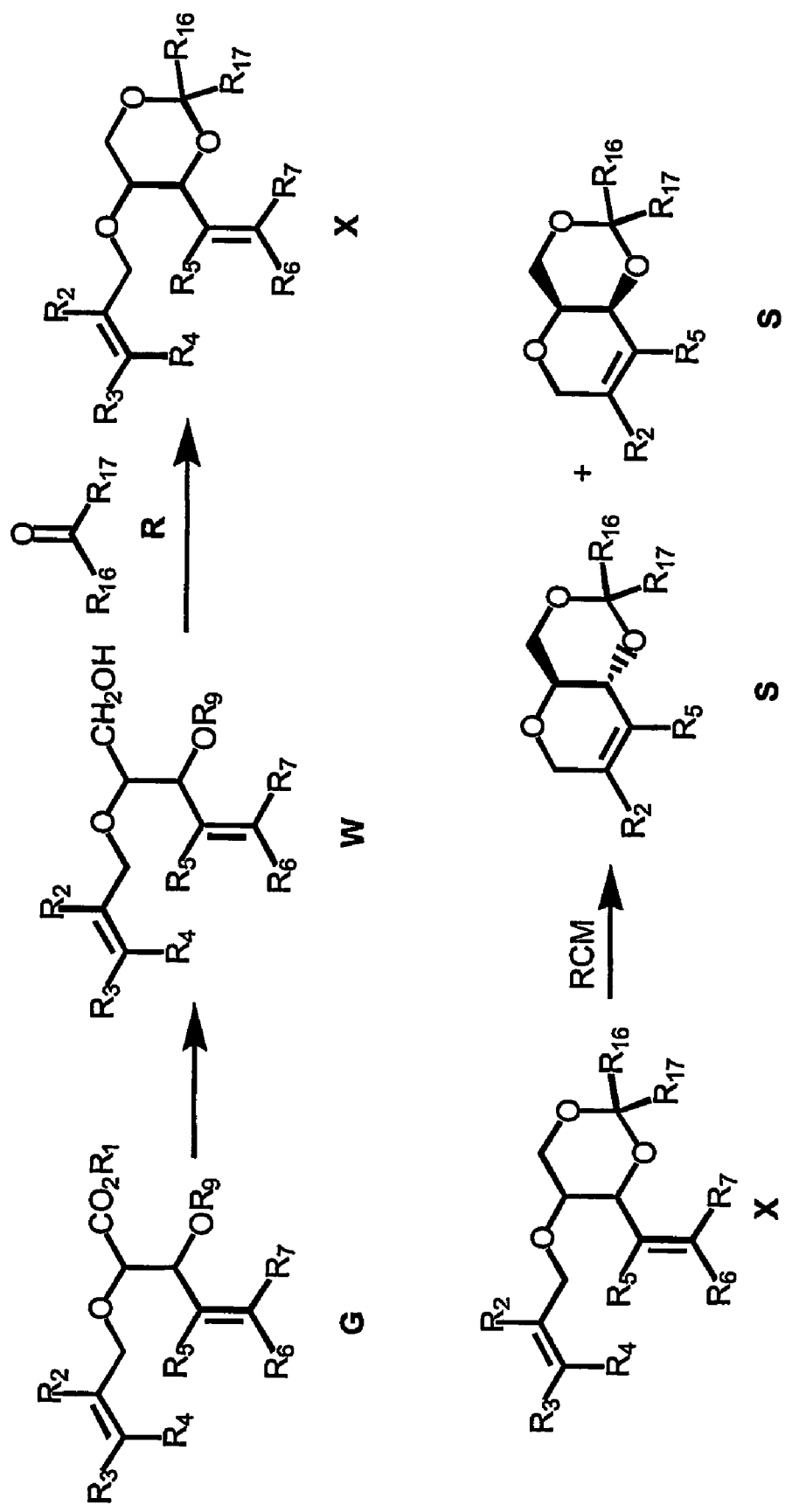
SCHEME 2

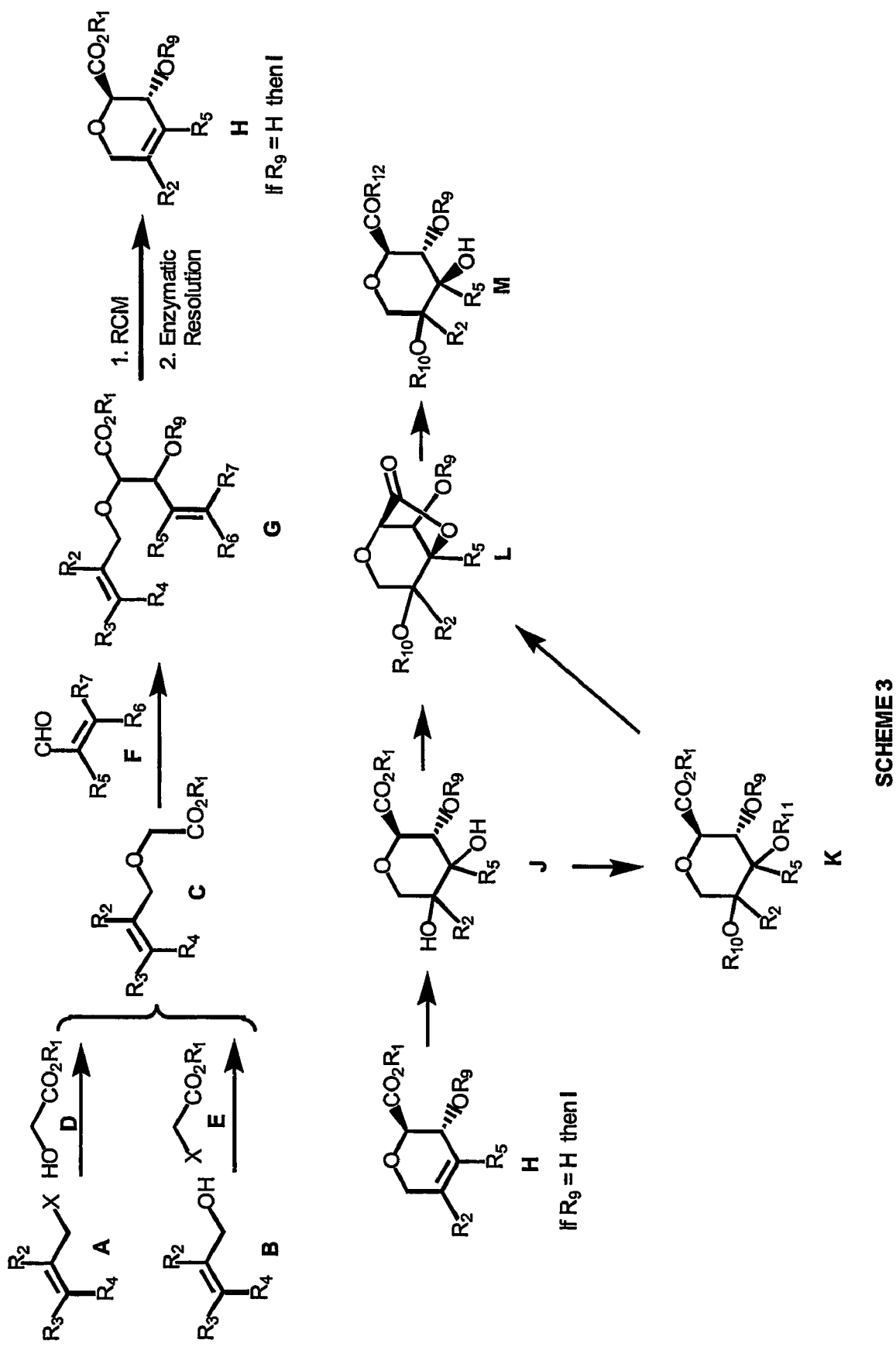
SCHEME 3

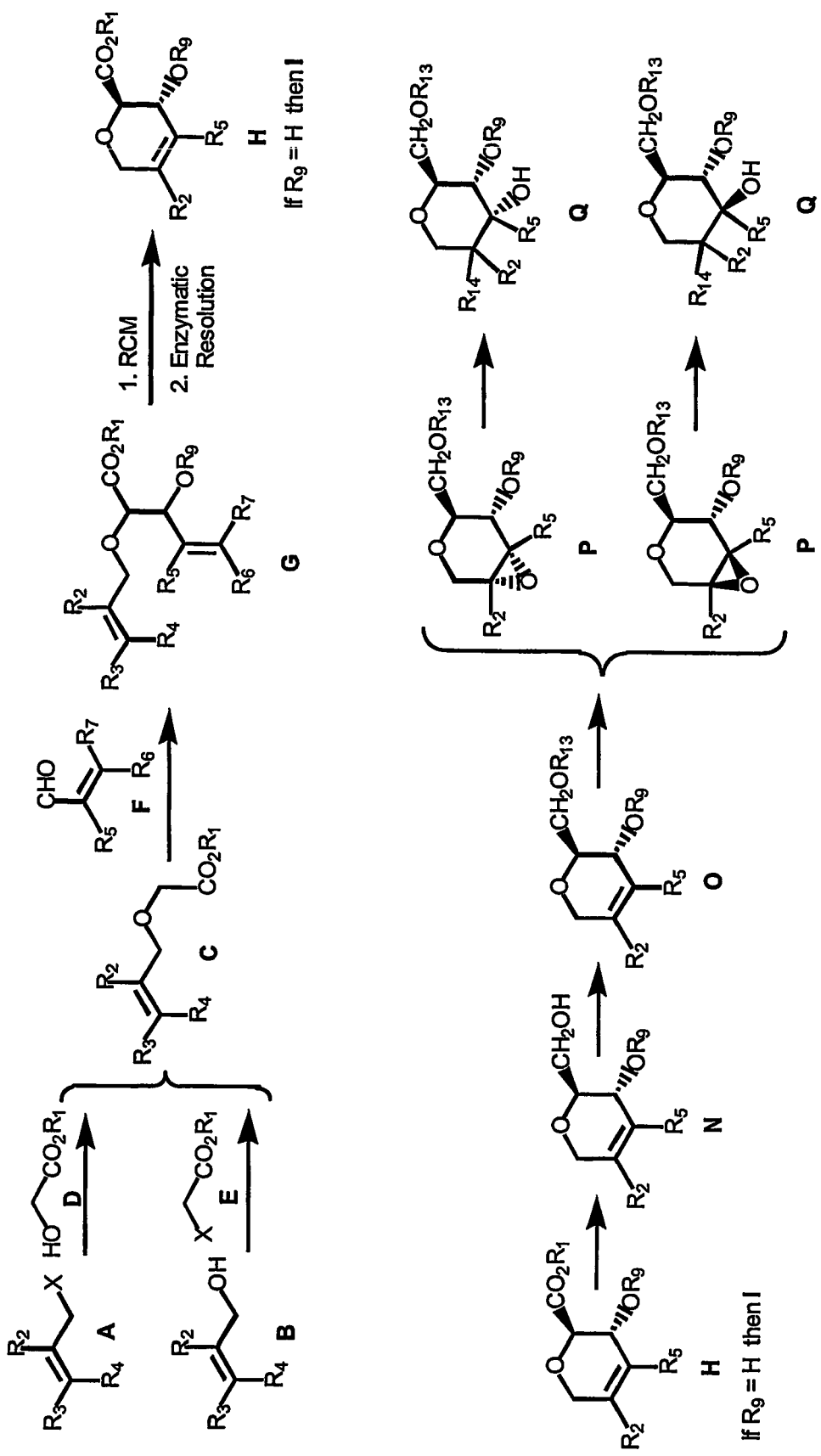
SCHEME 4

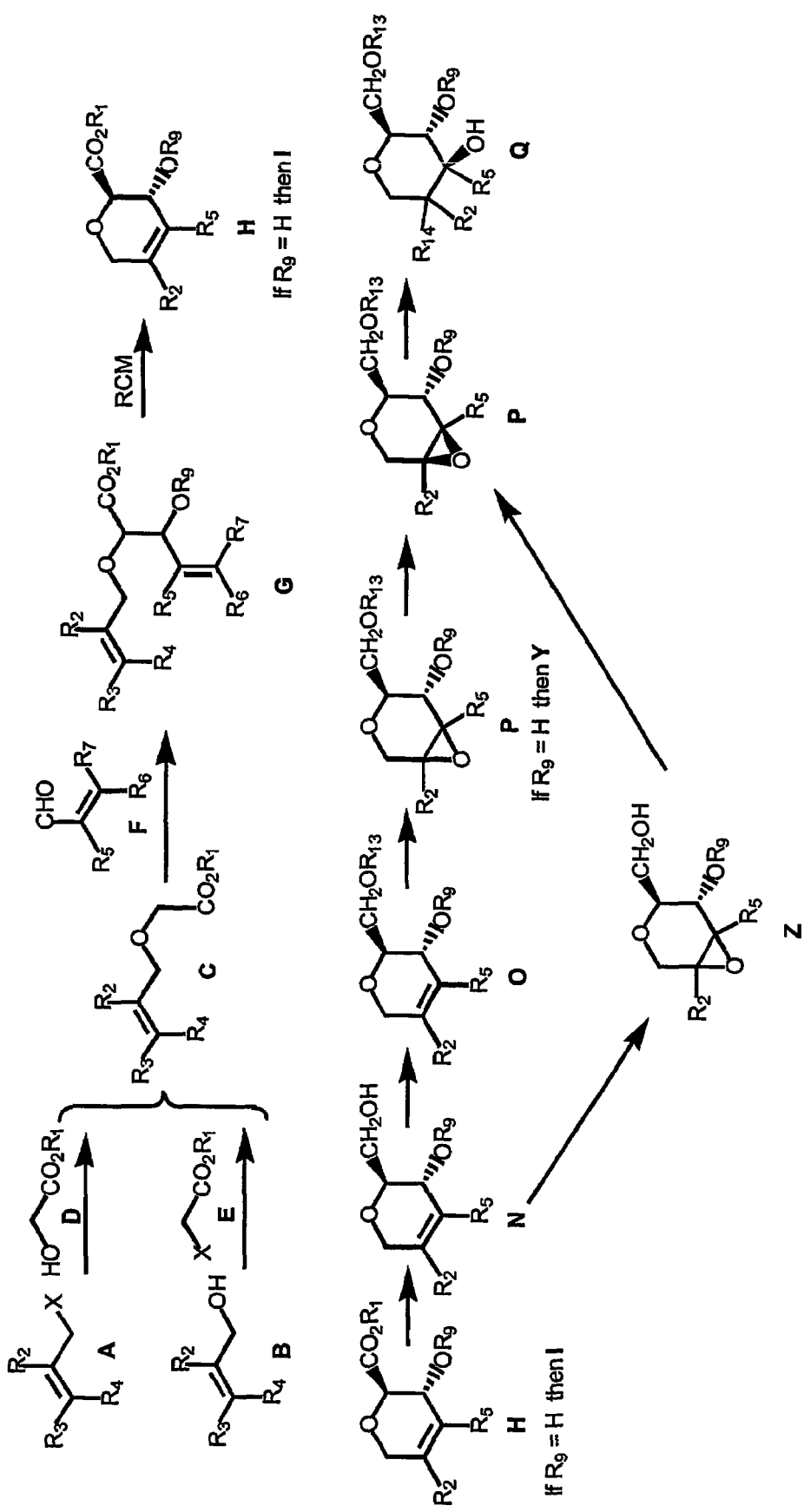
SCHEME 5

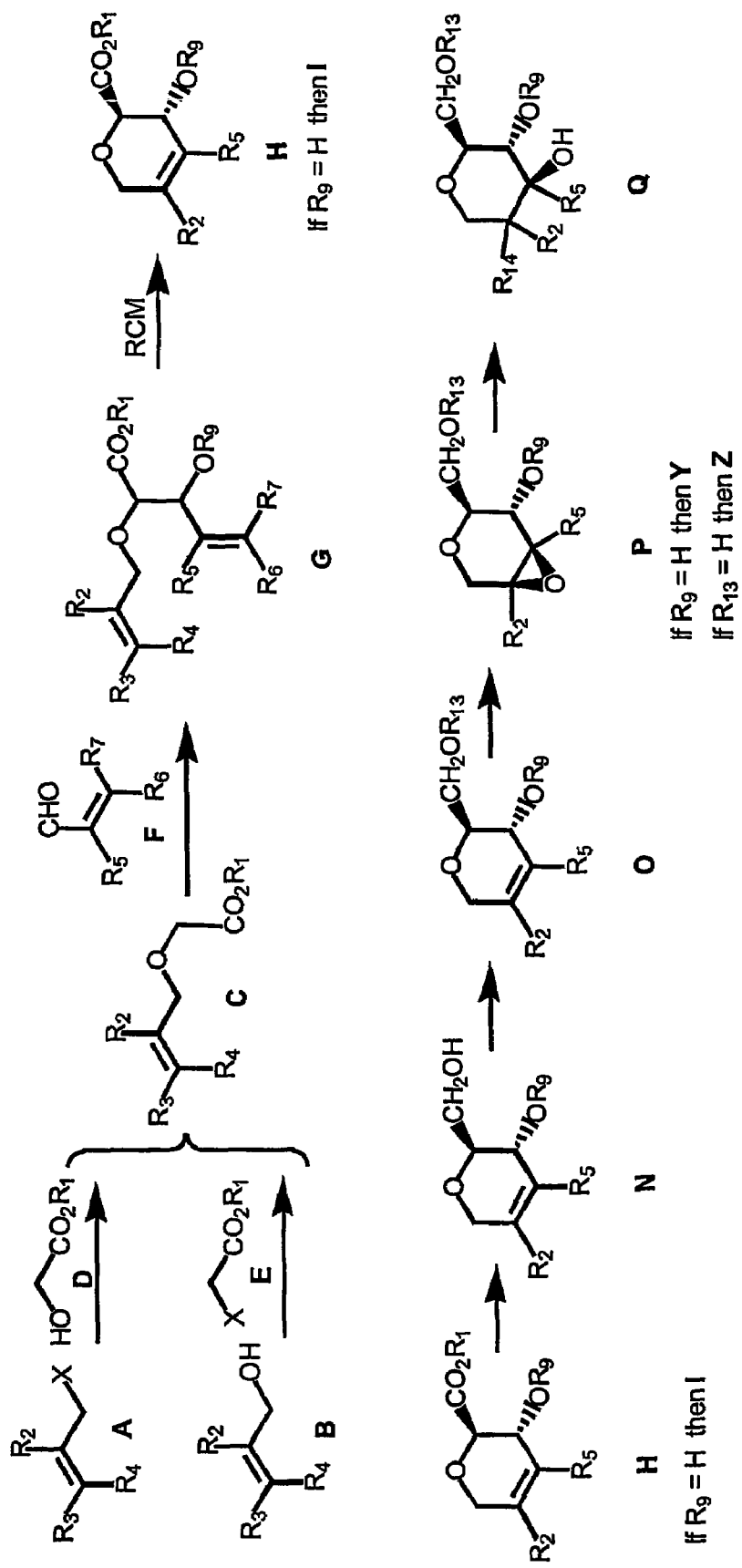
SCHEME 6

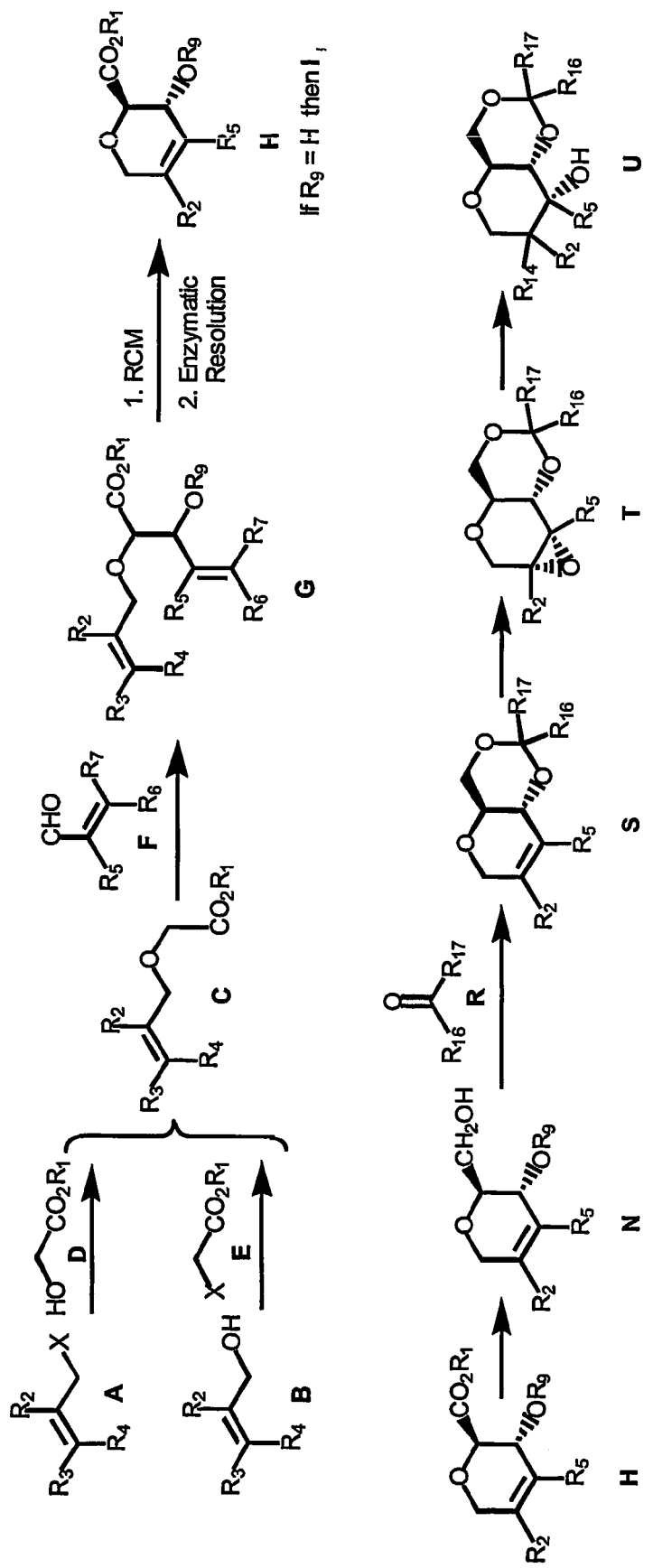
SCHEME 7

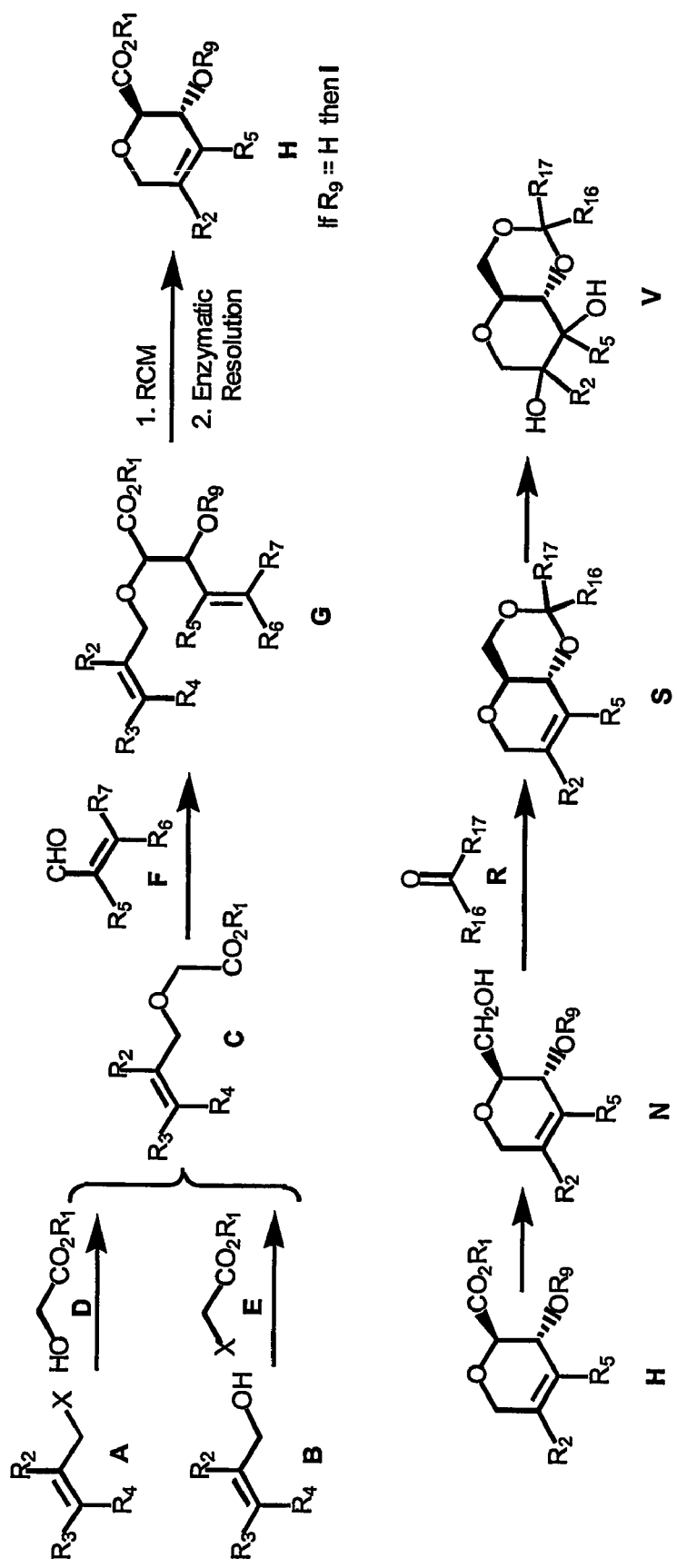
SCHEME 8

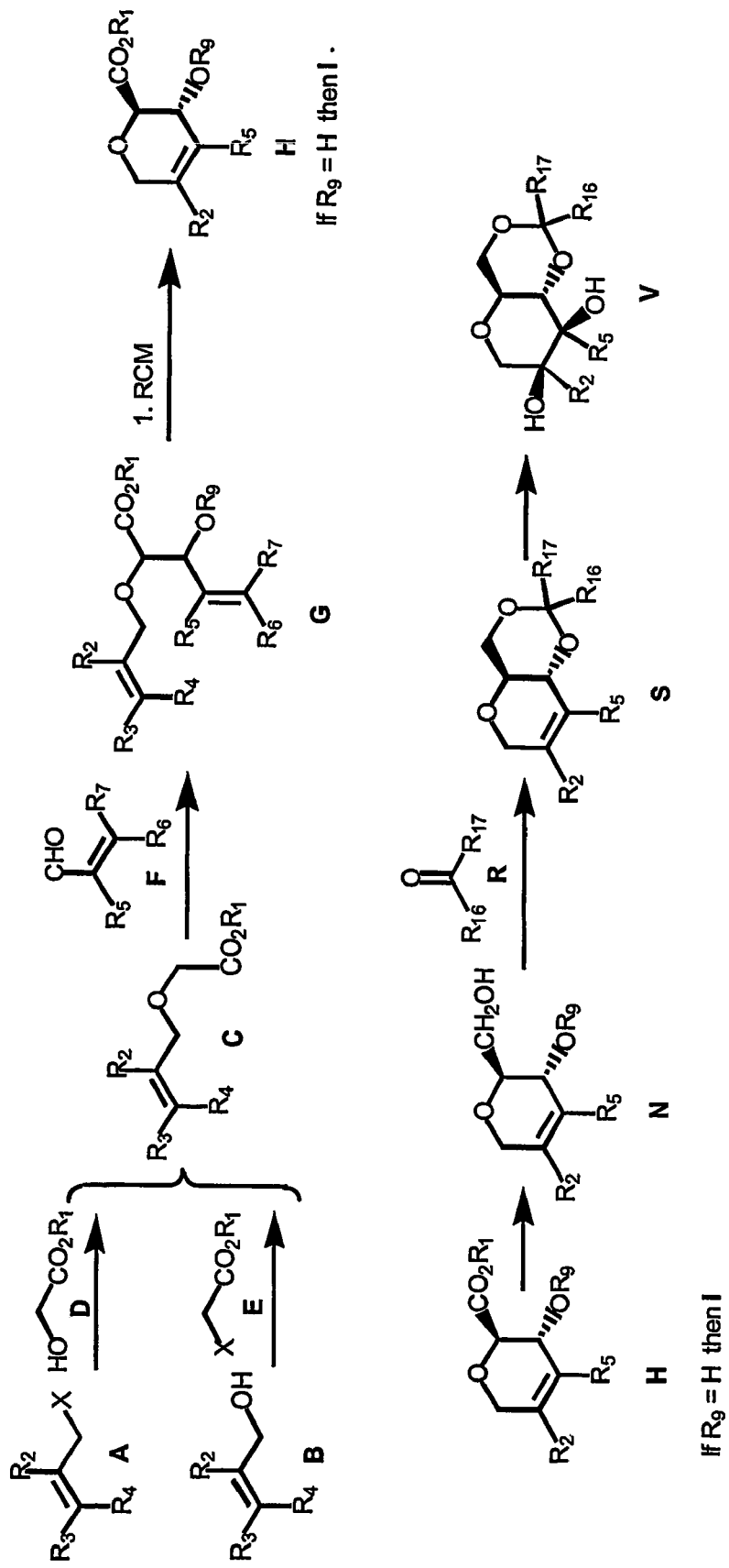
SCHEME 9

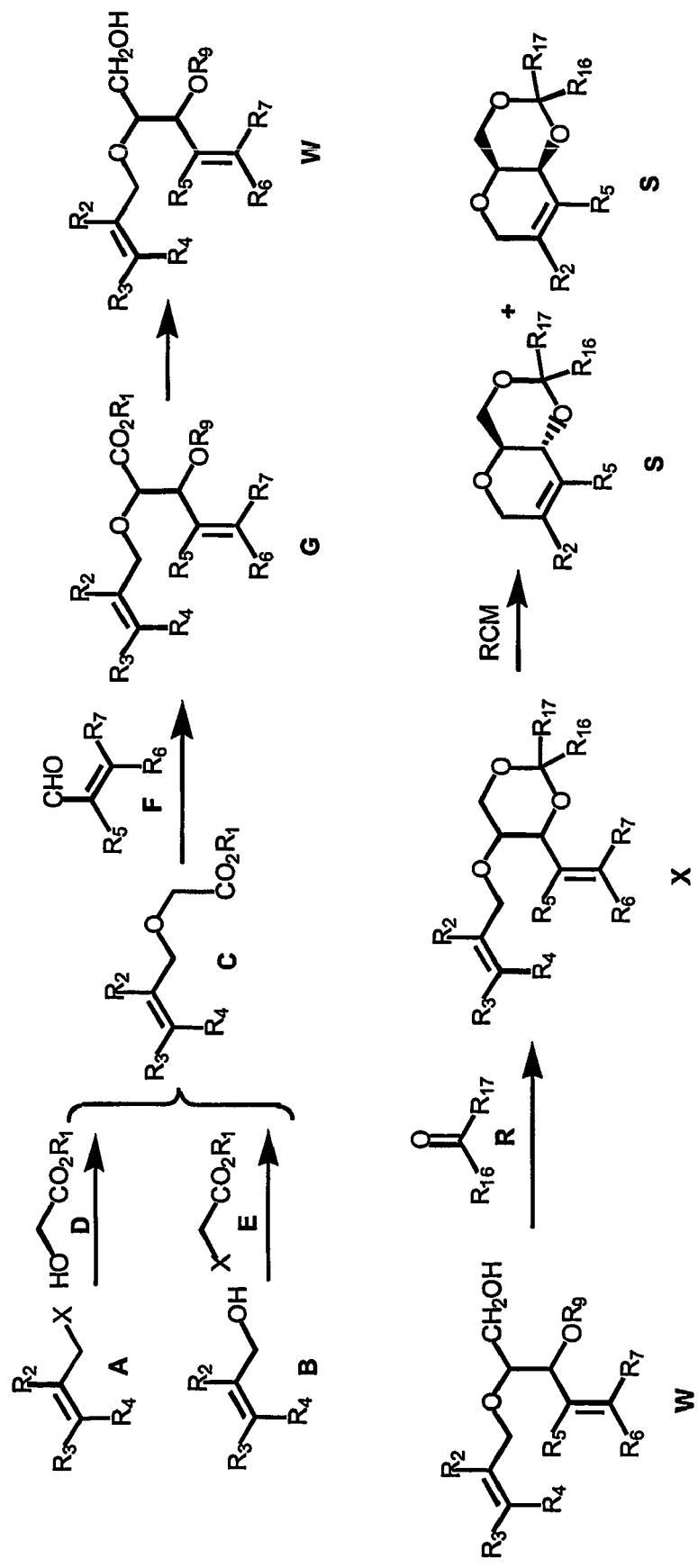
SCHEME 10

METHOD OF PREPARATION OF HETEROCYCLIC MOLECULES WITH PHARMACEUTICAL, PHARMACEUTICAL EXCIPIENT, COSMECEUTICAL, AGROCHEMICAL AND INDUSTRIAL USES

CROSS-REFERENCE TO RELATED APPLICATIONS

This application is a 35 USC 0371 National Stage application of PCT Application No. US2004/001344 filed Jan. 16, 2004; which claims the benefit under 35 USC 0119(e) to U.S. application Ser. No. 60/440,982 filed Jan. 17, 2003, now abandoned. The disclosure of each of the prior applications is considered part of and is incorporated by reference in the disclosure of this application.

BACKGROUND OF THE INVENTION

This invention pertains to processes that have utility in the construction of racemic and optically pure heterocyclic molecules that are to be screened for biological activities that would render them useful as pharmaceuticals, cosmeceuticals, pharmaceutical excipients or agrochemicals. More specifically, it pertains to the use of Ring-Closure olefin Metathesis (RCM) and Enzymatic Resolution (ER) for the production of optically pure synthetic intermediates during an organic synthesis and methods for elaboration of same.

BACKGROUND INFORMATION

Carbohydrates or saccharides are highly functionalized biomolecules present in plant and animal cells and tissues. These molecules play a key role in energy storage, cellular signaling and molecular recognition. Carbohydrates are critical in the early stages of inflammation and immune response and contribute to the progression of a number of diseases. In general, saccharides are poor therapeutic agents. These compounds are rapidly metabolized in the gut or the plasma and have low binding affinities to their targets. In addition, carbohydrates are difficult to synthesize and purify by conventional methods. The combination of the above drawbacks has considerably limited the use of saccharides as pharmaceuticals, cosmeceuticals, pharmaceutical excipients or agrochemicals. Such difficulties maybe overcome by the use of "carbohydrate mimetics" or optically active heterocyclic molecules that resemble, carbohydrates but have improved stability, target affinity and synthetic availability.

One strategy for increasing the stability of carbohydrate mimetics is to replace the heteroatom anomeric linkage of the carbohydrate ring system with a non-heteroatom linkage. Traditionally, these carbohydrate mimetics have been prepared by direct cleavage of the anomeric carbon-oxygen bond with a hydride equivalent, as set forth in Rolf, D. et al J. Amer. Chem. Soc. 1982, 104, 3539-3541. Such transformations are commonly carried out by reaction of the alkyl or acyl glycoside with a strong Lewis acid such as boron trifluoride etherate ($BF_3.Et_2O$), trifluoroacetic acid ($CF_3CO_2H$) and/or trimethylsilyl trifluoromethanesulfonate ($TMSOSO_2CF_3$) in the presence of an ionic hydride donor such as a trialkylsilane (FIG. 1). Said carbohydrate mimetics have also been prepared by direct cleavage of the anomeric carbon-oxygen bond with a cyanide equivalent, as set forth in Martin, J. et al Tetrahedron Lett. 1998, 39, 5927-5930. Such transformations are commonly carried out by reaction of the bromoglycoside with a free radical initiator (e.g. AIBN) in the presence of an alkyl isocyanide (FIG. 1). The use of trialkylsilyl cyanides for the preparation of cyano glycosides has also been described as set forth in Igarashi, Y. et al Bioorg. Med. Chem. Lett. 1997, 7(5), 613-616.

Such methodologies ultimately depend on the availability of the glycoside and are thereby limited in scope. Another drawback of the existing art is that the cleavage of the anomeric carbon-oxygen bond is not stereospecific and usually yields a mixture of stereoisomers. As such, there is an obvious and immediate need for novel methodology that provides rapid access to large quantities of optically pure heterocyclic molecules such as those set forth in this invention.

BRIEF DESCRIPTION OF THE INVENTION

Prior art preparations of carbohydrate mimetics are shown in FIG. 1.

The optically pure carbohydrate mimetics of the instant invention are shown in FIG. 2.

Schemes 1 to 10 on sheets 2 to 11 illustrate the chemical reactions used in making the optically pure carbohydrate mimetics of the invention.

SUMMARY OF THE INVENTION

Relative to traditional methods, efficiency is introduced into the syntheses of these carbohydrate mimetics by combining starting materials according to formulae A and D, or formulae B and E, to provide esters according to formula C. Compounds according to formula C can then react with aldehydes according to formula F to provide acyclic intermediates according to formula G. Application of a stereoselective Ring Closure olefin Metathesis (RCM) reaction to compounds according to formula G provides the 3,6-dihydro-2H-pyrans according to formulae H or I. These intermediates are subsequently transformed into optically pure stereoisomers via enzymatic resolution (Scheme 1). It is to be understood that the transformation of compounds according to formula G to optically pure compounds according to formulae H or I can also be carried out by way of an enantioselective Ring Closure olefin Metathesis (RCM) reaction.

Efficiency is also introduced into the syntheses of these carbohydrate mimetics by reduction of compounds according to formula G to compounds according to formula W. Subsequent reaction of compounds according to formula W with carbonyl compounds according to formula R provides acyclic intermediates according to formula X. Application of a stereoselective Ring Closure olefin Metathesis (RCM) reaction to compounds according to formula X provides the 3,6-dihydro-2H-pyrans according to formula S (Scheme 2). It is to be understood that the transformation of compounds according to formula X to optically pure compounds according to formula S can also be carried out by way of an enantioselective Ring Closure olefin Metathesis (RCM) reaction. When subjected to other synthetic transformations, compounds according to formula H, I and S provide a variety optically pure carbohydrate mimetics according to formulae J, K, L, M, N, O, P, Q, T, U, V, Y and Z (FIG. 2).

One advantage of this method over existing state of the art is that it provides rapid access to large quantities of optically pure compounds according to formulae H, I, J, K, L, M, N, O, P, Q, S, T, U, V, Y and Z. Another advantage of this method is that it allows the introduction of a variety of substituents into compounds according to formulae H, I, J, K, L, M, N, O, P, Q, S, T, U, V, Y and Z.

In one aspect of this invention, said carbohydrate mimetics can be used to generate molecules or diverse compound libraries with potential pharmaceutical, pharmaceutical excipient, cosmeceutical, agrochemical or industrial applications.

In another aspect of this invention, said carbohydrate mimetics can be linked to polymeric supports and/or other molecules in order to generate diverse compound libraries with potential pharmaceutical, pharmaceutical excipient, cosmeceutical, agrochemical or industrial applications.

In still another aspect of this invention, said carbohydrate mimetics can be coordinated to metals in order to generate organometallic complexes or catalysts with potential pharmaceutical, pharmaceutical excipient, cosmeceutical, agrochemical or industrial applications as set forth in Kanai, M. et al Tetrahedron Lett. 2000, 41, 2405-2409; Groaning, M. D. et al Tetrahedron Lett. 1998, 39, 5485-5488; Bell, D. et al U.S. Pat. No. 5,916,975 Jun. 29, 1999; and RajanBabu, T. V. et al J. Org. Chem. 1997, 62, 6012-6028.

Accordingly, the present invention describes a process shown in scheme 3 for preparing pharmaceuticals, pharmaceutical excipients, cosmeceuticals or agrochemicals comprising:

1. An allylic halide reagent A is first reacted with an α-hydroxycarboxylic ester D forming an oxygen-carbon bond and forming ether C; alternatively, an allylic alcohol reagent B is first reacted with an α-substituted ester D forming an oxygen-carbon bond and forming ether C.
2. The resulting compound according to formula C is reacted in a subsequent synthetic step with an α,β-unsaturated carbonyl compound according to formula F forming a carbon-carbon bond and forming a compound according to formula G;
3. The resulting compound according to formula G is reacted with a ring-closing olefin metathesis (RCM) catalyst forming a carbon-carbon bond and forming substituted 3,6-dihydro-2H-pyrans according to formulae H or I.
4. The resulting compound according to formulae H or I is reacted with an enzyme producing the optically pure substituted 3,6-dihydro-2H-pyrans according to formulae H or I.
5. The resulting compound according to formulae H or I is reacted with an oxidant forming substituted tetrahydropyran according to formula J.
6. The resulting compound according to formula J is reacted with an enzyme or an electrophilic reagent producing the compound according to formula K.
7. The resulting compound according to formula K or alternatively the compound according to formula J is reacted under microwave radiation forming substituted bicyclo[3.2.1]lactone according to formula L.
8. The resulting compound according to formula L is reacted with a nucleophilic reagent forming substituted tetrahydropyran according to formula M.

It is to be understood that the process shown in scheme 3 applies to all stereoisomers of compounds G, H, I, J, K, L and M.

Accordingly, the present invention also describes a process shown in scheme 4 for preparing pharmaceuticals, pharmaceutical excipients, cosmeceuticals or agrochemicals comprising:

1. An allylic halide reagent A is first reacted with an α-hydroxycarboxylic ester D forming an oxygen-carbon bond and forming ether C; alternatively, an allylic alcohol reagent B is first reacted with an α-substituted ester D forming an oxygen-carbon bond and forming ether C.
2. The resulting compound according to formula C is reacted in a subsequent synthetic step with an α,β-unsaturated carbonyl compound according to formula F forming a carbon-carbon bond and forming a compound according to formula G;
3. The resulting compound according to formula G is reacted with a ring-closing olefin metathesis (RCM) catalyst forming a carbon-carbon bond and forming substituted 3,6-dihydro-2H-pyrans according to formulae H or I.
4. The resulting compound according to formulae H or I is reacted with an enzyme producing the optically pure substituted 3,6-dihydro-2H-pyrans according to formulae H or I.
5. The resulting compound according to formulae H or I is reacted with a reducing reagent forming substituted 3,6-dihydro-2H-pyran according to formula N.
6. The resulting compound according to formula N is reacted with an electrophilic reagent forming substituted 2,6-dihydro-2H-pyran according to formula O.
7. The resulting compound according to formula O is reacted with an epoxidation reagent forming substituted 3,7-dioxabicyclo[4.1.0]heptane according to formula P.
8. The resulting compound according to formula P is reacted with a nucleophilic reagent forming substituted tetrahydropyran according to formula Q.

It is to be understood that the process shown in scheme 4 applies to all stereoisomers of compounds G, H, I, N, O, P and Q.

Accordingly, the present invention also describes a process shown in scheme 5 for preparing pharmaceuticals, pharmaceutical excipients, cosmeceuticals or agrochemicals comprising:

1. An allylic halide reagent A is first reacted with an α-hydroxycarboxylic ester D forming an oxygen-carbon bond and forming ether C; alternatively, an allylic alcohol reagent B is first reacted with an α-substituted ester D forming an oxygen-carbon bond and forming ether C.
2. The resulting compound according to formula C is reacted in a subsequent synthetic step with an α,β-unsaturated carbonyl compound according to formula F forming a carbon-carbon bond and forming a compound according to formula G;
3. The resulting compound according to formula G is reacted with a ring-closing olefin metathesis (RCM) catalyst forming a carbon-carbon bond and forming substituted 3,6-dihydro-2H-pyrans according to formulae H or I.
4. The resulting compound according to formulae H or I is reacted with a reducing reagent forming substituted 3,6-dihydro-2H-pyran according to formula N.
5. The resulting compound according to formula N is reacted with an electrophilic reagent forming substituted 2,6-dihydro-2H-pyran according to formula O.
6. The resulting compound according to formula O is reacted with an epoxidation reagent forming substituted 3,7-dioxabicyclo[4.1.0]heptane according to formulae P or Y.
7. The resulting compound according to formulae P or Y is reacted with an enzyme producing the optically pure substituted 3,7-dioxabicyclo[4.1.0]heptane according to formula P.
8. Alternatively, the compound according to formula N is reacted with an epoxidation reagent forming substituted 3,7-dioxabicyclo[4.1.0]heptane according to formula Z.

9. The resulting compound according to formula Z is reacted with an enzyme producing the optically pure substituted 3,7-dioxabicyclo[4.1.0]heptane according to formula P.

10. The resulting compound according to formula P is reacted with a nucleophilic reagent forming substituted tetrahydropyran according to formula Q.

It is to be understood that the process shown in scheme 5 applies to all stereoisomers of compounds G, H, I, N, O, P, Q, Y and Z.

Accordingly, the present invention also describes a process shown in scheme 6 for preparing pharmaceuticals, pharmaceutical excipients, cosmeceuticals or agrochemicals comprising:

1. An allylic halide reagent A is first reacted with an α-hydroxycarboxylic ester D forming an oxygen-carbon bond and forming ether C; alternatively, an allylic alcohol reagent B is first reacted with an α-substituted ester D forming an oxygen-carbon bond and forming ether C.

2. The resulting compound according to formula C is reacted in a subsequent synthetic step with an α,β-unsaturated carbonyl compound according to formula F forming a carbon-carbon bond and forming a compound according to formula G;

3. The resulting compound according to formula G is reacted with a ring-closing olefin metathesis (RCM) catalyst forming a carbon-carbon bond and forming substituted 3,6-dihydro-2H-pyrans according to formulae H or I.

4. The resulting compound according to formulae H or I is reacted with a reducing reagent forming substituted 3,6-dihydro-2H-pyran according to formula N.

5. The resulting compound according to formula N is reacted with an electrophilic reagent forming substituted 2,6-dihydro-2H-pyran according to formula O.

6. The resulting compound according to formula O is reacted with an epoxidation reagent forming the optically pure substituted 3,7-dioxabicyclo[4.1.0]heptane according to formulae P, Y or Z.

7. The resulting compound according to formulae P, Y or Z is reacted with a nucleophilic reagent forming substituted tetrahydropyran according to formula Q.

It is to be understood that the process shown in scheme 6 applies to all stereoisomers of compounds G, H, I, N, O, P, Q, Y and Z.

Accordingly, the present invention also describes a process shown in scheme 7 for preparing pharmaceuticals, pharmaceutical excipients, cosmeceuticals or agrochemicals comprising:

1. An allylic halide reagent A is first reacted with an α-hydroxycarboxylic ester D forming an oxygen-carbon bond and forming ether C; alternatively, an allylic alcohol reagent B is first reacted with an α-substituted ester D forming an oxygen-carbon bond and forming ether C.

2. The resulting compound according to formula C is reacted in a subsequent synthetic step with an α,β-unsaturated carbonyl compound according to formula F forming a carbon-carbon bond and forming a compound according to formula G;

3. The resulting compound according to formula G is reacted with a ring-closing olefin metathesis (RCM) catalyst forming a carbon-carbon bond and forming substituted 3,6-dihydro-2H-pyrans according to formulae H or I.

4. The resulting compound according to formulae H or I is reacted with an enzyme producing the optically pure substituted 3,6-dihydro-2H-pyrans according to formulae H or I.

5. The resulting compound according to formulae H or I is reacted with a reducing reagent forming substituted 3,6-dihydro-2H-pyran according to formula N.

6. The resulting compound according to formula N is reacted with a carbonyl compound according to formula R forming substituted tetrahydropyran according to formula S.

7. The resulting compound according to formula S is reacted with an epoxidation reagent forming substituted hexahydro-1,3,5,7-tetraoxacyclopropa[a]naphthalene according to formula T.

8. The resulting compound according to formula T is reacted with a nucleophilic reagent forming substituted tetrahydropyran according to formula U.

It is to be understood that the process shown in scheme 7 applies to all stereoisomers of compounds G, H, I, N, S, T and U.

Accordingly, the present invention also describes a process shown in scheme 8 for preparing pharmaceuticals, pharmaceutical excipients, cosmeceuticals or agrochemicals comprising:

1. An allylic halide reagent A is first reacted with an α-hydroxycarboxylic ester D forming an oxygen-carbon bond and forming ether C; alternatively, an allylic alcohol reagent B is first reacted with an α-substituted ester D forming an oxygen-carbon bond and forming ether C.

2. The resulting compound according to formula C is reacted in a subsequent synthetic step with an α,β-unsaturated carbonyl compound according to formula F forming a carbon-carbon bond and forming a compound according to formula G;

3. The resulting compound according to formula G is reacted with a ring-closing olefin metathesis (RCM) catalyst forming a carbon-carbon bond and forming substituted 3,6-dihydro-2H-pyrans according to formulae H or I.

4. The resulting compound according to formulae H or I is reacted with an enzyme producing the optically pure substituted 3,6-dihydro-2H-pyrans according to formulae H or I.

5. The resulting compound according to formulae H or I is reacted with a reducing reagent forming substituted 3,6-dihydro-2H-pyran according to formula N.

6. The resulting compound according to formula N is reacted with a carbonyl compound according to formula R forming substituted tetrahydropyran according to formula S.

7. The resulting compound according to formula S is reacted with an oxidant forming substituted tetrahydropyran according to formula V.

It is to be understood that the process shown in scheme 8 applies to all stereoisomers of compounds G, H, I, N, S and V.

Accordingly, the present invention also describes a process shown in scheme 9 for preparing pharmaceuticals, pharmaceutical excipients, cosmeceuticals or agrochemicals comprising:

1. An allylic halide reagent A is first reacted with an α-hydroxycarboxylic ester D forming an oxygen-carbon bond and forming ether C; alternatively, an allylic alcohol reagent B is first reacted with an α-substituted ester D forming an oxygen-carbon bond and forming ether C.

2. The resulting compound according to formula C is reacted in a subsequent synthetic step with an α,β-unsaturated carbonyl compound according to formula F forming a carbon-carbon bond and forming a compound according to formula G;

3. The resulting compound according to formula G is reacted with a ring-closing olefin metathesis (RCM) catalyst forming a carbon-carbon bond and forming substituted 3,6-dihydro-2H-pyrans according to formulae H or I.

4. The resulting compound according to formulae H or I is reacted with a reducing reagent forming substituted 3,6-dihydro-2H-pyran according to formula N.

5. The resulting compound according to formula N is reacted with a carbonyl compound according to formula R forming substituted tetrahydropyran according to formula S.

6. The resulting compound according to formula S is reacted with an oxidant forming optically pure substituted tetrahydropyran according to formula V.

It is to be understood that the process shown in scheme 8 applies to all stereoisomers of compounds G, H, I, N, S and V.

Accordingly, the present invention also describes a process shown in scheme 10 for preparing pharmaceuticals, pharmaceutical excipients, cosmeceuticals or agrochemicals comprising:

1. An allylic halide reagent A is first reacted with an α-hydroxycarboxylic ester D forming an oxygen-carbon bond and forming ether C; alternatively, an allylic alcohol reagent B is first reacted with an α-substituted ester D forming an oxygen-carbon bond and forming ether C.

2. The resulting compound according to formula C is reacted in a subsequent synthetic step with an α,β-unsaturated carbonyl compound according to formula F forming a carbon-carbon bond and forming a compound according to formula G;

3. The resulting compound according to formula G is reacted with a reducing reagent forming an alcohol according to formula W.

4. The resulting compound according to formula W is reacted with a carbonyl compound according to formula R forming a compound according to formula X.

5. The resulting compound according to formula X is reacted with a ring-closing olefin metathesis (RCM) catalyst forming a carbon-carbon bond and forming substituted tetrahydropyrans according to formula S.

6. The resulting compound according to formula S is then reacted according to schemes 7, 8 or 9 forming optically pure substituted tetrahydropyrans according to formula T, U and V.

It is to be understood that the process shown in scheme 8 applies to all stereoisomers of compounds G, W, X, and S.

Accordingly, the present invention also describes processes for preparing pharmaceuticals, pharmaceutical excipients, cosmeceuticals or agrochemicals comprising:

1. Compounds according to formulae H, I, J, K, L, M, N, O, P, Q, S, T, U, V, Y and Z can be linked to polymeric supports and/or other molecules in order to generate diverse compound libraries with potential pharmaceutical, pharmaceutical excipient, cosmeceutical, or agrochemical use.

2. Compounds according to formulae H, I, J, K, L, M, N, O, P, Q, S, T, U, V, Y and Z can be linked to metals and/or other metal containing molecules in order to generate diverse compound libraries with potential pharmaceutical, pharmaceutical excipient, cosmeceutical, or agrochemical use.

3. Compounds according to formulae H, I, J, K, L, M, N, O, P, Q, S, T, U, V, Y and Z can be linked to metals and/or other metal containing molecules and thereby serve as chiral catalysts in order to generate diverse compound libraries with potential pharmaceutical, pharmaceutical excipient, cosmeceutical, or agrochemical use.

4. Compounds according to formulae H, I, J, K, L, M, N, O, P, Q, S, T, U, V, Y and Z can be linked to achiral reagents and thereby serve as chiral auxiliaries in order to generate diverse compound libraries with potential pharmaceutical, pharmaceutical excipient, cosmeceutical, or agrochemical use.

5. Compounds according to formulae H, I, J, K, L, M, N, O, P, Q, S, T, U, V, Y and Z can be linked to other molecules and thereby serve as solubilizing agents in order to generate diverse compound libraries with potential pharmaceutical, pharmaceutical excipient, cosmeceutical, or agrochemical use.

6. Compounds according to formulae H, I, J, K, L, M, N, O. P, Q, S, T, U, V, Y and Z can be, linked to other molecules in order to generate diverse compound libraries of prodrugs with potential pharmaceutical, pharmaceutical excipient, cosmeceutical, or agrochemical use.

DEFINITIONS

The compounds according to this invention contain one or more asymmetric carbon atoms and thus occur as racemates and racemic mixtures, single enantiomers, diastereomeric mixtures and individual diastereomers. The term "stereoisomer" refers to a chemical compound having the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers may have an optical rotation that is so slight that it is undetectable with present instrumentation. The compounds described herein may have one or more asymmetrical carbon atoms and therefore include various stereoisomers. All such isomeric forms of these compounds are expressly included in the present invention.

Each stereogenic carbon may be of R or S configuration. Although the specific compounds exemplified in this application may be depicted in a particular configuration, compounds having either the opposite stereochemistry at any given chiral center or mixtures thereof are also envisioned. When chiral centers are found in the derivatives of this invention, it is to be understood that this invention encompasses all possible stereoisomers. For example, in compounds according to formula H, the carbon atoms to which —$OR_9$ and —$CO_2R_1$ are attached may have an R,R or S,S or S,R or R,S configuration. Similarly, in formula Q, the carbon atoms to which $R_2$, $R_5$, $R_{14}$, —$OR_9$ and —$CH_2OR_{13}$ are attached may have an R,R,R,R or S,S,S,S or S,R,R,R or R,S,S,S or R,S,R,R or S,R,S,S or R,R,S,R or S,S,R,S or R,R,R,S or S,S,S,R or S,S,R,R or R,R,S,S or S,R,S,R or R,S,R,S or S,R,R,S or R,S,S,R configuration.

The terms "optically pure compound" or "optically pure isomer" refers to a single stereoisomer of a chiral compound regardless of the configuration of the said compound.

For purpose of this application, all sugars are referenced using conventional three-letter nomenclature. All sugars are assumed to be in the D-form unless otherwise noted, except for fucose, which is in the L-form. Further, all sugars are in the pyranose form.

The following examples of nomenclature, numbering systems and stereochemical assignments are provided for reference.

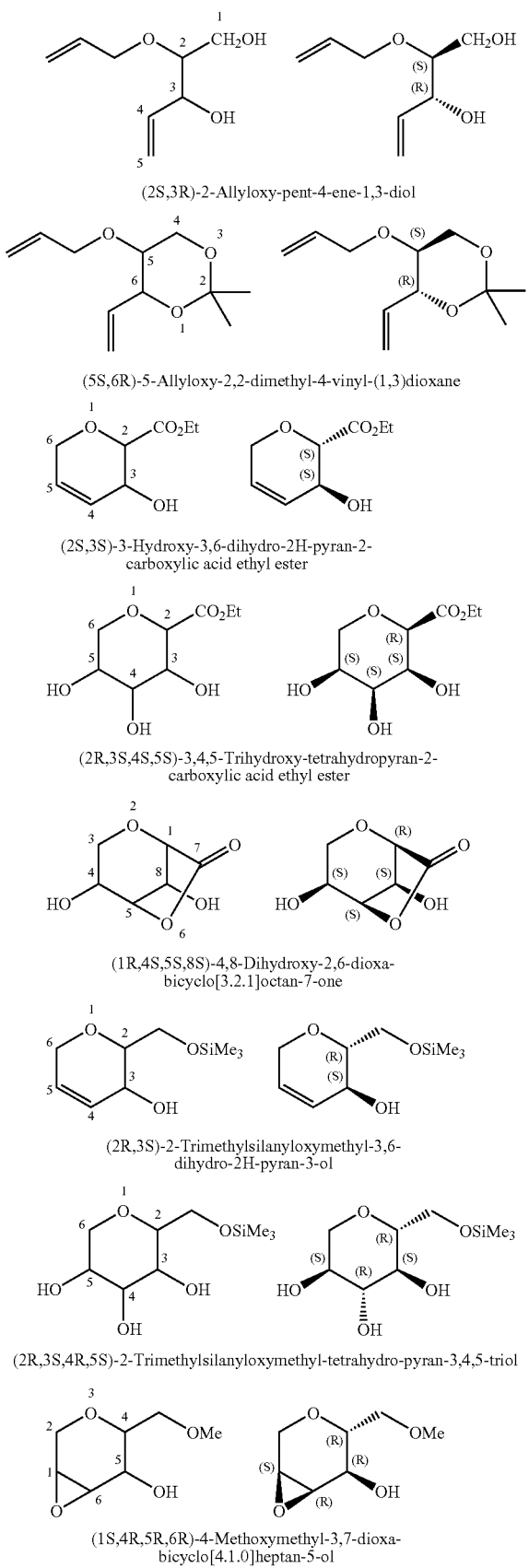
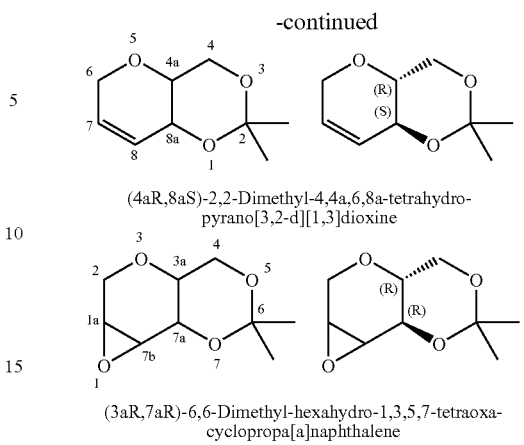

The term "substantially homogeneous" refers to collections of molecules wherein at least 80%, preferably at least about 90% and more preferably at least about 95% of the molecules are a single compound or a single stereoisomer thereof.

As used herein, the term "attached" signifies a stable covalent bond, certain preferred points of attachment being apparent to those skilled in the art.

The term "Lewis acid" refers to a molecule that can accept an unshared pair of electrons and as such would be obvious to one of ordinary skill and knowledge in the art. The definition of "Lewis acid" includes but is not limited to: boron trifluoride, boron trifluoride etherate, boron trifluoride tetrahydrofuran complex, boron trifluoride tert-butyl-methyl ether complex, boron trifluoride dibutyl ether complex, boron trifluoride dihydrate, boron trifluoride di-acetic acid complex, boron trifluoride dimethyl sulfide complex, boron trichloride, boron trichloride dimethyl sulfide complex, boron tribromide, boron tribromide dimethyl sulfide complex, boron triiodide, triimethoxyborane, triethoxyborane, trimethylaluminum, triethylaluminum, aluminum trichloride, aluminum trichloride tetrahydrofuran complex, aluminum tribromide, titanium tetrachloride, titanium tetrabromide, titanium iodide, titanium tetraethoxide, titanium tetraisopropoxide, scandium (III) trifluoromethanesulfonate, yttrium (III) trifluoromethanesulfonate, ytterbium (III) trifluoromethanesulfonate, lanthanum (III) trifluoromethanesulfonate, zinc (II) chloride, zinc (II) bromide, zinc (II) iodide, zinc (II) trifluoromethanesulfonate, zinc (II) sulfate, magnesium sulfate, lithium perchlorate, copper (II) trifluoromethanesulfonate, copper (II) tetrafluoroborate and the like. Certain Lewis acids may have optically pure ligands attached to the electron acceptor atom, as set forth in Corey, E. J. Angewandte Chemie, International Edition (2002), 41(10), 1650-1667; Aspinall, H. C. Chemical Reviews (Washington, D.C., United States) (2002), 102(6), 1807-1850; Groger, H. Chemistry—A European Journal (2001), 7(24), 5246-5251; Davies, H. M. L. Chemtracts (2001), 14(11), 642-645; Wan, Y. Chemtracts (2001), 14(11), 610-615; Kim, Y. H. Accounts of Chemical Research (2001), 34(12), 955-962; Seebach, D. Angewandte Chemie, International Edition (2001), 40(1), 92-138; Blaser, H. U. Applied Catalysis, A: General (2001), 221(1-2), 119-143; Yet, L. Angewandte Chemie, International Edition (2001), 40(5), 875-877; Jorgensen, K. A. Angewandte Chemie, International Edition (2000), 39(20), 3558-3588; Dias, L. C. Current Organic Chemistry (2000), 4(3), 305-342; Spindler, F. Enantiomer (1999), 4(6), 557-568; Fodor, K. Enantiomer (1999), 4(6), 497-511; Shimizu, K. D.; Comprehensive Asymmetric Catalysis I-III (1999), 3, 1389-1399; Kagan, H. B. Comprehensive Asymmetric Catalysis I-III (1999), 1, 9-30; Mikami, K. Lewis Acid Reagents (1999), 93-136 and all references cited therein. Such Lewis acids maybe used by one of ordinary skill and knowledge in the art to produce optically pure compounds from achiral starting materials.

The term "acylating agent" refers to a molecule that can transfer an alkylcarbonyl, substituted alkylcarbonyl or aryl carbonyl group to another molecule. The definition of "acylating agent" includes but is not limited to ethyl acetate, vinyl acetate, vinyl propionate, vinyl butyrate, isopropenyl acetate, 1-ethoxyvinyl acetate, trichloroethyl butyrate, trifluoroethyl butyrate, trifluoroethyl laureate, S-ethyl thiooctanoate, biacetyl monooxime acetate, acetic anhydride, succinic anhydride, diketene, diallyl carbonate, carbonic acid but-3-enyl ester cyanomethyl ester, amino acid and the like.

The term "nucleophile" or "nucleophilic reagent" refers to a negatively charged or neutral molecule that has an unshared pair of electrons and as such would be obvious to one of ordinary skill and knowledge in the art. The definition of "nucleophile" includes but is not limited to: water, alkylhydroxy, alkoxy anion, arylhydroxy, aryloxy anion, alkylthiol, alkylthio anion, arylthiol, arylthio anion, ammonia, alkylamine, arylamine, alkylamine anion, arylamine anion, hydrazine, alkyl hydrazine, arylhydrazine, alkylcarbonyl hydrazine, arylcarbonyl hydrazine, hydrazine anion, alkyl hydrazine anion, arylhydrazine anion, alkylcarbonyl hydrazine anion, arylcarbonyl hydrazine anion, cyanide, azide, hydride, alkyl anion, aryl anion and the like.

The term "electrophile" or "electrophilic reagent" refers to a positively charged or neutral molecule that has an open valence shell and as such would be obvious to one of ordinary skill and knowledge in the art. The definition of "electrophile" includes but is not limited to: hydronium, acylium, lewis acids, such as for example, boron trifluoride and the like, halogens, such as for example $Br_2$ and the like, carbocations, such as for example tert-butyl cation and the like, diazomethane, trimethylsilyidiazomethane, alkyl halides, such as for example methyl iodide, benzyl bromide and the like, alkyl triflates, such as for example methyl triflate and the like, alkyl sulfonates, such as for example ethyl toluenesulfonate, butyl methanesulfonate and the like, acyl halides, such as for example acetyl chloride, benzoyl bromide and the like, acid anhydrides, such as for example acetic anhydride, succininc anhydride, maleic anhydride and the like, isocyanates, such as for example methyl isocyanate, phenylisocyanate and the like, chloroformates, such as for example methyl chloroformate, ethyl chloroformate, benzyl chloroformate and the like, sulfonyl halides, such as for example methanesulfonyl chloride, p-tolunesulfonyl chloride and the like, silyl halides, such as for example trimethylsilyl chloride, tertbutyldimethyl silyll chloride and the like, phosphoryl halide such as for example dimethyl chlorophosphate and the like, alpha-beta-unsaturated carbonyl compounds such as for example acrolein, methyl vinyl ketone, cinnamaldehyde and the like.

The term "oxidant" refers to any reagent that will increase the oxidation state of a carbon atom in the starting material by either adding an oxygen atom to this carbon or removing an electron from this carbon and as such would be obvious to one of ordinary skill and knowledge in the art. The definition of "oxidant" includes but is not limited to: osmium tetroxide, ruthenium tetroxide, ruthenium trichloride, potassium permanganate, meta-chloroperbenzoic acid, hydrogen peroxide, dimethyl dioxirane and the like.

The term "metal ligand" refers to a molecule that has an unshared pair of electrons and can coordinate to a metal atom and as such would be obvious to one of ordinary skill and knowledge in the art. The definition of "metal ligand" includes but is not limited to: water, alkoxy anion, alkylthio anion, ammonia, trialkylamine, triarylamine, trialkylphosphine, triarylphosphine, cyanide, azide and the like.

The term "epoxidation reagent" refers to any reagent that will transform an alkene into an epoxide. The definition of "epoxidation reagent" includes but is not limited to: oxygen, tert-butyl hydroperoxide, meta-chloroperbenzoic acid, dimethyl dioxirane, oxone, sodium hypochlorite, sodium periodate, iodosylbenzene and the like. Certain transition metals and ligands facilitate the epoxidation of alkenes. Examples of such transition metal reagents include: titanium tetraisopropoxide, polymer supported cyclopentadienyl titanium trichloride, zirconium tetraethoxide, hafnium tetraisopropoxide, vanadium pentoxide, niobium pentaethoxide, tantalum pentaisopropoxide, manganese (II) trifluoromethanesulfonate, iron (III) acetylacetonate, molybdenum hexacarbonyl, ruthenium dichloride tris(triphenylphosphine), cobalt (II) trifluoromethanesulfonate, and the like. Examples of such ligands include: (R,R) diethyl tartarate, (S,S) diethyl tartarate, N-ethyl ephedrine, N-methylprolinol, porphyrin, 2,2'-[[(1S,2S)-1,2-diphenyl-1,2-ethanediyl]-bis(nitrilomethylidyne)]bis[6-(1,1-dimethylethyl)-4-methyl-phenol, 2,2'-[[(1R,2R)-1,2-diphenyl-1,2-ethanediyl]-bis(nitrilomethylidyne)]bis[6-(1,1-dimethylethyl)-4-methyl-phenol, 2,2'-[(1R,2R)-1,2-cyclohexanediylbis[(E)-nitrilomethylidyne]]bis[6-(1,1-dimethylethyl)-4-methyl-phenol and the like. Such chiral ligands maybe used by one of ordinary skill and knowledge in the art to produce optically pure epoxides from alkene starting materials.

The term "reducing reagent" refers to any reagent that will decrease the oxidation state of a carbon atom in the starting material by either adding a hydrogen atom to this carbon or adding an electron to this carbon and as such would be obvious to one of ordinary skill and knowledge in the art. The definition of "reducing reagent" includes but is not limited to: borane-dimethyl sulfide complex, 9-borabicyclo[3.3.1.] nonane (9-BBN), catechol borane, lithium borohydride, sodium borohydride, sodium borohydride-methanol complex, potassium borohydride, sodium hydroxyborohydride, lithium triethylborohydride, lithium n-butylborohydride, sodium cyanoborohydride, calcium (II) borohydride, lithium aluminum hydride, diisobutylaluminum hydride, n-butyl-diisobutylaluminum hydride, sodium bis-methoxyethoxyaluminum hydride, triethoxysilane, diethoxymethylsilane, lithium hydride, lithium, sodium, hydrogen Ni/B, and the like. Certain acidic and Lewis acidic reagents enhance the activity of reducing reagents. Examples of such acidic reagents include: acetic acid, methanesulfonic acid, hydrochloric acid, and the like. Examples of such Lewis acidic reagents include: trimethoxyborane, triethoxyborane, aluminum trichloride, lithium chloride, vanadium trichloride, dicyclopentadienyl titanium dichloride, cesium fluoride, potassium fluoride, zinc (II) chloride, zinc (II) bromide, zinc (II) iodide, and the like.

The term "coupling reagent" refers to any reagent that will activate the carbonyl of a carboxylic acid and facilitate the formation of an ester or amide bond. The definition of "coupling reagent" includes but is not limited to: acetyl chloride, ethyl chloroformate, dicyclohexylcarbodiimide (DCC), diisopropyl carbodiimide (DIC), 1-ethyl-3-(3-dimethylaminopropyl)carbodiimide (EDCl), N-hydroxybenzotriazole (HOBT), N-hydroxysuccinimide (HOSu), 4-nitrophenol, pentafluorophenol, 2-(1H-benzotriazole-1-yl)-1,1,3,3-tetramethyluronium tetrafluoroborate (TBTU), O-benzotriazole-N,N,N'N'-tetramethyluronium hexafluorophosphate (HBTU), benzotriazole-1-yl-oxy-tris-(dimethylamino)-phosphonium hexafluorophosphate (BOP), benzotriazole-1-yl-oxy-tris-pyrrolidino-phosphonium hexafluorophosphate, bromo-trispyrrolidino-phosphonium hexafluorophosphate, 2-(5-norbornene-2,3-dicarboximido)-1,1,3,3-tetramethyluronium tetrafluoroborate (TNTU), O-(N-succinimidyl)-1,1,3,3-tetramethyluronium tetrafluoroborate (TSTU), tetramethylfluoroformamidinium hexafluorophosphate and the like.

The terms "resin", "resin bound", "polymeric resin", "polymeric resin support", "polymeric support" or "solid support" refer to, at all occurrences, a bead or other solid support, which would be obvious to one of ordinary skill and knowledge in the art. The preferred polymer resins for use herein are the Merrifield, hydroxymethyl, aminomethyl, benzhydrylamine, 4-methylbenhydrylamine, Wang and Rink resins and the like (available commercially from Advanced Chemtech, Chemimpex and the like). Other solid supports that are suitably substituted and made of a cross-linked polystyrene resin or polyethylene glycol-polystyrene resin can also be used. Additionally, a "linker", defined here as any aliphatic or aromatic reagent that tethers a given organic or organometallic compound to the solid-support and which lacks functionality that will participate in any synthetic chemistry subsequently carried out on the solid-support, can be used.

The term "removable protecting group" or "protecting group" refers to any group which when bound to a functionality, such as the oxygen atom of a hydroxyl or carboxyl group or the nitrogen atom of an amino group, prevents reactions from occurring at these functional groups and which protecting group can be removed by conventional chemical or enzymatic steps to reestablish the functional group. The particular removable protecting group employed is not critical.

The definition of "hydroxyl protecting group" includes but is not limited to:

a) Methyl, tert-butyl, allyl, propargyl, p-chlorophenyl, p-methoxyphenyl, p-nitrophenyl, 2,4-dinitrophenyl, 2,3,5,6-tetrafluoro-4-(trifluoromethyl)phenyl, methoxymethyl, methylthiomethyl, (phenyldimethylsilyl)methoxymethyl, benzyloxymethyl, p-methoxy-benzyloxymethyl, p-nitrobenzyloxymethyl, o-nitrobenzyloxymethyl, (4-methoxyphenoxy)methyl, gualacolmethyl, tert-butoxymethyl, 4-pentenyloxymethyl, tert-butyidimethylsiloxymethyl, thexyldimethylsiloxymethyl, tert-butyldiphenylsiloxymethyl, 2-methoxyethoxymethyl, 2,2,2-trichloroethoxymethyl, bis(2-chloroethoxy)methyl, 2-(trimethylsilyl)ethoxymethyl, menthoxymethyl, 1-ethoxyethyl, 1-(2-chloroethoxy)ethyl, 1-[2-(trimethylsilyl)ethoxy]ethyl, 1-methyl-1-ethoxyethyl, 1-methyl-1-benzyloxyethyl, 1-methyl-1-benzyloxy-2-fluoroethyl, 1-methyl-1-phenoxyethyl, 2,2,2-trichloroethyl, 1-dianisyl-2,2,2-trichloroethyl, 1,1,1,3,3,3-hexafluoro-2-phenylisopropyl, 2-trimethylsilylethyl, 2-(benzylthio)ethyl, 2-(phenylselenyl)ethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydropyranyl S,S-dioxide, 1-[(2-chloro-4-methyl)phenyl]-4-methoxypiperidin-yl, 1-(2-fluorophenyl)-4-methoxypiperidin-4-yl, 1,4-dioxan-2-yl, tetrahydrofuranyl, tetrahydrothiofuranyl and the like;

b) Benzyl, 2-nitrobenzyl, 2-trifluoromethylbenzyl, 4-methoxybenzyl, 4-nitrobenzyl, 4-chlorobenzyl, 4-bromobenzyl, 4-cyanobenzyl, 4-phenylbenzyl, 4-acylaminobenzyl, 4-azidobenzyl, 4-(methylsulfinyl)benzyl, 2,4-dimethoxybenzyl, 4-azido-3-chlorobenzyl, 3,4-dimethoxybenzyl, 2,6-dichlorobenzyl, 2,6-difluorobenzyl, 1-pyrenylmethyl, diphenylmethyl, 4,4'-dinitrobenzhydryl, 5-benzosuberyl, triphenylmethyl (Trityl), α-naphthyidiphenylmethyl, (4-Methoxyphenyl)-diphenyl-methyl, di-(p-methoxyphenyl)-phenylmethyl, tri-(p-methoxyphenyl)methyl, 4-(4'-bromophenacyloxy)-phenyldiphenylmethyl, 4,4',4"-tris(4,5-dichlorophthalimidophenyl)methyl, 4,4',4"-tris(levulinoyloxyphenyl)methyl, 4,4'-dimethoxy-3"-[N-(imidazolylmethyl)]trityl, 4,4'-dimethoxy-3"-[N-(imidazolylethyl)carbamoyl]trityl, 1,1-bis(4-methoxyphenyl)-1'-pyrenylmethyl, 4-(17-tetrabenzo[a,c,g,i]fluorenylmethyl)-4,4'-dimethoxytrityl, 9-anthryl, 9-(9-phenyl)xanthenyl, 9-(9-phenyl-10-oxo)anthryl and the like;

c) Trimethylsilyl, triethylsilyl, triisopropylsilyl, dimethylisopropylsilyl, diethylisopropylsilyl, dimethylhexylsilyl, tert-butyldimethylsilyl, tert-butyidiphenylsilyl, tribenzylsilyl, tri-p-xylylsilyl, triphenylsilyl, diphenylmethylsilyl, di-tert-butylmethylsilyl, tris(trimethylsilyl)silyl, (2-hydroxystyryl)dimethylsilyl, (2-hydroxystyryl)diisopropylsilyl, tert-butylmethoxyphenylsilyl, tert-butoxydiphenylsilyl and the like;

d) —C(O)R$^8$, where R$^8$ is selected from alkyl, substituted alkyl, aryl and more specifically R$^8$=hydrogen, methyl, ethyl, tert-butyl, adamantyl, crotyl, chloromethyl, dichloromethyl, trichloromethyl, trifluoromethyl, methoxymethyl, triphenylmethoxymethyl, phenoxymethyl, 4-chlorophenoxymethyl, phenylmethyl, diphenylmethyl, 4-methoxycrotyl, 3-phenylpropyl, 4-pentenyl, 4-oxopentyl, 4,4-(ethylenedithio)pentyl, 5-[3-bis(4-methoxyphenyl)hydroxymethylphenoxy]-4-oxopentyl, phenyl, 4-methylphenyl, 4-nitrophenyl, 4-fluorophenyl, 4-chlorophenyl, 4-methoxyphenyl, 4-phenylphenyl, 2,4,6-trimethylphenyl, α-naphthyl, benzoyl and the like;

e) —C(O)OR$^8$, where R$^8$ is selected from alkyl, substituted alkyl, aryl and more specifically R$^8$=methyl, methoxymethyl, 9-fluorenylmethyl, ethyl, 2,2,2-trichloromethyl, 1,1-dimethyl-2,2,2-trichloroethyl, 2-(trimethylsilyl)ethyl, 2-(phenylsulfonyl)ethyl, isobutyl, tert-Butyl, vinyl, allyl, 4-nitrophenyl, benzyl, 2-nitrobenzyl, 4-nitrobenzyl, 4-methoxybenzyl, 2,4-dimethoxybenzyl, 3,4-dimethoxybenzyl, 2-(methylthiomethoxy)ethyl, 2-dansenylethyl, 2-(4-nitrophenyl)ethyl, 2-(2,4-dinitrophenyl)ethyl, 2-cyano-1-phenylethyl, thiobenzyl, 4-ethoxy-1-naphthyl and the like.

The definition of "amino protecting group" includes but is not limited to:

a) 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 1-methyl-1-(triphenylphosphonio)ethyl, 1,1-dimethyl-2-cyanoethyl, 2-dansylethyl, 2-(4-nitrophenyl)ethyl, 4-phenylacetoxybenzyl, 4-azidobenzyl, 4-azidomethoxybenzyl, m-chloro-p-acyloxybenzyl, p-(dihydroxyboryl)benzyl, 5-benzisoxazolylmethyl, 2-(trifluoromethyl)-6-chromonylmethyl, m-nitrophenyl, 3.5-dimethoxybenzyl, 1-methyl-1-(3,5-dimethoxyphenyl)ethyl, o-nitrobenzyl, α-methylnitropiperonyl, 3,4-dimethoxy-6-nitrobenzyl, N-benzenesulfenyl, N-o-nitrobenzenesulfenyl, N-2,4-dinitrobenzenesulfenyl, N-pentachlorobenzenesulfenyl. N-2-nitro-4-methoxybenzenesulfenyl, N-triphenylmethylsulfenyl, N-1-(2,2,2-trifluoro-1,1-diphenyl)ethylsulfenyl, N-3-nitro-2-pyridinesulfenyl, N-p-toluenesulfonyl, N-benzenesulfonyl, N-2,3,6-trimethyl-4-methoxybenzenesulfonyl, N-2,4,6-trimethoxybenzene-sulfonyl, N-2,6-dimethyl-4-methoxybenzenesulfonyl, N-pentamethylbenzenesulfonyl, N-2,3,5,6-tetramethyl-4-methoxybenzenesulfonyl and the like;

b) —C(O)OR$^8$, where R$^8$ is selected from alkyl, substituted alkyl, aryl and more specifically R$^8$=methyl, ethyl, 9-fluorenylmethyl, 9-(2-sulfo)fluorenylmethyl. 9-(2,7-dibromo)fluorenylmethyl, 17-tetrabenzo[a,c,g,i]fluorenylmethyl.

2-chloro-3-indenylmethyl, benz[f]inden-3-ylmethyl, 2,7-di-t-butyl-[9-(10,10-dioxo-10,10,10,10-tetrahydrothloxanthyl)]methyl, 1,1-dioxobenzo[b]thiophene-2-ylmethyl, 2,2,2-trichloroethyl, 2-trimethylsilylethyl, 2-phenylethyl, 1-(1-adamantyl)-1-methylethyl, 2-chloroethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-tert-butylphenyl)-1-methylethyl, 2-(2'-pyridyl)ethyl, 2-(4'-pyridyl)ethyl, 2,2-bis(4'-nitrophenyl)ethyl, N-(2-pivaloylamino)-1,1-dimethylethyl, 2-[(2-nitrophenyl) dithio]-1-phenylethyl, tert-butyl, 1-adamantyl, 2-adamantyl, Vinyl, allyl, 1-Isopropylallyl, cinnamyl. 4-nitrocinnamyl, 3-(3'-pyridyl)prop-2-enyl, 8-quinolyl, N-Hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl, diphenylmethyl, tert-amyl, S-benzyl thiocarbamate, butynyl, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N'-dimethylcarboxamido)benzyl, 1,1-dimethyl-3-(N,N'-dimethylcarboxamido)propyl, 1,1-dimethylpropynyl, di(2-pyridyl)methyl, 2-furanylmethyl, 2-Iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(p-phenylazophenyl)ethyl, 1-methyl-1-phenylethyl, 1methyl-1-4'-pyridylethyl, phenyl, p-(phenylazo)benzyl, 2,4,6-trimethylphenyl, 4-(trimethylammonium)benzyl, 2,4,6-trimethylbenzyl and the like.

The definition of "carboxyl protecting group" includes but is not limited to:

2-N-(morpholino)ethyl, choline, methyl, methoxyethyl, 9-Fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, pivaloyloxymethyl, phenylacetoxymethyl, triisopropylsilylmethyl, cyanomethyl, acetol, p-bromophenacyl, α-methylphenacyl, p-methoxyphenacyl, desyl, carboxamidomethyl, p-azobenzenecarboxamido-methyl, N-phthalimidomethyl, (methoxyethoxy)ethyl, 2,2,2-trichloroethyl, 2-fluoroethyl, 2-chloroethyl, 2-bromoethyl, 2-iodoethyl, 4-chlorobutyl, 5-chloropentyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(p-methoxyphenyl)ethyl, 2-(diphenylphosphino)ethyl, 1-methyl-1-phenylethyl, 2-(4-acetyl-2-nitrophenyl)ethyl, 2-cyanoethyl, heptyl, tert-butyl, 3-methyl-3-pentyl, dicyclopropylmethyl, 2,4-dimethyl-3-pentyl, cyclopentyl, cyclohexyl, allyl, methallyl, 2-methylbut-3-en-2-yl, 3-methylbut-2-(prenyl), 3-buten-1-yl, 4-(trimethylsilyl)-2-buten-1-yl, cinnamyl, α-methylcinnamyl, propargyl, phenyl, 2,6-dimethylphenyl, 2,6-diisopropylphenyl, 2,6-di-tert-butylmethylphenyl, 2,6-di-tert-butyl-4-methoxyphenyl, p-(methylthio)phenyl, pentafluorophenyl, benzyl, triphenylmethyl, diphenylmethyl, bis(o-nitrophenyl) methyl, 9-anthrylmethyl, 2-(9,10-dioxo)anthrylmethyl. 5-dibenzosuberyl, 1-pyrenylmethyl, 2-(trifluoromethyl)-6-chromonylmethyl, 2,4,6-trimethylbenzyl, p-bromobenzyl, o-nitrobenzyl, p-nitrobenzyl, p-methoxybenzyl, 2.6-dimethoxybenzyl, 4-(methylsulfinyl)benzyl, 4-Sulfobenzyl, 4-azidomethoxybenzyl, 4-{a/-[1-(4,4-dimethyl-2,6-dioxocyclohexylidene)-3-methylbutyl]amino}benzyl, piperonyl, 4-picolyl, trimethylsilyl, triethylsilyl, tert-butyldimethylsilyl, isopropyldimethylsilyl, phenyldimethylsilyl, di-tert-butylmethylsilyl, triisopropylsilyl and the like.

The term "Amino acid" refers to any of the naturally occurring amino acids, as well as synthetic analogs and derivatives thereof. Alpha-Amino acids comprise a carbon atom to which is bonded an amino group, a carboxy group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine), substituted arylalkyl (e.g., as in tyrosine), heteroarylalkyl (e.g., as in tryptophan, histidine) and the like. One of skill in the art will appreciate that the term "amino acid" can also include beta-, gamma-, delta-, omega-amino acids, and the like. Unnatural amino acids are also known in the art, as set forth in, Natchus, M. G. Organic Synthesis: Theory and Applications (2001), 5, 89-196; Ager, D. J. Current Opinion in Drug Discovery & Development (2001), 4(6), 800; Reginato, G. Recent Research Developments in Organic Chemistry (2000), 4(Pt. 1), 351-359; Dougherty, D. A. Current Opinion in Chemical Biology (2000), 4(6), 645-652; Lesley, S. A. Drugs and the Pharmaceutical Sciences (2000), 101(Pepfide and Protein Drug Analysis), 191-205; Pojitkov, A. E. Journal of Molecular Catalysis B: Enzymatic (2000), 10(1-3), 47-55; Ager, D. J. Speciality Chemicals (1999), 19(1), 10-12, and all references cited therein. Stereoisomers (e.g., D-amino acids) of the twenty conventional amino acids, unnatural amino acids such as alpha, alpha-disubstituted amino acids and other unconventional amino acids may also be suitable components for compounds of the present invention. Examples of unconventional amino acids include: 4-hydroxyproline, 3-methylhistidine, 5-hydroxylysine, and other similar amino acids and imino acids (e.g., 4-hydroxyproline).

The term "N-protected amino acid" refers to any amino acid which has a protecting group bound to the nitrogen of the amino functionality. This protecting group prevents reactions from occurring at the amino functional group and can be removed by conventional chemical or enzymatic steps to reestablish the amino functional group. The particular protecting group employed is not critical.

The term "O-protected amino acid" refers to any amino acid which has a protecting group bound to the oxygen of the carboxyl functionality. This protecting group prevents reactions from occurring at the carboxyl functional group and can be removed by conventional chemical or enzymatic steps to reestablish the carboxyl functional group. The particular protecting group employed is not critical.

The term "ring-closing metathesis catalyst" refers to an organometallic compound that catalyzes the formation of a cyclic molecule from an acyclic precursor in a single synthetic step. The definition of "ring-closing metathesis catalyst" includes but is not limited to: 2,6-diisopropylphenylimidoneophylidene molybdenum (IV) bis-(tert-butoxide), 2,6-diisopropylphenylimidoneophylidene molybdenum (IV) bis-(hexafluoro-tert-butoxide), 2,6-diisopropylphenylimidoneophylidene[racemic-BIPHEN] molybdenum (IV). 2,6-diisopropylphenylimidoneophylidene[(R)-(+)-BIPHEN] molybdenum (IV), 2,6-diisopropylphenylimidoneophylidene[(S)-(−)-BIPHEN] molybdenum (IV), bis-(tricyclohexylphosphine)benzylidine ruthenium (IV) dichloride, bis-(tricyclohexylphosphine)-3-methyl-2-butenylidene ruthenium (IV) dichloride, bis-(tricyclopentylphosphine)benzylidine ruthenium (IV) dichloride, bis-(tricyclopentylphosphine)-3-methyl-2-butenylidene ruthenium (IV) dichloride, tricyclohexylphosphine-(1,3-bis (2,4,6-trimethylphenyl)-4,5-dihydroimidazol-2-ylidene)-benzylidine ruthenium (IV) dichloride, tricyclohexylphosphine-(1,3-bis(2,6-diisopropylphenyl)-4,5-dihydroimidazol- 2-ylidene)-benzylidine ruthenium (IV) dichloride, (1,3-bis (2,4,6-trimethylphenyl)-4,5-dihydroimidazol-2-ylidene)-2-isopropoxyphenylmethylene ruthenium (IV) dichloride, (tricyclopentylphosphine)-2-isopropoxyphenylmethylene ruthenium (IV) dichloride, (tricyclopentylphosphine)-2-methoxy-3-naphthylmethylene ruthenium (IV) dichloride, and the like. Such ring-closing metathesis catalysts maybe used by one of ordinary skill and knowledge in the art to produce optically pure compounds from achiral starting materials.

The term "resolving enzyme" refers to a lipase, esterase, peptidase, acylase or protease enzyme of mammalian, plant, fungal or bacterial origin. The source of the "resolving enzyme" includes human pancreas, pig pancreas, pig kidney, pig liver, rabbit liver, wheat germ, *Achromobacter* sp., *Alcaligenes* sp., *Aspergillus niger*, *Aspergillus oryzae*, *Bacillus licheniformis*, *Bacillus* sp., *Bacillus thermocatenulatus*, *Candida antartica* type A, *Candida antartica* type B, *Candida lipolytica*, *Candida rugosa* (or *Candida cylindracea*), *E. coli*, *Geotrichum candidum*, *Humicola* sp., *Mucor javanicus* (or *Rhizomucor javanicus*), *Mucor miehei* (or *Rhizomucor miehel*), *Penicillium camembertil* (or *Penicillium cyclopium*), *Penicillium roquefortii*, *Penicillium* sp., *Pseudomonas cepacia* (or *Burkholderia cepacia*), *Pseudomonas fluorescens*, *Pseudomonas fragi*, *Pseudomonas glumae* (or *Chromobacterium viscosum*), *Pseudomonas* sp., *Pseudomonas stutzeri*, *Rhizopus delemar*, *Rhizopus javanicus*, *Rhizopus niveus*, *Rhizopus oryzae*, *Thermomyces lanuginose* (or *Humicola lanuginose*) and the like.

The definition of "resolving enzyme" includes but is not limited to:

1. Amano Lipase A (from *Aspergillus niger*), Amano Lipase M (from *Mucor javanicus*), Amano Lipase F (from *Rhizopus oryzae*), Amano Lipase G (from *Penicillium camembertii*), Amano Lipase R (from *Penicillium roquefortii*), Amano Newlase F (from *Rhizopus niveus*), Amano lipase AY (from *Candida rugosa*), Amano lipase PS (from *Pseudomonas cepacia*), Amano Lipase AK (from *Pseudomonas fluorescens*), Amano lipase CHE (from *Pseudomonas* sp.), Amano Lipase PPL (from pig pancreas), Amano Lipase D (from *Rhizopus delemar*), Amano Lipase L (from *Candida lipolytica*), Amano Lipase AH (from *Pseudomonas cepacia*), Lipase Amano lipase PS-D (immobilized lipase from *Pseudomonas cepacia*), Amano Lipase PS-C (immobilized lipase from *Pseudomonas cepacia*) and the like.

2. Roche (cholesterol esterase, lyophilizate, from *Candida Rugosa*), Roche (cholesterol esterase, sodium chloride solution, from *Candida Rugosa*), Roche (esterase, suspension, from pig liver), Roche Chirazyme E-1 (esterase, lyophilizate, from pig liver, fraction 1), Roche Chirazyme E-1 (esterase, carrier-fixed, lyophilizate, from pig liver, fraction 1), Roche Chirazyme E-2 (esterase, lyophilizate, from pig liver, fraction 2), Roche Chirazyme L-1 (lipase, from *Bacillus thermocatenulatus*), Roche Chirazyme L-2 (lipase, solution, from *Candida antartica*, type B), Roche Chirazyme L-2 (lipase, lyophilizate, from *Candida antartica*, type B), Roche Chirazyme L-2 (lipase, carrier-fixed, carrier 1, lyophilizate, from *Candida antartica*, type B), Roche Chirazyme L-2 (lipase, carrier-fixed, carrier 2, lyophilizate, from *Candida antartica*, type B), Roche Chirazyme L-2 (lipase, carrier-fixed, carrier 3, lyophilizate, from *Candida antartica*, type B), Roche Chirazyme L-3 (lipase, lyophilizate, from *Candida Rugosa*), Roche Chirazyme L-3 (purified lipase, lyophilizate, from *Candida Rugosa*), Roche Chirazyme L-3 (purified lipase, carrier-fixed, carrier 2, lyophilizate, from *Candida rugosa*), Roche Chirazyme L-5 (lipase, solution, from *Candida antartica*, type A), Roche Chirazyme L-5 (lipase, lyophilizate, from *Candida antartica*, type A), Roche Chirazyme L-5 (lipase, carrier-fixed, carrier 1, lyophilizate, from *Candida antartica*, type A), Roche Chirazyme L-6 (lipase, lyophilizate, from *Pseudomonas* sp.), Roche Chirazyme L-7 (lipase, lyophilizate, from porcine pancreas), Roche Chirazyme L-8 (lipase, solution, from *Thermomyces lanuginosus*), Roche Chirazyme L-8 (lipase, lyophilizate, from *Thermomyces lanuginosus*), Roche Chirazyme L-9 (lipase, solution, from *Mucor miehel*), Roche Chirazyme L-9 (lipase, lyophilizate, from *Mucor miehei*), Roche Chirazyme L-9 (lipase, carrier-fixed, carrier 1, dry, from Mucormiehei), Roche Chirazyme L-9 (lipase, carrier-fixed, carrier 2, lyophilizate, from *Mucor miehei*), Roche Chirazyme L-10 (lipase, lyophilizate, from *Alcaligenes* sp.), Roche (lipase, from pig pancreas) and the like.

3. Altus Biologics 1 (esterase from pig liver), Altus Biologics 2 (lipase from *Pseudomonas cepacia*), Altus Biologics 3 (lipase from pig pancreas), Altus Biologics 4 (lipase from *Candida rugosa*), Altus Biologics 5 (α-chymotrypsin), Altus Biologics 5 (penicillin acylase), Altus Biologics 7 (lipase from *Aspergillus niger*), Altus Biologics 8 (lipase from *Mucor miehel*), Altus Biologics 9 (ChiroCLEC™-CR; slurry, lipase, from *Candida rugosa*), Altus Biologics 10 (Subtilisin Carlsberg), Altus Biologics 11 (lipase from *Candida antartica* type A), Altus Biologics 12 (lipase from *Candida lipolytica*), Altus Biologics 13 (lipase from *Candida antartica* type B), Altus Biologics 14 (lipase from *Humicola lanuginosa*), Altus Biologics 15 (protease from *Bacillus* species), Altus Biologics 16 (ChiroCLEC™-BL, slurry, peptidase from *Bacillus licheniformis*), Altus Biologics 17 (ChiroCLEC™-CR, dry, lipase from *Candida rugosa*), Altus Biologics 18 (ChiroCLEC™-BL, dry, peptidase from *Bacillus licheniformis*), Altus Biologics 19 (ChiroCLEC™-PC, slurry, lipase from *Pseudomonas cepacia*), Altus Biologics 20 (ChiroCLEC™-PC, dry, lipase from *Pseudomonas cepacia*), Altus Biologics 21 (ChiroCLEC™-EC, slurry, lipase from *E. coli*), Altus Biologics 22 (ChiroCLEC™-EC, dry, lipase from *E. coli*), Altus Biologics 23 (lipase from *Rhizopus delemar*), Altus Biologics 24 (lipase from *Rhizopus niveus*), Altus Biologics 25 (lipase from *Rhizopus oryzae*), Altus Biologics 26 (lipase from *Pseudomonas glumae*), Altus Biologics 27 (lipase from *Alcaligenes* sp.), Altus Biologics 28 (lipase from *Geotrichum candidum*), Altus Biologics 29 (lipase from *Mucor javanicus*), Altus Biologics 30 (protease from *Aspergillus oryzae*), Altus Biologics 31 (esterase from *Candida rugosa*), Altus Biologics 41 (protease from *Aspergillus niger*), Altus Biologics 42 (protease from *Aspergillus oryzae*), Altus Biologics 43 (protease from *Penicillium* sp.), Altus Biologics 45 (protease from *Aspergillus* sp.), Altus Biologics 51, Altus Biologics 52, Altus Biologics 54, Altus Biologics 55.

4. Sigma acylase (from pig kidney), Sigma esterase (solution from pig liver), Sigma esterase (from pig liver), Sigma esterase (from rabbit liver), Sigma lipase (from human pancreas), Sigma lipase (from pig pancreas), Sigma lipase (from wheat germ), Sigma lipase (from *Candida rugosa*), Sigma lipase (from *Mucor javanicus*), Sigma lipase (from *Mucor miehei*), Sigma lipase (from *Pseudomonas cepacia*), Sigma lipase (from *Rhizopus niveus*), Sigma lipase (immobilized on cellulose from *Pseudomonas* sp.), Sigma lipase (from *Candida rugosa*), Sigma lipase (from *Rhizopus arrhizus*), Sigma lipase (from *Chromobacterium viscosum*), Sigma lipase (from *Pseudomonas* sp.) and the like.

5. Novozym 435 (lipase from *Candida antarctica*), Novozym™ CALB L (lipase from *Candida Antarctica*), Lecitase Novo™ (esterase from *Aspergillus oryzae*), Lecitase Ultra™ (esterase from *Thermomyces lanuginosus*), Lipozyme™ RM IM (lipase from *Rhizomucor miehei*), Lipozymem TL 100 L (lipase from *Thermomyces lanuginosus*), Lipozyme™ TL IM (lipase from *Thermomyces lanuginosus*) and the like.

6. Meito Sangyo Lipase MY (from *Candida cylindracea*), Meito Sangyo Lipase OF (from *Candida cylindracea*), Meito Sangvo Lipase AL (from *Achrombacter* sp.), Meito Sangyo Lipase ALC/ALG (from *Achromobacter* sp.), Meito Sangyo Lipase PL (from *Alcaligenes* sp.), Meito Sangyo Lipase PLC/PLG (from *Alcaligenes* sp.), Meito Sangyo Lipase QLM (from *Alcaligenes* sp.), Meito Sangyo Lipase QLC/QLG (from *Alcaligenes* sp.), Meito Sangyo Lipase SL (from *Burkholderia cepacia*), Meito Sangyo Lipase TL (from *Pseudomonas stutzeri*), Meito Sangyo Lipase UL (from *Rhizopus* sp.) and the like The term "Prodrug" refers to an agent that is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A prodrug may be converted into the parent drug by various mechanisms, including enzymatic processes and metabolic hydrolysis. See Harper, "Drug Latentiation" in Jucker, ed. Progress in Drug Research 4:221-294 (1962); Morozowich et al., "Application of Physical Organic Principles to Prodrug Design" in E. B. Roche ed. Design of Biopharmaceutical Properties through Prodrugs and Analogs, APHA Acad. Pharm. Sci. (1977); Bioreversible Carriers in Drug in Drug Design, Theory and Application, E. B. Roche, ed., APHA Acad. Pharm. Sci. (1987); Design of Prodrugs, H. Bundgaard, Elsevier (1985); Wang et al. "Prodrug approaches to the improved delivery of peptide drug" in Curr. Pharm. Design. 5(4):265-287 (1999); Pauletti et al. (1997) Improvement in peptide bioavailability: Peptidomimetics and Prodrug Strategies, Adv. Drug. Delivery Rev. 27:235-256; Mizen et al. (1998) "The Use of Esters as Prodrugs for Oral Delivery of .beta.-Lactam antibiotics," Pharm. Biotech. 11:345-365; Gaignault et al. (1996) "Designing Prodrugs and Bioprecursors I. Carrier Prodrugs," Pract. Med. Chem. 671-696; Asghamejad, "Improving Oral Drug Transport", in Transport Processes in Pharmaceutical Systems, G. L. Amidon, P. 1. Lee and E. M. Topp, Eds., Marcell Dekker, p. 185-218 (2000); Balant et al., "Prodrugs for the improvement of drug absorption via different routes of administration", Eur. J. Drug Metab. Pharmacokinet., 15(2): 143-53 (1990); Balimane and Sinko, "Involvement of multiple transporters in the oral absorption of nucleoside analogues", Adv. Drug Delivery Rev., 39(1-3):183-209 (1999); Browne, "Fosphenyloin (Cerebyx)", Clin. Neuropharmacol. 20(1): 1-12 (1997); Bundgaard, "Bioreversible derivatization of drugs—principle and applicability to improve the therapeutic effects of drugs", Arch. Pharm. Chemi 86(1): 1-39 (1979); Bundgaard H. "Improved drug delivery by the prodrug approach", Controlled Drug Delivery 17: 179-96 (1987); Bundgaard H. "Prodrugs as a means to improve the delivery of peptide drugs", Adv. Drug Delivery Rev. 8(1): 1-38 (1992); Fleisher et al. "Improved oral drug delivery: solubility limitations overcome by the use of prodrugs", Adv. Drug Delivery Rev. 19(2): 115-130 (1996); Fleisher et al. "Design of prodrugs for improved gastrointestinal absorption by intestinal enzyme targeting", Methods Enzymol. 112 (Drug Enzyme Targeting, Pt. A): 360-81, (1985); Farquhar D, et al., "Biologically Reversible Phosphate-Protective Groups", J. Pharm. Sci., 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," J. Chem. Soc., Chem. Commun., 875-877 (1991); Friis and Bundgaard, "Prodrugs of phosphates and phosphonates: Novel lipophilic alpha-acyloxyalkyl ester derivatives of phosphate- or phosphonate containing drugs masking the negative charges of these groups", Eur. J. Pharm. Sci. 4: 49-59 (1996); Gangwar et al., "Pro-drug, molecular structure and percutaneous delivery", Des. Biopharm. Prop. Prodrugs Analogs, [Symp.] Meeting Date 1976, 409-21. (1977); Nathwani and Wood, "Penicillins: a current review of their clinical pharmacology and therapeutic use", Drugs 45(6): 866-94 (1993); Sinhababu and Thakker, "Prodrugs of anticancer agents", Adv. Drug Delivery Rev. 19(2): 241-273 (1996); Stella et al., "Prodrugs. Do they have advantages in clinical practice?", Drugs 29(5): 455-73 (1985); Tan et al. "Development and optimization of anti-HIV nucleoside analogs and prodrugs: A review of their cellular pharmacology, structure-activity relationships and pharmacokinetics", Adv. Drug Delivery Rev. 39(1-3): 117-151 (1999); Taylor, "Improved passive oral drug delivery via prodrugs", Adv. Drug Delivery Rev., 19(2): 131-148 (1996); Valentino and Borchardt, "Prodrug strategies to enhance the intestinal absorption of peptides", Drug Discovery Today 2(4): 148-155 (1997); Wiebe and Knaus, "Concepts for the design of anti-HIV nucleoside prodrugs for treating cephalic HIV infection", Adv. Drug Delivery Rev.: 39(1-3):63-80 (1999); Waller et al., "Prodrugs", Br. J. Clin. Pharmac. 28: 497-507 (1989).

The terms "halogen", "halide" or "halo" include fluorine, chlorine, bromine, and iodine.

The terms "alkyl" and "substituted alkyl" are interchangeable and include substituted and unsubstituted $C_1$-$C_{10}$ straight chain saturated aliphatic hydrocarbon groups, substituted and unsubstituted $C_2$-$C_{10}$ straight chain unsaturated aliphatic hydrocarbon groups, substituted and unsubstituted $C_4$-$C_{10}$ branched saturated aliphatic hydrocarbon groups, substituted and unsubstituted $C_4$-$C_{10}$ branched unsaturated aliphatic hydrocarbon groups, substituted and unsubstituted $C_3$-$C_8$ cyclic saturated aliphatic hydrocarbon groups, substituted and unsubstituted $C_5$-$C_8$ cyclic unsaturated aliphatic hydrocarbon groups having the specified number of carbon atoms. For example, the definition of "alkyl" shall include but is not limited to: methyl (Me), ethyl (Et), propyl (Pr), butyl (Bu), pentyl, hexyl, heptyl, octyl, nonyl, decyl, undecyl, ethenyl, propenyl, butenyl, penentyl, hexenyl, heptenyl, octenyl, nonenyl, decenyl, undecenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, cyclopentenyl, cyclohexenyl, cycloheptenyl, cyclooctenyl, methylcyclopropyl, ethylcyclohexenyl, butenylcyclopentyl, adamantyl, norbornyl and the like. Alkyl substituents are independently selected from the group comprising halogen, —OH, —SH, —NH$_2$, —CN, —NO$_2$, =O, =CH$_2$, trihalomethyl, carbamoyl, arylC$_{0-10}$alkyl, heteroarylC$_{0-10}$alkyl, C$_{1-10}$alkyloxy, arylC$_{0-10}$alkyloxy, C$_{1-10}$alkylthio, arylC$_{0-10}$alkylthio, C$_{1-10}$alkylamino, arylC$_{0-10}$alkylamino, N-aryl-N-C$_{0-10}$alkylamino, C$_{1-10}$alkylcarbonyl, arylC$_{0-10}$alkylcarbonyl, C$_{1-10}$alkylcarboxy, arylC$_{0-10}$alkylcarboxy, C$_{1-10}$alkylcarbonylamino, arylC$_{0-10}$alkylcarbonylamino, tetrahydrofuryl, morpholinyl, piperazinyl, hydroxypyronyl, —C$_{0-10}$alkylCOOR$_{21}$ and —C$_{0-10}$alkylCONR$_{22}$R$_{23}$ wherein R$_{21}$, R$_{22}$ and R$_{23}$ are independently selected from hydrogen, alkyl, aryl, or R$_{22}$ and R$_{23}$ are taken together with the nitrogen to which they are attached forming a saturated cyclic or unsaturated cyclic system containing 3 to 8 carbon atoms with at least one substituent as defined herein.

The term "alkyloxy" (e.g. methoxy, ethoxy, propyloxy, allyloxy, cyclohexyloxy) represents an alkyl or substituted alkyl group as defined above having the indicated number of carbon atoms attached through an oxygen bridge. The term "alkyloxyalkyl" represents an alkyloxy group attached through an alkyl or substituted alkyl group as defined above having the indicated number of carbon atoms.

The term "alkylthio" (e.g. methylthio, ethylthio, propylthio, cyclohexenylthio and the like) represents an alkyl or substituted alkyl group as defined above having the indicated number of carbon atoms attached through a sulfur bridge. The term "alkylthioalkyl" represents an alkylthio group attached through an alkyl or substituted alkyl group as defined above having the indicated number of carbon atoms.

The term "alkylamino" (e.g. methylamino, diethylamino, butylamino, N-propyl-N-hexylamino, (2-cyclopentyl)propylamino, hexenylamino, and the like) represents one or two alkyl or substituted alkyl groups as defined above having the indicated number of carbon atoms attached through an amine bridge. The alkyl or substituted alkyl groups maybe taken together with the nitrogen to which they are attached forming a cyclic system containing 3 to 10 carbon atoms with at least one substituent as defined above. The term "alkylaminoalkyl" represents an alkylamino group attached through an alkyl or substituted alkyl group as defined above having the indicated number of carbon atoms.

The term "alkylhydrazino" (e.g. methylhydrazino, ethylhydrazino, butylhydrazino, (2-cyclopentyl)propylhydrazino, cyclohexanehydrazino, and the like) represents one alkyl or substituted alkyl group as defined above having the indicated number of carbon atoms attached through a hydrazine bridge. The term "alkylhydrazinoalkyl" represents an alkylhydrazino group attached through an alkyl or substituted alkyl group as defined above having the indicated number of carbon atoms.

The term "alkylcarbonyl" (e.g. cyclooctylcarbonyl, pentylcarbonyl, 3-hexenylcarbonyl and the like) represents an alkyl or substituted alkyl group as defined above having the indicated number of carbon atoms attached through a carbonyl group. The term "alkylcarbonylalkyl" represents an alkylcarbonyl group attached through an alkyl or substituted alkyl group as defined above having the indicated number of carbon atoms.

The term "alkylcarboxy" (e.g. heptylcarboxy, cyclopropylcarboxy, 3-pentenylcarboxy and the like) represents an alkylcarbonyl group as defined above wherein the carbonyl is in turn attached through an oxygen. The term "alkylcarboxyalkyl" represents an alkylcarboxy group attached through an alkyl group as defined above having the indicated number of carbon atoms.

The term "alkylcarbonylamino" (e.g. hexylcarbonylamino, cyclopentylcarbonyl-aminomethyl, methylcarbonylaminophenyl and the like) represents an alkylcarbonyl group as defined above wherein the carbonyl is in turn attached through the nitrogen atom of an amino group. The nitrogen group may itself be substituted with an alkyl or aryl group. The term "alkylcarbonylaminoalkyl" represents an alkylcarbonylamino group attached through an alkyl group as defined above having the indicated number of carbon atoms. The nitrogen group may itself be substituted with an alkyl or aryl group.

The term "alkylcarbonylhydrazino" (e.g. ethylcarbonylhydrazino, tert-butylcarbonylhydrazino and the like) represents an alkylcarbonyl group as defined above wherein the carbonyl is in turn attached through the nitrogen atom of a hydrazino group.

The term "aryl" represents an unsubstituted, mono-, di- or trisubstituted monocyclic, polycyclic, biaryl aromatic groups covalently attached at any ring position capable of forming a stable covalent bond, certain preferred points of attachment being apparent to those skilled in the art (e.g., 3-phenyl, 4-naphtyl and the like). The aryl substituents are independently selected from the group consisting of halo, —OH, —SH, —CN, —NO$_2$, trihalomethyl, hydroxypyronyl, $C_{1-10}$alkyl, aryl$C_{0-10}$alkyl, $C_{0-10}$alkyloxy$C_{0-10}$alkyl, aryl$C_{0-10}$alkyloxy$C_{0-10}$alkyl, $C_{0-10}$alkylthio$C_{0-10}$alkyl, aryl$C_{0-10}$alkylthio$C_{0-10}$alkyl, $C_{0-10}$alkylamino$C_{0-10}$alkyl, aryl$C_{0-10}$alkylamino$C_{0-10}$alkyl, N-aryl-N-$C^{0-10}$alkylamino$C_{0-10}$alkyl, $C_{1-10}$alkylcarbonyl$C_{0-10}$alkyl, aryl$C_{0-10}$alkylcarbonyl$C_{0-10}$alkyl, $C_{0-10}$alkylcarboxy$C_{0-10}$alkyl, aryl$C_{0-10}$alkylcarboxy$C_{0-10}$alkyl, $C_{1-10}$alkylcarbonylamino$C_{0-10}$alkyl, aryl$C_{0-10}$alkylcarbonylamino$C_{0-10}$alkyl, —$C_{0-10}$alkylCOOR$_{21}$, and —$C_{0-10}$alkylCONR$_{22}$R$_{23}$ wherein R$_{21}$, R$_{22}$ and R$_{23}$ are independently selected from hydrogen, $C_1$-$C_{10}$alkyl, aryl$C_0$-$C_{10}$alkyl, or R$_{22}$ and R$_{23}$ are taken together with the nitrogen to which they are attached forming a cyclic system containing 3 to 8 carbon atoms with at least one substituent as defined above.

The definition of "aryl" includes but is not limited to phenyl, biphenyl, naphthyl, dihydronaphthyl, tetrahydronaphthyl, indenyl, indanyl, azulenyl, anthryl, phenanthryl, fluorenyl, pyrenyl and the like.

The term "arylalkyl" (e.g. (4-hydroxyphenyl)ethyl, (2-aminonaphthyl)hexenyl and the like) represents an aryl group as defined above attached through an alkyl or substituted alkyl group as defined above having the indicated number of carbon atoms.

The term "arylcarbonyl" (e.g. 2-thiophenylcarbonyl, 3-methoxyanthrylcarbonyl and the like) represents an aryl group as defined above attached through a carbonyl group.

The term "arylalkylcarbonyl" (e.g. (2,3-dimethoxyphenyl) propylcarbonyl, (2-chloronaphthyl)pentenyl-carbonyl, imidazolylcyclopentylcarbonyl and the like) represents an arylalkyl group as defined above wherein the alkyl group is in turn attached through a carbonyl.

The term "aryloxy" (e.g. phenoxy, naphthoxy, 3-methylphenoxy, and the like) represents an aryl or substituted aryl group as defined above having the indicated number of carbon atoms attached through an oxygen bridge. The term "aryloxyalkyl" represents an aryloxy group attached through an alkyl or substituted alkyl group as defined above having the indicated number of carbon atoms.

The term "arylthio" (e.g. phenylthio, naphthylthio, 3-bromophenylthio, and the like) represents an aryl or substituted aryl group as defined above having the indicated number of carbon atoms attached through a sulfur bridge. The term "arylthioalkyl" represents an arylthio group attached through an alkyl or substituted alkyl group as defined above having the indicated number of carbon atoms.

The term "arylamino" (e.g. phenylamino, diphenylamino, naphthylamino, N-phenyl-N-naphthylamino, o-methylphenylamino, p-methoxyphenylamino, and the like) represents one or two aryl groups as defined above having the indicated number of carbon atoms attached through an amine bridge. The term "arylaminoalkyl" represents an arylamino group attached through an alkyl group as defined above having the indicated number of carbon atoms. The term "arylalkylamine" represents an aryl group attached through an alkylamino group as defined above having the indicated number of carbon atoms. The term "N-aryl-N-alkylamino" (e.g. N-phenyl-N-methylamino, N-naphthyl-N-butylamino, and the like) represents one aryl and one alkyl or substituted alkyl group as defined above having the indicated number of carbon atoms independently attached through an amine bridge.

The term "arylhydrazino" (e.g. phenylhydrazino, naphthylhydrazino, p-methoxyphenylhydrazino, and the like) represents one aryl or substituted aryl group as defined above having the indicated number of carbon atoms attached through a hydrazine bridge. The term "arylhydrazinoalkyl" represents an arylhydrazino group attached through an alkyl or substituted alkyl group as defined above having the indicated number of carbon atoms.

The term "arylcarbonylamino" (e.g. phenylcarbonylamino, naphthylcarbonylamino and the like) represents an arylcarbonyl group as defined above wherein the carbonyl is in turn attached through the nitrogen atom of an amino group. The nitrogen group may itself be substituted with an alkyl or aryl group. The term "arylcarbonylaminoalkyl" represents an arylcarbonylamino group attached through an alkyl group as defined above having the indicated number of carbon atoms. The nitrogen group may itself be substituted with an alkyl or aryl group.

The term "arylcarbonylhydrazino" (e.g. phenylcarbonylhydrazino, naphthylcarbonylhydrazino and the like) represents an arylcarbonyl group as defined above wherein the carbonyl is in turn attached through the nitrogen atom of a hydrazino group.

The terms "heteroaryl", "heterocycle" or "heterocyclic" refers to a monovalent unsaturated group having a single ring or multiple condensed rings, from 1 to 8 carbon atoms and from 1 to 4 hetero atoms selected from nitrogen, sulfur or oxygen within the ring. For the purposes of this application, the terms "heteroaryl", "heterocycle" or "heterocyclic" do not include carbohydrate rings (i.e. mono- or oligosaccharides).

Unless otherwise constrained by the definition for the "heteroaryl" substituent, such heterocyclic groups can be optionally substituted with 1 to 3 substituents selected from the group comprising: halo, —OH, —SH, —CN, —NO$_2$, trihalomethyl, hydroxypyronyl, C$_{1-10}$alkyl, arylC$_{0-10}$alkyl, C$_{0-10}$alkyloxyC$_{0-10}$alkyl, arylC$_{0-10}$alkyloxyC$_{0-10}$alkyl, C$_{0-10}$alkylthioC$_{0-10}$alkyl, arylC$_{0-10}$alkylthioC$_{0-10}$alkyl, C$_{0-10}$alkylaminoC$_{0-10}$alkyl, arylC$_{0-10}$alkylaminoC$_{0-10}$alkyl, N-aryl-N-C$_{0-10}$alkylaminoC$_{0-10}$alkyl, C$_{1-10}$alkylcarbonylC$_{0-10}$alkyl, arylC$_{0-10}$alkylcarbonylC$_{0-10}$alkyl, C$_{1-10}$alkylcarboxyC$_{0-10}$alkyl, arylC$_{0-10}$alkylcarboxyC$_{0-10}$alkyl, C$_{1-10}$alkylcarbonylaminoC$_{0-10}$alkyl, arylC$_{0-10}$alkylcarbonylaminoC$_{0-10}$alkyl, —C$_{0-10}$alkylCOOR$_{21}$, and —C$_{0-10}$alkylCONR$_{22}$R$_{23}$ wherein R$_{21}$, R$_{22}$ and R$_{23}$ are independently selected from hydrogen, C$_1$-C$_{10}$alkyl, arylC$_0$-C$_{10}$alkyl, or R$_{22}$ and R$_{23}$ are taken together with the nitrogen to which they are attached forming a cyclic system containing 3 to 8 carbon atoms with at least one substituent as defined above.

The definition of "heteroaryl" includes but is not limited to thienyl, benzothienyl, isobenzothienyl, 2,3-dihydrobenzothienyl, furyl, pyranyl, benzofuranyl, isobenzofuranyl, 2,3-dihydrobenzofuranyl, pyrrolyl, pyrrolyl-2,5-dione, 3-pyrrolinyl, indolyl, isoindolyl, 3H-indolyl, indolinyl, indolizinyl, indazolyl, phthalimidyl (or isoindoly-1,3-dione), imidazolyl, 2H-imidazolinyl, benzimidazolyl, pyridyl, pyrazinyl, pyradazinyl, pyrimidinyl, triazinyl, quinolyl, isoquinolyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, chromanyl, benzodioxolyl, piperonyl, purinyl, pyrazolyl, triazolyl, tetrazolyl, thiazolyl, isothiazolyl, benzthiazolyl, oxazolyl, isoxazolyl, benzoxazolyl, oxadiazolyl, thiadiazolyl, pyrrolidinyl-2,5-dione, imidazolidinyl-2,4-dione, 2-thioxo-imidazolidinyl-4-one, imidazolidinyl-2,4-dithione, thiazolidinyl-2,4-dione, 4-thioxo-thiazolidinyl-2-one, piperazinyl-2,5-dione, tetrahydro-pyridazinyl-3,6-dione, 1,2-dihydro-[1,2,4,5]tetrazinyl-3,6-dione, [1,2,4,5] tetrazinanyl-3,6-dione, dihydro-pyrimidinyl-2,4-dione, pyrimidinyl-2,4,6-trione, 1H-pyrimidinyl-2,4-dione, 5-iodo-1H-pyrimidinyl-2,4-dione, 5-chloro-1H-pyrimidinyl-2,4-dione, 5-methyl-1H-pyrimidinyl-2,4-dione, 5-isopropyl-1H-pyrimidinyl-2,4-dione, 5-propynyl-1H-pyrimidinyl-2,4-dione, 5-trifluoromethyl-1H-pyrimidinyl-2,4-dione, 6-amino-9H-purinyl, 2-amino-9H-purinyl, 4-amino-1H-pyrimidinyl-2-one, 4-amino-5-fluoro-1H-pyrimidinyl-2-one, 4-amino-5-methyl-1H-pyrimidinyl-2-one, 2-amino-1,9-dihydro-purinyl-6-one, 1,9-dihydro-purinyl-6-one, 1H-[1,2,4] triazolyl-3-carboxylic acid amide, 2,6-diamino-N$_6$-cyclopropyl-9H-purinyl, 2-amino-6-(4-methoxyphenylsulfanyl)-9H-purinyl, 5,6-dichloro-1H-benzoimidazolyl, 2-isopropylamino-5,6-dichloro-1H-benzoimidazolyl, 2-bromo-5,6-dichloro-1H-benzoimidazolyl, and the like.

The term "saturated heterocyclic" represents an unsubstituted, mono-, di- or trisubstituted monocyclic, polycyclic saturated heterocyclic group covalently attached at any ring position capable of forming a stable covalent bond, certain preferred points of attachment being apparent to those skilled in the art (e.g., 1-piperidinyl, 4-piperazinyl and the like).

The saturated heterocyclic substituents are independently selected from the group consisting of halo, —OH, —SH, —CN, —NO$_2$, trihalomethyl, hydroxypyronyl, C$_{1-10}$alkyl, arylC$_{0-10}$alkyl, C$_{0-10}$alkyloxyC$_{0-10}$alkyl, arylC$_{0-10}$alkyloxyC$_{0-10}$alkyl, C$_{0-10}$alkylthioC$_{0-10}$alkyl, arylC$_{0-10}$alkylthioC$_{0-10}$alkyl, C$_{0-10}$alkylaminoC$_{0-10}$alkyl, arylC$_{0-10}$alkylaminoC$_{0-10}$alkyl, N-aryl-N—C$_{0-10}$alkylaminoC$_{0-10}$alkyl, C$_{1-10}$alkylcarbonylC$_{0-10}$alkyl, arylC$_{0-10}$alkylcarbonyl C$_{0-10}$alkyl, C$_{1-10}$alkylcarboxyC$_{0-10}$alkyl, arylC$_{0-10}$alkylcarboxyC$_{0-10}$alkyl, C$_{1-10}$alkylcarbonylaminoC$_{0-10}$alkyl, arylC$_{0-10}$alkylcarbonylaminoC$_{0-10}$alkyl, —C$_{0-10}$alkylCOOR$_{21}$, and —C$_{0-10}$alkylCONR$_{22}$R$_{23}$ wherein R$_{21}$, R$_{22}$ and R$_{23}$ are independently selected from hydrogen, C$_1$-C$_{10}$alkyl, arylC$_0$-C$_{10}$alkyl, or R$_{22}$ and R$_{23}$ are taken together with the nitrogen to which they are attached forming a cyclic system containing 3 to 8 carbon atoms with at least one substituent as defined above.

The definition of saturated heterocyclic includes but is not limited to pyrrolidinyl, pyrazolidinyl, piperidinyl, 1,4-dioxanyl, morpholinyl, 1,4-dithienyl, thiomorpholinyl, piperazinyl, quinuclidinyl and the like.

The term "alpha-beta-unsaturated carbonyl" refers to a molecule that has a carbonyl group directly attached to a double or triple bonded carbon and which would be obvious to one of ordinary skill and knowledge in the art. The definition of alpha-beta-unsaturated carbonyl heterocyclic includes but is not limited to acrolein, methylvinyl ketone, and the like.

The term "acetal" refers to a molecule that contains a carbon atom C$_1$ that is directly attached to a hydrogen atom (H$_1$), a substituted carbon atom (C$_2$) and two oxygen atoms (O$_r$ and O$_2$). These oxygen atoms are in turn attached to other substituted carbon atoms (C$_3$ and C$_4$), which would be obvious to one of ordinary skill and knowledge in the art. The definition of acetal includes but is not limited to 1,1-dimethoxypropane, 1,1-bis-allyloxybutane and the like.

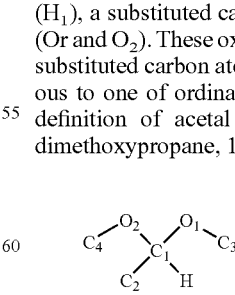

The term "cyclic acetal" refers to an acetal as defined above where C$_3$ and C$_4$, together with the oxygen atoms to which they are attached, combine thru an alkyl bridge to form a 5- to 10-membered ring, which would be obvious to one of ordinary skill and knowledge in the art. The definition of cyclic acetal includes but is not limited to 2-methyl-[1,3]dioxolane, 2-ethyl-[1,3]dioxane, 2-phenyl-[1,3]dioxane, 2 2-phenyl-hexahydro-pyrano[3,2-d][1,3]dioxine and the like.

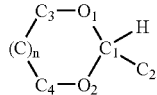

n = 1 to 5

The term "ketal" refers to a molecule that contains a carbon atom $C_1$ that is directly attached to two substituted carbon atom ($C_2$ and $C_3$) and two oxygen atoms ($O_1$ and $O_2$). These oxygen atoms are in turn attached to other substituted carbon atoms ($C_4$ and $C_5$), which would be obvious to one of ordinary skill and knowledge in the art. The definition of acetal includes but is not limited to 2,2-dimethoxy-butane, 3,3-diethoxy-pentane and the like.

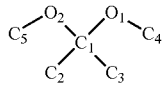

The term "cyclic ketal" refers to a ketal as defined above where $C_4$ and $C_5$, together with the oxygen atoms to which they are attached, combine thru an alkyl bridge to form a 5- to 10-membered ring, which would be obvious to one of ordinary skill and knowledge in the art. The definition of cyclic acetal includes but is not limited to 2,2,4,5-tetramethyl-[1,3] dioxolane, 2,2-diethyl-[1,3]dioxepane, 2,2-dimethyl-hexahydro-pyrano[3,2-d][1,3]dioxine and the like.

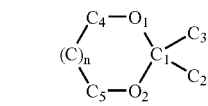

n = 1 to 5

DETAILED DESCRIPTION

In one embodiment, the present invention provides a process for preparing a compound of formula G. Such a process can be performed, for example, by contacting a compound of formula C with a compound of formula F under conditions suitable to form compound of formula G, as set forth below:

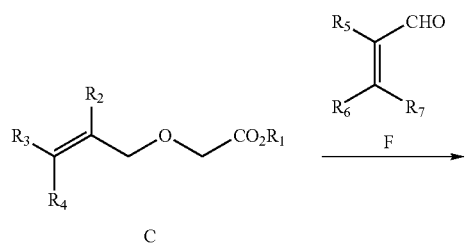

C

-continued

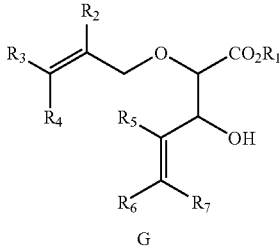

G

In the scheme shown above, $R_1$ is typically alkyl, substituted alkyl, or aryl; $R_2$ and $R_5$ are each independently hydrogen, alkyl, substituted alkyl and aryl; $R_3$, $R_4$, $R_6$ and $R_7$ are either all hydrogen or, of $R_3$, $R_4$, $R_6$ and $R_7$, three are hydrogen and the fourth is alkyl, substituted alkyl, or aryl. In one embodiment, $R_1$ is ethyl and $R_2$, $R_3$, $R_4$, $R_6$, and $R_7$ are hydrogen. In another embodiment, $R_1$ is ethyl, $R_6$ is methyl, and $R_2$, $R_3$, $R_4$, $R_6$, and $R_7$ are hydrogen. In still another embodiment, $R_1$ is ethyl, $R_5$ is phenyl, and $R_2$, $R_3$, $R_4$, $R_6$, and $R_7$ are hydrogen.

Solvents contemplated for use in the practice of this particular invention process are typically ethereal solvents, such as for example, diethyl ether, dioxane, tetrahydrofuran, and the like, or any suitable mixtures thereof. The process is typically carried out at a temperature in the range of about −100° C. up to about 30° C.

Compound C is typically contacted with compound F In the presence of an organometallic reagent. Organometallic reagents contemplated for use include, for example, lithium diisopropyl amide, tert-butyl lithium, lithium hexamethyldisilazide, sodium hexamethyldisilazide, potassium hexamethyldisilazide, lithium diisopropyl amide-spartein complex, triethyl amine-dicyclohexyl boron triflate complex, and the like.

In yet another embodiment of the invention, there are provided compounds having the structure G:

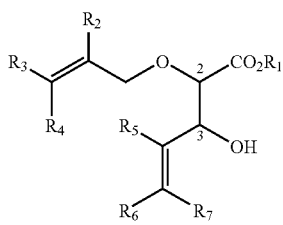

G wherein:
$R_1$ is alkyl, substituted alkyl, or aryl, $R_2$ and $R_5$ are each independently hydrogen, alkyl, substituted alkyl and aryl; $R_3$, $R_4$, $R_6$ and $R_7$ are either all hydrogen or, of $R_3$, $R_4$, $R_6$ and $R_7$, three are hydrogen and the fourth is alkyl, substituted alkyl, or aryl. In one embodiment, R. Is ethyl and $R_2$, $R_3$, $R_4$, $R_5$, $R_6$, and $R_7$ are hydrogen.

Invention compounds having structure G maybe optically pure and include (2R,3R)-2-allyloxy-3-hydroxy-pent-4-enoic acid ethyl ester; (2S,3S)-2-allyloxy-3-hydroxy-pent-4-enoic acid ethyl ester; (2R,3S)-2-allyloxy-3-hydroxy-pentenoic acid ethyl ester; and (2S,3R)-2-allyloxy-3-hydroxy-pent-4-enoic acid ethyl ester.

In one embodiment, the present invention provides a process for preparing a compound of formula H. Such a process can be performed, for example, by contacting a compound of formula G under conditions suitable to form compound of formula H, as set forth below:

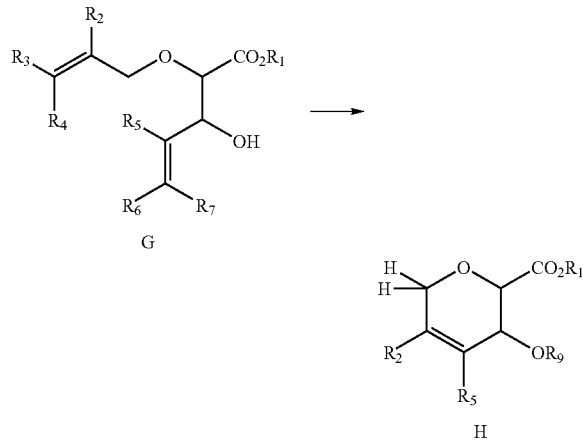

In the scheme shown above, $R_1$ is typically alkyl, substituted alkyl, or aryl; $R_2$ and $R_5$ are each independently hydrogen, alkyl, substituted alkyl and aryl; $R_3$, $R_4$, $R_6$ and $R_7$ are either all hydrogen or, of $R_3$, $R_4$, $R_6$ and $R_7$, three are hydrogen and the fourth is alkyl, substituted alkyl, or aryl; $R_9$ is hydrogen, alkyl, substituted alkyl, aryl or hydroxyl protecting group. In another embodiment, $R_1$ is ethyl, and $R_2$, $R_3$, $R_4$, $R_5$, $R_6$, $R_7$ and $R_9$ are hydrogen. In another embodiment, $R_1$ is ethyl, $R_6$ is methyl, and $R_2$, $R_3$, $R_4$, $R_6$, $R_7$ and $R_9$ are hydrogen. In still another embodiment, $R_1$ is ethyl, $R_6$ is phenyl, and $R_2$, $R_3$, $R_4$, $R_6$, $R_7$ and $R_9$ are hydrogen.

In one embodiment, the present invention provides a process for preparing compound of formula H as a mixture of stereoisomers, such as for example, cis or trans stereoisomers and the like. In another embodiment, the invention provides a process for separating such stereoisomers, such as for example, chromatography, crystallization, re-crystallization, distillation and the like. In still another embodiment, the invention provides a process for preparing compound H as an optically pure isomer.

Solvents contemplated for use in the practice of this particular invention process are typically water, halogenated solvents, such as for example, dichloromethane, dichloroethane and the like, ethereal solvents, such as for example, diethyl ether, dioxane, tetrahydrofuran and the like, polar non-protic solvents, such as for example, acetonitrile, dimethyl formamide, dimethyl acetamide, N-methylpyrrolidine, dimethyl sulfoxide and the like, aromatic solvents, such as for example, benzene, toluene, dichlorobenzene, xylene and the like, alcoholic solvents, such as for example, methanol, ethanol, isopropanol and the like, or any suitable mixtures thereof. The process is typically carried out at a temperature in the range of about 0° C. up to about 150° C.

Compound G Is typically contacted with a ring-closing metathesis catalyst. Ring-closing metathesis catalysts contemplated for use include, for example, 2,6-diisopropylphenylimidoneophylidene molybdenum (IV) bis-(tert-butoxide), 2,6-diisopropylphenylimidoneophylidene molybdenum (IV) bis-(hexafluoro-tert-butoxide), 2,6-diisopropylphenylimidoneophylidene[racemic-BIPHEN]molybdenum (IV), 2,6-diisopropylphenylimidoneophylidene[(R)-(+)-BIPHEN]molybdenum (IV), 2,6-diisopropylphenylimidoneophylidene[(S)-(−)-BIPHEN]molybdenum (IV), bis-(tricyclohexylphosphine)benzylidine ruthenium (IV) dichloride, bis-(tricyclohexylphosphine)-3-methyl-2-butenylidene ruthenium (IV) dichloride, bis-(tricyclopentylphosphine)benzylidine ruthenium (IV) dichloride, bis-(tricyclopentylphosphine)-3-methyl-2-butenylidene ruthenium (IV) dichloride, tricyclohexylphosphine-(1,3-bis(2,4,6-trimethylphenyl)-4,5-dihydroimidazol-2-ylidene)-benzylidine ruthenium (IV) dichloride, tricyclohexylphosphine-(1,3-bis(2,6-diisopropylphenyl)-4,5-dihydroimidazol-2-ylidene)-benzylidine ruthenium (IV) dichloride, (1,3-bis(2,4,6-trimethylphenyl)-4,5-dihydroimidazol-2-ylidene)-2-isopropoxyphenylmethylene ruthenium (IV) dichloride, (tricyclopentylphosphine)-2-isopropoxyphenylmethylene ruthenium (IV) dichloride, (tricyclopentylphosphine)-2-methoxy-3-naphthylmethylene ruthenium (IV) dichloride and the like.

In yet another embodiment of the invention, there are provided compounds having the structure H:

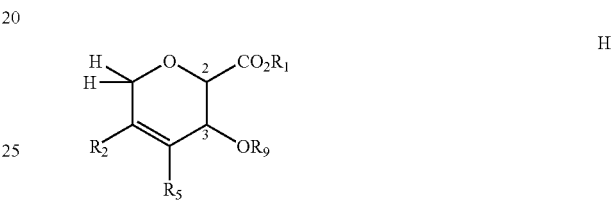

wherein:
$R_1$ is alkyl, substituted alkyl, or aryl; $R_2$ and $R_5$ are each independently hydrogen, alkyl, substituted alkyl and aryl; $R_9$ is hydrogen, alkylcarbonyl, substituted alkylcarbonyl, arylcarbonyl or hydroxyl protecting group.

Invention compounds having structure H maybe optically pure and include 3-hydroxy-3,6-dihydro-2H-pyran-2-carboxylic acid ethyl ester, (2R,3)-3-hydroxy-3,6-dihydro-2H-pyran-2-carboxylic acid ethyl ester, (2S,3S)-3-hydroxy-3,6-dihydro-2H-pyran-2-carboxylic acid ethyl ester, (2S,3R)-3-hydroxy-3,6-dihydro-2H-pyran-2-carboxylic acid ethyl ester, (2R,3S)-3-hydroxy-3,6-dihydro-2H-pyran-2-carboxylic acid ethyl ester, (2R,3R) 3-acetoxy-3,6-dihydro-2H-pyran-2-carboxylic acid ethyl ester, (2S,3S) 3-acetoxy-3,6-dihydro-2H-pyran-2-carboxylic acid ethyl ester, (2R,3S) 3-acetoxy-3,6-dihydro-2H-pyran-2-carboxylic acid ethyl ester, (2S,3R) 3-acetoxy-3,6-dihydro-2H-pyran-2-carboxylic acid ethyl ester In one embodiment, the present invention provides a process for preparing a compound of formula H. Such a process can be performed, for example, by contacting a compound of formula I with a resolving enzyme and an acylating agent under conditions suitable to form compound of formula H, as set forth below:

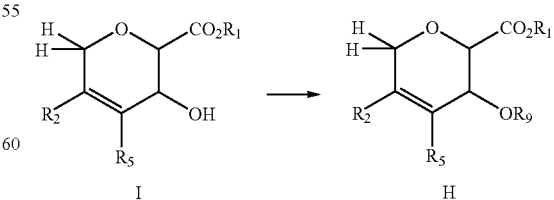

In the scheme shown above, $R_1$ is typically alkyl, substituted alkyl, or aryl; $R_2$ and $R_5$ are each independently hydrogen, alkyl, substituted alkyl and aryl; $R_1$ is hydrogen, alkylcarbonyl, substituted alkylcarbonyl, or arylcarbonyl. In another embodiment, R$_1$ is ethyl, R$_2$ and R$_5$ are hydrogen, and R$_9$ is hydrogen or acetyl.

Solvents contemplated for use in the practice of this particular invention process are typically water, halogenated solvents, such as for example, dichloromethane, dichloroethane and the like, ethereal solvents, such as for example, diethyl ether, dioxane, tetrahydrofuran and the like, polar non-protic solvents, such as for example, acetonitrile, dimethyl formamide, dimethyl acetamide, N-methylpyrrolidine, dimethyl sulfoxide and the like, aromatic solvents, such as for example, benzene, toluene, dichlorobenzene, xylene and the like, alcoholic solvents, such as for example, methanol, ethanol, isopropanol and the like, or any suitable mixtures thereof. The process is typically carried out at a temperature in the range of about 0° C. up to about 40° C.

Compound I is typically contacted with a resolving enzyme in the presence of an acylating agent. Resolving enzymes contemplated for use include lipase, esterase, peptidase, acylase or protease enzymes of mammalian, plant, fungal or bacterial origin, such as for example, Lipase Amano lipase PS-4 (immobilized lipase from *Pseudomonas cepacia*), Amano Lipase PS-C (immobilized lipase from *Pseudomonas cepacia*), Roche Chirazyme L-3 (lipase, lyophilizate, from *Candida Rugosa*), Roche Chirazyme L-3 (purified lipase, lyophilizate, from *Candida Rugosa*), Roche Chirazyme L-3 (purified lipase, carrier-fixed, carrier 2, lyophilizate, from *Candida rugosa*), Roche Chirazyme L-5 (lipase, solution, from *Candida antartica*, type A), Roche Chirazyme L-5 (lipase, lyophilizate, from *Candida antarfica*, type A), Roche Chirazyme L-5 (lipase, carrier-fixed, carrier 1, lyophilizate, from *Candida antartica*, type A), Roche Chirazyme L-10 (lipase, lyophilizate, from *Alcaligenes* sp.), Altus Biologics 8 (lipase from Mucormiehei) and Altus Biologics 27 (lipase from *Alcaligenes* sp.) and the like. Acylating agents contemplated for use include, for example, ethyl acetate, vinyl acetate, vinyl propionate, vinyl butyrate, isopropenyl acetate, 1-ethoxyvinyl acetate, trichloroethyl butyrate, trifluoroethyl butyrate, trifluoroethyl laureate, S-ethyl thiooctanoate, biacetyl monooxime acetate, acetic anhydride, succinic anhydride, amino acid, diketene and the like.

In one embodiment, the present invention provides a process for preparing compound of formula H as a mixture of optically pure compounds, such as for example, a mixture of (2R,3R) 3-acetoxy-3,6-dihydro-2H-pyran-2-carboxylic acid ethyl ester and (2S,3S) 3-hydroxy-3,6-dihydro-2H-pyran-2-carboxylic acid ethyl ester, or a mixture of (2S,3R) 3-acetoxy-3,6-dihydro-2H-pyran-2-carboxylic acid ethyl ester and (2R, 3S) 3-hydroxy-3,6-dihydro-2H-pyran-2-carboxylic acid ethyl ester. In another embodiment, the invention provides a process for separating such optically pure compounds, such as for example, chromatography, crystallization, re-crystallization, distillation and the like.

In one embodiment, the present invention provides a process for preparing a compound of formula J. Such a process can be performed, for example, by contacting a compound of formula H under conditions suitable to form compound of formula J, as set forth below:

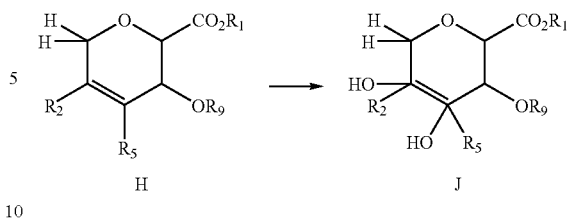

In the scheme shown above, R$_1$ is typically alkyl, substituted alkyl, or aryl; R$_2$ and R$_5$ are each independently hydrogen, alkyl, substituted alkyl and aryl; R$_9$ is hydrogen, alkyl, substituted alkyl, alkylcarbonyl, substituted alkylcarbonyl, aryl, arylcarbonyl or hydroxyl protecting group. In another embodiment, R$_1$ is ethyl, R$_2$ and R$_5$ are hydrogen, and R$_9$ is hydrogen or acetyl.

Solvents contemplated for use in the practice of this particular invention process are typically water, halogenated solvents, such as dichloromethane and the like, alcoholic solvents, such as for example 2-methyl-2-propanol and the like, ethereal solvents, such as for example tetrahydrofuran and the like, or any suitable mixtures thereof. The process is typically carried out at a temperature in the range of about −78° C. up to about 60° C.

Compound H is typically contacted with a suitable mixture of an oxidant, a co-oxidant and a ligand, or any suitable mixtures thereof. Oxidants contemplated for use include, for example, osmium tetroxide, potassium permanganate, thallium acetate, potassium periodate, silver acetate and the like, co-oxidants contemplated for use include, for example, N-methylmorpholine oxide, trimethylamine oxide, tert-butyl peroxide, iodine, potassium ferricyanide and the like, ligands contemplated for use include, for example, pyridine, quinuclidine, dihydroquinine acetate, dihydroquinidine acetate, dihydroquinine anthraquinone-1,4-diyl diether ((DHQ)$_2$AQN), dihydroquinine phthalazine-1,4-diyl diether ((DHQ)$_2$PHAL), dihydroquinine 2,5-diphenyl-4,6-pyrimidinedlyl diether ((DHQ)$_2$PYR), dihydroquinidine anthraquinone-1,4-diyl diether ((DHQD)$_2$AQN), dihydroquinidine phthalazine-1,4-diyl diether ((DHQD)$_2$PHAL), dihydroquinidine 2,5-diphenyl-4,6-pyrimidinediyl diether ((DHQD)$_2$PYR), tetraethyl ammonium hydroxide, tetraethyl ammonium acetate, N,N,N'N'-tetramethylethylene diamine (TMEDA) and the like.

In yet another embodiment of the invention, there are provided compounds having the structure J:

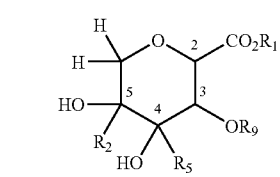

wherein:
R$_1$ is hydrogen, alkyl, substituted alkyl, or aryl; R$_2$ and R$_5$ are each independently hydrogen, alkyl, substituted alkyl, and aryl; R$_9$ is hydrogen, alkyl, substituted alkyl, substituted alkylcarbonyl, alkylcarbonyl, aryl, arylcarbonyl or hydroxyl protecting group.

With the proviso that:
stereoisomers (2R,3R,4S,5S), (2R,3S,4S,5R), (2R,3R,4R,5R), (2R,3R,4S,5R), (2S,3R,4R,5R) cannot have $R_1$=hydrogen or methyl and $R_2$=$R_5$=$R_9$=hydrogen; and, stereoisomer (2S,3S,4R,5R) cannot have $R_1$=hydrogen or methyl and $R_2$=$R_5$=$R_9$=hydrogen;

Invention compounds having structure J maybe optically pure and include (1R,2R,3R,4R) 3-acetoxy-4,5-dihydroxy-tetrahydropyran-2-carboxylic acid ethyl ester; (1R,2R,3S,4S) 3-acetoxy-4,5-dihydroxy-tetrahydropyran-2-carboxylic acid ethyl ester; (1S,2S,3R,4R) 3-acetoxy-4,5-dihydroxy-tetrahydropyran-2-carboxylic acid ethyl ester; (1S,2S,3S,4S) 3-acetoxy-4,5-dihydroxy-tetrahydropyran-2-carboxylic acid ethyl ester; (1R,2S,3R,4R) 3-acetoxy-4,5-dihydroxy-tetrahydropyran-2-carboxylic acid ethyl ester; (1R,2S,3S,4S) 3-acetoxy-4,5-dihydroxy-tetrahydropyran-2-carboxylic acid ethyl ester; (1S,2R,3R,4R) 3-acetoxy-4,5-dihydroxy-tetrahydropyran-2-carboxylic acid ethyl ester; (1S,2R,3S,4S) 3-acetoxy-4,5-dihydroxy-tetrahydropyran-2-carboxylic acid ethyl ester; (1R,2R,3R,4R) 3-4,5-trihydroxy-tetrahydropyran-2-carboxylic acid ethyl ester; (1R,2R,3S,4S) 3-4,5-trihydroxy-tetrahydropyran-2-carboxylic acid ethyl ester; (1S,2S,3R,4R) 3-4,5-trihydroxy-tetrahydropyran-2-carboxylic acid ethyl ester; (1S,2S,3S,4S) 3-4,5-trihydroxy-tetrahydropyran-2-carboxylic acid ethyl ester; (1R,2S,3R,4R) 3-4,5-trihydroxy-tetrahydropyran-2-carboxylic acid ethyl ester; (1R,2S,3S,4S) 3-4,5-trihydroxy-tetrahydropyran-2-carboxylic acid ethyl ester; (1S,2R,3R,4R) 3-4,5-trihydroxy-tetrahydropyran-2-carboxylic acid ethyl ester; and (1S,2R,3S,4S) 3-4,5-trihydroxy-tetrahydropyran-2-carboxylic acid ethyl ester.

In one embodiment, the present invention provides a process for preparing a compound of formula K. Such a process can be performed, for example, by contacting a compound of formula J under conditions suitable to form a compound of formula K, as set forth below:

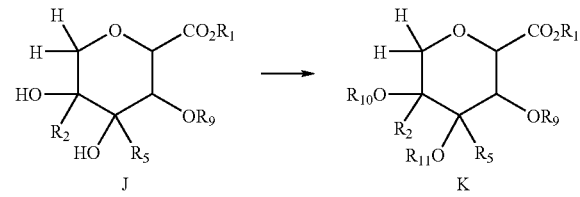

In the scheme shown above, $R_1$ is typically alkyl, substituted alkyl, or aryl; $R_2$ and $R_5$ are each independently hydrogen, alkyl, substituted alkyl and aryl; $R_9$, $R_{10}$ and $R_{11}$ are each independently hydrogen, alkyl, substituted alkyl, alkylcarbonyl, substituted alkylcarbonyl, aryl, arylcarbonyl and hydroxyl protecting group.

Solvents contemplated for use in the practice of this particular invention process are typically water, halogenated solvents, such as for example, dichloromethane, dichloroethane and the like, ethereal solvents, such as for example, diethyl ether, dioxane, tetrahydrofuran and the like, polar non-protic solvents, such as for example, acetonitrile, dimethyl formamide, dimethyl acetamide, N-methylpyrrolidine, dimethyl sulfoxide and the like, aromatic solvents, such as for example, benzene, toluene, dichlorobenzene, xylene and the like, alcoholic solvents, such as for example, methanol, ethanol, isopropanol and the like, or any suitable mixtures thereof. The process is typically carried out at a temperature in the range of about 0° C. up to about 40° C.

Compound J is typically contacted with a resolving enzyme in the presence of an acylating agent. Resolving enzymes contemplated for use include lipase, esterase, peptidase, acylase or protease enzymes of mammalian, plant, fungal or bacterial origin, such as for example, Lipase Amano lipase PS-D (immobilized lipase from *Pseudomonas cepacia*), Amano Lipase PS-C (immobilized lipase from *Pseudomonas cepacia*), Roche Chirazyme L-3 (lipase, lyophilizate, from *Candida Rugosa*), Roche Chirazyme L-3 (purified lipase, lyophilizate, from *Candida Rugosa*), Roche Chirazyme L-3 (purified lipase, carrier-fixed, carrier 2, lyophilizate, from *Candida rugosa*), Roche Chirazyme L-5 (lipase, solution, from *Candida antartica*, type A), Roche Chirazyme L-5 (lipase, lyophilizate, from *Candida antartica*, type A), Roche Chirazyme L-5 (lipase, carrier-fixed, carrier 1, lyophilizate, from *Candida antartica*, type A), Roche Chirazyne L-10 (lipase, lyophilizate, from *Alcaligenes* sp.), Altus Biologics 8 (lipase from *Mucor miehei*) and Altus Biologics 27 (lipase from *Alcaligenes* sp.) and the like. Acylating agents contemplated for use include, for example, ethyl acetate, vinyl acetate, vinyl propionate, vinyl butyrate, isopropenyl acetate, 1-ethoxyvinyl acetate, trichloroethyl butyrate, trifluoroethyl butyrate, trifluoroethyl laureate, S-ethyl thiooctanoate, biacetyl monooxime acetate, acetic anhydride, succinic anhydride, amino acid, diketene and the like.

Compound J can also be contacted with an electrophilic reagent. Electrophilic reagents contemplated for use include, for example, diazomethane, trimethylsilyldiazomethane, alkyl halides, such as for example methyl iodide, benzyl bromide and the like, alkyl triflates, such as for example methyl triflate and the like, alkyl sulfonates, such as for example ethyl toluenesulfonate, butyl methanesulfonate and the like, acyl halides, such as for example acetyl chloride, benzoyl bromide and the like, acid anhydrides, such as for example acetic anhydride, succininc anhydride, maleic anhydride and the like, isocyanates, such as for example methyl isocyanate, phenylisocyanate and the like, chloroformates, such as for example methyl chloroformate, ethyl chloroformate, benzyl chloroformate and the like, sulfonyl halides, such as for example methanesulfonyl chloride, p-tolunesulfonyl chloride and the like, silyl halides, such as for example trimethylsilyl chloride, tertbutyidimethyl silyll chloride and the like, phosphoryl halide such as for example dimethyl chlorophosphate and the like, alpha-beta-unsaturated carbonyl such as for example acrolein, methyl vinyl ketone, cinnamaldehyde and the like.

Compound J can also be contacted with an alcohol in the presence of an azodicarboxylate and a phosphine base, or any suitable mixtures thereof. Azodicarboxylates contemplated for use include, for example, diethyl azodicarboxylate, dicyclohexyl azodicarboxylate, diisopropyl azodicarboxylate and the like. Phosphine bases contemplated for use include, for example, triethylphosphine, tricyclopentylphosphine, tricyclohexylphosphine, triphenylphosphine, tri-o-tolylphosphine, and the like.

Compound J can also be contacted with a carboxylic acid or an amino acid in the presence of a coupling agent and a base, or any suitable mixtures thereof. Coupling agents contemplated for use include, for example, dicyclohexylcarbodiimide (DCC), diisopropyl carbodiiimide (DIC), 1-ethyl-3-(3-dimethylaminopropyl)-carbodiimide (EDCl), N-hydroxybenzotriazole (HOBT), N-hydroxysuccinimide (HOSu), 4-nitrophenol, pentafluorophenol, 2-(1H-benzotriazole-1-yl-1,1,3,3-tetramethyluronium tetrafluoroborate (TBTU), O-benzotriazole-N,N,N'N'-tetramethyluronium hexafluorophosphate (HBTU), benzotriazole-1-yl-oxy-tris-(dimethylaminoyphosphonium hexafluorophosphate (BOP), benzotriazole-1-yl-oxy-tris-pyrrolidinophosphonium hexafluorophosphate, bromo-trispyrrolidino-phosphonium hexafluorophosphate, 2-(5-norbornene-2,3-dicarboximido)-1,1,3,3-tetramethyluronium tetrafluoroborate (TNTU), 0-(N-succinimidyl)-1,1,3,3-tetramethyluronium tetrafluoroborate (TSTU), tetramethylfluoroformamidinium hexafluorophosphate and the like. Bases contemplated for use include, for example, triethylamine, diisopropylethylamine, pyridine, 4-dimethylaminopyridine, and the like.

In another embodiment, the present invention provides a process for preparing compound of formula K as a mixture of optically pure compounds, such as for example, (2R,3R,4R,5R)-3-acetoxy-4,5-dihydroxy-tetrahydropyran-2-carboxylic acid ethyl ester and (2R,3R,4S,5S-3,5-diacetoxy-4-hydroxy-tetrahydropyran-2-carboxylic acid ethyl ester. In another embodiment, the invention provides a process for separating such optically pure compounds, such as for example, chromatography, crystallization, re-crystallization, distillation and the like.

In yet another embodiment of the invention, there are provided compounds having the structure K:

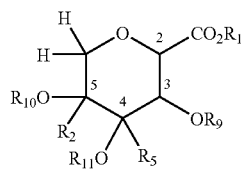

K wherein:
R₁ is alkyl, substituted alkyl, or aryl; $R_2$ and $R_5$ are each independently hydrogen, alkyl, substituted alkyl and aryl; $R_9$, $R_{10}$ and $R_{11}$ are each independently hydrogen, alkyl, substituted alkyl, alkylcarbonyl, substituted alkylcarbonyl, aryl, arylcarbonyl and hydroxyl protecting group.

With the proviso that
stereoisomers (2R, 3R, 4S, 5S), (2R, 3S, 4S, 5R), (2R, 3R, 4R, 5R), (2R, 3R, 4S, 5R), (2S, 3R, 4R, 5R), (2S, 3S, 4R, 5S), (2R, 3S, 4R, 5S) cannot have $R_1$=methyl and $R_2$=$R_5$=hydrogen and $R_9$=$R_{10}$=$R_{11}$=acetyl; stereoisomers (2R, 3R, 4S, 5S), (2R, 3S, 4S, 5R), (2R, 3R, 4R, 5R), (2R, 3R, 4S, 5R), (2S, 3R, 4R, 5R), (2S, 3S, 4R, 5R) cannot have $R_1$=methyl and $R_2$=$R_5$=$R_9$=$R_{10}$=$R_{11}$=hydrogen; stereoisomers (2R, 3R, 4S, 5S), (2R, 3S, 4S, 5R), (2R, 3R, 4R, 5R), (2R, 3R, 4S, 5R), (2S, 3R, 4R, 5R), (2S, 3S, 4R, 5R) cannot have $R_1$=$R_2$=$R_5$=$R_9$=$R_{10}$=$R_{11}$=hydrogen; stereoisomers (2S, 3S, 4R, 5R), (2R, 3S, 4R, 5R) cannot have $R_1$=$R_{10}$=$R_{11}$=methyl and $R_2$=$R_5$=hydrogen and $R_9$=acetyl; stereoisomers (2S, 3S, 4R, 5R), (2R, 3S, 4R, 5R) cannot have $R_1$=$R_{10}$=$R_{11}$=methyl and $R_2$=$R_5$=hydrogen and $R_9$=benzoyl; stereoisomer (2S, 3R, 4R, 5S) cannot have $R_1$=$R_2$=$R_5$=hydrogen and $R_9$=$R_{10}$=$R_{11}$=acetyl; and stereoisomer (1S, 4R, 5R, 8S) cannot have $R_1$=methyl $R_2$=$R_5$=$R_{11}$=hydrogen and $R_9$=$R_{10}$=benzyl.

In one embodiment, the present invention provides a process for preparing a compound of formula L. Such a process can be performed, for example, by contacting a compound of formula K under conditions suitable to form a compound of formula L, as set forth below:

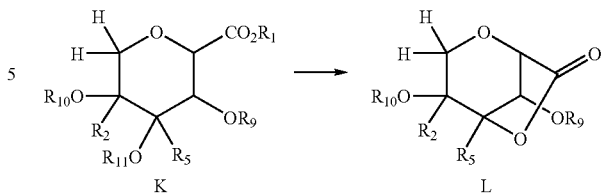

In the scheme shown above, $R_1$ is typically alkyl, substituted alkyl, or aryl; $R_2$ and $R_5$ are each independently hydrogen, alkyl, substituted alkyl and aryl; $R_9$ and $R_{10}$ are each independently hydrogen, alkyl, substituted alkyl, alkylcarbonyl, substituted alkylcarbonyl, aryl, arylcarbonyl and hydroxyl protecting group; $R_{11}$ is hydrogen.

Solvents contemplated for use in the practice of this particular invention process are typically water, halogenated solvents, such as for example, dichloromethane, dichloroethane and the like, ethereal solvents, such as for example, diethyl ether, dioxane, tetrahydrofuran and the like, polar non-protic solvents, such as for example, acetonitrile, dimethyl formamide, dimethyl acetamide, N-methylpyrrolidine, dimethyl sulfoxide and the like, aromatic solvents, such as for example, benzene, toluene, dichlorobenzene, xylene and the like, alcoholic solvents, such as for example, methanol, ethanol, isopropanol and the like, or any suitable mixtures thereof. The process is typically carried out at a temperature in the range of about 0° C. up to about 200° C.

In one embodiment, compound K is contacted with focused microwave radiation. The process is typically carried out using a quartz reactor at a pressure in the range of about 1 atm to about 25 atm and a power setting in the range of about 1 W per liter of solvent to about 900 W per liter of solvent.

In another embodiment, compound K is contacted with a dehydrating reagent in the presence or absence of a base. Dehydrating reagents contemplated for use include, for example, acetic acid, hydrochloric acid, sulfuric acid, toluenesulfonic acid, acetyl chloride, benzoyl chloride, oxalyl chloride, acetic anhydride, methyl chloroformate, dicyclohexylcarbodiimide, diethyl azodicarboxylate, 2,4,6-trichloro-[1,3,5]triazine, dibutyltin oxide, dibutyltin chloride, zinc chloride, molecular sieves, silica gel, alumina, catechol borane, mercuric acetate, silver perchlorate and the like. Bases contemplated for use include, for example, pyridine, triethylamine, diisopropylethylamine, triphenylphosphine, imidazole, tert-butyl lithium, tert-butyl magnesium chloride, potassium hydride, sodium hydride, potassium tert-butoxide, sodium methoxide, potassium carbonate, potassium bicarbonate, sodium carbonate, cesium carbonate, potassium hydroxide, sodium hydroxide and the like.

In yet another embodiment of the invention, there are provided compounds having the structure L:

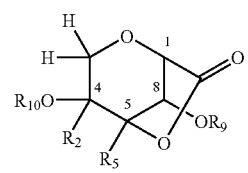

L wherein:

R$_2$ and R$_5$ are each independently hydrogen, alkyl, substituted alkyl and aryl; R$_9$ and R$_{10}$ are each independently hydrogen, alkyl, substituted alkyl, alkylcarbonyl, substituted alkylcarbonyl, aryl, arylcarbonyl and hydroxyl protecting group.

With the proviso that:
stereoisomer (1S, 4R, 5R, 8S) cannot have R$_2$=R$_5$=R$_9$=R$_{10}$=hydrogen; stereoisomer (1S, 4R, 5R, 8S) cannot have R$_2$=R$_5$=R$_{10}$=hydrogen and R$_9$=benzoyl; stereoisomer (1S, 4R, 5R, 8S) cannot have R$_2$=R=hydrogen and R$_9$=R$_{10}$=benzoyl; stereoisomer (1S, 4R, 5R, 8S) cannot have R$_2$=hydrogen and R$_9$=R$_{10}$=benzyl Invention compounds having structure L maybe optically pure and include (1R,4S,5S,8R)-8-acetoxy-4-hydroxy-2,6-dioxa-bicyclo[3.2.1]octan-7-one and (1R,4S,5S,8R)-4,8-hydroxy-2,6-dioxa-bicyclo[3.2.1]octan-7-one.

In one embodiment, the present invention provides a process for preparing a compound of formula M. Such a process can be performed, for example, by contacting a compound of formula L with a nucleophile under conditions suitable to form a compound of formula M, as set forth below:

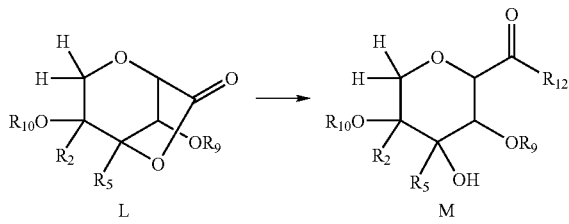

R$_2$ and R$_5$ are each independently hydrogen, alkyl, substituted alkyl and aryl; R$_9$ and R$_{10}$ are each independently hydrogen, alkyl, substituted alkyl, alkylcarbonyl, substituted alkylcarbonyl, aryl, arylcarbonyl and hydroxyl protecting group; R$_{12}$ is typically alkyl, substituted alkyl, aryl, hydroxy, alkyloxy, substituted alkyloxy, aryloxy, amino, alkylamino, arylamino, hydrazine, alkylhydrazino, arylhydrazino, alkylcarbonylhydrazino, arylcarbonylhydrazino, nitrogen containing saturated heterocyclic compound, O-protected amino acid, or solid support; with the proviso that compound of formula L cannot be the stereoisomer (1S,4R,5R,8S) where R$_2$=R$_5$=hydrogen and R$_9$=R$_{10}$=benzyl and R$_{12}$=methoxy.

Solvents contemplated for use in the practice of this particular invention process are typically water, halogenated solvents, such as for example, dichloromethane, dichloroethane and the like, ethereal solvents, such as for example, diethyl ether, dioxane, tetrahydrofuran and the like, polar non-protic solvents, such as for example, acetonitrile, dimethyl formamide, dimethyl acetamide, N-methylpyrrolidine, dimethyl sulfoxide and the like, aromatic solvents, such as for example, benzene, toluene, dichlorobenzene, xylene and the like, alcoholic solvents, such as for example, methanol, ethanol, isopropanol and the like, or any suitable mixtures thereof. The process is typically carried out at a temperature in the range of about 0° C. up to about 150° C.

Compound L is typically contacted with a nucleophile in the presence or absence of a Lewis acidic reagent. Nucleophiles contemplated for use include, for example, water, potassium hydroxide, methanol, sodium ethoxide, benzyl alcohol, 3,5-dimethylphenol, sodium phenoxide, ethyl thiol, potassium phenyl thiolate, ammonia, ammonium hydroxide, methylamine, benzylamine, dibutylamine, aniline, 3-methoxyaniline, diphenylamine, sodium amide, Lithium dimethylamide, potassium benzylmethylamide, lithium anilide, hydrazine, potassium hydrizide, methylhydrazine, phenylhydrazine, benzoylhydrazine, acetylhydrazine, piperidine, morpholine, piperazine, thiomorpholine, pyrrolidine, lithium piperidide, potassium morpholinide, glycine methyl ester, serine tert-butyl ester, valine ethyl ester lithium salt, methyl lithium, ethyl magnesium bromide, phenyl lithium, diethyl zinc, diethyl mercury, trimethyl aluminum, triethyl indium, trimethyl gallium, Merrifield resin, Wang resin, Rink resin, Wang resin lithium salt and the like. Lewis acidic reagents contemplated for use include, for example, boron trifluoride, boron trifluoride etherate, boron trifluoride tetrahydrofuran complex, boron trifluoride tert-butyl-methyl ether complex, boron trifluoride dibutyl ether complex, boron trifluoride dihydrate, boron trifluoride di-acetic acid complex, boron trifluoride dimethyl sulfide complex, boron trichloride, boron trichloride dimethyl sulfide complex, boron tribromide, boron tribromide dimethyl sulfide complex, boron triiodide, trimethoxyborane, triethoxyborane, trimethylaluminum, triethylaluminum, aluminum trichloride, aluminum trichloride tetrahydrofuran complex, aluminum tribromide, titanium tetrachloride, titanium tetrabromide, titanium iodide, titanium tetraethoxide, titanium tetraisopropoxide, scandium (III) trifluoromethanesulfonate, yttrium (III) trifluoromethanesulfonate, ytterbium (III) trifluoromethanesulfonate, lanthanum (Ill) trifluoromethanesulfonate, zinc (II) chloride, zinc (II) bromide, zinc (II) iodide, zinc (II) trifluoromethanesulfonate, zinc (II) sulfate, magnesium sulfate, lithium perchlorate, copper (II) trifluoromethanesulfonate, copper (II) tetrafluoroborate and the like.

In yet another embodiment of the invention, there are provided compounds having the structure M:

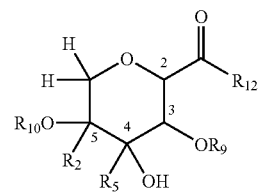

wherein:
R$_2$ and R$_5$ are each independently hydrogen, alkyl, substituted alkyl and aryl; R$_9$ and R$_{10}$ are each independently hydrogen, alkyl, substituted alkyl, alkylcarbonyl, substituted alkylcarbonyl, aryl, arylcarbonyl and hydroxyl protecting group; R$_{12}$ is alkyl, substituted alkyl, aryl, hydroxy, alkyloxy, substituted alkyloxy, aryloxy, amino, alkylamino, arylamino, nitrogen containing saturated heterocyclic compound, O-protected amino acid, or solid support.

With the proviso that
stereoisomers (2R, 3R, 4S, 5S), (2R, 3S, 4S, 5R), (2R, 3R, 4R, 5R), (2R, 3R, 4S, 5R), (2S, 3R, 4R, 5R), (2S, 3S, 4R, 5R) cannot have R$_{12}$=hydroxy and R$_2$→R$_5$=R$_9$=R$_{10}$=hydrogen; stereoisomers (2R, 3R, 4S, 5S), (2R, 3S,4S, 5R), (2R, 3R, 4R, 5R), (2R, 3R, 4S, 5R), (2S, 3R, 4R, 5R), (2S, 3S, 4R, 5R) cannot have R$_{12}$=methoxy and R$_2$=R$_5$=R$_9$=R$_{10}$=hydrogen; stereoisomers (2R, 3R, 4S, 5S), (2R, 3S, 4S, 5R), (2R, 3R, 4R, 5R), (2R, 3R, 4S, 5R), (2S, 3R, 4R, 5R), (2S, 3S, 4R, 5R) cannot have R$_{12}$=amino and $R_2=R_5=R_9=R_{10}$=hydrogen; and, stereoisomer (1S, 4R, 5R, 8S) cannot have $R_2=R_5$=hydrogen and $R_9=R_{10}$=benzyl and $R_{12}$=methoxy.

In one embodiment, the present invention provides a process for preparing a compound of formula N. Such a process can be performed, for example, by contacting a compound of formula H under conditions suitable to form a compound of formula N, as set forth below:

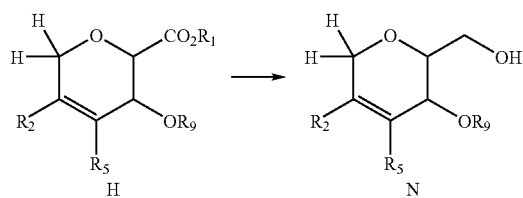

$R_1$ is typically alkyl, substituted alkyl, or aryl; $R_2$ and $R_5$ are each independently hydrogen, alkyl, substituted alkyl and aryl; $R_9$ is hydrogen, alkyl, substituted alkyl, alkylcarbonyl, substituted alkylcarbonyl, aryl, arylcarbonyl, or hydroxyl protecting group. In another embodiment, $R_1$ is ethyl, $R_2$, $R_5$ and $R_9$ are hydrogen. In still another embodiment, $R_1$ is ethyl, $R_2$ and $R_5$ are hydrogen, and $R_9$ is acetyl.

Solvents contemplated for use in the practice of this particular invention process are typically water, ammonia, ethereal solvents, such as for example, diethyl ether, dioxane, tetrahydrofuran and the like, alcoholic solvents, such as for example, methanol, ethanol, isopropanol, 1,2-ethanediol, polyethylene glycol and the like, or any suitable mixtures thereof. The process is typically carried out at a temperature in the range of about $-100°$ C. up to about $100°$ C.

Compound H is typically contacted with a reducing reagent in the presence or absence of an acidic reagent or a Lewis acidic reagent. Reducing reagents contemplated for use include, for example, borane-dimethyl sulfide complex, 9-borabicyclo[3.3.1.]nonane (9-BBN), catechol borane, lithium borohydride, sodium borohydride, sodium borohydride-methanol complex, potassium borohydride, sodium hydroxyborohydride, lithium triethylborohydride, lithium n-butylborohydride, sodium cyanoborohydride, calcium (II) borohydride, lithium aluminum hydride, diisobutylaluminum hydride, n-butyl-diisobutylaluminum hydride, sodium bis-methoxyethoxyaluminum hydride, triethoxysilane, diethoxymethylsilane, lithium hydride, lithium, sodium, hydrogen NUB, and the like. Acidic reagents contemplated for use include, for example, acetic acid, methanesulfonic acid, hydrochloric acid, and the like. Lewis acidic reagents contemplated for use include, for example, trimethoxyborane, triethoxyborane, aluminum trichloride, lithium chloride, vanadium trichloride, dicyclopentadienyl titanium dichloride, cesium fluoride, potassium fluoride, zinc (II) chloride, zinc (II) bromide, zinc (II) iodide, and the like.

In yet another embodiment of the invention, there are provided compounds having the structure N:

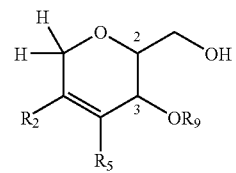

wherein:
$R_2$ and $R_5$ are each independently hydrogen, alkyl, substituted alkyl, and aryl; $R_9$ is hydrogen, alkyl, substituted alkyl, alkylcarbonyl, substituted alkylcarbonyl, aryl, arylcarbonyl, or hydroxyl protecting group
With the proviso that:
stereoisomers (2R,3S), (2S,3R) and (2R,3R) cannot have $R_2=R_9$=hydrogen.
Invention compounds having structure N maybe optically pure and include (2S,3S-2-hydroxymethyl-3,6-dihydro-2H-pyran-3-ol).

In yet another embodiment of the invention, there are provided compounds having the structure O:

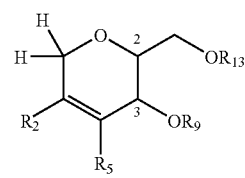

wherein:
$R_2$ and $R_5$ are each independently hydrogen, alkyl, substituted alkyl, and aryl; $R_9$ is alkyl, substituted alkyl, alkylcarbonyl, substituted alkylcarbonyl, aryl, arylcarbonyl, or hydroxyl protecting group; $R_{13}$ is hydrogen, alkyl, substituted alkyl, aryl, alkylcarbonyl, arylcarbonyl, or hydroxyl protecting group.
With the proviso that
stereoisomers (2R,3S), (2S,3R) and (2R,3R) cannot have $R_9=R_{13}$=acetyl; stereoisomer (2R,3S) cannot have $R_9$=2-bromoallyl and $R_{13}$=tert-butyldimethylsilyl; stereoisomer (2R,3S) cannot have $R_9$=2-bromobenzyl and $R_{13}$=tert-butyldimethylsilyl; stereoisomer (2R,3S) cannot have $R_9$=2-bromocyclopent-1-ene and $R_{13}$=tert-butyldimethylsilyl; stereoisomer (2R,3S) cannot have $R_9$=2-bromocyclohex-1-ene and $R_{13}$=tert-butyldimethylsilyl; stereoisomer (2R,3S) cannot have $R_9$=tichloromethylimidate [C($=$NH)CCl$_3$] and $R_{13}$=acetyl; stereoisomer (2R,3S) cannot have $R_9$=trichloromethylimidate [C($=$NH)CCl$_3$] and $R_{13}$=tert-butyldimethylsilyl; stereoisomer (2R, 3S) cannot have $R_9$=4-methoxyphenylaminocarboxy [4-CH$_3$OC$_6$H$_4$NHC($=$O)] and $R_{13}$=benzoyl; stereoisomer (2R,3S) cannot have $R_9$=4-methoxyphenylaminocarboxy[4-CH$_3$OC$_6$H$_4$NHC($=$O)] and $R_{13}$=tert-butyldimethylsilyl; stereoisomer (2S,3R) cannot have $R_9$=allyl and $R_{13}$=tosyl; stereoisomer (2R,3R) cannot have $R_9=R_{13}$=benzoyl; and, stereoisomer (2R,3R) cannot have $R_9$=2-bromoallyl and $R_{13}$=tert-butyldimethylsilyl In one embodiment, the present invention provides a process for preparing a compound of formula P. Such a process can be performed, for example, by contacting a compound of formula O under conditions suitable to form a compound of formula P, as set forth below:

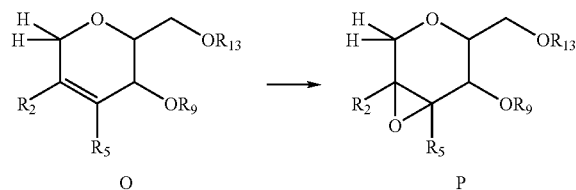

In the scheme shown above, $R_2$ and $R_5$ are each independently hydrogen, alkyl, substituted alkyl, and aryl; $R_9$ and $R_{13}$ are each independently hydrogen, alkyl, substituted alkyl, alkylcarbonyl, substituted alkylcarbonyl, aryl, arylcarbonyl, and hydroxyl protecting group, with the proviso that stereoisomer (1S,4R,5R,6R) cannot have $R_9$=hydrogen and $R_{13}$=tert-butyldimethylsilyl; and, stereoisomer (1S,4R,5R,6R) cannot have $R_9$=hydrogen and $R_{13}$=tert-butyldiphenylsilyl.

In another embodiment, compound of formula O is the (2R,3R) stereoisomer; $R_2$ and $R_5$ are each independently hydrogen, alkyl, substituted alkyl, and aryl; $R_9$ and $R_{13}$ are each independently hydrogen, alkyl, substituted alkyl, alkylcarbonyl, substituted alkylcarbonyl, aryl, arylcarbonyl, and hydroxyl protecting group.

In still another embodiment, compound of formula O is the (2S,3S) stereoisomer; $R_2$ and $R_5$ are each independently hydrogen, alkyl, substituted alkyl, and aryl; $R_9$ and $R_{13}$ are each independently hydrogen, alkyl, substituted alkyl, alkylcarbonyl, substituted alkylcarbonyl, aryl, arylcarbonyl, and hydroxyl protecting group.

Solvents contemplated for use in the practice of this particular invention process are typically water, halogenated solvents, such as for example, dichloromethane, dichloroethane and the like, ethereal solvents, such as for example, diethyl ether, dioxane, tetrahydrofuran and the like, polar non-protic solvents, such as for example, acetonitrile, dimethyl formamide, dimethyl acetamide, N-methylpyrrolidine, dimethyl sulfoxide and the like, aromatic solvents, such as for example, benzene, toluene, dichlorobenzene, xylene and the like, alcoholic solvents, such as for example, methanol, ethanol, isopropanol and the like, or any suitable mixtures thereof. The process is typically carried out at a temperature in the range of about −100° C. up to about 100° C.

Compound O is typically contacted with an epoxidation reagent in the presence or absence of a transition metal reagent and in the presence or absence of a ligand. Epoxidation reagents contemplated for use include, for example, oxygen, tert-butyl hydroperoxide, meta-chloroperbenzoic acid, dimethyl dioxirane, oxone, sodium hypochlorite, sodium periodate, iodosylbenzene and the like. Transition metal reagents contemplated for use include, for example, titanium tetraisopropoxide, polymer supported cyclopentadienyl titanium trichloride, zirconium tetraethoxide, hafnium tetraisopropoxide, vanadium pentoxide, niobium pentaethoxide, tantalum pentaisopropoxide, manganese (II) trifluoromethanesufonate, iron (III) acetylacetonate, molybdenum hexacarbonyl, ruthenium dichloride tris(triphenylphosphine), cobalt (II) trifluoromethanesulfonate, and the like. Ligands contemplated for use include, for example, (R,R) diethyl tartarate, (S,S) diethyl tartarate, N-ethyl ephedrine, N-methylprolinol, porphyrin, 2,2'-[[(1S,2S)-1,2-diphenyl-1,2-ethanediyl]-bis(nitrilomethylidyne)]bis[6-(1, 1-dimethylethyl)-4-methyl-phenol, 2,2'-[[(1R,2R)-1,2-diphenyl-1,2-ethanediyl]-bis(nitrilomethylidyne)]bis[6-(1, 1-dimethylethyl)-4-methyl-phenol, 2,2'-[(1R,2R)-1,2-cyclohexanediylbis[(E)-nitrilomethylidyne]]bis[6-(1,1-dimethylethyl)-4-methyl-phenol and the like.

In yet another embodiment of the invention, there are provided compounds having the structure P:

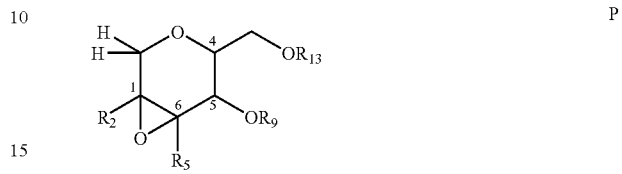

wherein:
$R_2$ and $R_5$ are each independently hydrogen, alkyl, substituted alkyl, or aryl; $R_9$ and $R_{13}$ are each independently hydrogen, alkyl, substituted alkyl, alkylcarbonyl, substituted alkylcarbonyl, aryl, arylcarbonyl, or hydroxyl protecting group;
With the proviso that:
stereoisomer (1S,4R,5R,6R) cannot have $R_9$ hydrogen and $R_{13}$=tert-butyldimethylsilyl; and, stereoisomer (1S,4R,5R,6R) cannot have $R_9$=hydrogen and $R_{13}$=tert-butyldiphenylsilyl;

Invention compounds having structure P maybe optically pure and include stereoisomer (1R,4S,5S,6S) where $R_2$=$R_5$=$R_9$=hydrogen and $R_{13}$=tert-butyldimethylsilyl; stereoisomer (1S,4S,5S,6R) where $R_2$=$R_5$=$R_9$=hydrogen and $R_{13}$=tert-butyldimethylsilyl; stereoisomer (1R,4R,5R,6S) where $R_2$=$R_9$=hydrogen and $R_{13}$=tert-butyldimethylsilyl; stereoisomer (1R,4S,5R,6S) where $R_2$=$R_5$=$R_9$=hydrogen and $R_{13}$=tert-butyldimethylsilyl; stereoisomer (1S,4R,5S,6R) where $R_2$=$R_5$=$R_9$=hydrogen and $R_{13}$=tert-butyldimethylsilyl; stereoisomer (1S,4S,5R,6R) where $R_2$=$R_5$=$R_9$=hydrogen and $R_{13}$=tert-butyldimethylsilyl; stereoisomer (1R,4R,5S,6S) where $R_2$=$R_5$=$R_9$=hydrogen and $R_{13}$=tert-butyldimethylsilyl.

In one embodiment, the present invention provides a process for preparing a compound of formula Q. Such a process can be performed, for example, by contacting a compound of formula P with a nucleophile under conditions suitable to form a compound of formula Q, as set forth below:

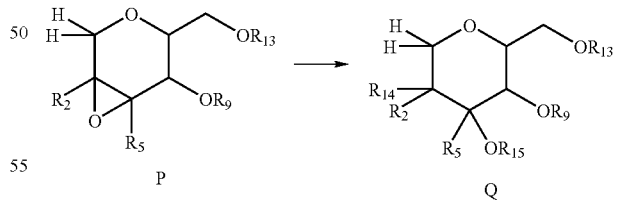

In the scheme shown above, $R_2$ and $R_5$ are each independently hydrogen, alkyl, substituted alkyl, and aryl; $R_9$ is hydrogen, alkyl, substituted alkyl, alkylcarbonyl, substituted alkylcarbonyl, aryl, arylcarbonyl, or hydroxyl protecting group. $R_{13}$ is alkyl, substituted alkyl and aryl, alkylcarbonyl, substituted alkylcarbonyl, arylcarbonyl, or hydroxyl protecting group. $R_{14}$ is hydrogen, halogen, alkyl, substituted alkyl, aryl, heteroaryl, saturated heteroaryl, cyano, azido, amino, alkylamino, arylamino, hydrazine, alkylhydrazino, arylhydrazino, alkylcarbonylhydrazino, arylcarbonylhydrazino, hydroxy, alkoxy, aryloxy, alkylthio, arylthio, alkylcarboxy, arylcarboxy, N-protected amino acid, 0protected amino acid, or a solid support; and $R_{15}$ is hydrogen. In another embodiment, $R_2$ and $R_5$ are each independently hydrogen, alkyl, substituted alkyl, and aryl; $R_9$ is hydrogen, alkyl, substituted alkyl, alkylcarbonyl, substituted alkylcarbonyl, aryl, arylcarbonyl, or hydroxyl protecting group. $R_{13}$ is alkyl, substituted alkyl and aryl, alkylcarbonyl, substituted alkylcarbonyl, arylcarbonyl, or hydroxyl protecting group, $R_{14}$ is hydrogen; and $R_{15}$ is hydrogen. In still another embodiment, $R_2$ and $R_5$ are each independently hydrogen, alkyl, substituted alkyl, and aryl; $R_9$ is hydrogen, alkyl, substituted alkyl, alkylcarbonyl, substituted alkylcarbonyl, aryl, arylcarbonyl, or hydroxyl protecting group. $R_{13}$ is alkyl, substituted alkyl and aryl, alkylcarbonyl, substituted alkylcarbonyl, arylcarbonyl, or hydroxyl protecting group, $R_{14}$ is fluorine, chlorine, bromine or iodine, and $R_{15}$ is hydrogen. In yet another embodiment, $R_2$ and $R_5$ are each independently hydrogen, alkyl, substituted alkyl, and aryl; $R_9$ is hydrogen, alkyl, substituted alkyl, alkylcarbonyl, substituted alkylcarbonyl, aryl, arylcarbonyl, or hydroxyl protecting group. $R_{13}$ is alkyl, substituted alkyl and aryl, alkylcarbonyl, substituted alkylcarbonyl, arylcarbonyl, or hydroxyl protecting group, $R_{14}$ is cyano; and $R_{15}$ is hydrogen, trimethylsilyl, or tert-butyldimethylsilyl.

Solvents contemplated for use in the practice of this particular invention process are typically water, halogenated solvents, such as for example, dichloromethane, dichloroethane and the like, ethereal solvents, such as for example, diethyl ether, dioxane, tetrahydrofuran and the like, polar non-protic solvents, such as for example, acetonitrile, dimethyl formamide, dimethyl acetamide, N-methylpyrrolidine, dimethyl sulfoxide and the like, aromatic solvents, such as for example, benzene, toluene, dichlorobenzene, xylene and the like, alcoholic solvents, such as for example, methanol, ethanol, isopropanol and the like, or any suitable mixtures thereof. The process is typically carried out at a temperature in the range of about −100° C. up to about 150° C.

Compound P is typically contacted with a nucleophile in the presence or absence of a Lewis acidic reagent. Nucleophiles contemplated for use include, for example, water, potassium cyanide, trimethylsilyl cyanide, sodium azide, potassium iodide, sodium fluoride, potassium hydroxide, methanol, sodium ethoxide, benzyl alcohol, 3,5-dimethylphenol, sodium phenoxide, ethyl thiol, potassium phenyl thiolate, ammonia, ammonium hydroxide, hydrazine, ethyl hydrazine, phenyl hydrazine, benzoylhydrazine, methylamine, benzylamine, dibutylamine, aniline, 3-methoxyaniline, diphenylamine, sodium amide, Lithium dimethylamide, potassium benzylmethylamide, lithium anilide, hydrazine, potassium hydrizide, methylhydrazine, phenylhydrazine, benzoylhydrazine, acetylhydrazine, piperidine, morpholine, piperazine, thiomorpholine, pyrrolidine, lithium piperidide, potassium morpholinide, phthalimide, maleimide, adenine, guanine, uracil, thymine, cytosine, imidazole, pyrrole, indole, tetrazole, glycine methyl ester, serine tert-butyl ester, valine ethyl ester lithium salt, N-benzylleucine, methyl lithium, ethyl magnesium bromide, phenyl lithium, diethyl zinc, diethyl mercury, trimethyl aluminum, triethyl indium, trimethyl gallium, Merrifield resin, Wang resin, Rink resin, Wang resin lithium salt, compound of formula N and the like. Lewis acidic reagents contemplated for use include, for example, boron trifluoride, boron trifluoride etherate, boron trifluoride tetrahydrofuran complex, boron trifluoride tert-butyl-methyl ether complex, boron trifluoride dibutyl ether complex, boron trifluoride dihydrate, boron trifluoride di-acetic acid complex, boron trifluoride dimethyl sulfide complex, boron trichloride, boron trichloride dimethyl sulfide complex, boron tribromide, boron tribromide dimethyl sulfide complex, boron triiodide, trimethoxyborane, triethoxyborane, trimethylaluminum, triethylaluminum, aluminum trichloride, aluminum trichloride tetrahydrofuran complex, aluminum tribromide, titanium tetrachloride, titanium tetrabromide, titanium iodide, titanium tetraethoxide, titanium tetraisopropoxide, scandium (III) trifluoromethanesulfonate, yttrium (III) trifluoromethanesulfonate, ytterbium (III) trifluoromethanesulfonate, lanthanum (III) trifluoromethanesulfonate, zinc (II) chloride, zinc (II) bromide, zinc (II) iodide, zinc (II) trifluoromethanesulfonate, zinc (II) sulfate, magnesium sulfate, lithium perchlorate, copper (II) trifluoromethanesulfonate, copper (II) tetrafluoroborate and the like.

In yet another embodiment of the invention, there are provided compounds having the structure Q:

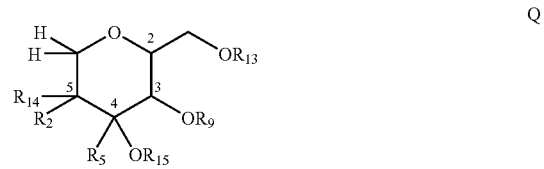

wherein:

$R_2$ and $R_5$ are each independently hydrogen, alkyl, substituted alkyl, and aryl; $R_9$ is hydrogen, alkyl, substituted alkyl, alkylcarbonyl, substituted alkylcarbonyl, aryl, arylcarbonyl, or hydroxyl protecting group; $R_{13}$ is —C(O)OR$^8$, where R$^8$ is selected from the group consisting of alkyl, substituted alkyl and aryl and more specifically $R_8$ is methyl, methoxymethyl, 9-fluorenylmethyl, ethyl, 2,2,2-trichloromethyl, 1,1-dimethyl-2,2,2-trichloroethyl, 2-(trimethylsilyl)ethyl, 2-(phenylsulfonyl)ethyl, isobutyl, tert-Butyl, vinyl, allyl, 4-nitrophenyl, benzyl, 2-nitrobenzyl, 4-nitrobenzyl, 4-methoxybenzyl, 2,4-dimethoxybenzyl, 3,4-dimethoxybenzyl, 2-(methylthiomethoxy)ethyl, 2-dansenylethyl, 2-(4-nitrophenyl)ethyl, 2-(2,4-dinitrophenyl)ethyl, 2-cyano-1-phenylethyl, thiobenzyl, or 4-ethoxy-1-naphthyl; $R_{14}$ is hydrogen, halogen, alkyl, substituted alkyl, aryl, heteroaryl, saturated heteroaryl, cyano, azido, amino, alkylamino, arylamino, hydroxy, alkoxy, aryloxy, alkylthio, arylthio, alkylcarboxy, arylcarboxy, N-protected amino acid, O-protected amino acid, or a solid support; and $R_{15}$ is hydrogen.

In yet another embodiment of the invention, there are provided compounds having the structure Q:

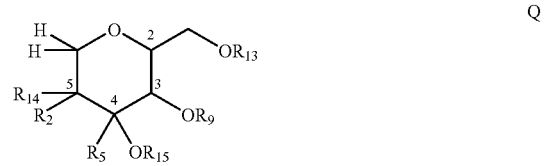

wherein:

$R_2$ and $R_5$ are each independently hydrogen, alkyl, substituted alkyl, and aryl; $R_9$ is hydrogen, alkyl, substituted alkyl, alkylcarbonyl, substituted alkylcarbonyl, aryl, arylcarbonyl, or hydroxyl protecting group; $R_{13}$=—Si ($R^8$)$_3$, where $R_8$ is alkyl, substituted alkyl and aryl and more specifically $R_{13}$ is trimethylsilyl, triethylsilyl, triisopropylsilyl, dimethylisopropylsilyl, diethylisopropylsilyl, dimethylhexylsilyl, tert-butyldimethylsilyl, tert-butyidiphenylsilyl, tribenzylsilyl, tri-p-xylylsilyl, triphenylsilyl, diphenylmethylsilyl, di-tert-butylmethylsilyl, tris(trimethylsilyl)silyl, (2-hydroxystyryl)dimethylsilyl, (2-hydroxystyryl)diisopropylsilyl, tert-butylmethoxyphenylsilyl, or tert-butoxydiphenylsilyl; $R_{14}$ is hydrogen, halogen, alkyl, substituted alkyl, aryl, heteroaryl, saturated heteroaryl, cyano, azido, amino, alkylamino, arylamino, hydroxy, alkoxy, aryloxy, alkylthio, arylthio, alkylcarboxy, arylcarboxy, N-protected amino acid, O-protected amino acid, or a solid support; and $R_{15}$ is hydrogen.

With the proviso that:

stereoisomer (2R,3S,4R) cannot have $R_9$=benzyl and $R_2$=$R_{14}$=hydrogen and $R_{13}$=tert-butyidimethylsilyl; stereoisomer (2R,3S,4R) cannot have $R_9$=$R_2$=$R_5$, $R_{14}$=hydrogen and $R_{13}$=tert-butyldimethylsilyl; stereoisomer (2R,3S,4R) cannot have $R_9$=$R_2$=$R_5$=$R_{14}$=hydrogen and $R_{13}$=tert-butyldiphenylsilyl; stereoisomer (2R,3S,4S,5S) cannot have $R_2$=$R_5$=$R_9$=hydrogen and $R_{13}$=tert-butyidiphenylsilyl and $R_{14}$=p-toluenecarboxy; stereoisomer (2R,3S,4S,5S) cannot have $R_2$=$R_5$=$R_9$=hydrogen and $R_{13}$=tert-butyldimethylsilyl and $R_{14}$=tricholoroacetamide; and, stereoisomers (2R,3S,4S,5R) and (2S,3R,4R,5S) cannot have $R_2$=$R_5$=$R_9$=hydrogen and $R_{13}$=tert-butyldimethylsilyl and $R_{14}$=5,6-dichlorobenzimidazole.

In yet another embodiment of the invention, there are provided compounds having the structure Q:

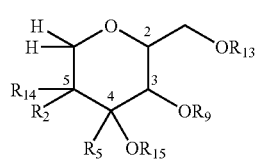

Q wherein:

$R_2$ and $R_5$ are each independently hydrogen, alkyl, substituted alkyl, and aryl; $R_9$ is hydrogen, alkyl, substituted alkyl, alkylcarbonyl, substituted alkylcarbonyl, aryl, arylcarbonyl, or hydroxyl protecting group; $R_{13}$ is benzyl, 2-nitrobenzyl, 2-trifluoromethylbenzyl, 4-methoxybenzyl, 4-nitrobenzyl, 4-chlorobenzyl, 4-bromobenzyl, 4-cyanobenzyl, 4-phenylbenzyl, 4-acylaminobenzyl, 4-azidobenzyl, 4-(methylsulfinyl)benzyl, 2,4-dimethoxybenzyl, 4-azido-3-chlorobenzyl, 3,4-dimethoxybenzyl, 2,6-dichlorobenzyl, 2,6-difluorobenzyl, 1-pyrenylmethyl, diphenylmethyl, 4,4'-dinitrobenzhydryl, 5-benzosuberyl, triphenylmethyl (trityl), α-naphthyldiphenylmethyl, (4-methoxyphenyl)-diphenyl-methyl (MMT), di-(p-methoxyphenyl)-phenylmethyl, tri-(p-methoxyphenyl)methyl, 4-(4'-bromophenacyloxy)-phenyldiphenylmethyl, 4,4',4'-tris(4,5-dichlorophthalimidophenyl)methyl, 4,4',4"-tris(levulinoyloxyphenyl)methyl, 4,4'-dimethoxy-3"-[N-(imidazolylmethyl)]trityl, 4,4'-dimethoxy-3'-[N-(imidazolyiethyl)carbamoyl]trityl, 1,1-bis(4-methoxyphenyl)-1'-pyrenylmethyl, 4-(17-tetrabenzo[a,c,g,i]fluorenylmethyl)-4,4'-dimethoxytrityl, 9-anthryl, 9-(9-phenyl)xanthenyl, or 9-(9-phenyl-10-oxo)anthryl; $R_{14}$ is hydrogen, halogen, alkyl, substituted alkyl, aryl, heteroaryl, saturated heteroaryl, cyano, azido, amino, alkylamino, arylamino, hydroxy, alkoxy, aryloxy, alkylthio, arylthio, alkylcarboxy, arylcarboxy, N-protected amino acid, O-protected amino acid, or a solid support; and $R_{15}$ is hydrogen.

With the proviso that:

stereoisomer (2R, 3S, 4S, 5R) cannot have $R_2$=$R_5$=hydrogen and $R_9$=benzoyl and $R_{13}$=(4-methoxyphenyl)-diphenyl-methyl and $R_{14}$=N-(9H-purin-6-yl)-benzamide; stereoisomer (2R, 3S, 4S, 5R) cannot have $R_2$=$R_5$=hydrogen and $R_9$=benzoyl and $R_{13}$=(4-methoxyphenyl)-diphenyl-methyl and $R_{14}$=1H-pyrimidine-2,4-dione; stereoisomer (2R, 3S, 4S, 5R) cannot have $R_2$=$R_5$=hydrogen and $R_9$=benzoyl and $R_{13}$=(4-methoxyphenyl)-diphenyl-methyl and $R_{14}$=N-(2-oxo-1,2-dihydro-pyrimidin-4-yl)-benzamide; stereoisomer (2R, 3S, 4S, 5R) cannot have $R_2$=$R_5$=hydrogen and $R_9$=benzoyl and $R_{13}$=(4-methoxyphenyl)-diphenyl-methyl and $R_{14}$=N,N-dimethyl-N'-(6-oxo-6,9-dihydro-1H-purin-2-yl)-formamidine; stereoisomer (2R, 3S, 4R) cannot have $R_2$=$R_5$=$R_9$=$R_{14}$=hydrogen and $R_{13}$=triphenylmethyl; stereoisomer (2R, 3S, 4S) cannot have $R_2$=$R_5$=$R_9$=$R_{14}$=hydrogen and $R_{13}$=benzyl; stereoisomers (2R, 3S, 4R, 5R) and (2R, 3S, 4R, 5S) cannot have $R_2$=$R_5$=$R_9$=hydrogen and $R_{13}$=triphenylmethyl and $R_{14}$=hydroxy; and, stereoisomer (2R, 3R, 4R) and (2S, 3S, 4S) cannot have $R_2$=$R_9$=$R_{14}$=hydrogen and $R_5$=methyl and $R_{13}$=triphenylmethyl.

In yet another embodiment of the invention, there are provided compounds having the structure Q:

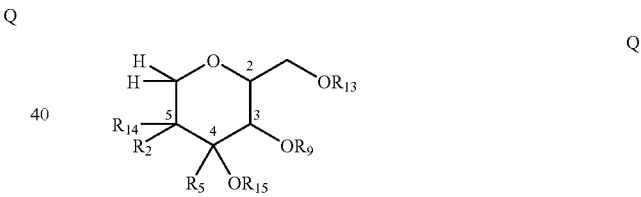

Q wherein:

$R_2$ and $R_5$ are each independently hydrogen, alkyl, substituted alkyl, and aryl; $R_9$ is hydrogen, alkyl, substituted alkyl, alkylcarbonyl, substituted alkylcarbonyl, aryl, arylcarbonyl, or hydroxyl protecting group; $R_{13}$ is alkyl, substituted alkyl and aryl and more specifically $R_{13}$ is methyl, tert-butyl, allyl, propargyl, p-chlorophenyl, p-methoxyphenyl, p-nitrophenyl, 2,4-dinitrophenyl, 2,3,5,6-tetrafluoro-4-trifluoromethyl)phenyl, methoxymethyl, methylthiomethyl, (phenyldimethylsilyl)methoxymethyl, benzyloxymethyl, p-methoxy-benzyloxymethyl, p-nitrobenzyloxymethyl, o-nitrobenzyloxymethyl, (4-methoxyphenoxy)methyl, gualacolmethyl, tert-butoxymethyl, 4-pentenyloxymethyl, tert-butyldimethylsiloxymethyl, thexyldimethylsiloxymethyl, tert-butyldiphenyllsioxymethyl, 2-methoxyethoxymethyl, 2,2,2-trichloroethoxymethyl, bis(2-chloroethoxy)methyl, 2-(trimethylsilyl)ethoxymethyl, methoxymethyl, 1-ethoxyethyl, 1-(2-chloroethoxy)ethyl, 1-[2-(trimethylsilyl)ethoxy]ethyl, 1-methyl-1-ethoxyethyl, 1-methyl-1-benzyloxyethyl, 1-methyl-1-benzyloxy-2-fluoroethyl, 1-methyl-1-phenoxyethyl, 2,2,2-trichloroethyl, 1-dianisyl-2,2,2-trichloroethyl, 1,1,1,3,3,3-hexafluoro-2-phenylisopropyl, 2-trimethylsilylethyl, 2-(benzylthio)ethyl, 2-(phenylselenyl)ethyl, tetrahydropyranyl, 3-bromotetrahydropyranyl, tetrahydrothiopyranyl, 1-methoxycyclohexyl, 4-methoxytetrahydropyranyl, 4-methoxytetrahydrothlopyranyl, 4-methoxytetrahydropyranyl S,S-dioxide, 1-(2-chloro-4-methyl)phenyl]4 methoxypiperidin-4-yl, 1-(2-fluorophenyl)-4-methoxypiperidin-4-yl, 1,4-dioxan-2-yl, tetrahydrofuranyl, tetrahydrothiofuranyl, $R_{14}$ is hydrogen, halogen, alkyl, substituted alkyl, aryl, heteroaryl, saturated heteroaryl, cyano, azido, amino, alkylamino, arylamino, hydroxy, alkoxy, aryloxy, alkylthio, arylthio, alkylcarboxy, arylcarboxy, N-protected amino acid, O-protected amino acid, or a solid support; and $R_{15}$ is hydrogen.

With the proviso that

Compounds of formula Q cannot have $R_2=R_5=R_9$=hydrogen and $R_{13}$=allyl and $R_{14}$=hydroxy; Compounds of formula Q cannot have $R_2=R_5$=hydrogen and $R_9=R_{13}$=methyl and $R_{14}$=methoxy; stereoisomer (2R,3S,4R,5S) cannot have $R_2=R_5$=hydrogen and $R_9=R_{13}$=methyl and $R_{14}$=methoxy; stereoisomer (2R,3S,4R,5S) cannot have $R_2=R_5$=hydrogen and $R_9$=benzyl and $R_{13}$=methyl and $R_{14}$=hydroxy; stereoisomer (2R,3S,4R,5S) cannot have $R_2=R_5$=hydrogen and $R_9$=benzyl and $R_{13}$=methyl and $R_{14}$=methoxy; stereoisomer (2R,3S,4S,5S) cannot have $R_2=R_5=R_9$=hydrogen and $R_{13}$=methyl and $R_{14}$=methoxy; stereoisomer (2R, 3S, 4R) cannot have $R_2=R_5=R_{14}$=hydrogen and $R_9=R_{13}$=methyl.

In yet another embodiment of the invention, there are provided compounds having the structure Q:

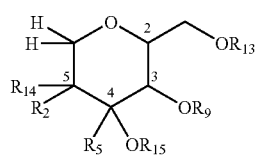

wherein:

$R_2$ and $R_5$ are each independently hydrogen, alkyl, substituted alkyl, and aryl; $R_9$ is hydrogen, alkyl, substituted alkyl, alkylcarbonyl, substituted alkylcarbonyl, aryl, arylcarbonyl, or hydroxyl protecting group; $R_{13}$ is —C(O)$R^8$, where $R^8$ is alkyl, substituted alkyl, or aryl and more specifically $R_8$ is hydrogen, methyl, ethyl, tert-butyl, adamantyl, crotyl, chloromethyl, dichloromethyl, trichloromethyl, trifluoromethyl, methoxymethyl, triphenylmethoxymethyl, phenoxymethyl, 4-chlorophenoxymethyl, phenylmethyl, diphenylmethyl, 4-methoxycrotyl, 3-phenylpropyl, 4-pentenyl, 4-oxopentyl, 4,4-(ethylenedithio)pentyl, 5-[3-bis(4-methoxyphenyl)hydroxymethylphenoxy]-4-oxopentyl, phenyl, 4-methylphenyl, 4-nitrophenyl, 4-fluorophenyl, 4-chlorophenyl, 4-methoxyphenyl, 4-phenylphenyl, 2,4,6-trimethylphenyl, α-naphthyl, benzoyl; $R_{14}$ is hydrogen, halogen, alkyl, substituted alkyl, aryl, heteroaryl, saturated heteroaryl, cyano, azido, amino, alkylamino, arylamino, hydroxy, alkoxy, aryloxy, alkylthio, arylthio, alkylcarboxy, arylcarboxy, N-protected amino acid, O-protected amino acid, or a solid support; and $R_{15}$ is hydrogen.

With the proviso that stereoisomer (2R,3S,4R,5R) cannot have $R_2=R_5=R_9$=hydrogen and $R_{13}$=acetyl and $R_{14}$=N-acetamido; stereoisomer (2R,3R,4S,5S) cannot have $R_2=R_5=R_9$=hydrogen and $R_{13}$=acetyl and $R_{14}$=acetoxy; stereoisomer (2R,3S,4R) cannot have $R_2=R_5=R_{14}$=hydrogen and $R_9=R_{13}$=tert-butylcarbonyl; stereoisomer (2R,3S,4R) cannot have $R_2=R_5=R_9=R_{14}$=hydrogen and $R_{13}$=1-naphthoyl; stereoisomer (2R,3S,4R) cannot have $R_2=R_5=R_9=R_{14}$=hydrogen and $R_{13}$=2-naphthoyl; stereoisomer (2R,3S,4R) cannot have $R_2=R_5=R_9=R_{14}$=hydrogen and $R_{13}$=benzoyl; stereoisomer (2R,3S,4R) cannot have $R_2=R_5=R_9=R_{14}$=hydrogen and $R_{13}$=4-methoxybenzoyl; stereoisomer (2R, 3S, 4S, 5R) cannot have $R_2=R_5=R_9$=hydrogen and $R_{13}$=3,4,5-trihydroxybenzoyl and $R_{14}$=(3,4,5-trihydroxyphenyl)carboxy; stereoisomer (2R, 3S, 4R, 5R) cannot have $R_2=R_5=R_9$=hydrogen and $R_{13}$=benzoyl and $R_{14}$=phenylcarboxy; stereoisomer (2R, 3R, 4R, 5R) cannot have $R_2=R_5=R_9$=hydrogen and $R_{13}$=benzoyl and $R_{14}$=phenylcarboxy; stereoisomer (2R, 3S, 4R, 5R) cannot have $R_2=R_5$=hydrogen and $R_9=R_{13}$=benzoyl and $R_{14}$=phenylcarboxy; stereoisomer (2R, 3S, 4R, 5R) cannot have $R_2=R_5$=hydrogen and $R_9=R_{13}$=benzoyl and $R_{14}$=hydroxy; compounds of formula Q cannot have $R_2=R_9$=hydrogen and $R_{13}$=3-(3,4,5-trimethoxyphenyl)acryloyl and $R_{14}$=hydroxy; compounds of formula Q cannot have $R_2=R_5=R_9$=hydrogen and $R_{13}$=formyl and $R_{14}$=hydroxy; compounds of formula Q cannot have $R_2=R_5=R_9$=hydrogen and $R_{13}$=ethylcarbonyl and $R_{14}$=hydroxy; compounds of formula Q cannot have $R_2=R_5=R_9$=hydrogen and $R_{14}$=hydroxy and $R_{13}$=aminomethylcarbonyl; compounds of formula Q cannot have $R_2=R_5=R_9$=hydrogen and $R_{14}$=hydroxy and $R_{13}$=10-aminodecylcarbonyl; compounds of formula Q cannot have $R_2=R_5=R_9$=hydrogen and $R_{14}$=hydroxy and $R_{13}$=5-aminopentylcarbonyl; compounds of formula Q cannot have $R_2=R_5=R_9$=hydrogen and $R_{14}$=hydroxy and $R_{13}$=succinoyl; and, compounds of formula Q cannot have $R_2=R_5=R_5$=hydrogen and $R_{13}$=3,4,5-trihydroxybenzoyl and $R_{14}$=hydroxy.

In yet another embodiment of the invention, there are provided compounds having the structure Q:

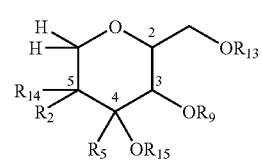

wherein:

$R_2$ and $R_5$ are each independently hydrogen, alkyl, substituted alkyl, and aryl; $R_9$, $R_{13}$, $R_{15}$ are each independently hydrogen, alkylcarbonyl, substituted alkylcarbonyl, arylcarbonyl, and hydroxyl protecting group, $R_{14}$ is cyano; $R_{15}$ is hydrogen, trimethylsilyl, or tert-butyidimethylsilyl.

In yet another embodiment of the invention, there are provided compounds having the structure Q:

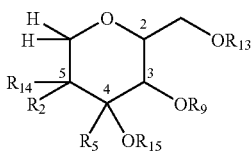

wherein:
R$_2$ and R$_5$ are each independently hydrogen, alkyl, substituted alkyl, and aryl; R$_9$, R$_{13}$ and R$_1$ are each independently hydrogen, alkyl, substituted alkyl, aryl, alkylcarbonyl, substituted alkylcarbonyl, arylcarbonyl, bimethylsilyl, tert-butyldimethylsilyl, and hydroxyl protecting group; R$_{14}$ is alkylthio, or arylthio With the proviso that:
stereoisomer (2R,3R,4S,5R) and (2R,3R,4S,5S) cannot have R$_2$=R$_5$=hydrogen, R$_5$=R$_{13}$=R$_{15}$=acetyl, and R$_{14}$=ethylthio; stereoisomer (2R,3R,4S,5R) and (2R,3R,4S,5S) cannot have R$_2$=R$_5$=hydrogen, R$_9$=R$_{13}$=R$_{15}$=acetyl, and R$_{14}$=n-propylthio; stereoisomers (2R,3S,4S,5R) and (2R,3S,4S,5S) cannot have R$_2$=R$_5$=R$_9$=R$_{13}$=R$_{15}$=hydrogen and R$_{14}$=benzylthio; stereoisomers (2R,3R,4S,5R) and (2R,3R,4S,5S) cannot have R$_2$=R$_5$=hydrogen, R$_9$=R$_{13}$=R$_{15}$=acetyl, and R$_{14}$=benzylthio.

In yet another embodiment of the invention, there are provided compounds having the structure Q:

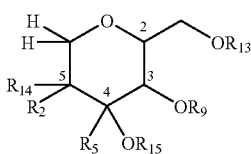

wherein:
R$_2$ and R$_5$ are each independently hydrogen, alkyl, substituted alkyl, and aryl; R$_9$ is hydrogen, alkyl, substituted alkyl, aryl, alkylcarbonyl, substituted alkylcarbonyl, arylcarbonyl, trimethylsilyl, tert-butyldimethylsilyl, or hydroxyl protecting group; R$_{13}$ is alkyl, substituted alkyl, aryl, alkylcarbonyl, substituted alkylcarbonyl, arylcarbonyl, trimethylsilyl, tert-butyldimethylsilyl, or hydroxyl protecting group; R$_{14}$ is NHR$_{18}$ where R$_{18}$ is hydrogen, alkyl, substituted alkyl, aryl, alkylcarbonyl, substituted alkylcarbonyl, arylcarbonyl, or amino protecting group; R$_{15}$ is hydrogen With the proviso that:
stereoisomers (2R,3S,4R,5R) cannot have R$_2$=R$_5$=R$_9$=R$_{15}$=hydrogen, R$_{13}$=acetyl, and R$_{14}$=acetamido; stereoisomers (2R,3S,4S,5S) and (2R,3R,4R,5S) cannot have R$_2$=R$_5$=R$_9$=R$_{15}$=hydrogen, R$_{13}$=tert-butyltrimethylsilyl, and R$_{14}$=trichloroacetamido.

In yet another embodiment of the invention, there are provided compounds having the structure Q:

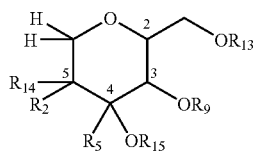

wherein:
R$_2$ and R$_5$ are each independently hydrogen, alkyl, substituted alkyl, and aryl; R$_9$ and R$_{15}$ are each independently hydrogen, alkyl, substituted alkyl, aryl, alkylcarbonyl, substituted alkylcarbonyl, arylcarbonyl, trimethylsilyl, tert-butyldimethylsilyl, and hydroxyl protecting group; R$_{13}$ is alkyl, substituted alkyl, aryl, alkylcarbonyl, substituted alkylcarbonyl, arylcarbonyl, trimethylsilyl, tert-butyldimethylsilyl, or hydroxyl protecting group; R$_{14}$ is phthalimide, substituted phthalimide, maleimide substituted maleimide, or NR$_{18}$R$_{19}$ where R$_{18}$ and R$_{19}$ are each independently alkyl, substituted alkyl, alkylcarbonyl, substituted alkylcarbonyl, aryl, arylcarbonyl, heteroaryl, saturated heteroaryl, and amino protecting group, and R$_{18}$ and R$_{19}$ maybe taken together with the nitrogen to which they are attached forming a cyclic system containing 3 to 10 carbon atoms with at least one substituent as defined for a substituted alkyl.

With the proviso that:
stereoisomer (2R,3R,4R,5R) cannot have R$_2$, R$_5$=hydrogen, R$_9$=R$_{13}$=R$_{15}$=acetyl, and R$_{14}$=phtalimido; stereoisomer (2R,3S,4R,5S) cannot have R$_2$=R$_5$=R$_9$=R$_{13}$=R$_{15}$=hydrogen, and R$_{14}$=dimethylamino hydrogen chloride; stereoisomer (2S,3S,4R,5S) cannot have R$_2$=R$_5$=R$_9$=R$_{13}$=R$_{15}$=hydrogen, and R$_{14}$=trimethylaminoiodide; and, stereoisomer (2R,3S,4R,5S) cannot have R$_2$=R$_5$=R$_9$=R$_{13}$=R$_{15}$=hydrogen, and R$_{14}$=N,N-(benzyloxycarboxy)methylamino.

Invention compounds having structure Q maybe optically pure and include 6-(tert-butyldimethylsiloxymethyl)-5-hydroxy-4-(trimethylsiloxy)tetrahydropyran-3-carbonitrile; 6-(tert-Butyldimethylsiloxymethyl)-5-hydroxy-4(-tert-butyldimethylsiloxy)-tetrahydropyran-3-carbonitrile; 6-(tert-butyldimethylsiloxymethyl)-5-hydroxy-4(-trimethylsiloxy)-tetrahydropyran-3-carbonitrile; 5-benzyloxy-2-hydroxymethyl-tetrahydropyran-3,4-diol, 5-benzylamino-2-tert-butyldimethylsilanyloxymethyl)-tetrahydropyran-3,4-diol; 2-hydroxymethyl-tetrahydropyran-3,4,5-triol; 6-(tert-butyldimethylsilanyloxymethyl)-5-hydroxy-4-trimethylsilanyloxy-tetrahydro-pyran-3-carbonitrile; 2-(tert-butyldimethylsilanyloxymethyl)-tetrahydropyran-3,5-diol; 5-azido-2-(tert-butyldimethylsilanyloxymethyl-tetrahydropyran-3,4-diol; 2-(tert-butyldimethylsilanyloxymethyl)-5-(3-methoxyphenylamino)-tetrahydropyran-3,4-diol; 2-hydroxymethyl-5-phenylsulfanyl-tetrahydropyran-3,4-diol In one embodiment, the present invention provides a process for preparing a compound of formula S. Such a process can be performed, for example, by contacting a compound of formula N with a compound of formula R under conditions suitable to form a compound of formula S, as set forth below:

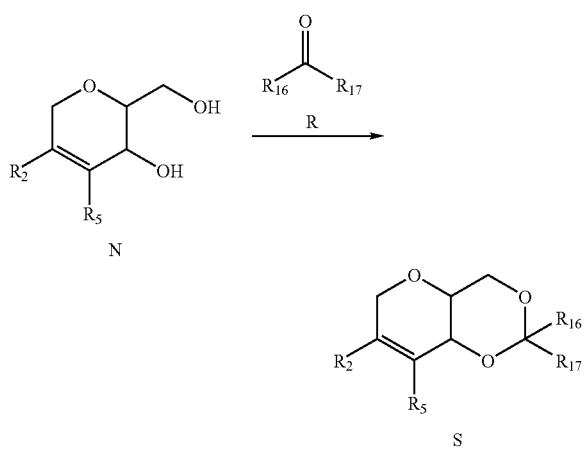

In the scheme shown above, $R_2$, $R_5$, $R_{16}$ and $R_{17}$ are each independently hydrogen, alkyl, substituted alkyl, and aryl.

Solvents contemplated for use in the practice of this particular invention process are typically halogenated solvents, such as for example, dichloromethane, dichloroethane and the like, ethereal solvents, such as for example, diethyl ether, dioxane, tetrahydrofuran and the like, polar non-protic solvents, such as for example, acetonitrile and the like, aromatic solvents, such as for example, benzene, toluene, dichlorobenzene, xylene and the like, or any suitable mixtures thereof. The process is typically carried out at a temperature in the range of about 0° C. up to about 150° C.

Compound N is typically contacted with compound R in the presence of an acidic reagent or a Lewis acidic reagent. Acidic reagents contemplated for use include, for example, formic acid, acetic acid, fumaric acid, phthalic acid, oxalic acid, pyridinium p-toluenesulfonate, p-toluenesulfonic acid, methanesulfonic acid, Montmorillonite Clay K-10, Montmorillonite Clay KSF, ammonium chloride, sulfuric acid, phosphoric acid, hydrochloric acid, hydrobromic acid, hydroiodic acid, and the like. Lewis acidic reagents contemplated for use include, for example, boron trifluoride, trimethylsilyl chloride, trimethylsilylbromide, trimethylsilyl iodide, trimethylsilyl trifluoromethylsulfonate, cerium (III) chloride, scandium (III) trifluoromethanesulfonate, yttrium (III) trifluoromethanesulfonate, ytterbium (III) trifluoromethanesulfonate, lanthanum (III) trifluoromethanesulfonate, iron (III) chloride, zinc (II) chloride, zinc (II) bromide, zinc (II) iodide, zinc (II) trifluoromethanesulfonate, zinc (II) sulfate, magnesium sulfate, lithium perchlorate, copper (II) trifluoromethanesulfonate, copper (II) tetrafluoroborate.

In yet another embodiment of the invention, there are provided compounds having the structure S:

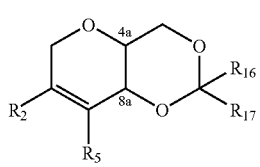

wherein:
$R_2$, $R_5$, $R_{16}$ and $R_{17}$ are each independently hydrogen, alkyl, substituted alkyl, and aryl.

With the proviso that:
stereoisomer (4aR,8aS) cannot have $R_2=R_5=R_{16}$=hydrogen and $R_{17}$=phenyl; and, stereoisomer (4aR,8aS) cannot have $R_2=R_{10}$=hydrogen, $R_5$=(4-methoxyphenyl)-diphenylmethoxymethyl and $R_{17}$=phenyl Invention compounds having structure S maybe optically pure and include 2,2-dimethyl-4,4a,6,8a-tetrahydropyrano[3,2-d][1,3]dioxine); (4aR,8aR)-2,2-dimethyl-4,4a,6,8a-tetrahydropyrano[3,2-d][1,3]dioxine; (4aS,8aS)-2,2-dimethyl-4,4a,6,8a-tetrahydropyrano[3,2-d][1,3]dioxine; (4aR,8aS)-2,2-dimethyl-4,4a,6,8a-tetrahydropyrano[3,2-d][1,3]dioxine; (4aS,8aR)-2,2-dimethyl-4,4a,6,8a-tetrahydropyrano[3,2-d][1,3]dioxine In one embodiment, the present invention provides a process for preparing a compound of formula T. Such a process can be performed, for example, by contacting a compound of formula S under conditions suitable to form a compound of formula T, as set forth below:

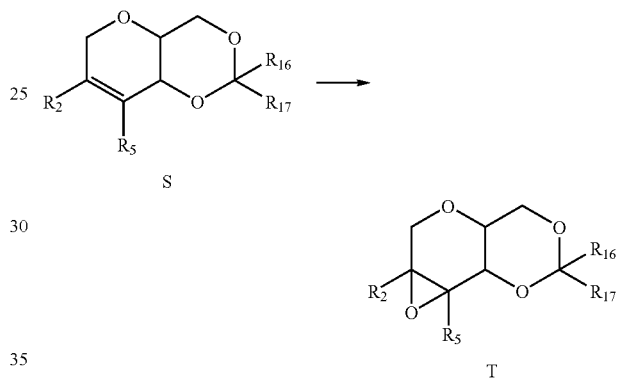

$R_2$, $R_1$, $R_{16}$ and $R_{17}$ are each independently hydrogen, alkyl, substituted alkyl, and aryl.

With the proviso that
For compound of formula S, stereoisomer (3aR,7aS) cannot have $R_2=R_5$=hydrogen and $R_{10}=R_{17}$=methyl Solvents contemplated for use in the practice of this particular invention process are typically water, halogenated solvents, such as for example, dichloromethane, dichloroethane and the like, ethereal solvents, such as for example, diethyl ether, dioxane, tetrahydrofuran and the like, polar non-protic solvents, such as for example, acetonitrile, dimethyl formamide, dimethyl acetamide, N-methylpyrrolidine, dimethyl sulfoxide and the like, aromatic solvents, such as for example, benzene, toluene, dichlorobenzene, xylene and the like, alcoholic solvents, such as for example, methanol, ethanol, isopropanol and the like, or any suitable mixtures thereof. The process is typically carried out at a temperature in the range of about −100° C. up to about 100° C.

Compound S is typically contacted with an epoxidation reagent in the presence or absence of a transition metal reagent, and in the presence or absence of a ligand. Epoxidation reagents contemplated for use include, for example, oxygen, tert-butyl hydroperoxide, meta-chloroperbenzoic acid, dimethyl dioxirane, oxone, sodium hypochlorite, sodium periodate, iodosylbenzene and the like. Transition metal reagents contemplated for use include, for example, titanium tetraisopropoxide, polymer supported cyclopentadienyl titanium trichloride, zirconium tetraethoxide, hafnium tetraisopropoxide, vanadium pentoxide, niobium pentaethoxide, tantalum pentaisopropoxide, manganese (II) trifluoromethanesulfonate, iron (III) acetylacetonate, molybdenum hexacarbonyl, ruthenium dichloride tris(triphenylphosphine), cobalt (II) trifluoromethanesulfonate, and the like. Ligands contemplated for use include, for example, (R,R) diethyl tartarate, (S,S) diethyl tartarate, N-ethyl ephedrine, N-methylprolinol, porphyrin, 2,2'-[[(1S,2S)-1,2-diphenyl-1,2-ethanediyl]-bis(nitrilomethylidyne)]bis[6-(1, 1-dimethylethyl)-4-methyl-phenol, 2,2'-[[(1R,2R)-1,2-diphenyl-1,2-ethanediyl]-bis(nitrilomethylidyne)]bis[6-(1, 1-dimethylethyl)-4-methyl-phenol, 2,2'-[(1R,2R)-1,2-cyclohexanediylbis[(E)-nitrilomethylidyne]]bis[6-(1,1-dimethylethyl)-4-methyl-phenol and the like.

In yet another embodiment of the invention, there are provided compounds having the structure T:

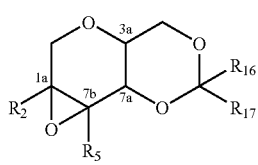

wherein:
$R_2$, $R_5$, $R_{16}$ and $R_{17}$ are each independently hydrogen, alkyl, substituted alkyl, and aryl;
With the proviso that:
stereoisomer (1aR,3aR,7aR,7bR) cannot have $R_2=R_5=R_{16}$=hydrogen and $R_{17}$=phenyl; stereoisomer (1aS,3aR,7aR,7bS) cannot have $R_2=R_5=R_{16}$=hydrogen and $R_{17}$=phenyl; and, stereoisomer (1aR,3aS,7aS,7bR) cannot have $R_2=R_5=R_{16}$=hydrogen and $R_{17}$=phenyl.

In one embodiment, the present invention provides a process for preparing a compound of formula U. Such a process can be performed, for example, by contacting a compound of formula T with a nucleophile under conditions suitable to form a compound of formula U, as set forth below.

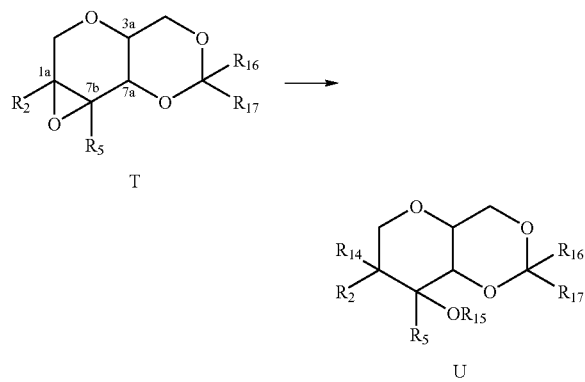

$R_2$, $R_5$, $R_{16}$ and $R_{17}$ are each independently hydrogen, alkyl, substituted alkyl, and aryl; $R_{14}$ is hydrogen, halogen, alkyl, substituted alky, aryl, heteroaryl, saturated heteroaryl, cyano, azido, amino, alkylamino, arylamino, hydrazine, alkylhydrazino, arylhydrazino, alkylcarbonylhydrazino, arylcarbonylhydrazino, hydroxy, alkoxy, aryloxy, alkylthio, arylthio, alkylcarboxy, arylcarboxy, N-protected amino acid, O-protected amino acid, or a solid support; $R_{15}$ is hydrogen, alkyl, substituted alkyl, alkylcarbonyl, substituted alkylcarbonyl, aryl, arylcarbonyl, or hydroxyl protecting group.

With the proviso that:
For compounds of formula T, stereoisomer (1aS,3aR,7aR, 7bS) cannot have $R_2=R_5=R_{16}$=hydrogen and $R_{17}$=phenyl Solvents contemplated for use in the practice of this particular invention process are typically water, halogenated solvents, such as for example, dichloromethane, dichloroethane and the like, ethereal solvents, such as for example, diethyl ether, dioxane, tetrahydrofuran and the like, polar non-protic solvents, such as for example, acetonitrile, dimethyl formamide, dimethyl acetamide, N-methylpyrrolidine, dimethyl sulfoxide and the like, aromatic solvents, such as for example, benzene, toluene, dichlorobenzene, xylene and the like, alcoholic solvents, such as for example, methanol, ethanol, isopropanol and the like, or any suitable mixtures thereof. The process is typically carried out at a temperature in the range of about 0° C. up to about 150° C.

Compound T is typically contacted with a nucleophile in the presence or absence of a Lewis acidic reagent. Nucleophiles contemplated for use include, for example, water, potassium cyanide, trimethylsilyl cyanide, sodium azide, potassium iodide, sodium fluoride, potassium hydroxide, methanol, sodium ethoxide, benzyl alcohol, 3,5-dimethylphenol, sodium phenoxide, ethyl thiol, potassium phenyl thiolate, ammonia, ammonium hydroxide, hydrazine, ethyl hydrazine, phenyl hydrazine, benzoylhydrazine, methylamine, benzylamine, dibutylamine, aniline, 3-methoxyaniline, diphenylamine, sodium amide, Lithium dimethylamide, potassium benzylmethylamide, lithium anilide, hydrazine, potassium hydrizide, methylhydrazine, phenylhydrazine, benzoylhydrazine, acetylhydrazine, piperidine, morpholine, piperazine, thiomorpholine, pyrrolidine, lithium piperidide, potassium morpholinide, phthalimide, maleimide, adenine, guanine, uracil, thymine, cytosine, imidazole, pyrrole, indole, tetrazole, glycine methyl ester, serine tert-butyl ester, valine ethyl ester lithium salt, N-benzylleucine, methyl lithium, ethyl magnesium bromide, phenyl lithium, diethyl zinc, diethyl mercury, trimethyl aluminum, triethyl indium, trimethyl gallium, Merrifield resin, Wang resin, Rink resin, Wang resin lithium salt, compound of formula N and the like. Lewis acidic reagents contemplated for use include, for example, boron trifluoride, boron trifluoride etherate, boron trifluoride tetrahydrofuran complex, boron trifluoride tert-butyl-methyl ether complex, boron trifluoride dibutyl ether complex, boron trifluoride dihydrate, boron trifluoride di-acetic acid complex, boron trifluoride dimethyl sulfide complex, boron trichloride, boron trichloride dimethyl sulfide complex, boron tribromide, boron tribromide dimethyl sulfide complex, boron triiodide, trimethoxyborane, triethoxyborane, trimethylaluminum, triethylaluminum, aluminum trichloride, aluminum trichloride tetrahydrofuran complex, aluminum tribromide, titanium tetrachloride, titanium tetrabromide, titanium iodide, titanium tetraethoxide, titanium tetraisopropoxide, scandium (III) trifluoromethanesulfonate, yttrium (III) trifluoromethanesulfonate, ytterbium (III) trifluoromethanesulfonate, lanthanum (III) trifluoromethanesulfonate, zinc (II) chloride, zinc (II) bromide, zinc (II) iodide, zinc (II) trifluoromethanesulfonate, zinc (II) sulfate, magnesium sulfate, lithium perchlorate, copper (II) trifluoromethanesulfonate, copper (II) tetrafluoroborate and the like.

In yet another embodiment of the invention, there are provided compounds having the structure U:

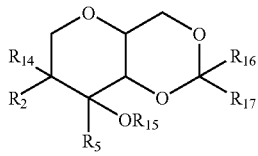

wherein:
  $R_2$, $R_5$, $R_{16}$ and $R_{17}$ are each independently hydrogen, alkyl, substituted alkyl, and aryl; $R_{14}$ is hydrogen, halogen, alkyl, substituted alkyl, aryl, heteroaryl, saturated heteroaryl, cyano, azido, amino, alkylamino, arylamino, hydrazine, alkylhydrazino, arylhydrazino, alkylcarbonylhydrazino, arylcarbonylhydrazino, hydroxy, alkoxy, aryloxy, alkylthio, arylthio, alkylcarboxy, arylcarboxy, N-protected amino acid, O-protected amino acid, or a solid support; and $R_{15}$ is hydrogen, alkyl, substituted alkyl, alkylcarbonyl, substituted alkylcarbonyl, aryl, arylcarbonyl, or hydroxyl protecting group.

With the proviso that
  if $R_{16}$ is methyl then $R_{17}$ cannot be methyl; if $R_{16}$ is hydrogen then $R_{17}$ cannot be phenyl; if $R_2=R_5=R_{15}=R_{10}=$hydrogen and $R_{14}=$hydroxy then $R_{17}$ cannot be 3-nitrophenyl; if $R_2=R_5=R_{14}=R_{15}=R_{16}=$hydrogen then $R_{17}$ cannot be 4-nitrophenyl; if $R_2=R_{14}=R_{15}=R_{16}=$hydrogen then $R_{17}$ cannot be 4-methoxyphenyl; if $R_2=R_5=R_{16}=$hydrogen and $R_{14}=$methoxy and $R_{15}=$methyl then $R_{17}$ cannot be 4-methoxyphenyl; and, if $R_2=R_5=R_{15}=R_{16}=$hydrogen and $R_{14}=$hydroxy then $R_{17}$ cannot be 4-methoxyphenyl.

In one embodiment, the present invention provides a process for preparing a compound of formula V. Such a process can be performed, for example, by contacting a compound of formula S under conditions suitable to form a compound of formula V, as set forth below:

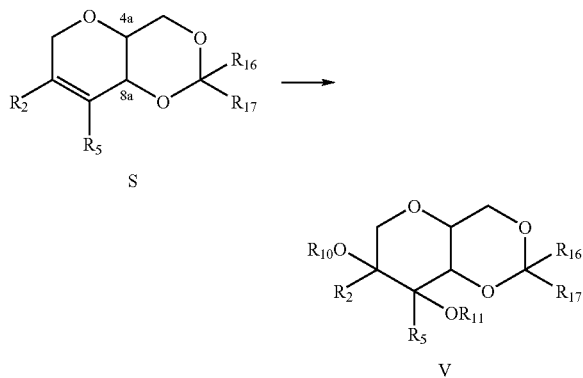

In the scheme shown above, $R_2$, $R_5$, $R_{16}$ and $R_{17}$ are independently selected from the group consisting of hydrogen, alkyl, substituted alkyl, and aryl; $R_{10}$ and $R_{11}$ are hydrogen With the proviso that:
  stereoisomer (4aR,8aS) cannot have $R_{16}=$hydrogen and $R_{17}=$phenyl Solvents contemplated for use in the practice of this particular Invention process are typically water, halogenated solvents, such as dichloromethane and the like, alcoholic solvents, such as for example 2-methyl-2-propanol and the like, ethereal solvents, such as for example tetrahydrofuran and the like, or any suitable mixtures thereof. The process is typically carried out at a temperature in the range of about −78° C. up to about 60° C.

Compound S is typically contacted with a suitable mixture of an oxidant, a co-oxidant and a ligand. Oxidants contemplated for use include, for example, osmium tetroxide, potassium permanganate, thallium acetate, potassium periodate, silver acetate and the like, co-oxidants contemplated for use include, for example, N-methylmorpholine oxide, trimethylamine oxide, tert-butyl peroxide, iodine, potassium ferricyanide and the like, ligands contemplated for use include, for example, pyridine, quinuclidine, dihydroquinine acetate, dihydroquinidine acetate, dihydroquinine anthraquinone-1,4-diyl diether ((DHQ)$_2$AQN), dihydroquinine phthalazine-1,4-diyl diether ((DHQ)$_2$PHAL), dihydroquinine 2,5-diphenyl-4,6-pyrimidinediyl diether ((DHQ)$_2$PYR), dihydroquinidine anthraquinone-1,4-diyl diether ((DHQD)$_2$AQN), dihydroquinidine phthalazine-1,4-diyl diether ((DHQD)$_2$PHAL), dihydroquinidine 2,5-diphenyl-4,6-pyrimidinediyl diether ((DHQD)$_2$PYR), tetraethyl ammonium hydroxide, tetraethyl ammonium acetate, N,N,N'N'-tetramethylethylene diamine (TMEDA) and the like.

In yet another embodiment of the invention, there are provided compounds having the structure V:

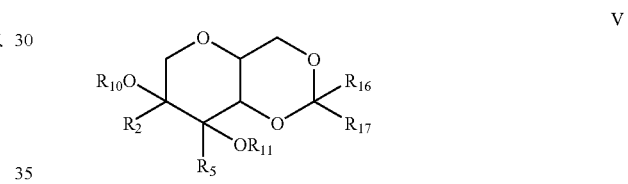

wherein:
  $R_2$, $R_5$, $R_{16}$ and $R_{17}$ are each independently hydrogen, alkyl, substituted alkyl, and aryl; $R_{10}$ and $R_{11}$ are each independently hydrogen, alkyl, substituted alkyl, alkylcarbonyl, substituted alkylcarbonyl, aryl, arylcarbonyl, and hydroxyl protecting group;

With the proviso that:
  If $R_{16}$ is methyl then $R_{17}$ cannot be methyl; if $R_{16}$ is hydrogen then $R_{17}$ cannot be phenyl; if $R_2=R_5=R_{10}=R_{11}=R_{16}=$hydrogen then $R_{17}$ cannot be 3-nitrophenyl; if $R_2=R_5=R_{16}=$hydrogen and $R_{14}=$hydroxy then $R_{17}$ cannot be 4-methoxyphenyl; and, if $R_2=R_5=R_{16}=$hydrogen and $R_{10}=R_{11}=$methyl then $R_{17}$ cannot be 4-methoxyphenyl.

Invention compounds having structure V maybe optically pure and include 2,2-dimethyl-hexahydro-pyrano[3,2-d][1,3]dioxine-7,8-diol; (4aS,7R,8R,8aR)-2,2-dimethyl-hexahydropyrano[3,2-d][1,3]dioxine-7,8-diol; (4aS,7S,8S,8aR)-2,2-dimethyl-hexahydropyrano[3,2-d][1,3]dioxine-7,8-diol; (4aR,7R,8R,8aS)-2,2-dimethyl-hexahydropyrano[3,2-d][1,3]dioxine-7,8-diol; (4aS,7R,8R,8aS)-2,2-dimethyl-hexahydropyrano[3,2-d][1,3]dioxine-7,8-diol; (4aR,7S,8S,8aR)-2,2-dimethyl-hexahydropyrano[3,2-d][1,3]dioxine-7,8-diol; (4aS,7S,8S,8aS)-2,2-dimethyl-hexahydropyrano[3,2-d][1,3]dioxine-7,8-diol; and, (4aR,7R,8R,8aR)-2,2-dimethyl-hexahydropyrano[3,2-d][1,3]dioxine-7,8-diol In one embodiment, the present invention provides a process for preparing a compound of formula W. Such a process can be performed, for example, by contacting a compound of formula G under conditions suitable to form a compound of formula W, as set forth below:

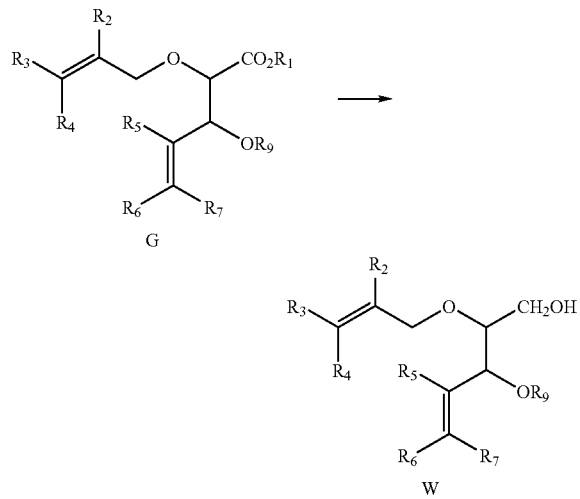

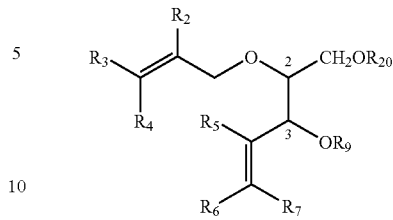

In the scheme shown above, $R_1$ is typically alkyl, substituted alkyl, or aryl; $R_2$ and $R_5$ are each independently hydrogen, alkyl, substituted alkyl, and aryl; $R_3$, $R_4$, $R_6$, $R_7$ are either all hydrogen or, of $R_3$, $R_4$, $R_5$, $R_7$ three are hydrogen and the fourth is alkyl, substituted alkyl, or aryl; $R_9$ is hydrogen, alkyl, substituted alkyl, alkylcarbonyl, substituted alkylcarbonyl, aryl, arylcarbonyl, or hydroxyl protecting group. In another embodiment, $R_1$ is ethyl, $R_2$-$R_7$ and $R_9$ are hydrogen.

Solvents contemplated for use in the practice of this particular invention process are typically water, ammonia, ethereal solvents, such as for example, diethyl ether, dioxane, tetrahydrofuran and the like, alcoholic solvents, such as for example, methanol, ethanol, isopropanol, 1,2-ethanediol, polyethylene glycol and the like, or any suitable mixtures thereof. The process is typically carried out at a temperature in the range of about −100° C. up to about 100° C.

Compound G is typically contacted with a reducing reagent in the presence or absence of an acidic reagent or a Lewis acidic reagent. Reducing reagents contemplated for use include, for example, borane-dimethyl sulfide complex, 9-borabicyclo[3.3.1.]nonane (9-BBN), catechol borane, lithium borohydride, sodium borohydride, sodium borohydride-methanol complex, potassium borohydride, sodium hydroxyborohydride, lithium triethylborohydride, lithium n-butylborohydride, sodium cyanoborohydride, calcium (II) borohydride, lithium aluminum hydride, diisobutylaluminum hydride, n-butyl-diisobutylaluminum hydride, sodium bis-methoxyethoxyaluminum hydride, triethoxysilane, diethoxymethylsilane, lithium hydride, lithium, sodium, hydrogen Ni/B, and the like. Acidic reagents contemplated for use include, for example, acetic acid, methanesulfonic acid, hydrochloric acid, and the like. Lewis acidic reagents contemplated for use include, for example, trimethoxyborane, triethoxyborane, aluminum trichloride, lithium chloride, vanadium trichloride, dicyclopentadienyl titanium dichloride, cesium fluoride, potassium fluoride, zinc (II) chloride, zinc (II) bromide, zinc (II) iodide, and the like.

In yet another embodiment of the invention, there are provided compounds having the structure W:

wherein:
$R_2$ and $R_5$ are each independently hydrogen, alkyl, substituted alkyl, and aryl; $R_3$, $R_4$, $R_5$, $R_7$ are either all hydrogen or, of $R_3$, $R_4$, $R_6$, $R_7$ three are hydrogen and the fourth is alkyl, substituted alkyl, or aryl; $R_9$ and $R_{20}$ are each independently hydrogen, alkyl, substituted alkyl, alkylcarbonyl, substituted alkylcarbonyl, aryl, arylcarbonyl, and hydroxyl protecting group With the proviso that:
stereoisomer (2R,3R) cannot have $R_3=R_4=R_5=R_7=R_9=R_{20}=$hydrogen; stereoisomer (2R,3R) cannot have $R_3=R_4=R_5=R_7=$hydrogen and $R_9=R_{20}=$benzoyl; stereoisomer (2R,3R) cannot have $R_3=R_4=R_7=R_9=R_{20}=$hydrogen and $R_6=$methyl; stereoisomer (2R,3R) cannot have $R_3=R_4=R_7=$hydrogen and $R_5=$methyl and $R_9=R_{20}=$benzoyl; and, if $R_{20}=$benzyl then $R_3$, $R_4$, $R_6$, $R_7$, $R_9$ cannot be hydrogen Invention compounds having structure W maybe optically pure and include 2-allyloxy-pent-4-ene-1,3-diol, (2S,3S)-2-allyloxy-pent-4-ene-1,3-diol; (2R,3S)-2-allyloxy-pent-4-ene-1,3-diol; (2S,3R)-2-allyloxy-pent-4-ene-1,3-diol.

In one embodiment, the present invention provides a process for preparing a compound of formula X. Such a process can be performed, for example, by contacting a compound of formula W with a compound of formula R under conditions suitable to form a compound of formula X, as set forth below:

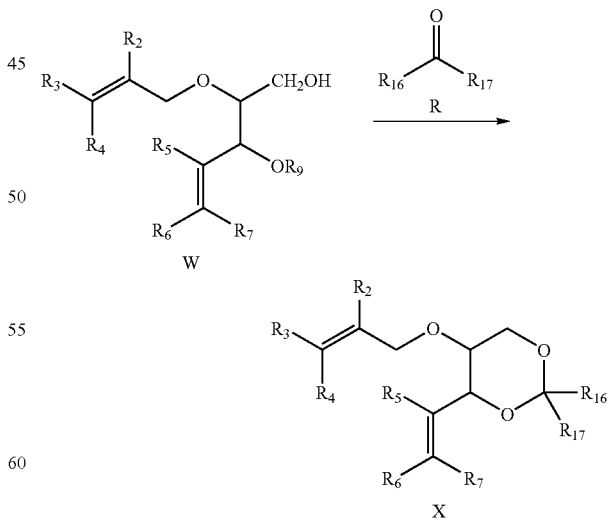

In the scheme shown above, $R_2$ and $R_5$ are each independently hydrogen, alkyl, substituted alkyl, and aryl; $R_3$, $R_4$, $R_6$, $R_7$ are either all hydrogen or, of $R_3$, $R_4$, $R_6$, $R_7$ three are hydrogen and the fourth is alkyl, substituted alkyl, or aryl; $R_{16}$ and $R_{17}$ are each independently hydrogen, alkyl, substituted alkyl, and aryl.

Solvents contemplated for use in the practice of this particular invention process are typically halogenated solvents, such as for example, dichloromethane, dichloroethane and the like, ethereal solvents, such as for example, diethyl ether, dioxane, tetrahydrofuran and the like, polar non-protic solvents, such as for example, acetonitrile and the like, aromatic solvents, such as for example, benzene, toluene, dichlorobenzene, xylene and the like, or any suitable mixtures thereof. The process is typically carried out at a temperature in the range of about 0° C. up to about 150° C.

Compound W is typically contacted with compound R in the presence of an acidic reagent or a Lewis acidic reagent. Acidic reagents contemplated for use include, for example, formic acid, acetic acid, fumaric acid, phthalic acid, oxalic acid, pyridinium p-toluenesulfonate, p-toluenesulfonic acid, methanesulfonic acid, Montmorillonite Clay K-10, Montmorillonite Clay KSF, ammonium chloride, sulfuric acid, phosphoric acid, hydrochloric acid, hydrobromic acid, hydroiodic acid, and the like. Lewis acidic reagents contemplated for use include, for example, boron trifluoride, trimethylsilyl chloride, trimethylsilylbromide, trimethylsilyl iodide, trimethylsilyl trifluoromethylsulfonate, cerium (III) chloride, scandium (III) trifluoromethanesulfonate, yttrium (III) trifluoromethanesulfonate, ytterbium (III) trifluoromethanesulfonate, lanthanum (III) trifluoromethanesulfonate, iron (III) chloride, zinc (II) chloride, zinc (II) bromide, zinc (II) iodide, zinc (II) trifluoromethanesulfonate, zinc (II) sulfate, magnesium sulfate, lithium perchlorate, copper (II) trifluoromethanesulfonate, copper (II) tetrafluoroborate.

In yet another embodiment of the invention, there are provided compounds having the structure X:

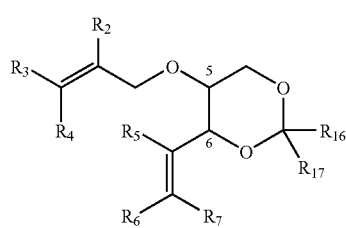

X wherein:

$R_2$ and $R_5$ are each independently hydrogen, alkyl, substituted alkyl, and aryl; $R_3$, $R_4$, $R_6$, $R_7$ are either all hydrogen or, of $R_3$, $R_4$, $R_6$, $R_7$ three are hydrogen and the fourth is alkyl, substituted alkyl, and aryl; $R_{16}$ and $R_{17}$ are each independently hydrogen, alkyl, substituted alkyl, and aryl Invention compounds having structure X maybe optically pure and include 5-allyloxy-2,2-dimethyl-4-vinyl-[1,3]dioxane; (5R,6R)-5-allyloxy-2,2-dimethyl-4-vinyl-[1,3]dioxane; (5S,6S-5-allyloxy-2,2-dimethyl-4-vinyl-[1,3]dioxane; (5S,6R-5-allyloxy-2,2-dimethyl-4-vinyl-[1,3]dioxane; (5R,6S)-5-allyloxy-2,2-dimethyl-4-vinyl-[1,3]dioxane.

In one embodiment, the present invention provides a process for preparing a compound of formula S. Such a process can be performed, for example, by contacting a compound of formula X under conditions suitable to form a compound of formula S, as set forth below:

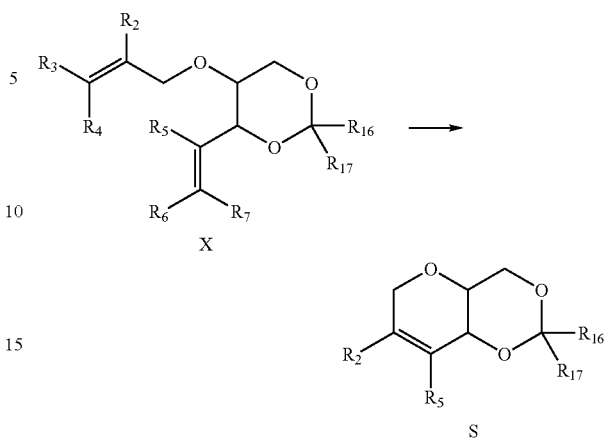

In the scheme shown above, $R_2$, $R_5$, $R_{16}$ and $R_{17}$ are each independently hydrogen, alkyl, substituted alkyl, and aryl. In another embodiment, $R_2$-$R_7$ are hydrogen and $R_{16}$ and $R_{17}$ are methyl; In still another embodiment, $R_2$, $R_3$, $R_4$, $R_5$, $R_7$ are hydrogen, and $R_5$, $R_{16}$, $R_{17}$ are methyl; in yet another embodiment, $R_2$, $R_3$, $R_4$, $R_5$, $R_7$ are hydrogen, $R_6$ is phenyl, and $R_{16}$-$R_{17}$ are methyl.

In one embodiment, the present invention provides a process for preparing compound of formula S as a mixture of stereoisomers, such as for example, cis or trans stereoisomers and the like. In another embodiment, the invention provides a process for separating such stereoisomers, such as for example, chromatography, crystallization, re-crystallization, distillation and the like. In still another embodiment, the invention provides a process for preparing compound S as an optically pure isomer.

Solvents contemplated for use in the practice of this particular invention process are typically water, halogenated solvents, such as for example, dichloromethane, dichloroethane and the like, ethereal solvents, such as for example, diethyl ether, dioxane, tetrahydrofuran and the like, polar non-protic solvents, such as for example, acetonitrile, dimethyl formamide, dimethyl acetamide, N-methylpyrrolidine, dimethyl sulfoxide and the like, aromatic solvents, such as for example, benzene, toluene, dichlorobenzene, xylene and the like, alcoholic solvents, such as for example, methanol, ethanol, isopropanol and the like, or any suitable mixtures thereof. The process is typically carried out at a temperature in the range of about 0° C. up to about 150° C.

Compound X is typically contacted with a ring-closing metathesis catalyst. Ring-closing metathesis catalysts contemplated for use include, for example, 2,6-diisopropylphenylimidoneophylidene molybdenum (IV) bis-(tert-butoxide), 2,6-diisopropylphenylimidoneophylidene molybdenum (IV) bis-(hexafluoro-tert-butoxide), 2,6-diisopropylphenylimidoneophylidene[racemic-BIPHEN]molybdenum (IV), 2,6-diisopropylphenylimidoneophylidene[(R)-(+)-BIPHEN]molybdenum (IV), 2,6-diisopropylphenylimidoneophylidene[(S)-(−)-BIPHEN]molybdenum (IV), bis-(tricyclohexylphosphine)benzylidine ruthenium (IV) dichloride, bis-(tricyclohexylphosphine)-3-methyl-2-butenylidene ruthenium (IV) dichloride, bis-(tricyclopentylphosphine)benzylidine ruthenium (IV) dichloride, bis-(tricyclopentylphosphine)-3-methyl-2-butenylidene ruthenium (IV) dichloride, tricyclohexylphosphine-(1,3-bis(2,4,6-trimethylphenyl)-4,5-dihydroimidazol-2-ylidene)-benzylidine ruthenium (IV) dichloride, tricyclohexylphosphine-(1,3-bis (2,6-diisopropylphenyl)-4,5-dihydroimidazol-2-ylidene) benzylidine ruthenium (IV) dichloride, (1,3-bis(2,4,6-trimethylphenyl)-4,5-dihydroimidazol-2-ylidene)-2-isopropoxyphenylmethylene ruthenium (IV) dichloride, (tricyclopentylphosphine)-2-isopropoxyphenylmethylene ruthenium (IV) dichloride, (tricyclopentylphosphine)-2-methoxy-3-naphthylmethylene ruthenium (IV) dichloride and the like.

In one embodiment, the present invention provides a process for preparing a compound of formula P. Such a process can be performed, for example, by contacting a compound of formula Y under conditions suitable to form a compound of formula P, as set forth below:

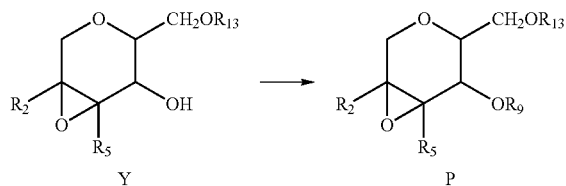

In the scheme shown above, $R_2$ and $R_5$ are each independently hydrogen, alkyl, substituted alkyl, and aryl; $R_9$ and $R_{13}$ are each independently hydrogen, alkyl, substituted alkyl, alkylcarbonyl, substituted alkylcarbonyl, aryl, arylcarbonyl, and hydroxyl protecting group.

Solvents contemplated for use in the practice of this particular invention process are typically water, halogenated solvents, such as for example, dichloromethane, dichloroethane and the like, ethereal solvents, such as for example, diethyl ether, dioxane, tetrahydrofuran and the like, polar non-protic solvents, such as for example, acetonitrile, dimethyl formamide, dimethyl acetamide, N-methylpyrrolidine, dimethyl sulfoxide and the like, aromatic solvents, such as for example, benzene, toluene, dichlorobenzene, xylene and the like, alcoholic solvents, such as for example, methanol, ethanol, isopropanol and the like, or any suitable mixtures thereof. The process is typically carried out at a temperature in the range of about 0° C. up to about 40° C.

Compound Y is typically contacted with a resolving enzyme in the presence of an acylating agent. Resolving enzymes contemplated for use include lipase, esterase, peptidase, acylase or protease enzymes of mammalian, plant, fungal or bacterial origin, such as for example, Lipase Amano lipase PS-D (immobilized lipase from *Pseudomonas cepacia*), Amano Lipase PS-C (immobilized lipase from *Pseudomonas cepacia*), Roche Chirazyme L-3 (lipase, lyophilizate, from *Candida Rugosa*), Roche Chirazyme L-3 (purified lipase, lyophilizate, from *Candida Rugosa*), Roche Chirazyme L-3 (purified lipase, carrier-fixed, carrier 2, lyophilizate, from *Candida rugosa*), Roche Chirazyme L-5 (lipase, solution, from *Candida antartica*, type A), Roche Chirazyme L-5 (lipase, lyophilizate, from *Candida antartica*, type A), Roche Chirazyme L-5 (lipase, carrier-fixed, carrier 1, lyophilizate, from *Candida antartica*, type A), Roche Chirazyme L-10 (lipase, lyophilizate, from *Alcaligenes* sp.), Altus Biologics 8 (lipase from *Mucor miehei*) and Altus Biologics 27 (lipase from *Alcaligenes* sp.) and the like. Acylating agents contemplated for use include, for example, ethyl acetate, vinyl acetate, vinyl propionate, vinyl butyrate, Isopropenyl acetate, 1-ethoxyvinyl acetate, trichloroethyl butyrate, trifluoroethyl butyrate, trifluoroethyl laureate, S-ethyl thiooctanoate, biacetyl monooxime acetate, acetic anhydride, succinic anhydride, amino acid, diketene and the like.

Compound Y can also be contacted with an electrophilic reagent. Electrophilic reagents contemplated for use include, for example, diazomethane, trimethylsilyidiazomethane, alkyl halides, such as for example methyl iodide, benzyl bromide and the like, alkyl triflates, such as for example methyl triflate and the like, alkyl sulfonates, such as for example ethyl toluenesulfonate, butyl methanesulfonate and the like, acyl halides, such as for example acetyl chloride, benzoyl bromide and the like, acid anhydrides, such as for example acetic anhydride, succininc anhydride, maleic anhydride and the like, isocyanates, such as for example methyl isocyanate, phenylisocyanate and the like, chloroformates, such as for example methyl chloroformate, ethyl chloroformate, benzyl chloroformate and the like, sulfonyl halides, such as for example methanesulfonyl chloride, p-tolunesulfonyl chloride and the like, silyl halides, such as for example trimethylsilyl chloride, tertbutyidimethyl silyll chloride and the like, phosphoryl halide such as for example dimethyl chlorophosphate and the like, alpha-beta-unsaturated carbonyl such as for example acrolein, methyl vinyl ketone, cinnamaldehyde and the like.

Compound Y can also be contacted with an alcohol in the presence of an azodicarboxylate and a phosphine base, or any suitable mixtures thereof. Azodicarboxylates contemplated for use include, for example, diethyl azodicarboxylate, dicyclohexyl azodicarboxylate, diisopropyl azodicarboxylate and the like. Phosphine bases contemplated for use include, for example, triethylphosphine, tricyclopentylphosphine, tricyclohexylphosphine, triphenylphosphine, tri-o-tolylphosphine, and the like.

Compound Y can also be contacted with a carboxylic acid or an amino acid in the presence of a coupling agent and a base, or any suitable mixtures thereof. Coupling agents contemplated for use include, for example, dicyclohexylcarbodiimide (DCC), diisopropyl carbodiimide (DIC), 1-ethyl-3-(3-dimethylaminopropyl)-carbodiimide (EDCl), N-hydroxybenzotriazole (HOBT), N-hydroxysuccinimide (HOSu), 4-nitrophenol, pentafluorophenol, 2-(1H-benzotriazole-1-yl)-1,1,3,3-tetramethyluronium tetrafluoroborate (TBTU), O-benzotriazole-N,N,N'N'-tetramethyluronium hexafluorophosphate (HBTU), benzotriazole-1-yl-oxy-tris-dimethylamino)-phosphonium hexafluorophosphate (BOP), benzotriazole-1-yl-oxy-tris-pyrrolidinophosphonium hexafluorophosphate, bromo-trispyrrolidino-phosphonium hexafluorophosphate, 2-(5-norbornene-2,3-dicarboximido)-1,1,3,3-tetramethyluronium tetrafluoroborate (TNTU), O-(N-succinimidyl)-1,1,3,3-tetramethyluronium tetrafluoroborate (TSTU), tetramethylfluoroformamidinium hexafluorophosphate and the like. Bases contemplated for use include, for example, triethylamine, diisopropylethylamine, pyridine, 4-dimethylaminopyridine, and the like.

In another embodiment, the invention provides a process for separating compound of formula P, such as for example, chromatography, crystallization, re-crystallization, distillation and the like.

In one embodiment, the present invention provides a process for preparing a compound of formula P. Such a process can be performed, for example, by contacting a compound of formula Z under conditions suitable to form a compound of formula P, as set forth below:

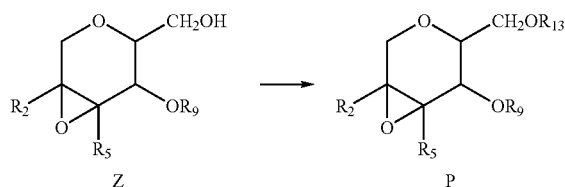

In the scheme shown above, $R_2$ and $R_5$ are each independently hydrogen, alkyl, substituted alkyl, and aryl; $R_9$ and $R_{13}$ are each independently hydrogen, alkyl, substituted alkyl, alkylcarbonyl, substituted alkylcarbonyl, aryl, arylcarbonyl, and hydroxyl protecting group.

Solvents contemplated for use in the practice of this particular invention process are typically water, halogenated solvents, such as for example, dichloromethane, dichloroethane and the like, ethereal solvents, such as for example, diethyl ether, dioxane, tetrahydrofuran and the like, polar non-protic solvents, such as for example, acetonitrile, dimethyl formamide, dimethyl acetamide, N-methylpyrrolidine, dimethyl sulfoxide and the like, aromatic solvents, such as for example, benzene, toluene, dichlorobenzene, xylene and the like, alcoholic solvents, such as for example, methanol, ethanol, Isopropanol and the like, or any suitable mixtures thereof. The process is typically carried out at a temperature in the range of about 0° C. up to about 40° C.

Compound Z is typically contacted with a resolving enzyme in the presence of an acylating agent. Resolving enzymes contemplated for use include lipase, esterase, peptidase, acylase or protease enzymes of mammalian, plant, fungal or bacterial origin, such as for example, Lipase Amano lipase PS-D (immobilized lipase from *Pseudomonas cepacia*), Amano Lipase PS-C (immobilized lipase from *Pseudomonas cepacia*), Roche Chirazyme L-3 (lipase, lyophilizate, from *Candida Rugosa*), Roche Chirazyme L-3 (purified lipase, lyophilizate, from *Candida Rugosa*), Roche Chirazyme L-3 (purified lipase, carrier-fixed, carrier 2, lyophilizate, from *Candida rugosa*), Roche Chirazyme L-5 (lipase, solution, from *Candida antartica*, type A), Roche Chirazyme L-5 (lipase, lyophilizate, from *Candida antartica*, type A), Roche Chirazyme L-5 (lipase, carrier-fixed, carrier 1, lyophilizate, from *Candida antartica*, type A), Roche Chirazyme L-10 (lipase, lyophilizate, from *Alcaligenes* sp.), Altus Biologics 8 (lipase from *Mucor miehei*) and Altus Biologics 27 (lipase from *Alcaligenes* sp.) and the like. Acylating agents contemplated for use include, for example, ethyl acetate, vinyl acetate, vinyl propionate, vinyl butyrate, isopropenyl acetate, 1-ethoxyvinyl acetate, trichloroethyl butyrate, trifluoroethyl butyrate, trifluoroethyl laureate, S-ethyl thiooctanoate, biacetyl monooxime acetate, acetic anhydride, succinic anhydride, amino acid, diketene and the like.

Compound Z can also be contacted with an electrophilic reagent Electrophilic reagents contemplated for use include, for example, diazomethane, trimethylsilyldiazomethane, alkyl halides, such as for example methyl iodide, benzyl bromide and the like, alkyl triflates, such as for example methyl triflate and the like, alkyl sulfonates, such as for example ethyl toluenesulfonate, butyl methanesulfonate and the like, acyl halides, such as for example acetyl chloride, benzoyl bromide and the like, acid anhydrides, such as for example acetic anhydride, succininc anhydride, maleic anhydride and the like, isocyanates, such as for example methyl isocyanate, phenylisocyanate and the like, chloroformates, such as for example methyl chloroformate, ethyl chloroformate, benzyl chloroformate and the like, sulfonyl halides, such as for example methanesulfonyl chloride, p-tolunesulfonyl chloride and the like, silyl halides, such as for example trimethylsilyl chloride, tertbutyidimethyl silyll chloride and the like, phosphoryl halide such as for example dimethyl chlorophosphate and the like, alpha-beta-unsaturated carbonyl such as for example acrolein, methyl vinyl ketone, cinnamaldehyde and the like.

Compound Z can also be contacted with an alcohol in the presence of an azodicarboxylate and a phosphine base, or any suitable mixtures thereof. Azodicarboxylates contemplated for use include, for example, diethyl azodicarboxylate, dicyclohexyl azodicarboxylate, diisopropyl azodicarboxylate and the like. Phosphine bases contemplated for use include, for example, triethylphosphine, tricyclopentylphosphine, tricyclohexylphosphine, triphenylphosphine, tri-o-tolylphosphine, and the like.

Compound Z can also be contacted with a carboxylic acid or an amino acid in the presence of a coupling agent and a base, or any suitable mixtures thereof. Coupling agents contemplated for use include, for example, dicyclohexylcarbodiimide (DCC), diisopropyl carbodiimide (DIC), 1-ethyl-3-(3-dimethylaminopropyl)-carbodiimide (EDCl), N-hydroxybenzotriazole (HOBT), N-hydroxysuccinimide (HOSu), 4-nitrophenol, pentafluorophenol, 2-(1H-benzotriazole-1-yl)-1,1,3,3-tetramethyluronium tetrafluoroborate (TBTU), O-benzotriazole-N,N,N'N'-tetramethyluronium hexafluorophosphate (HBTU), benzotriazole-1-yl-oxy-trisdimethylaminoyphosphonium hexafluorophosphate (BOP), benzotriazole-1-yl-oxy-tris-pyrrolidinophosphonium hexafluorophosphate, bromo-trispyrrolidino-phosphonium hexafluorophosphate, 2-(5-norbornene-2,3-dicarboximido)-1,3,3-tetramethyluronium tetrafluoroborate (TNTU), O-(N-succinimidyl)-1,1,3,3-tetramethyluronium tetrafluoroborate (TSTU), tetramethylfluoroformamidinium hexafluorophosphate and the like. Bases contemplated for use include, for example, triethylamine, diisopropylethylamine, pyridine, 4-dimethylaminopyridine, and the like.

In another embodiment, the invention provides a process for separating compound of formula P, such as for example, chromatography, crystallization, re-crystallization, distillation and the like.

General Methods of Preparation

Used herein, the following abbreviations have the following meanings: Me refers to methyl ($CH_3$—), Et refers to ethyl ($CH_3CH_2$—), i-Pr refers to isopropyl (($CH_3)_2CH_2$—), t-Bu or tert-butyl refers to tertiary butyl (($CH_3)_3CH$—), Ph refers to phenyl, Bn refers to benzyl ($PhCH_2$—), Bz refers to benzoyl (PhCO—), MOM refers to methoxymethyl, Ac refers to acetyl, TMS refers to trimethylsilyl, TBS refers to ter-butyldimethylsilyl, Ms refers to methanesulfonyl ($CH_3SO_2$—), Ts refers to p-toluenesulfonyl (p-$CH_3PhSO_2$—), Tf refers to trifluoromethanesulfonyl ($CF_3SO_2$—), TfO refers to trifluoromethanesulfonate ($CF_3SO_3$—), DMF refers to N,N-dimethylformamide, DCM refers to dichloromethane ($CH_2Cl_2$), THF refers to tetrahydrofuran, EtOAc refers to ethyl acetate, $Et_2O$ refers to diethyl ether, MeCN refers to acetonitrile ($CH_3CN$), NMP refers to 1-N-methyl-2-pyrrolidinone, DMA refers to N,N-dimethylacetamide, DMSO refers to dimethylsulfoxide, DCC refers to 1,3-dicyclohexyldicarbodiimide, EDCl refers to 1-(3-dimethylaminopropyl)-3-ethylcarbodiimide, Boc refers to tert-butylcarbonyl, Fmoc refers to 9-fluorenylmethoxycarbonyl, TBAF refers to tetrabutylammonium fluoride, TBAI refers to tetrabutylammonium iodide, TMEDA refers to N,N,N,N-tetramethylethylene diamine, Dess-Martin periodinane or Dess Martin reagent refers to 1,1,1-triacetoxy-1,1-dihydro-1,2-benziodoxol-3(1H)-one, DMAP refers to 4-N,N-dimethylaminopyridine, (i-Pr)$_2$NEt or DIEA or Hunig's base refers to N,N-diethylisopropylamine, DBU refers to 1,8-Diazabicyclo[5.4.0]undec-7-ene, (DHQ)$_2$AQN refers to dihydroquinine anthraquinone-1,4-diyl diether, (DHQ)$_2$PHAL refers to dihydroquinine phthalazine-1,4-diyl diether, (DHQ)$_2$PYR refers to dihydroquinine 2,5-diphenyl-4,6-pyrimidinediyl diether, (DHQD)$_2$AQN refers to dihydroquinidine anthraquinone-1,4-diyl diether, (DHQD)$_2$PHAL refers to dihydroquinidine phthalazine-1,4-diyl diether, (DHQD)$_2$PYR refers to dihydroquinidine 2,5-diphenyl-4,6-pyrimidinediyl diether, LDA refers to lithium diisopropylamide, LiTMP refers to lithium 2,2,6,6-tetramethylpiperdinamide, n-BuLi refers to n-butyllithium, t-BuLi refers to tert-butyl lithium, IBA refers to 1-hydroxy-1,2-benziodoxol-3(1H)-one 1-oxide, OsO$_4$ refers to osmium tetroxide, m-CPBA refers to meta-chloroperbenzoic acid, DMD refers to dimethyl dioxirane, PDC refers to pyridinium dichromate, NMO refers to N-methyl morpholine-N-oxide, NaHMDS refers to sodium hexamethyldisilazide, LiHMDS refers to lithium hexamethyldisilazide, HMPA refers to hexamethylphosphoramide, TMSCl refers to trimethylsilyl chloride, TMSCN refers to trimethylsilyl cyanide, TBSCl refers to tert-butyidimethylsilyl chloride, TFA refers to trifluoroacetic acid, TFM refers to trifluoroacetic anhydride, AcOH refers to acetic acid, Ac$_2$O refers to acetic anhydride, AcCl refers to acetyl chloride, TsOH refers to p-toluenesulfonic acid, TsCl refer to p-toluenesulfonyl chloride, MBHA refers to 4-methylbenzhydrylamine, BHA refers to benzhydrylamine, ZnCl$_2$ refers to zinc (II) dichloride, BF$_3$ refers to boron trifluoride, Y(OTf)$_2$ refers to yttrium (III) trifluoromethanesulfonate, Cu(BF$_4$)$_2$ refers to copper (II) tetrafluoroborate, LAH refers to lithium aluminum hydride (LiAlH$_4$), NaHCO$_3$ refers to sodium bicarbonate, K$_2$CO$_3$ refers to potassium carbonate, NaOH refers to sodium hydroxide, KOH refers to potassium hydroxide, LiOH refers to lithium hydroxide, HCl refers to hydrochloric acid, H$_2$SO$_4$ refers to sulfuric acid, MgSO$_4$ refers to magnesium sulfate, and Na$_2$SO$_4$ refers to sodium sulfate. 1H NMR refers to proton nuclear magnetic resonance, 13C NMR refers to carbon 13 nuclear magnetic resonance, NOE refers to nuclear overhauser effect, NOESY refers to nuclear overhauser and exchange spectroscopy, COSY refers to homonuclear correlation spectroscopy, HMQC refers to proton detected heteronuclear multiplet-quantum coherence, HMBC refers to heteronuclear multiple-bond connectivity, s refers to singlet, br s refers to broad singlet, d refers to doublet, br d refers to broad doublet, t refers to triplet, q refers to quartet, dd refers to double doublet, m refers to multiplet, ppm refers to parts per million, IR refers to infrared spectrometry, MS refers to mass spectrometry, HRMS refers to high resolution mass spectrometry, EI refers to electron impact, FAB refers to fast atom bombardment, CI refers to chemical ionization, HPLC refers to high pressure liquid chromatography, TLC refer to thin layer chromatography, R$_f$ refers to, R$_t$ refers to retention time, GC refers to gas chromatography, min is minutes, h is hours, rt or RT is room temperature, g is grams, mg is milligrams, L is liters, mL is milliliters, mol is moles and mmol is millimoles.

For all of the following examples, standard work-up and purification methods can be utilized and will be obvious to those skilled in the art. Synthetic methodologies that make up the invention are shown in Schemes 1-10. These Schemes are intended to describe the applicable chemistry through the use of specific examples and are not indicative of the scope of the invention.

EXAMPLES

The following non-limiting examples illustrate the inventors' preferred methods for carrying out the process of the invention.

Example 1

Preparation of Allyloxy-Acetic Acid Ethyl Ester

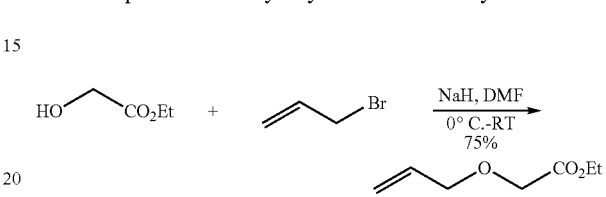

A round-bottom flask was charged with NaH (1.76 g, 44 mmol, 60% dispersion in mineral oil) and flushed with argon. Hexane (10 ml×2) was added and decanted. DMF (10 ml) was added into the flask and the resulting solution was cooled to 0° C. Ethyl glycolate (4.16 g, 40.0 mmol) was added over 10 min. The solution was allowed to gradually warm to 25° C. and was maintained at that temperature for 2H. The solution was cooled to 0° C. and allyl bromide (5.32 g, 44.0 mmol) was added over 10 min. The solution was allowed to gradually warm to 25° C. and stirred at that temperature for 2 h. Aqueous solution NH$_4$Cl (10 ml) was added to the reaction and the mixture was diluted with EtOAc (60 ml). The organic layer was separated and washed with H$_2$O (20 ml×2), dried over Na$_2$SO$_4$ and concentrated in vacuo. The crude product was purified by distillation under reduced pressure Yield=4.29 g, 75%; colorless liquid; bp=38-39° C., 2 mmHg;

IR (neat): 1985, 1756, 1724, 1203, 1130 cm$^{-1}$;

$^1$H NMR (CDCl$_3$, 400 MHz) δ 5.90-5.70 (m, 1H), 5.25-5.00 (m, 2H), 4.10-4.20 (m, 2H), 3.92-4.05 (m, 4H), 1.21 (t, J=7 Hz, 3H);

$^{13}$C NMR (CDCl$_3$, 100 MHz) δ 170.09 (C), 133.62 (CH), 117.78 (CH$_2$), 72.10 (CH$_2$), 66.99 (CH$_2$), 60.53 (CH$_2$), 13.94 (CH$_3$);

MS (m/z, relative intensity): 144 (M$^+$, 14), 115 (22), 103 (100), 83 (85); HRMS: calculated for C$_7$H$_{12}$O$_3$ (M$^+$): 144.0786; found 144.0783.

Example 2

Preparation of 2-allyloxy-3-hydroxypent-4-enoic acid ethyl ester

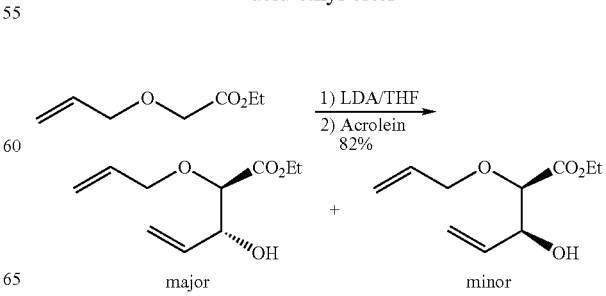

Under an atmosphere of argon, n-BuLi (3 mmol, 1.2 ml, 2.5 M in hexane) was added dropwise to a solution of diisopropylamine (281 mg, 2.78 mmol) in dry THF (20 ml) at −78° C. After stirring for 20-30 min, a solution of allyloxy-acetic acid ethyl ester (200 mg, 1.38 mmol) in THF (4 ml) was added and the mixture was stirred at −78° C. for 10 min. Acrolein (79 mg, 1.38 mmol) was added into the reaction mixture and stirring was maintained until all starting materials were consumed. The reaction was quenched by addition of EtOH (2 ml) and warmed to room temperature. The solution was diluted with EtOAc (60 ml), washed with $H_2O$ (20 ml×2), dried over $Na_2SO_4$ and concentrated in vacuo. The crude product was purified by flash chromatography with 20% EtOAc-hexane.

Yield=961 mg, 82%; colorless liquid; $R_f$=0.25 in 20% EtOAc-hexane)

IR (neat): 3300-3600, 2977, 1742, 1364, 1231, 1134, 1028, 927 $cm^{-1}$;

$^1H$ NMR ($CDCl_3$, 400 MHz) δ 6.0-5.8 (m, 2H), 5.3-5.1 (m, 4H), 4.44.2 (m, 1H), 4.2-4.0 (m, 3H), 3.9-3.8 (m, 2H), 2.73 (br s, 1H), 1.2 (t, J=7 Hz, 3H);

$^{13}C$ NMR ($CDCl_3$, 100 MHz, 2:1 isomeric forms, * denotes minor isomer) δ170.35* (C), 170.08 (C), 135.77* (CH), 135.42 (CH), 133.56 (CH), 133.47* (CH), 118.23* ($CH_2$), 118.12 ($CH_2$), 117.14* ($CH_2$), 116.96 ($CH_2$), 80.85 (one CH and one CH*), 73.32* (CH), 72.99 (CH), 71.88* ($CH_2$), 71.87 ($CH_2$), 60.99* ($CH_2$), 60.91 ($CH_2$), 14.08 ($CH_3$), 14.05* ($CH_3$);

MS (m/z, relative intensity): 200 ($M^+$, 7), 182 (27), 153 (41), 136 (51), 115 (37), 95 (100);

HRMS calculated for $C_{10}H_{16}O_4$ ($M^+$): 200.1048; found 200.1044.

Example 3

Preparation of 3-hydroxy-3,6-dihydro-2H-pyran-2-carboxylic acid ethyl ester

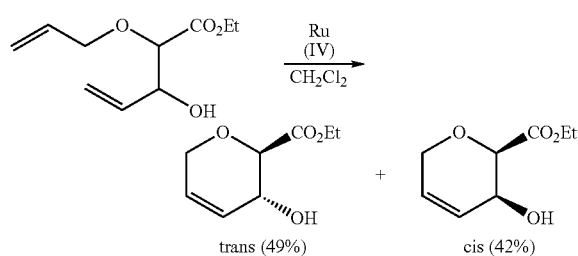

To a solution of 2-allyloxy-3-hydroxypent-4-enoic acid ethyl ester (200 mg, 1.0 mmol) in $CH_2Cl_2$ (10 ml) was added bis-(tricyclohexylphosphine)benzylidine ruthenium (IV) chloride (20 mg, 0.024 mmol) and the resulting mixture was stirred at ambient temperature for 4H. Bis-(tricyclohexylphosphine)benzylidine ruthenium (IV) chloride (20 mg, 0.024 mmol) was added again and the resulting mixture was stirred at ambient temperature for an additional 10 h. The solution was concentrated in vacuo. The crude product was purified by flash chromatography with 25 to 30% EtOAc-hexane trans 3-hydroxy-3,6-dihydro-2H-pyran-2-carboxylic acid ethyl ester Yield=84 mg (49%); $R_f$=0.29 in 40% EtOAc-hexane IR (neat): 3200-3600, 2976, 1747, 1185, 1111, 1024 $cm^{-1}$;

$^1H$ NMR ($CDC_3$, 400 MHz) δ 5.78 (br s, 2H), 4.10-4.35 (m, 5H), 3.93 (d, J=7 Hz, 1H), 3.07 (br s, 1H), 1.24 (t, J=7 Hz, 3H); $^{13}C$ NMR ($CDCl_3$, 100 MHz) δ 170.58 (C), 127.49 (CH), 126.54 (CH), 77.00 (CH), 64.98 ($CH_2$), 64.32 (CH), 61.53 ($CH_2$), 14.00 ($CH_3$); MS (m/z, relative intensity): 172 ($M^+$, 2), 141 (6), 112 (16), 81 (100); HRMS calculated for $C_8H_{12}O_4$ ($M^+$): 172.0735; found 172.0730.

cis 3-hydroxy-3,6-dihydro-2H-pyran-2-carboxylic acid ethyl ester

Yield=69 mg (42%); $R_f$=0.06 in 40% EtOAc-hexane

IR (neat): 3200-3600, 2975, 2926, 2841, 1746, 1642, 1182, 1097 $cm^{-1}$; $^1H$ NMR ($CDCl_3$, 500 MHz) δ 6.00-6.15 (m, 1H), 5.90-5.96 (m, 1H), 4.10-4.40 (m, 7H), 1.28 (t, J=7 Hz, 3H); $^{13}C$ NMR ($CDCl_3$, 100 MHz) δ 169.07 (C), 130.15 (CH), 125.96 (CH), 77.50 (CH), 66.09 ($CH_2$), 63.48 (CH), 61.36 ($CH_2$), 14.21 ($CH_3$); MS (m/z, relative intensity): 172 ($M^+$, 2), 141 (6), 112 (16), 81 (100); exact mass calculated for $C_8H_{12}O_4$ ($M^+$): 172.0735; found 172.0730.

Example 4

Resolution of racemic trans-3-hydroxy-3,6-dihydro-2H-pyran-2-carboxylic acid ethyl ester using lipase from *Mucor miehei*

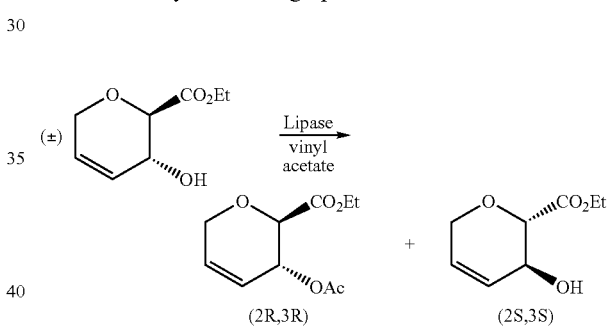

Vinyl acetate (200 μl) was added to a suspension of racemic trans-3-hydroxy-3,6-dihydro-2H-pyran-2-carboxylic acid ethyl ester (41 mg) and lipase from *Mucor miehei* (50 mg) in 5 ml of toluene. The mixture was agitated for 18H at ambient temperature. The mixture was filtered and the filtrate was concentrated in vacuo. The crude product was purified by flash chromatography with 20% EtOAc-hexane.

trans-(2R,3R)-3-Acetoxy-3,6-dihydro-2H-pyran-2-carboxylic acid ethyl ester

Yield=22 mg (43%); optical purity: >99.9% ee; Colorless liquid; $R_f$=0.64 in 40% EtOAc-hexane;

$^1H$ NMR ($CDCl_3$ 400 MHz) δ 5.96 (dd, J=10.4, 1.0 Hz, 1H), 5.80-5.85 (m, 1H), 5.44 (br s, 1H), 4.40 (dd, J=2.4, 17.3 Hz, 1H), 4.10-4.25 (m, 4H), 2.03 (s, 3H), 1.23 (t, J=7.1 Hz, 3H); $^{13}C$ NMR ($CDCl_3$, 100 MHz) δ 170.25 (C), 168.87 (C), 130.63 (CH), 122.00 (CH), 74.49 (CH), 65.33 (CH), 63.63 ($CH_2$), 61.50 ($CH_2$), 20.96 ($CH_3$), 14.02 ($CH_3$);

cis-(2S,3S)-3-hydroxy-3,6-dihydro-2H-pyran-2-carboxylic acid ethyl ester

Yield=17 mg (42%); optical purity: 89% ee; Colorless liquid, $R_f$=0.39 in 40% EtOAc-hexane. IR (neat): 3200-3600, 2976, 1747, 1185, 1111, 1024 $cm^{-1}$; $^1H$ NMR ($CDCl_3$, 400 MHz) δ 5.78 (br s, 2H), 4.10-4.35 (m, 5H), 3.93 (d, J=7 Hz, 1H), 3.07 (br s, 1H), 1.24 (t, J=7 Hz, 3H); $^{13}$C NMR (CDCl$_3$, 100 MHz) δ 170.58 (C), 127.49 (CH), 126.54 (CH), 77.00 (CH), 64.98 (CH$_2$), 64.32 (CH), 61.53 (CH$_2$), 14.00 (CH$_3$);

HRMS calculated for C$_8$H$_{12}$O$_4$ (M$^+$): 172.0735; found 172.0733.

Example 5

Resolution of racemic trans-3-hydroxy-3,6-dihydro-2H-pyran-2-carboxylic acid ethyl ester using lipase from *Alcaligenes* sp.

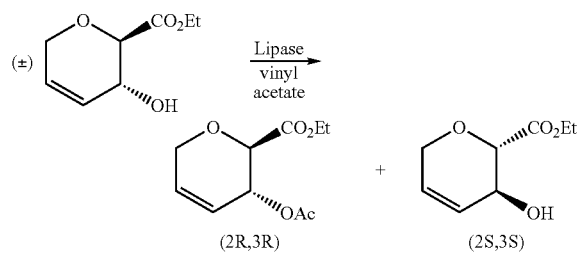

Vinyl acetate (200 μl) was added to a suspension of racemic trans-3-hydroxy-3,6-dihydro-2H-pyran-2-carboxylic acid ethyl ester (53 mg) and immobilized lipase from *Alcaligenes* sp. (50 mg) in 5 ml of toluene. The mixture was agitated for 14H at ambient temperature. The mixture was filtered and the filtrate was concentrated in vacuo. The crude product was purified by flash chromatography with 20% EtOAc-hexane.

trans-(2R,3R)-3-Acetoxy-3,6-dihydro-2H-pyran-2-carboxylic acid ethyl ester
  Yield=32 mg (49%); optical purity: >95% ee;

trans-2S,3S)-3-hydroxy-3,6-dihydro-2H-pyran-2-carboxylic acid ethyl ester
  Yield=25 mg (47%); optical purity: >99.9% ee;

Example 6

Resolution of racemic trans-3-hydroxy-3,6-dihydro-2H-pyran-2-carboxylic acid ethyl ester using lipase from *Candida antartica*, type A

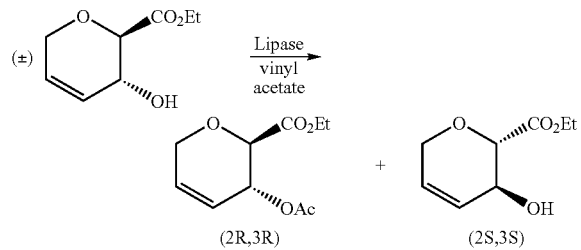

Vinyl acetate (10 μl) was added to a suspension of racemic trans-3-hydroxy-3,6-dihydro-2H-pyran-2-carboxylic acid ethyl ester (5 mg) and lipase from *Candida antartica*, type A (11 mg) in 1 ml of toluene. The mixture was agitated for 24H at ambient temperature. The mixture was filtered and the filtrate was concentrated in vacuo. The crude product was purified by flash chromatography with 20% EtOAc-hexane.

trans-(2R,3R)-3-Acetoxy-3,6-dihydro-2H-pyran-2-carboxylic acid ethyl ester
  optical purity: >99.5% ee;

trans-(2S,3S)-3-hydroxy-3,6-dihydro-2H-pyran-2-carboxylic acid ethyl ester
  optical purity: 88% ee;

Example 7

Resolution of racemic trans-3-hydroxy-3,6-dihydro-2H-pyran-2-carboxylic acid ethyl ester using lipase from *Alcaligenes* sp.

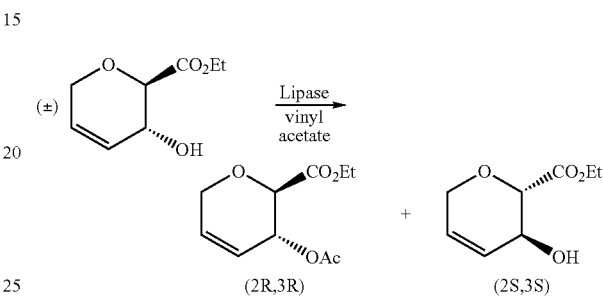

Vinyl acetate (10 μl) was added to a suspension of racemic trans-3-hydroxy-3,6-dihydro-2H-pyran-2-carboxylic acid ethyl ester (5 mg) and lipase from *Alcaligenes* sp. (11 mg) in 1 ml of toluene. The mixture was agitated for 24H at ambient temperature. The mixture was filtered and the filtrate was concentrated in vacuo. The crude product was purified by flash chromatography with 20% EtOAc-hexane.

trans-(2R,3R)-3-Acetoxy-3,6-dihydro-2H-pyran-2-carboxylic acid ethyl ester
  optical purity: >99.5% ee;

trans-(2S,3S)-3-hydroxy-3,6-dihydro-2H-pyran-2-carboxylic acid ethyl ester
  optical purity: 98.8% ee;

Example 8

Resolution of racemic trans-3-hydroxy-3,6-dihydro-2H-pyran-2-carboxylic acid ethyl ester using lipase from *Pseudomonas cepacia*

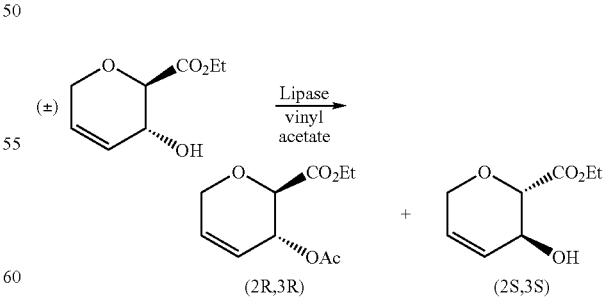

Vinyl acetate (10 μl) was added to a suspension of racemic trans-3-hydroxy-3,6-dihydro-2H-pyran-2-carboxylic acid ethyl ester (6 mg) and lipase from *Pseudomonas cepacia* (12 mg) in 1 ml of toluene. The mixture was agitated for 4H at ambient temperature. The mixture was filtered and the filtrate was concentrated in vacuo. The crude product was purified by flash chromatography with 20% EtOAc-hexane.

trans-(2R,3R-3-Acetoxy-3,6-dihydro-2H-pyran-2-carboxylic acid ethyl ester
  optical purity: >99.5% ee;

trans-(2S,3S)-3-hydroxy-3,6-dihydro-2H-pyran-2-carboxylic acid ethyl ester
  optical purity: 99.4% ee;

Example 9

Resolution of racemic cis-3-hydroxy-3,6-dlhydro-2H-pyran-2-carboxylic acid ethyl ester using lipase from *Mucor miehei*

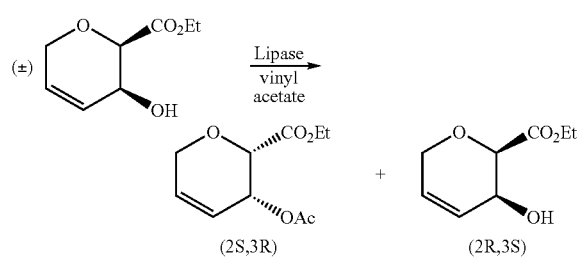

Vinyl acetate (200 μl) was added to a suspension of racemic cis-3-hydroxy-3,6-dihydro-2H-pyran-2-carboxylic acid ethyl ester (42 mg) and lipase from *Mucor miehei* (53 mg) in 5 ml of toluene. The mixture was agitated for 18H at ambient temperature. The mixture was filtered and the filtrate was concentrated in vacuo. The crude product was purified by flash chromatography with 20% EtOAc-hexane.

cis-(2S,3R)-3-Acetoxy-3,6-dihydro-2H-pyran-2-carboxylic acid ethyl ester
  Yield=24 mg (44%); optical purity: >99.9% ee; Colorless liquid; $R_f$=0.34 in 70% EtOAc-hexane;
  IR (neat): 2980, 2932, 2831, 1738, 1375, 1234, 1105, 1023 cm$^{-1}$;
  $^1$H NMR (CDCl$_3$, 400 MHz) δ 5.95-6.10 (m, 2H), 5.30-5.35 (m, 1H), 4.41 (dd, J=3.4, 1.6 Hz, 1H), 4.15-4.40 (m, 4H), 2.00 (s, 3H), 1.25 (t, J=7.2 Hz, 3H);
  $^{13}$C NMR (CDCl$_3$, 100 MHz) δ 170.12 (C), 167.91 (C), 132.06 (CH), 121.72 (CH), 75.12 (CH), 65.77 (CH$_2$), 64.87 (CH), 61.33 (CH$_2$), 20.67 (CH$_3$), 14.14 (CH$_3$);
  MS (m/z, relative intensity): 215 (M$^+$+1, 6), 213 (M$^+$-1, 18), 153 (100), 149 (30);
  HRMS calculated for C$_{10}$H$_{14}$O$_5$ (M$^+$): 214.0841; found 214.0839.

cis-(2R,3S)-3-hydroxy-3,6-dihydro-2H-pyran-2-carboxylic acid ethyl ester
  Yield=20 mg (48%); optical purity: 89% ee; Colorless liquid; $R_f$=0.61 in 70% EtOAc-hexane;
  IR (neat): 3200-3600, 2975, 2926, 2841, 1746, 1642, 1182, 1097 cm$^{-1}$; $^1$H NMR (CDCl$_3$, 500 MHz) δ 6.00-6.15 (m, 1H), 5.90-5.96 (m, 1H), 4.10-4.40 (m, 7H), 1.28 (t, J=7 Hz, 3H); $^{13}$C NMR (CDCl$_3$, 100 MHz) δ 169.07 (C), 130.15 (CH), 125.96 (CH), 77.50 (CH), 66.09 (CH$_2$), 63.48 (CH), 61.36 (CH$_2$), 14.21 (CH$_3$);
  MS (m/z, relative intensity): 172 (M$^+$, 2), 141 (6), 112 (16), 81 (100); exact mass calculated for C$_8$H$_{12}$O$_4$ (M$^+$): 172.0735; found 172.0730.

Example 10

Resolution of racemic cis-3-hydroxy-3,6-dihydro-2H-pyran-2-carboxylic acid ethyl ester using lipase from *Alcaligenes* sp.

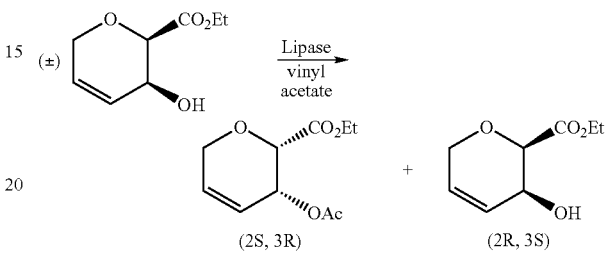

Vinyl acetate (200 μl) was added to a suspension of racemic cis-3-hydroxy-3,6-dihydro-2H-pyran-2-carboxylic acid ethyl ester (57 mg) and lipase from *Alcaligenes* sp. (51 mg) in 5 ml of toluene. The mixture was agitated for 14H at ambient temperature. The mixture was filtered and the filtrate was concentrated in vacuo. The crude product was purified by flash chromatography with 20% EtOAc-hexane.

cis-(2S,3R)-3-Acetoxy-3,6-dihydro-2H-pyran-2-carboxylic acid ethyl ester
  Yield=32 mg (49%); optical purity: 98.8% ee;

cis-(2R,3S)-3-hydroxy-3,6-dihydro-2H-pyran-2-carboxylic acid ethyl ester
  Yield=27 mg (48%); optical purity: >99.9% ee;

Example 11

Resolution of racemic cis-3-hydroxy-3,6-dihydro-2H-pyran-2-carboxylic acid ethyl ester using lipase from *Candida Rugosa*

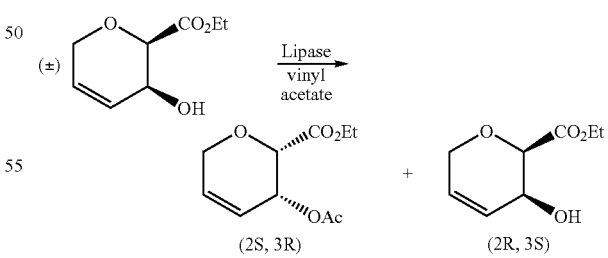

Vinyl acetate (10 μl) was added to a suspension of racemic cis-3-hydroxy-3,6-dihydro-2H-pyran-2-carboxylic acid ethyl ester (4 mg) and lipase from *Candida Rugosa* (20 mg) in 1 ml of toluene. The mixture was agitated for 34H at ambient temperature. The mixture was filtered and the filtrate was concentrated in vacuo. The crude product was purified by flash chromatography with 20% EtOAc-hexane.

cis-(2S,3R)-3-Acetoxy-3,6-dihydro-2H-pyran-2-carboxylic acid ethyl ester
  optical purity: >99.5% ee;

cis-(2R,3S)-3-hydroxy-3,6-dihydro-2H-pyran-2-carboxylic acid ethyl ester
  optical purity: >99.5% ee;

Example 12

Resolution of racemic cis-3-hydroxy-3,6-dihydro-2H-pyran-2-carboxylic acid ethyl ester using lipase from *Candida antartica*, type A

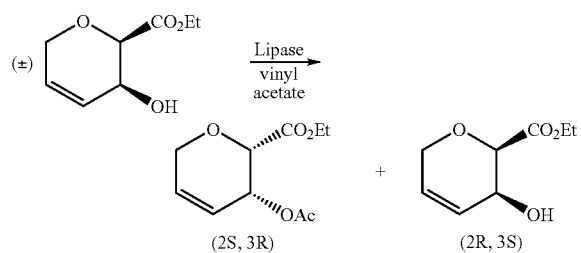

Vinyl acetate (10 μl) was added to a suspension of racemic cis-3-hydroxy-3,6-dihydro-2H-pyran-2-carboxylic acid ethyl ester (4 mg) and lipase from *Candida antartica*, type A (11 mg) in 1 ml of toluene. The mixture was agitated for 20 h at ambient temperature. The mixture was filtered and the filtrate was concentrated in vacuo. The crude product was purified by flash chromatography with 20% EtOAc-hexane.

cis-(2S,3R)-3-Acetoxy-3,6-dihydro-2H-pyran-2-carboxylic acid ethyl ester
  optical purity: >99.5% ee;

cis-(2R,3S)-3-hydroxy-3,6-dihydro-2H-pyran-2-carboxylic acid ethyl ester
  optical purity: >99.5% ee;

Example 13

Resolution of racemic cis-3-hydroxy-3,6-dihydro-2H-pyran-2-carboxylic acid ethyl ester using lipase from *Pseudomonas cepacia*

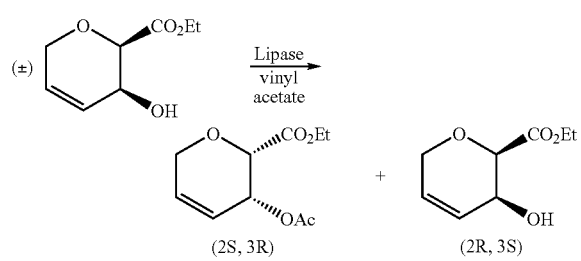

Vinyl acetate (10 μl) was added to a suspension of racemic cis-3-hydroxy-3,6-dihydro-2H-pyran-2-carboxylic acid ethyl ester (4 mg) and lipase from *Pseudomonas cepacia* (9 mg) in 1 ml of toluene. The mixture was agitated for 4H at ambient temperature. The mixture was filtered and the filtrate was concentrated in vacuo. The crude product was purified by flash chromatography with 20% EtOAc-hexane.

cis-(2S,3R)-3-Acetoxy-3,6-dihydro-2H-pyran-2-carboxylic acid ethyl ester
  optical purity: >99.5% ee;

cis-(2R,3S-3-hydroxy-3,6-dihydro-2H-pyran-2-carboxylic acid ethyl ester
  optical purity: >99.5% ee;

Example 14

Resolution of racemic cis-3-hydroxy-3,6-dihydro-2H-pyran-2-carboxylic acid ethyl ester using lipase from *Pseudomonas fluorescens*

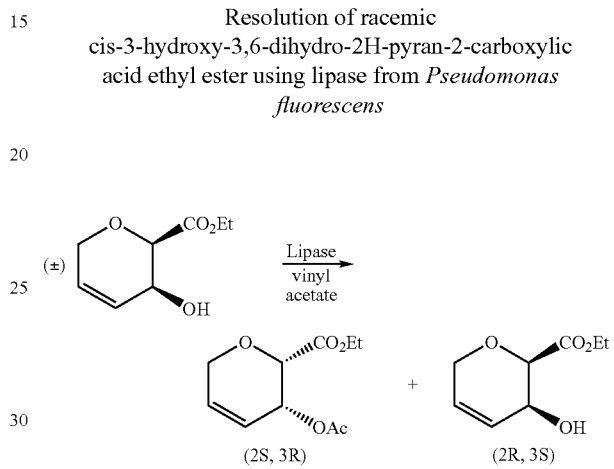

Vinyl acetate (10 μl) was added to a suspension of racemic cis-3-hydroxy-3,6-dihydro-2H-pyran-2-carboxylic acid ethyl ester (4 mg) and lipase from *Pseudomonas fluorescens* (10 mg) in 1 ml of toluene. The mixture was agitated for 38H at ambient temperature. The mixture was filtered and the filtrate was concentrated in vacuo. The crude product was purified by flash chromatography with 20% EtOAc-hexane.

cis-(2S,3R)-3-Acetoxy-3,6-dihydro-2H-pyran-2-carboxylic acid ethyl ester
  optical purity: >99.5% ee;

cis-(2R,3S)-3-hydroxy-3,6-dihydro-2H-pyran-2-carboxylic acid ethyl ester
  optical purity: >99.5% ee;

Example 15

Preparation of (2R,3R,4S,5S) and (2R,3R,4R,5R)-3-acetoxy-4,5-dihydroxy-tetrahydropyran-2-carboxylic acid ethyl esters

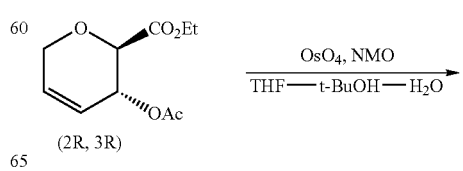

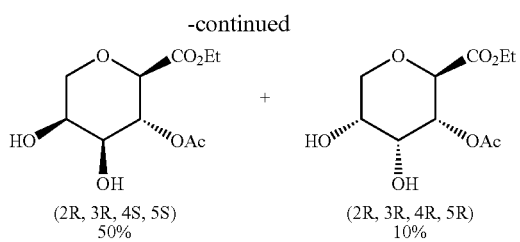

(2R, 3R, 4S, 5S)
50%

(2R, 3R, 4R, 5R)
10%

To (2R,3R)-3-acetoxy-3,6-dihydro-2H-pyran-2-carboxylic acid ethyl ester (300 mg, 1.40 mmol) in 27 ml of THF-tert-BuOH—H$_2$O (6:17.7:3 ml) was added NMO (612 mg, 4.47 mmol) and the solution was stirred for 5 min at ambient temperature. OsO$_4$ (0.3 ml, 2.5 wt % in tert-BuOH) was added and the mixture was stirred at ambient temperature for 72H. Sodium hydrosulphite (1.2 g), Florisil (12.0 g) and H$_2$O (10 ml) were added sequentially and the mixture was stirred for 30 min, washed with acetone (500 ml), filtered through filter paper and extracted with EtOAc (2×300 ml) in vacuo. The crude product was purified by flash chromatography with 90% EtOAc-hexane to give (2R,3R,4S,5S)- and (2R,3R,4R,5R)-3-acetoxy-4,5-dihydroxy-tetrahydropyran-2-carboxylic acid ethyl esters in 60% yield.

(2R,3R,4R,5R)-3-acetoxy-4,5-dihydroxy-tetrahydropyran-2-carboxylic acid ethyl ester Colorless oil; Yield: 10%; R$_f$=0.53 in EtOAc IR (neat): 3600-3200, 2952, 2925, 2868, 1738, 1458, 1375, 1242, 1039 cm$^{-1}$; $^1$H NMR (CDCl$_3$, 400 MHz) δ 4.83-4.90 (m, 1H), 4.22-4.32 (m, 3H), 4.15 (d, J=9.0 Hz, 1H), 3.80-3.90 (m, 2H), 3.74 (dd, J=10.1, 10.8 Hz, 1H), 2.09 (s, 3H), 1.31 (t, J=7.2 Hz, 3H); $^{13}$C NMR (CDCl$_3$, 100 MHz) δ 171.29 (C), 170.28 (C), 74.48 (CH), 69.44 (CH), 68.85 (CH), 67.39 (CH), 63.23 (CH$_2$), 62.32 (CH$_2$), 21.29 (CH$_3$), 14.48 (CH$_3$); EIMS (m/z, relative intensity): 248 (M$^+$, 2), 206 (4), 145 (30), 97 (20), 57 (38), 43 (100).

(2R,3R,4S,5S)-3-acetoxy-4,5-dihydroxy-tetrahydropyran-2-carboxylic acid ethyl ester Colorless liquid, Yield: 50%; R$_f$=0.5 in EtOAc IR (neat): 3640-3080, 2983, 1739, 1375, 1242, 1107, 1050 cm$^{-1}$; $^1$H NMR (CDCl$_3$, 400 MHz) δ 5.20 (dd, J=8.4, 8.4 Hz, 1H), 4.08-4.20 (m, 3H), 3.98 (d, J=1.7 Hz, 1H), 3.84 (d, J=8.3 Hz, 1H), 3.75 (d, J=8.4 Hz, 1H), 3.58 (dd, J=10.6, 1.7 Hz, 1H), 3.09 (s, 3H), 2.07 (s, 3H), 1.24 (t, J=7.2 Hz, 3H); $^{13}$C NMR (CDCl$_3$, 400 MHz) δ 170.83 (C), 168.48 (C), 75.95 (CH), 71.33 (CH), 70.82 (CH), 68.59 (CH$_2$), 67.84 (CH), 61.85 (CH$_2$), 20.85 (CH$_2$), 13.94 (CH$_3$); EIMS (m/z, relative intensity): 248 (M$^+$, 1), 230 (3), 205 (18), 157 (26), 115 (40), 97 (68), 43 (100); exact mass calculated for C$_{10}$H$_{16}$O$_7$ (M$^+$): 248.0896; found 248.0887

X-ray crystal structure of (2R,3R,4S,5S)-3-acetoxy-4,5-dihydroxy-tetrahydropyran-2-carboxylic acid ethyl ester

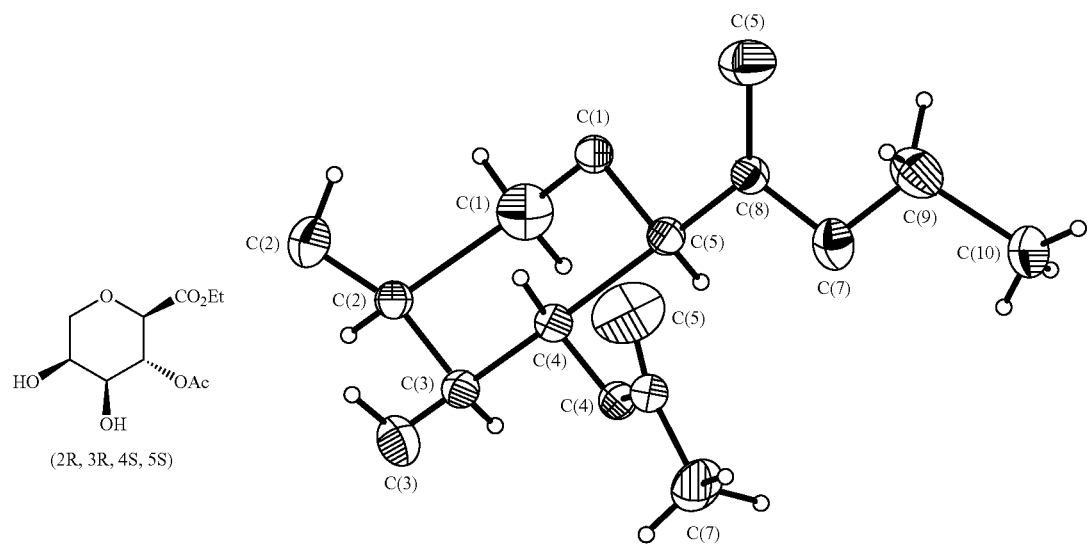

Example 16

Preparation of (2S,3S,4R,5R) and (2S,3S,4S,5S)-3,4,5-trihydroxy-tetrahydropyran-2-carboxylic acid ethyl esters

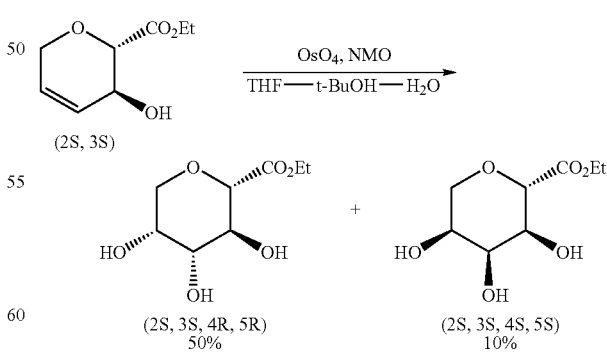

(2S, 3S)

(2S, 3S, 4R, 5R)
50%

(2S, 3S, 4S, 5S)
10%

To (2S,3S)-3-hydroxy-3,6-dihydro-2H-pyran-2-carboxylic acid ethyl ester (100 mg, 0.58 mmol) in 9 ml of THF-tert-BuOH—H$_2$O (2:5.9:1) was added NMO (235 mg, 1.72 mmol) and the solution was stirred for 5 min at ambient temperature. OsO$_4$ (0.1 ml, 2.5 wt % in tert-BuOH) was added and the mixture was stirred at ambient temperature for 24 H. Sodium hydrosulphite (0.4 g), Florisil (4.0 g) and H$_2$O (10 ml) were sequentially added and the mixture was stirred for 30 minutes, washed with acetone (200 ml), filtered through filter paper and extracted with EtOAc (2×100 ml). The combined organic layers were washed with brine (100 ml), dried over Na$_2$SO$_4$, and concentrated in vacuo. The crude product was purified by flash chromatography with 90% EtOAc-hexane to give (2S,3S,4R,5R)- and (2S,3S,4S,5S)-3,4,5-trihydroxy-tetrahydropyran-2-carboxylic acid ethyl esters in 60% yield.

(2S,3S,4R,5R)-3,4,5-trihydroxy-tetrahydropyran-2-carboxylic acid ethyl ester

Colorless oil; Yield: 50%;

IR (neat): 3640-3080, 2980, 2920, 1732, 1235, 1102, 629 cm$^{-1}$; $^1$H NMR (CDCl$_3$, 400 MHz) 67 4.34 (br s, 3H), 4.21 (q, J=7.2 Hz, 2H), 4.05 (d, J=1.7 Hz, 1H), 4.04 (dd, J=12.6, 1.7 Hz, 1H), 3.90-3.98 (m, 1H), 3.68 (d, J=9.4 Hz, 1H), 3.66-3.60 (m, 1H), 3.55 (d, J=12.2 Hz, 1H), 1.27 (t, J=7.2 Hz, 3H); $^{13}$C NMR (CDCl$_3$, 400 MHz) δ 170.30 (C), 78.88 (CH), 73.84 (CH), 70.27 (CH$_2$), 68.92 (CH), 68.70 (CH), 61.84 (CH$_2$), 13.99 (CH$_3$); EIMS (m/z, relative intensity): 207 (M$^+$+1, 100), 133 (5), 115 (7), 73 (32), 57 (12); exact mass calculated for C$_8$H$_{14}$O$_6$ (M$^+$): 206.0790; found 206.0788.

(2S,3S,4S,5S)-3,4,5-trihydroxy-tetrahydropyran-2-carboxylic acid ethyl ester

Colorless oil; Yield: 10%;

IR (neat): 3640-3080, 2980, 2926, 1732, 1645, 1381, 1204, 1099, 1043 cm$^{-1}$; $^1$H NMR (CDCl$_3$, 400 MHz) δ 4.22-4.30 (m, 2H), 4.11-4.13 (d, J=8.6 Hz, 1H), 3.70-3.90 (m, 3H), 3.52-3.62 (m, 2H), 1.30 (t, J=7.2 Hz, 3H); EIMS (m/z, relative intensity): 206 (M$^+$, 17), 188 (4), 167 (18), 149 (49), 73 (70), 57 (83), 43(100);

Example 17

Preparation of (+)-(2S,3R,4S,5S)-3-acetoxy-4,5-dihydroxy-tetrahydropyran-2-carboxylic acid ethyl ester

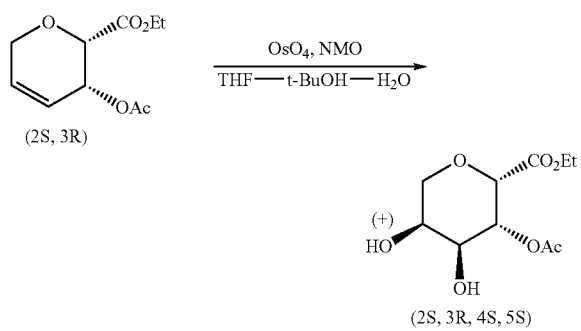

To (2S,3R)-3-acetoxy-3,6-dihydro-2H-pyran-2-carboxylic acid ethyl ester (200 mg, 0.93 mmol) in 18 ml of THF-tert-BuOH—H$_2$O (4:11.8:2) was added NMO (408 mg, 2.98 mmol) and the solution was stirred for 5 min at ambient temperature. OsO$_4$ (0.2 ml, 2.5 wt % in tert-BuOH) was added and the solution was stirred at ambient temperature for 72 H. Sodium hydrosulphite (0.83 g), Florisil (2.0 g) and H$_2$O (2 ml) were added sequentially and the mixture was stirred for 30 minutes, washed with 200 ml EtOAc, filtered through filter paper and the solvent was evaporated. The crude product was purified by flash chromatography with 20-80% EtOAc-hexane to give (2S,3R,4S,5S)-3-acetoxy-4,5-dihydroxy-tetrahydropyran-2-carboxylic acid ethyl ester Yield: 65%; Colorless oil; R$_f$=0.4 in 100% EtOAc;

IR (neat): 3600-3200, 2923, 2851, 1740, 1483, 1376, 1233, 1121, 1065 cm$^{-1}$; $^1$H NMR (CDCl$_3$, 400 MHz) δ 5.21 (dd, J=1.7 Hz, 3.8 Hz, 1H), 4.45 (d, J=1.7 Hz, 1H), 4.14-4.20 (m, 2H), 4.02-4.04 (m, 1H), 3.81-3.94 (m, 2H), 3.55 (dd, J=10.2, 10.2 Hz, 1H), 3.31 (br s, 2H), 2.02 (s, 3H), 1.21 (t, J=7.2 Hz, 3H); $^{13}$C NMR (CDC3, 400 MHz) δ 170.13 (C), 168.75 (C), 72.42 (CH), 71.93 (CH), 66.97 (CH), 65.52 (CH$_2$), 64.08 (CH), 61.63 (CH$_2$), 20.61 (CH$_3$), 14.00 (CH$_3$); EIMS (m/z, relative intensity): 249 (M$^+$+1, 5), 206 (8), 175 (10), 157 (39), 115 (37), 43 (100); exact mass calculated for C$_{10}$H$_{16}$O$_7$ (M$^+$): 248.0896; found 248.0887.

Example 18

Preparation of (+)-(2R,3S,4R,5R)-3,4,5-trihydroxy-tetrahydropyran-2-carboxylic acid ethyl ester

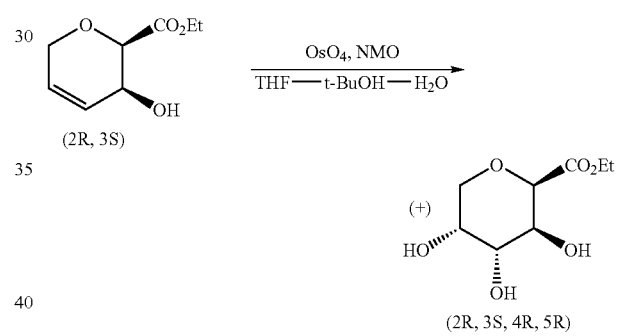

To (2R,3S)-3-hydroxy-3,6-dihydro-2H-pyran-2-carboxylic acid ethyl ester (200 mg, 1.16 mmol) in 18 ml THF-tert-BuOH—H$_2$O (4:11.8:2) was added NMO (408 mg, 3.43 mmol) and the solution was stirred for 5 min at ambient temperature. OsO$_4$ (0.2 ml, 2.5 wt % in tert-BuOH) was added and the mixture was stirred at ambient temperature for 72 H. Sodium hydrosulphite (0.83 g), Florisil (2.0 g) and H$_2$O (2 ml) were added sequentially and the mixture was stirred for 30 minutes, washed with 200 ml EtOAc, filtered through filter paper and the solvent was evaporated. The crude product was purified by flash chromatography with 20-80% EtOAc-hexane to give (2R,3S,4R,5R)-3,4,5-trihydroxy-tetrahydropyran-2-carboxylic acid ethyl ester Yield=65%; Colorless oil; R$_f$=0.4 in 100% EtOAc;

$^1$H NMR (CDC3, 400 MHz) δ 4.36 (s, 1H), 4.18-4.26 (m, 2H), 4.00-4.16 (m, 6H), 3.80-3.90 (m, 1H), 3.48-3.58 (m, 1H), 1.26 (t, J=7.1 Hz, 3H); $^{13}$C NMR (CDCl$_3$, 100 MHz) δ 170.59 (C), 74.20 (CH), 70.75 (CH), 69.69 (CH), 65.56 (CH$_2$), 64.10 (CH), 61.74 (CH$_2$), 14.04 (CH$_3$); EIMS (m/z, relative intensity): 207 (M$^+$+1, 11), 206 (19), 133 (23), 115 (61), 73 (85), 57 (80), 43 (100); Exact mass calculated for C$_8$H$_{14}$O$_6$ (M$^+$): 206.0790; found 206.0787.

Example 19

Preparation of (2R,3R,4S,5S)-3,5-diacetoxy-4-hydroxy-tetrahydropyran-2-carboxylic acid ethyl ester using lipase from *Alcaligenes* sp.

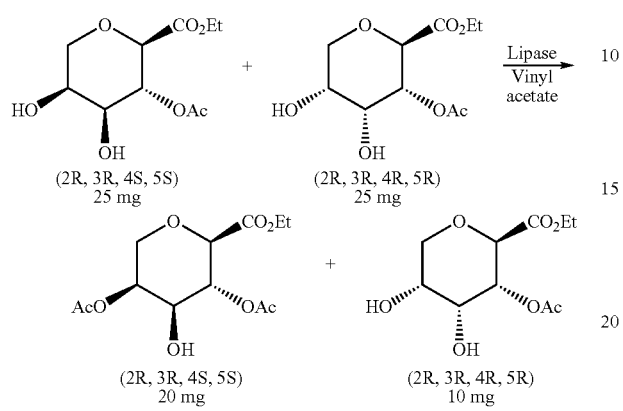

To a 1:1 mixture of (2R,3R,4S,5S) and (2R,3R,4R,5R)-3-acetoxy-4,5-dihydroxy-tetrahydropyran-2-carboxylic acid ethyl esters (50 mg, 0.2 mmol) in toluene (3 ml) was added *Alcaligenes* sp. (40 mg) followed by vinyl acetate (26 µl). The solution was stirred for 5 H at ambient temperature, filtered and the solvent was removed in vacuo. The product was purified by flash chromatography with 20% EtOAc-hexane to give 20 mg of (2R,3R,4S,5S)-3,5-diacetoxy-4-hydroxy-tetrahydropyran-2-carboxylic acid ethyl ester 10 mg of the (2R,3R,4R,5R) diol.

(2R,3R,4S,5S)-3,5-diacetoxy-4-hydroxy-tetrahydropyran-2-carboxylic acid ethyl ester Colorless oil; $R_f$=0.75 in 100% EtOAc.
$^1$H NMR (CDCl$_3$, 400 MHz) δ 5.27 (d, J=8.2 Hz, 1H), 5.10-5.13 (m, 1H), 4.12-4.25 (m, 4H), 3.90-3.95 (m, 2H), 2.14 (s, 3H), 2.10 (s, 3H), 1.27 (t, J=7.2 Hz, 3H).

Example 20

Preparation of (−)-(1R,4S,5S,8R)-8-acetoxyhydroxy-2,6-dioxa-bicyclo[3.2.1]octan-7-one

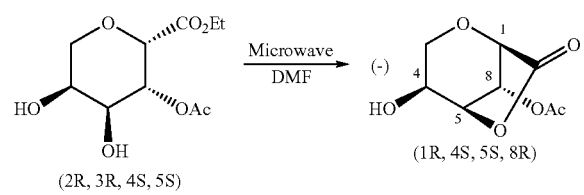

(2R,3R,4S,5S)-3-acetoxy-4,5-dihydroxy-tetrahydropyran-2-carboxylic acid ethyl ester (300 mg, 1.2 mmol) was dissolved in DMF (5 ml) and the solution was subjected to microwave irradiation at 150° C. for 4H. After cooling, the solvent was removed in vacuo. The crude product was purified by flash chromatography with 20% EtOAc-hexane to give (−)-(1R,4S,5S,8R)-8-acetoxy-4-hydroxy-2,6-dioxa-bicyclo[3.2.1]octan-7-one
Yield=12%; .

IR (neat): 2957, 2923, 2852, 1733, 1463, 1260, 1092, 1019, 799 cm$^{-1}$;

$^1$H NMR (CDCl$_3$, 400 MHz) δ 4.77 (br s, 1H), 4.58 (br s, 1H), 4.41 (br s, 1H), 4.03 (dd, J=10.5, 2.8 Hz, 1H), 3.96 (d, J=10.5 Hz, 1H), 3.86 (brs, 1H), 2.18 (s, 3H); $^{13}$C NMR (CDCl$_3$, 400 MHz) δ 171.82 (C), 167.19 (C), 79.35 (CH), 77.32 (CH), 72.02 (CH), 70.71 (CH), 64.90 (CH$_2$), 20.70 (CH$_3$); EIMS (m/z, relative intensity): 279 (M$^+$+77, 17), 160 (37), 159 (57), 148(62), 54(70), 42(99), 31(100);

Example 21

Preparation of (+)-(2R,3R,4S,5S)-3-acetoxy-4,5-dihydroxy-tetrahydropyran-2-carboxylic acid

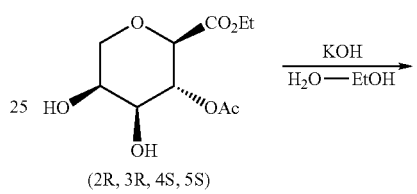

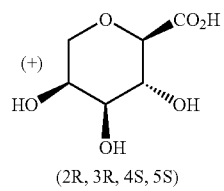

A solution of (2R,3R,4S,5S-3-acetoxy-4,5-dihydroxy-tetrahydropyran-2-carboxylic acid ethyl ester (370 mg, 1.49 mmol) in 19 ml of water-ethanol (4:1) was cooled to 0° C. and 1M KOH (2.1 ml) was added dropwise over 30 min. The resulting solution was stirred at 0° C. for 30 min and neutralized by addition of DOWEX-50W-X8 ion exchange resin. The resin was removed by filtration and the filtrate was concentrated in vacuo. The crude product was triturated with isopropanol (2 ml) to afford acid (+)-(2R,3R,4S,5S)-3-acetoxy-4,5-dihydroxy-tetrahydropyran-2-carboxylic acid.

Yield=65%;
IR (neat): 3600-3100, 2924, 1731, 1243, 1101, 1064, 778, 628 cm$^{-1}$;

$^1$H NMR (CD$_3$OD, 400 MHz) δ 3.84-3.88 (m, 1H), 3.75-3.86 (m, 4H), 3.61 (d, J=8.4 Hz, 1H), 3.49-3.51 (m, 1H), 3.45-3.48 (m, 2H); $^{13}$C NMR (CD$_3$OD, 100 MHz) δ 173.12 (C), 80.10 (CH), 74.54 (CH), 70.40 (CH), 70.39 (CH$_2$), 69.52 (CH); EIMS (m/z, relative intensity): 177 (M$^+$−1, 5), 160 (12), 149 (22), 73 (43), 57 (65), 43 (100).

Example 22

Preparation of (+)-(1R,4S,5S,8R)-4,8-hydroxy-2,6-dioxa-bicyclo[3.2.1]octan-7-one

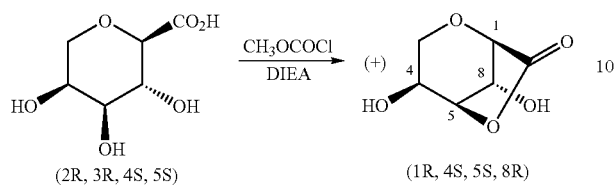

To (2R,3R,4S,5S)-3-acetoxy-4,5-dihydroxy-tetrahydro-pyran-2-carboxylic acid (25 mg, 0.14 mmol) was added diisopropylethylamine (30 μL, 0.169 mmol) followed by dry THF (3 ml) and the resulting solution was cooled to 0° C. Methyl chloroformate (12 μL, 0.154 mmol) was added dropwise over 5 min and the reaction mixture was stirred at room temperature for 36 H. The solvent was removed in vacuo and the crude product was purified by flash chromatography with 70% EtOAc-hexane to give (+)-(1R,4S,5S,8R)-4,8-hydroxy-2,6-dioxa-bicyclo[3.2.1]octan-7-one Yield=50%;

IR (neat): 3550-3100, 2924, 1732 cm$^{-1}$;

$^1$H NMR (CD$_3$OD, 200 MHz) δ 3.80-4.05 (m, 2H), 3.62-3.78 (m, 2H), 3.50-3.60 (m, 1H), 3.20-3.30 (m, 1H).

Example 23

Preparation of trans-2-hydroxymethyl-3,6-dihydro-2H-pyran-3-ol

To a solution of trans-3-acetoxy-3,6-dihydro-2H-pyran-2-carboxylic acid ethyl ester (56 mg, 0.26 mmol) in THF (5 ml) was added LiAlH$_4$ (62 mg, 1.64 mmol). The resulting solution was stirred at ambient temperature for 15 min and quenched by addition of H$_2$O (10 ml). The solution was diluted with EtOAc (50 ml×2), washed with brine (50 ml), dried over Na$_2$SO$_4$, concentrated in vacuo and purified by flash chromatography with 20% EtOAc-hexane (R$_f$=0.25 in EtOAc) to give 2-hydroxymethyl-3,6-dihydro-2H-pyran-3-ol as a colorless liquid Yield: 30 mg, 89%.

IR (neat): 3100-3600, 2983, 1642, 1376, 1186, 1114, 1038 cm$^{-1}$; $^1$H NMR (CDCl$_3$, 400 MHz) δ 5.77-5.84 (m, 2H), 4.16-4.19 (m, 3H), 3.88 (dd, J=11.5, 3.9 Hz, 1H), 3.78 (dd, J=11.5, 5.5 Hz, 1H), 3.30-3.33 (m, 1H), 1.77 (br s, 2H); $^{13}$C NMR (CDCl$_3$, 100 MHz) δ 128.41 (CH), 127.80 (CH), 78.46 (CH), 65.31 (CH$_2$), 64.42 (CH), 63.24 (CH$_2$); MS (m/z, relative intensity): 130 (M$^+$, 8), 112 (29), 97 (61), 81 (100); exact mass calculated for C$_6$H$_{10}$O$_3$ (M$^+$): 130.0630; found 130.0633.

Example 24

Preparation of trans-2-hydroxymethyl-3,6-dihydro-2H-pyran-3-ol

To a stirred solution of trans-3-hydroxy-3,6-dihydro-2H-pyran-2-carboxylic acid ethyl ester (0.480 g, 2.79 mmol) in THF (20 ml) at RT, was added in portions LiAlH$_4$ (0.126 g, 3.384 mmol) and the resulting mixture was stirred for 30 min. EtOAc (10 ml) was added, the mixture was stirred for 10 min and extracted with water (10 ml×2). The organic layer was dried over anhydrous Na$_2$SO$_4$. The solvent was removed in vacuo and the crude product purified by flash chromatography (25-30% EtOAc in hexane).

Yield: 0.37 g, 94%;

Example 25

Preparation of cis-2-hydroxymethyl-3,6-dihydro-2H-pyran-3-ol

To a solution of cis-3-acetoxy-3,6-dihydro-2H-pyran-2-carboxylic acid ethyl ester (52 mg, 0.25 mmol) in THF (5 ml) was added LiAlH$_4$ (60 mg, 1.60 mmol). The resulting solution was stirred at ambient temperature for 15 min. The reaction was quenched by addition of H$_2$O (10 ml). The solution was diluted with EtOAc (50 ml×2), washed with brine (50 ml), dried over Na$_2$SO$_4$, concentrated in vacuo and purified by flash chromatography with 20% EtOAc-hexane to give cis-2-hydroxymethyl-3,6-dihydro-2H-pyran-3-ol Colorless liquid; Yield: 28 mg, 90%; R$_f$=0.20 in EtOAc IR (neat): 3050-3600, 2932, 1644, 1447, 1378, 1297, 1185, 1103, 1040 cm$^{-1}$; $^1$H NMR (CDCl$_3$, 400 MHz) δ 5.95-6.05 (m, 2H), 4.12-4.30 (m, 2H), 3.88-3.94 (m, 2H), 3.75-3.85 (m, 1H), 3.55-3.60 (m, 1H), 1.86 (brs, 2H); $^{13}$C NMR (CDCl$_3$, 100 MHz) δ 130.60 (CH), 126.41 (CH), 77.87 (CH), 66.18 (CH$_2$), 63.50 (CH), 63.11 (CH$_2$); MS (m/z, relative intensity): 129 (M$^+$-1, 22), 112 (5), 111 (17), 70 (100); exact mass calculated for C$_6$H$_{10}$O$_3$ (M$^+$): 130.0630; found 130.0634.

Example 26

Preparation of cis-2-hydroxymethyl-3,6-hydro-2H-pyran-3-ol

To a stirred solution of cis-3-hydroxy-3,6-dihydro-2H-pyran-2-carboxylic acid ethyl ester (0.60 g, 3.48 mmol) in THF (20 ml) at RT, was added in portions LiAlH$_4$ (0.204 g, 4.89 mmol) and the resulting mixture was stirred for 30 min. EtOAc (10 ml) was added, the mixture was stirred for 10 min and extracted with water (10 ml×2). The organic layer was dried over anhydrous Na$_2$SO$_4$. The solvent was removed in vacuo and the crude product purified by flash chromatography (25-30% EtOAc in hexane).

Colorless oil; Yield: 0.42 g, 85%. R$_f$=0.18 (EtOAc).

Example 27

Preparation of trans-2-(tert-butyldimethylsilanyloxymethyl)-3,6-dihydro-2H-pyran-3-ol

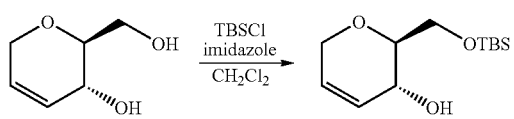

To a 0° C., stirred solution of trans-2-hydroxymethyl-3,6-dihydro-2H-pyran-3-ol (OA g, 2.84 mmol) in CH$_2$Cl$_2$ (40 ml) under an Argon atmosphere was added imidazole (0.231 g, 3.4 mmol) followed by TBSCl (0.428 g, 3.4 mmol). The resulting mixture was stirred for 1H at 0° C. The reaction mixture was washed with water (10 ml×2) and brine (10 ml). The organic phase was dried over anhydrous Na$_2$SO$_4$ The solvent was removed in vacuo and the crude product purified by flash chromatography (25-40% EtOAc in hexane).

Colorless oil. Yield: 0.618 g, 84%. R$_f$=0.72 (1:1 ether-hexane).

IR (neat): 3600-3100, 3037, 2929, 2857, 1463, 1254, 1099, 837, 778 cm$^{-1}$;

$^1$H NMR (CDCl$_3$, 400 MHz) δ 5.76-5.77 (m, 2H), 4.15-4.20 (m, 1H), 4.06-4.10 (m, 2H), 3.89 (dd, J=10.0, 5.2 Hz, 1H), 3.71 (dd, J=7.4, 10.0 Hz, 1H), 3.30-3.36 m, 1H), 0.88 (s, 9H), 0.08 (s, 6H);

$^{13}$C NMR (CDCl$_3$, 100 MHz) δ 127.97 (CH), 127.05 (CH), 77.32 (CH), 67.02 (CH), 65.73 (CH$_2$), 65.21 (CH$_2$), 25.83 (3×CH$_3$), 18.21 (C), -5.53 (CH$_3$), -5.59 (CH$_3$),

MS (m/z, relative intensity): 189 (4, M$^+$-tert-But), 118 (78), 116 (100)

Example 28

Preparation of cis-2-(tert-butyldimethylsilanyloxymethyl)-3,6-dihydro-2H-pyran-3-ol

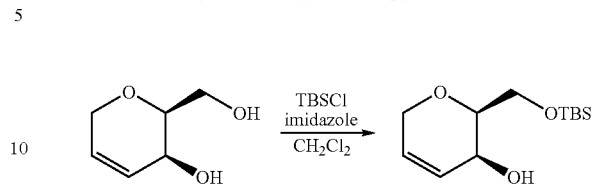

To a 0° C., stirred solution of cis-2-hydroxymethyl-3,6-dihydro-2H-pyran-3-ol (0.4 g, 2.84 mmol) in CH$_2$Cl$_2$ (40 ml) under an Argon atmosphere was added imidazole (0.231 g, 3.4 mmol) followed by TBSCl (0.428 g, 3.4 mmol). The resulting mixture was stirred for 1H at 0° C. The reaction mixture was washed with water (10 ml×2) and brine (10 ml). The organic phase was dried over anhydrous Na$_2$SO$_4$. The solvent was removed in vacuo and the crude product purified by flash chromatography (25-40% EtOAc in hexane).

Colorless oil. Yield: 0.478 g, 65%. R$_f$=0.6 (1:1, ether-hexane).

IR (neat): 3500-3150, 2928, 2925, 1103 cm$^{-1}$;

$^1$H NMR (CDCl$_3$, 400 MHz) δ 5.99-6.03 (m, 1H), 5.89-5.93 (m, 1H), 4.19 (dd, J=3.4, 1.7 Hz, 1H), 4.11 (dd, J=16.9, 2.0 Hz, 1H), 3.93-3.95 (m, 1H), 3.50-3.85 (m, 2H), 3.49-3.52 (m, 1H), 1.90-2.00 (m, 1H), 0.88 (s, 9H), 0.07 (s, 6H)

$^{13}$C NMR (CDCl$_3$, 100 MHz) δ 130.26 (CH), 126.62 (CH), 78.12 (CH), 66.14 (CH$_2$), 62.85 (CH$_2$), 62.57 (CH), 25.87 (3×CH$_3$), 18.28 (C), -5.36 (CH$_3$), -5.41 (CH$_3$)

MS (m/z, relative intensity): 203 (M+-41), 185 (25), 173 (48), 143 (41), 131 (71), 117 (100).

MS (EI) calcd. for C$_{12}$H$_{24}$O$_3$Si 244.1495.

Example 29

Preparation of 4-(tert-buyldimethylsilanyloxymethyl)-3,7-dioxa-bicyclo[4.1.0]heptan-5-ol

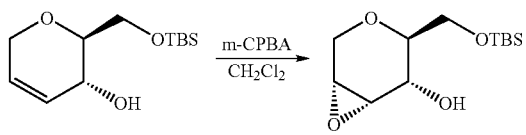

To a 0° C., stirred solution of trans-2-(tert-butyldimethylsilanyloxymethyl)-3,6-dihydro-2H-pyran-3-ol (0.110 g, 0.45 mmol) in CH$_2$Cl$_2$ (10 ml) was added m-CPBA (75%, 0.108 g, 1.08 mmol) and the mixture was stirred for 1 h at 0° C. Dimethyl sulfide (0.01 ml) was added and stirring was continued for 10 min. The solvent was removed in vacuo and the crude product was diluted with EtOAc (30 ml). The resulting solution was washed successively with saturated aqueous Na$_2$CO$_3$ (10 ml), water (10 ml×2) and brine (10 ml). The organic phase was dried over anhydrous Na$_2$SO$_4$. The solvent was removed in vacuo and the crude product was purified by flash chromatography (2540% EtOAc in hexane).

Colorless oil. Yield: 0.094 g, 80%. R$_f$=0.47 (1:1 ether-hexane).

IR (neat): 3550-3100, 2954, 2928, 2856, 1463, 1254, 1146, 1102, 837, 778 cm$^{-1}$;

$^1$H NMR (acetone-d$_6$, 400 MHz) δ 4.11 (d, J=7.2 Hz, 1H), 4.03 (dd, J=13.4, 3.9 Hz, 1H), 3.87 (dd, J=10.5, 2.2 Hz, 1H), 3.84-3.81 (m, 1H), 3.73-3.64 (m, 2H), 3.45 (dd, J=4.2, 4.2 Hz, 1H), 3.35-3.38 (m, 1H), 3.20-3.15 (m, 1H), 0.89 (s, 9H), 0.05 (s, 6H);

$^{13}$C NMR (acetone-d$_6$, 100 MHz) δ 76.75 (CH), 66.45 (CH), 65.19 (CH$_2$), 64.31 (CH$_2$), 55.73 (CH), 54.95 (CH), 26.25 (3×CH$_3$), 18.90 (C), −5.11 (CH$_3$), −5.14 (CH$_3$); MS (m/z, relative intensity): 203 (M$^+$-t-Bu, 17), 173 (3), 117 (53), 75 (100).

Example 30

Preparation of (1S,4S,5R,6R) and (1R,4S,5R,6S)-4-(tert-butyl-dimethylsilanyloxymethyl)-3,7-dioxa-bicyclo[4.1.0]heptan-5-ol

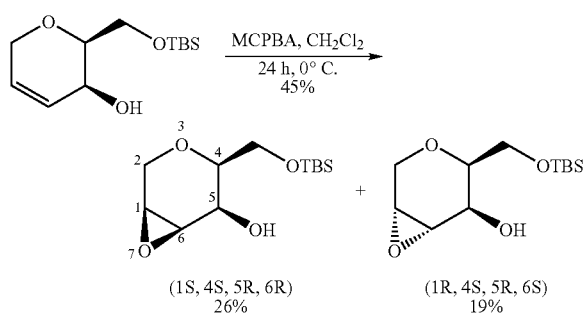

(1S, 4S, 5R, 6R)
26%

(1R, 4S, 5R, 6S)
19%

To a 0° C., stirred solution of cis-2-(tert-butyldimethylsilanyloxymethyl)-3,6-dihydro-2H-pyran-3-ol (0.200 g, 0.91 mmol) in CH$_2$Cl$_2$ (15 ml) was added m-CPBA (75%, 0.46 g, 2.68 mmol) and the mixture was stirred for 1 H at 0° C. Dimethyl sulfide (0.01 ml) was added and stirring was continued for 10 min. The solvent was removed in vacuo and the crude product was diluted with EtOAc (30 ml). The resulting solution was washed successively with saturated aqueous Na$_2$CO$_3$ (10 ml), water (10 ml×2) and brine (10 ml). The organic phase was dried over anhydrous Na$_2$SO$_4$. The solvent was removed in vacuo and the crude product was purified by flash chromatography (25-40% EtOAc in hexane).

(1S,4S,5R,6R)-4-(tert-butyl-dimethylsilanyloxymethyl)-3,7-dioxa-bicyclo[4.1.0]heptan-5-ol Yield: 0.083 g, 39%. R$_f$=0.52 (30% EtOAc-hexane).

IR (neat): 3550-3150, 2928, 2855, 1256, 1099, 839, 777 cm$^{-1}$; $^1$H NMR (CDCl$_3$, 400 MHz) δ 4.16 (d, J=13.4 Hz, 1H), 3.89-3.95 (m, 1H), 3.70-3.78 (m, 2H), 3.62 (dd, J=10.5, 6.3 Hz, 1H), 3.55 (dd, J=5.6, 4.0 Hz, 1H), 3.23 (d, J=3.9 Hz, 1H), 3.14 (ddd, J=8.7, 6.4, 2.4 Hz, 1H), 2.37 (d, J=11.0 Hz, 1H), 1.23 (brs, 1H), 0.88 (s, 9H), 0.05 (s, 6H);

$^{13}$C NMR (CDCl$_3$, 100 MHz) δ 78.86 (CH), 64.70 (CH$_2$), 61.66 (CH$_2$), 61.31 (CH), 52.26 (CH), 51.63 (CH), 25.86 (3×CH$_3$), 18.28 (C), −5.37 (CH$_3$), −5.44 (CH$_3$);

MS (m/z, relative intensity): 203 (M+-t-Bu, 4), 185 (22), 173 (45), 131 (70), 117 (100).

(1R,4S,5R,6S)-4(tert-butyl-dimethylsilanyloxymethyl)-3,7-dioxa-bicyclo[4.1.0]heptan-5-ol Yield: 0.10 g, 41%. R$_f$=0.32 (30% EtOAc-hexane).

IR (neat): 3550-3100, 2928, 2856, 1254, 1103, 837, 777 cm$^{-1}$; $^1$H NMR (CDCl$_3$, 400 MHz) δ 4.18 (dd, J=13.6, 3.9 Hz, 1H), 1.43 (d, J=6.4 Hz, 1H), 3.93 (d, J=13.5 Hz, 1H), 3.75 (dd, J=5.7, 2.4 Hz, 2H), 3.42-3.39 (m, 1H), 3.38-3.36 (m, 1H), 3.28 (dd, J=4.0, 4.0 Hz, 1H), 2.87 (d, J=7.0 Hz, 1H), 1.62 br s, 1H), 0.86 (s, 9H), 0.07 (s, 6H); $^{13}$C NMR (CDCl$_3$, 100 MHz) δ 72.51 (CH), 65.32 (CH), 65.07 (CH$_2$), 63.33 (CH$_2$), 52.74 (CH), 51.26 (CH), 25.86 (3×CH$_3$), 18.22 (C), −5.50 (2×CH$_3$);

Example 31

Preparation of 5-benzyloxy-2-hydroxymethyl-tetrahydropyran-3,4-diol

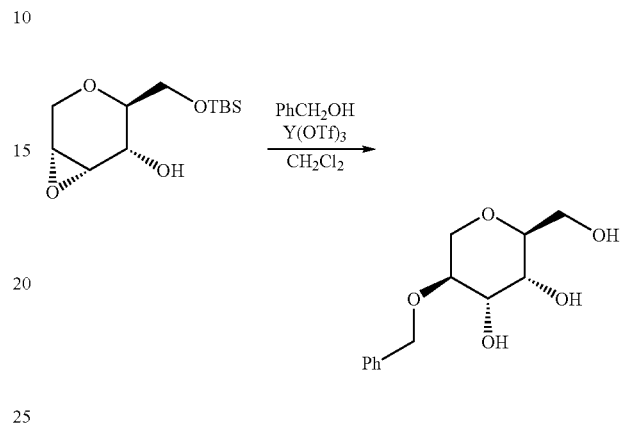

A solution of 4-(tert-butyldimethylsilanyloxymethyl)-3,7-dioxabicyclo[4.1.0]heptan-5-ol (0.06 g, 0.228 mmol) in CH$_2$Cl$_2$ (10 ml) was stirred under Argon atmosphere at RT for 15 min. Yttrium triflate (0.048 g, 0.08 mmol) was added and the slurry was stirred for 10 min. Benzyl alcohol (120 µl, 0.912 mmol) was added and the mixture was stirred for 24 H. The solvent was removed and the crude product was diluted with EtOAc (20 ml), washed with water (10 ml), saturated aqueous NaHCO$_3$ (5 ml×2) and brine (5 ml). The organic phase was dried over anhydrous Na$_2$SO$_4$. The crude product was purified by flash chromatography using 60% MeOH in EtOAc Yield: 0.030 g, 51%. R$_f$=0.18 (EtOAc).

IR (neat): 3600-3100, 3030, 2928, 2856, 1454, 1254, 1103, 837, 698 cm$^{-1}$;

$^1$H NMR (CDCl$_3$, 400 MHz) δ 7.28-7.33 (m, 5H), 4.48-4.62 (d, 1H, J=12 Hz), 4.57 (d, 1H, J=12 Hz, 2.3 Hz), 4.07-4.12 (m, 2H), 3.93-4.0 (m, 1H), 3.83-3.9 (m, 1H), 3.8-3.85 (m, 1H), 3.75-3.78 (m, 1H), 3.54-3.5.8 (m, 1H), 3.53-3.54 (m, 1H);

$^{13}$C NMR (CDCl$_3$, 100 MHz) δ 138.29 (C), 128.90 (2×CH), 128.27 (CH), 128.09 (2×CH), 76.50 (CH), 75.01 (CH), 71.66 (CH$_2$), 68.77 (CH), 67.25 (CH), 64.69 (CH$_2$), 63.99 (CH$_2$); MS (m/z, relative intensity): 255 (M$^+$+1, 17), 254 (M$^+$, 16), 206 (6), 176 (10), 107 (20), 91 (100); HRMS calcd. for C$_{13}$H$_{18}$O$_5$: 254.1155; observed: 254.1164.

Example 32

Preparation of 5-benzylamino-2-(tert-butyldimethylsilanyloxymethyl)-tetrahydropyran-3,4-diol

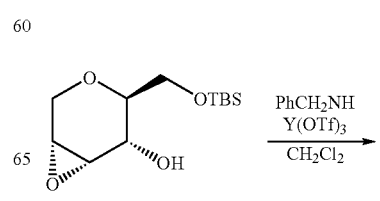

-continued

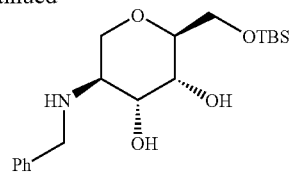

Following the procedure of example 32, the crude product was purified by flash chromatography using 10-20% EtOAc in hexane.

Yield: 0.045 g (53% yield). $R_f$=0.18 (1:1 EtOAc-hexane).

IR (neat): 3580, 3500-3200, 2927, 2857, 1464, 1252, 1086, 1062, 838, 780 cm$^{-1}$;

$^1$H NMR (CDCl$_3$, 200 MHz) δ 7.20-7.30 (m, 5H), 4.00-4.03 (m, 1H), 3.72-3.90 (m, 5H), 3.60-3.70 (m, 2H), 3.48-3.58 (m, 1H), 2.81 (dd, J=3.5, 1.7 Hz, 1H), 0.89 (s, 9H), 0.08 (s, 6H). $^{13}$C NMR (CDCl$_3$, 100 MHz) δ 139.88 (C), 128.44 (2×CH), 128.09 (2×CH), 127.10 (CH), 73.78 (CH), 69.53 (CH), 69.11 (CH), 65.78 (CH$_2$), 64.78 (CH$_2$), 56.80 (CH), 51.66 (CH$_2$), 25.80 (3×CH$_3$), 18.16 (C), −5.57 (CH$_3$), −5.62 (CH$_3$); MS (m/z, relative intensity): 367 (M$^+$, 11), 310 (M-t-Bu, 22), 148 (22), 91 (PhCH$_2^+$, 100); MS (EI) calcd. for C$_{19}$H$_{33}$NO$_4$Si: 367.2179; observed: 367.2171.

X-ray crystal structure of 5-benzylamino-2-(tert-butyldimethylsilanyloxymethyl)-tetrahydropyran-3,4-diol

Example 33

Preparation of 2-hydroxymethyl-tetrahydropyran-3,4,5-triol

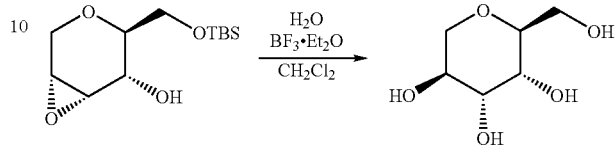

A solution of 4-(tert-butyldimethylsilanyloxymethyl)-3,7-dioxabicyclo[4.1.0]heptan-5-ol (0.06 g, 0.23 mmol) in CH$_2$Cl$_2$ (10 ml) was stirred under Argon atmosphere at RT for 15 min. BF$_3$·OEt$_2$ (1.5 ml, 0.013 mmol) was added followed by water (12 ml, 0.65 mmol). After stirring the mixture for 24 h, the solvent was removed and the crude product was purified by flash chromatography using 10% MeOH in EtOAc.

Yield: 0.015 g, 44%. $R_f$=0.1 (EtOAc).

$^1$H NMR (D$_2$O, 400 MHz) δ 4.04 (dd, J=13.8, 1.5 Hz, 1H), 3.84 (dd, J=11.6, 2.1 Hz, 1H), 3.78-3.70 (m, 2H), 3.60 (dd, J=4.2, 4.2 Hz, 1H), 3.50-3.42 (m, 2H), 3.22-3.15 (m, 1H);

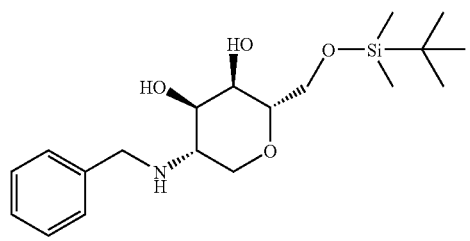

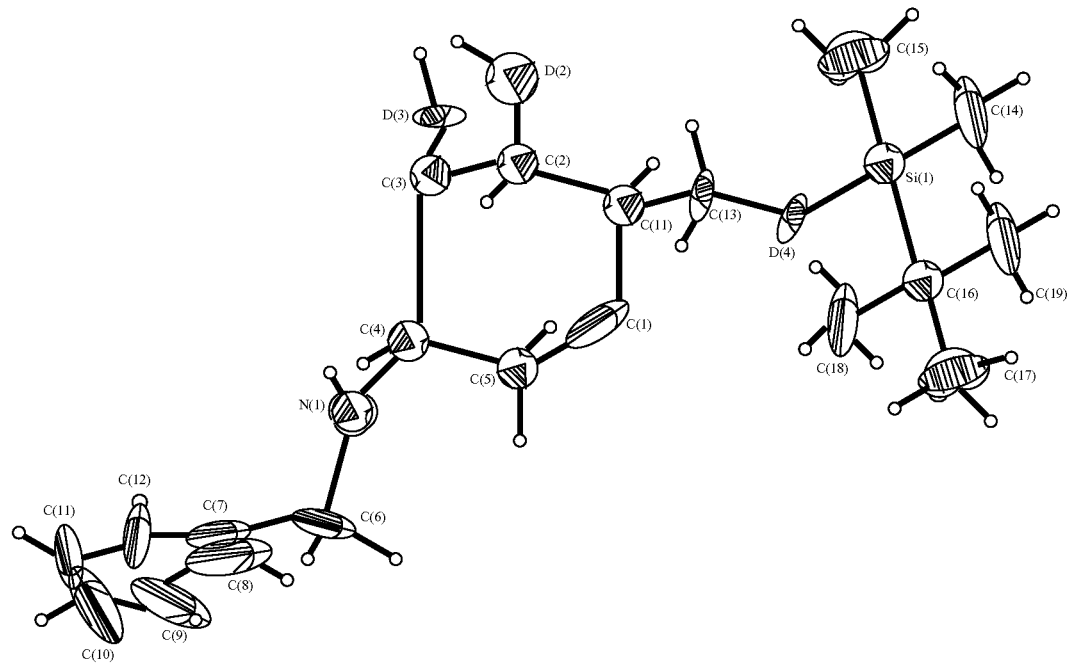

$^{13}$C NMR (D$_2$O, 100 MHz) δ 75.36, 65.13, 64.44, 61.43, 56.58, 54.99.

Example 34

Preparation of 6-(tert-butyldimethylsilanyloxymethyl)-5-hydroxy-4-trimethylsilanyloxy-tetrahydropyran-3-carbonitrile

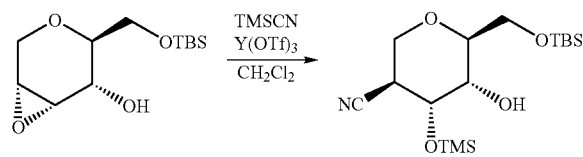

A solution of 4-(tert-butyldimethylsilanyloxymethyl)-3,7-dioxabicyclo[4.1.0]heptan-5-ol (0.02 g, 0.077 mmol) in CH$_2$Cl$_2$ (5 ml) was stirred under Argon atmosphere at RT for 15 min. Yttrium triflate (0.024 g, 0.04 mmol) was added and the slurry was stirred for 10 min. TMSCN (0.022 g, 25 ml, 0.228 mmol) was added and the mixture was stirred for 24 H. The solvent was removed and the crude product was diluted with EtOAc (20 ml), washed with water (10 ml), saturated aqueous NaHCO$_3$ (5 ml×2) and brine (5 ml). The organic phase was dried over anhydrous Na$_2$SO$_4$. The crude product was purified by flash chromatography using 10% EtOAc in hexane.

Yield: 0.018 g, 64%. R$_f$=0.73 (1:1 EtOAc-hexane).
IR (neat): 3550-3100, 2925, 2359, 774 cm$^{-1}$;
$^1$H NMR (CDCl$_3$, 400 MHz) δ 4.00-4.10 (m, 2H), 3.72-3.82 (m, 2H), 3.60-3.70 (m, 1H), 3.42 (dd, J=4.1, 4.1 Hz, 1H), 3.28-3.30 (m, 1H), 3.15-3.20 (m, 1H), 0.87 (s, 9H), 0.17 (s, 9H), 0.03 (s, 6H);
$^{13}$C NMR (CDCl$_3$, 100 MHz) δ 76.02 (CH), 66.50 (CH), 64.95 (CH$_2$), 63.03 (CH$_2$), 56.04 (CH), 55.03 (CH), 26.40 (3×CH$_3$), 18.90 (C), 0.74 (3×CH$_3$), -4.77 (2×CH$_3$), 4.89 (2×CH$_3$);
MS (m/z, relative intensity): 333 (M$^+$-CN, 78), 307 (100), 289 (70).

Example 35

Preparation of 5-azido-2-(tert-butyldimethylsilanyloxymethyl)-tetrahydropyran-3,4-diol

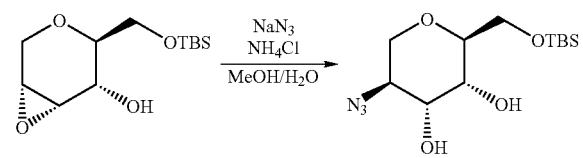

A solution of 4-(tert-butyldimethylsilanyloxymethyl)-3,7-dioxabicyclo[4.1.0]heptan-5-ol (0.03 g, 0.12 mmol) in MeOH (4 ml) was treated with water (1 ml) and NaN$_3$ (0.042 g, 0.65 mmol). The resulting mixture was heated to reflux for 12 H. The solvent was removed in vacuo. The crude product was diluted with EtOAc (10 ml), washed with water (5 ml×2), saturated aqueous Na$_2$CO$_3$ solution (5 ml) and brine (5 ml). The organic phase was dried over anhydrous Na$_2$SO$_4$. The crude product was purified by flash chromatography using 20-25% EtOAc in hexane.

Yield: 0.021 g, 58%. R$_f$=0.47 (1:1 EtOAc-hexane).
IR (neat): 3500-3100, 2928, 2108, 1256, 1101, 837, 776 cm$^{-1}$;
$^1$H NMR (CDCl$_3$, 400 MHz) δ 4.40 (d, J=3.4 Hz, 1H), 3.85-3.95 (m, 3H), 3.64-3.82 (m, 3H), 3.49-3.55 (m, 1H), 2.89 (brs, 2H), 0.89 (s, 9H), 0.07 (s, 6H);
$^{13}$C NMR (CDCl$_3$, 100 MHz) δ 77.88, 69.58, 65.91, 64.46, 64.13, 61.94, 26.26 (three CH$_3$), 18.89, -5.11, -5.12;
MS (m/z, relative intensity): 304 (20, M$^+$+1), 246 (38), 75 (100).

Example 36

Preparation of 2-(tert-butyldimethylsilanyloxymethyl)-5-(3-methoxyphenylamino)-tetrahydropyran-3,4-diol

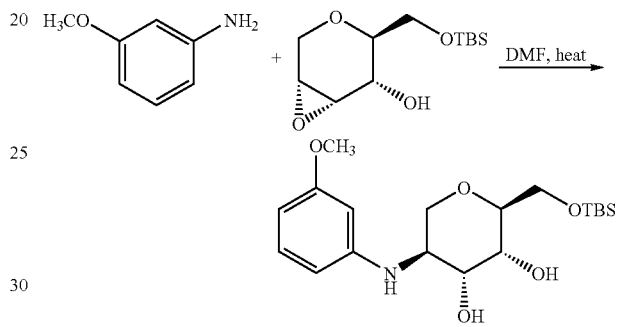

A solution of 4-(tert-butyldimethylsilanyloxymethyl)-3,7-dioxabicyclo[4.1.0]heptan-5-ol (0.03 g, 0.13 mmol) and m-anisidine (0.08 g, 0.65 mmol) in DMF (4 ml) was heated to reflux for 12H. The solvent was removed in vacuo and the crude product was purified by flash chromatography using 15-25% EtOAc in hexane.

Yield: 0.027 g, 53%. R$_f$0.48 (1:1 EtOAc-hexane).
IR (neat): 3550-3100, 2953, 2928, 2856, 1615, 1254, 1092, 836, 778 cm$^{-1}$;
$^1$H NMR (CDCl$_3$, 200 MHz) δ 7.00-7.19 (m, 1H), 6.16-6.39 (m, 2H), 3.50-4.20 (m, 8H), 3.75 (s, 3H), 0.89 (s, 9H), 0.06 (s, 6H);

Example 37

Preparation of 2-(tert-butyl-dimethylsilanyloxymethyl)-5-phenylsulfanyl-tetrahydropyran-3,4-diol

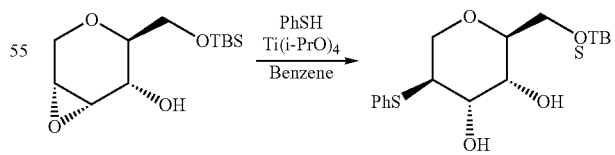

A solution of 4-(tert-butyldimethylsilanyloxymethyl)-3,7-dioxabicyclo[4.1.0]heptan-5-ol (30 mg, 0.115 mmol) in benzene (5 mL) was stirred under Argon atmosphere. Titanium tetraisopropoxide (85 mg, 0.3 mmol) and thiophenol (12 μL, 13 mg, 0.115 mmol) were added sequentially and the resulting mixture was stirred for 24 H. The solvent was removed in vacuo and the residue was diluted with EtOAc (20 mL), washed with water (5 mL×2), saturated aqueous sodium carbonate solution (5 mL) and brine (5 mL). The organic phase was dried over anhydrous $Na_2SO_4$. The solvent was removed in vacuo and the crude product was purified by flash chromatography using 10-20% EtOAc-hexane.

Yield: 0.019 g, 45%. $R_f$=0.82 (1:1 EtOAc-hexane).

IR (neat): 3500-3100, 2925, 1090, 775 $cm^{-1}$;

$^1$H NMR (CDCl$_3$, 200 MHz) δ 7.38-7.42 (m, 2H), 7.24-7.31 (m, 3H), 4.20-3.20 (m, 6H), 2.89-2.86 (m, 2H), 0.89 (s, 9H), 0.10 (s, 3H), 0.07 (s, 3H);

MS (EI) calcd. for $C_{18}H_{30}O_4SSi$ 370.1634; observed. 313 (6, $M^+$-t-Bu), 312 (7), 204 (20), 123 (48), 118 (78), 117 (100).

Example 38

Preparation of (2S,3S,4S,5R)-5-benzylamino-2-(tert-butyldimethylsilanyloxymethyl)-tetrahydropyran-3,4-diol

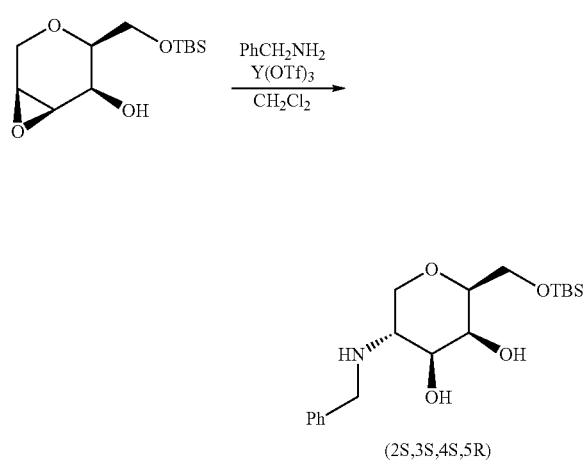

(2S,3S,4S,5R)

Following the procedure of example 32, the crude product was purified by flash chromatography using 60% EtOAc in hexane.

Yield: 72%. $R_f$=0.3 (1:1 EtOAc-hexane).

IR (neat): 3550-3200, 2927, 2855, 1254, 1104, 837, 776, 699 $cm^{-1}$;

$^1$H NMR (CDCl$_3$, 400 MHz) δ 7.23-7.34 (m, 5H), 3.80-4.05 (m, 7H), 3.86 (br s, 2H), 3.67 (brs, 1H), 3.50 (brs, 1H), 3.12 (brs, 1H), 0.89 (s, 9H), 0.09 (s, 3H), 0.08 (s, 3H).

$^{13}$C NMR (CDCl$_3$, 100 MHz) δ 139.88 (C), 128.49 (2×CH), 128.02 (2×CH), 127.24 (CH), 72.95 (CH), 71.34 (CH), 69.35 (CH$_2$), 68.23 (CH), 66.29 (CH$_2$), 58.72 (CH), 52.32 (CH$_2$), 25.77 (3×CH$_3$), 18.18 (C), -5.52 (CH$_3$), -5.66 (CH$_3$);

MS (m/z, relative intensity): 367 ($M^+$, 2), 311 (10), 179 (15), 149 (15), 106 (15), 91 (100);

MS (EI) calcd. for $C_{19}H_{33}NO_4Si$: 367.2179; observed: 367.2184.

Example 39

Preparation of (2S,3S,4R,5S)-5)-benzylamino-2-(tert-butyldimethylsilanyloxymethyl)-tetrahydropyran-3,4-diol

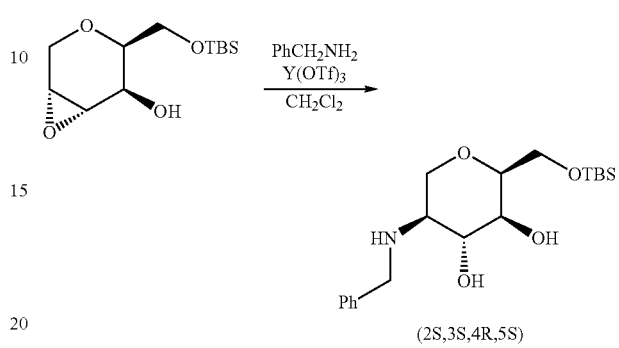

(2S,3S,4R,5S)

Following the procedure of example 32, the crude product was purified by column chromatography using 60% EtOAc in hexane.

Yield: 63%. $R_f$=0.33 (1:1 EtOAc-hexane).

IR (neat): 3550-3200, 2927, 2856, 1462, 1254, 1074, 838, 778, 750, 699 $cm^{-1}$;

$^1$H NMR (CDCl$_3$, 400 MHz) δ 7.24-7.34 (m, 5H), 4.12-4.13 (m, 1H), 4.01 (d, J=1.4 Hz, 1H), 3.90-3.70 (m, 6H), 3.64 (br s, 1H), 2.77 (br s, 1H), 1.24 (br s, $_1$H), 0.88 (s, 9H), 0.08 (s, 3H), 0.06 (s, 3H); $^{13}$C NMR (CDCl$_3$, 100 MHz) δ 138.31 (C), 128.71 (2×CH), 128.25 (2×CH), 127.60 (CH), 76.01 (CH), 69.90 (CH), 66.37 (CH), 66.11 (CH$_2$), 63.24 (CH$_2$), 57.00 (CH), 51.54 (CH$_2$), 25.94 (C), 18.37 (3×CH$_3$), -5.33 (CH$_3$), -5.37 (CH$_3$); MS (m/z, relative intensity): 367 ($M^+$, 11), 311 (31), 149 (30), 107 (39), 92 (100); MS (EI) calcd. for $C_{19}H_{33}NO_4SI$: 367.2179; observed: 367.2175.

Example 40

Preparation of 2-allyloxy-3-hydroxy-hex-4-enoic acid ethyl ester

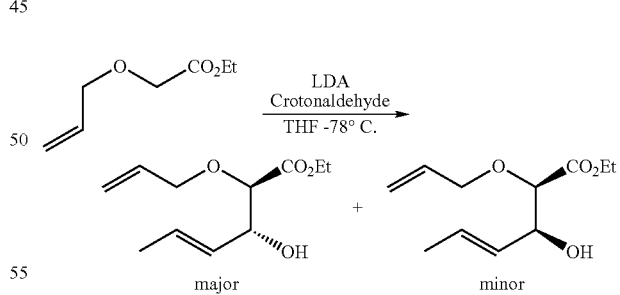

major          minor

A solution of lithium diisopropylamide (LDA) in THF/n-heptane (4.27 mL, 2M, 8.28 mmol) was added to THF (40 mL) at -78° C. and the mixture was stirred for 5 min under argon atmosphere. A solution of allyloxyacetic acid ethyl ester (1 g, 6.9 mmol) in THF (10 mL) was added and stirring was maintained for 5 min. Distilled crotonaldehyde (0.68 mL, 8.28 mmol) was added into the reaction mixture and the resulting solution was allowed to stir for 25 min. The reaction was quenched by the addition of EtOH (5 mL) and the solution was allowed to warm to RT. The solution was diluted with EtOAc (50 mL) and washed with water (10 mL). The organic layer was dried over $Na_2SO_4$, concentrated in vacuo and the residue was purified by flash chromatography with 15% EtOAc-hexane.

Yield=0.76 g (51%); $R_f$=0.33, 40% EtOAc-hexane $^1$H NMR (200 MHz, $CDCl_3$) δ 1.25 (t, J=7.0 Hz, 3H), 1.68 (d, J=5.8 Hz, 3H), 3.85-4.05 (m, 1H), 4.08-4.30 (m, 4H), 5.12-5.38 (m, 2H), 5.40-5.60 (m, 1H), 5.62-6.00 (m, 2H); $^{13}$C NMR (125 MHz, ca. 2:1, for major isomer): δ 170.21 (C), 133.71 (CH), 129.46 (CH), 128.24 (CH), 118.26 ($CH_2$), 81.06 (CH), 74.92 (CH), 73.44 ($CH_2$), 60.94 ($CH_2$), 17.72 ($CH_3$), 14.19 ($CH_3$); MS (m/z, relative intensity): 214 ($M^+$, 3), 196 (36), 155 (58), 127 (21), 71 (100).

HRMS calculated for $C_{11}H_{18}O_4$: 214.1205, found 214.1204.

Example 41

Preparation of cis- and trans-3-hydroxy-3,6-dihydro-2H-pyran-2-carboxylic acid ethyl ester

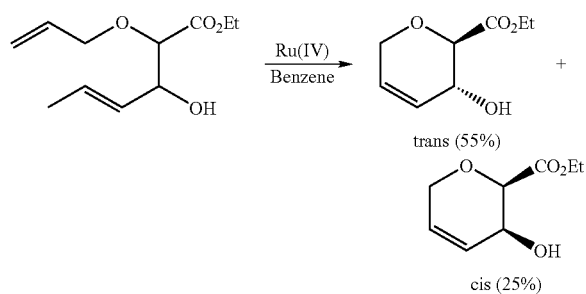

To a stirred solution of 2-allyloxy-3-hydroxy-hex-4-enoic acid ethyl ester (0.1 g, 0.47 mmol) in dry benzene (20 mL) was added bis-(tricyclohexylphosphine)-benzylidine rutherium (IV) chloride (15 mg, 0.018 mmol) and the mixture was stirred at ambient temperature. The solvent was removed and the residue was purified by flash chromatography with 20-40% EtOAc-hexane.

trans-3-hydroxy-3,6-dihydro-2H-pyran-2-carboxylic acid ethyl ester

Yield=56%;

cis-3-hydroxy-3,6-dihydro-2H-pyran-2-carboxylic acid ethyl ester

Yield=25%

Example 42

Preparation of 2-allyloxy-3-hydroxy-5-phenyl-pent 4-enoic acid ethyl ester

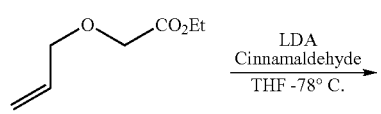

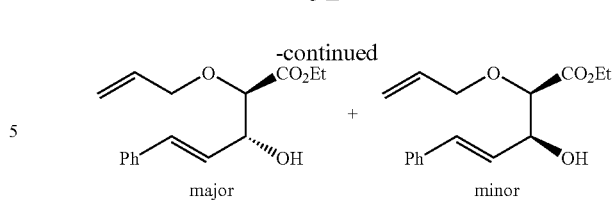

A 2.0M solution of LDA in THF/n-heptane (4.27 mL, 8.28 mmol) was added to THF (40 mL) at −78° C. and stirred for 5 min under argon atmosphere. A solution of allyloxyacetic acid ethyl ester (1 g, 6.9 mmol) in THF (20 mL) was added and the reaction mixture was stirred for 25 min. Distilled cinnamaldehyde (1 mL, 8.28 mmol) was added into the reaction mixture and the resulting solution was allowed to stir for 15 min. The reaction was quenched by the addition of EtOH (5 mL) and the solution was allowed to warm to RT. EtOAc (150 mL) was added and the organic layer was washed with water (10 mL), dried over $Na_2SO_4$, concentrated in vacuo and the residue was purified by flash chromatography with 18% EtOAc-hexane.

Yield=1.37 g (68%); $R_f$=0.25, 20% EtOAc-hexane $^1$H NMR (500 MHz, $CDCl_3$, two isomers): δ 7.20-7.40 (m, 5H), 6.66 (dd, J=15.5, 6.0 Hz, 1H), 6.30-6.20 (m, 1H), 5.95-5.85 (m, 1H), 5.22 (dd, J=10.5, 1.0 Hz, 2H), 4.65-4.50 (m, 1H), 4.35-4.18 (m, 2H), 4.15-3.95 (m, 2H), 1.23 (t, J=7.0 Hz, 3H);

$^{13}$C NMR (125 MHz, $CDCl_3$, two isomers, ca. 1:1 ratio): δ 170.44 (C), 170.15 (C), 136.34 (C), 136.25 (C), 133.57 (CH), 133.46 (CH), 132.53 (CH), 132.31 (CH), 128.46 (2×CH) 128.41 (2×CH) 128.33 (CH), 127.81 (CH), 127.72 (CH), 126.72 (CH), 126.54 (2×CH), 126.51 (2×CH), 118.48 ($CH_2$), 118.36 ($CH_2$), 81.20 (CH), 80.95 (CH), 73.36 (CH), 72.95 (CH), 71.99 (2×$CH_2$), 61.12 ($CH_2$), 61.02 ($CH_2$), 14.16 ($CH_3$), 14.11 ($CH_3$).

MS (m/z, relative intensity): 276 ($M^+$, 2), 263 (10), 144 (51), 133 (63), 115 (50), 103 (100);

HRMS calculated for $C_{16}H_{20}O_4$: 276.1362; found 276.1360.

Example 43

Preparation of cis- and trans-3-hydroxy-3,6-dihydro-2H-pyran-2-carboxylic acid ethyl ester

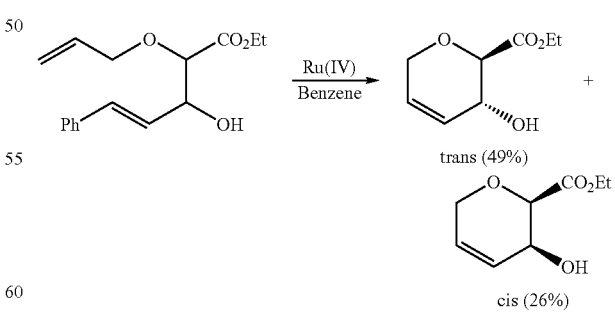

To a stirred solution of 2-allyloxy-3-hydroxy-5-phenyl-pent-4-enoic acid ethyl ester (90 mg, 0.33 mmol) in dry DCM (20 mL) was added bis-(tricyclohexylphosphine)-benzylidine rutherium (IV) chloride (16 mg, 0.018 mmol) and the mixture was stirred at ambient temperature for 30 h. The solvent was removed and the residue was purified by flash chromatography with 20-40% EtOAc-hexane.

trans-3-hydroxy-3,6-dihydro-2H-pyran-2-carboxylic acid ethyl ester
Yield=49%;

cis-3-hydroxy-3,6-dihydro-2H-pyran-2-carboxylic acid ethyl ester
Yield=26%;

Example 44

Preparation of 3-acetoxy-2-allyloxy-pent-4-enoic acid ethyl ester

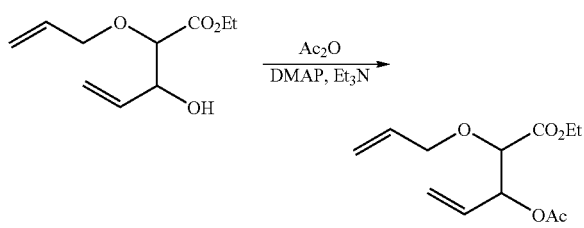

To a solution of 2-allyloxy-3-hydroxy-pent-4-enoic acid ethyl ester (100 mg, 0.5 mmol) and DMAP (30 mg, 0.25 mmol) in $CH_2Cl_2$-$Et_3N$ (9:1, 10 mL) was added $Ac_2O$ (76 mg, 0.75 mmol). The resulting solution was stirred at ambient temperature for 1H. The solution was diluted with $CH_2Cl_2$ (40 mL), washed with $H_2O$ (20 mL×2), dried over $Na_2SO_4$, concentrated in vacuo and purified by flash chromatography with 20% EtOAc-hexane.

Yield=119 mg, 99% yield; colorless liquid; $R_f$=0.58 in 20% EtOAc-hexane.

IR (neat): 2967, 1747, 1369, 1236, 1028, 932 cm$^{-1}$;

$^1$H NMR (CDCl$_3$, 400 MHz): δ 5.80-6.00 (m, 2H), 5.50-5.68 (m, 1H), 5.15-5.40 (m, 4H), 3.90-4.30 (m, 5H), 2.02 (br s, 3H), 1.25 (t, J=7 Hz, 3H);

$^{13}$C NMR (CDCl$_3$, 100 MHz, 2:1 isomeric forms, * denotes minor isomer): δ 169.64* (C), 169.53 (C), 169.34* (C), 169.29 (C), 133.55* (CH), 133.49 (CH), 132.02* (CH), 131.59 (CH), 119.31 (CH$_2$), 119.16* (CH$_2$), 118.27* (CH$_2$), 118.10 (CH$_2$), 79.00 (CH), 78.89* (CH), 74.44 (CH), 74.17* (CH), 72.08* (CH$_2$), 71.89 (CH$_2$), 61.11 (*CH$_2$ and CH$_2$), 20.90 (CH$_3$), 20.80* (CH$_3$), 14.12 (CH$_3$), 14.06* (CH$_3$);

MS (m/z, relative intensity): 242 (M$^+$, 19), 200 (22), 169 (41), 142 (13), 110 (100); HRMS calculated for $C_{12}H_{18}O_5$ (M$^+$): 242.1154; found 242.1160.

Example 45

Preparation of cis- and trans-3-acetoxy-3,6-dihydro-2H-pyran-2-carboxylic acid ethyl ester

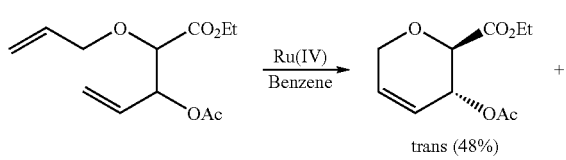

trans (48%)

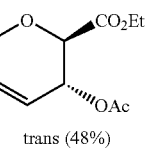

cis (43%)

To a solution of 3-acetoxy-2-allyloxy-pentenoic acid ethyl ester (300 mg, 1.23 mmol) in $CH_2Cl_2$ (10 mL) was added bis-(tricyclohexylphosphine)-benzylidine rutherium (IV) chloride (20 mg, 0.024 mmol), the resulting mixture was stirred at ambient temperature for 4 H and bis-(tricyclohexylphosphine)-benzylidine rutherium (IV) chloride (20 mg, 0.024 mmol) was added again. The resulting mixture was stirred at ambient temperature for an additional 10 h. The solution was concentrated in vacuo and purified by flash chromatography with 15 to 20% EtOAc-hexane.

trans-3-acetoxy-3,6-dihydro-2H-pyran-2-carboxylic acid ethyl ester

Yield=127 mg, 48%; $R_f$=0.43 in 20% EtOAc-hexane; IR (neat): 2967, 1747, 1374, 1231, 1028 cm$^{-1}$; $^1$H NMR (CDCl$_3$, 400 MHz) δ 5.96 (dd, J=10.4, 1.0 Hz, 1H), 5.80-5.85 (m, 1H), 5.44 (br s, 1H), 4.40 (dd, J=2.4, 17.3 Hz, 1H), 4.10-4.25 (m, 4H), 2.03 (s, 3H), 1.23 (t, J=7.1 Hz, 3H); $^{13}$C NMR (CDCl$_3$, 100 MHz) δ 170.25 (C), 168.87 (C), 130.63 (CH), 122.00 (CH), 74.49 (CH), 65.33 (CH), 63.63 (CH$_2$), 61.50 (CH$_2$), 20.96 (CH$_3$), 14.02 (CH$_3$); MS (m/z, relative intensity): 215 (M$^+$+1, 6), 213 (M$^+$-1, 18), 153 (100), 149 (30); HRMS calculated for $C_{10}H_{14}O_5$ (M$^+$): 214.0841; found 214.0844.

cis-3-acetoxy-3,6-dihydro-2H-pyran-2-carboxylic acid ethyl ester

Yield=117 mg, 43%; $R_f$=0.16 in 20% EtOAc-hexane; IR (neat): 2980, 2932, 2831, 1738, 1375, 1234, 1105, 1023 cm$^{-1}$; $^1$H NMR (CDCl$_3$, 400 MHz) δ 5.95-6.10 (m, 2H), 5.30-5.35 (m, 1H), 4.41 (dd, J=3.4, 1.6 Hz, 1H), 4.15-4.40 (m, 4H), 2.00 (s, 3H), 1.25 (t, J=7.2 Hz, 3H); $^{13}$C NMR (CDCl$_3$, 100 MHz) δ 170.12 (C), 167.91 (C), 132.06 (CH), 121.72 (CH), 75.12 (CH), 65.77 (CH$_2$), 64.87 (CH), 61.33 (CH$_2$), 20.67 (CH$_3$), 14.14 (CH$_3$); MS (m/z, relative intensity): 215 (M$^+$+1, 6), 213 (M$^+$-1, 18), 153 (100), 149 (30); exact mass calculated for $C_{10}H_{14}O_5$ (M$^+$): 214.0841; found 214.0839.

Example 46

Preparation of trans-3-acetoxy-3,6-dihydro-2H-pyran-2-carboxylic acid ethyl ester

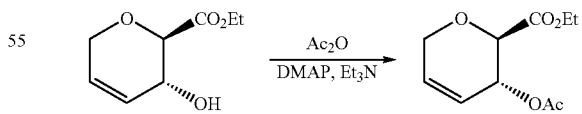

To a solution of trans-3-hydroxy-3,6-dihydro-2H-pyran-2-carboxylic acid ethyl ester (70 mg, 0.41 mmol) and DMAP (24 mg, 0.2 mmol) in $CH_2Cl_2$-$Et_3N$ (9:1, 5 mL) was added $Ac_2O$ (54 mg, 0.53 mmol). The resulting solution was stirred at ambient temperature for 2 H. The solution was diluted with $CH_2C_{12}$ (40 mL), washed with $H_2O$ (20 mL×2), dried over $Na_2SO_4$, concentrated in vacuo and purified by flash chromatography with 20% EtOAc-hexane.

Yield=68 mg, 79%; colorless liquid; $R_f$=0.16 in 20% EtOAc-hexane;

Example 47

Preparation of 2-allyloxy-pent-4-ene-1,3-diol

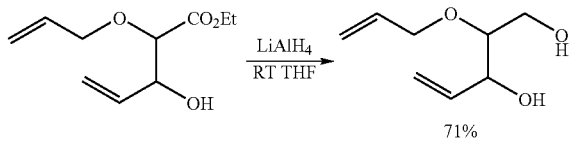

To a solution of 2-allyloxy-3-hydroxy-pentenoic acid ethyl ester (200 mg, 1.00 mmol) in THF (5 mL) was added LiAlH$_4$ (151 mg, 4.00 mmol). The resulting solution was stirred at ambient temperature for 15 min. H$_2$O (10 mL) was added and the mixture was diluted with EtOAc (50 mL×2), washed with brine (50 mL), dried over Na$_2$SO$_4$, concentrated in vacuo and purified by flash chromatography with 50% EtOAc-hexane Yield=112 mg, 71% yield; colorless liquid; $R_f$=0.33 in 60% EtOAc-hexane.

IR (neat): 3100-3700, 2880, 1644, 1425, 1055, 996 cm$^{-1}$; $^1$H NMR (CDCl$_3$, 400 MHz) δ 5.79-5.89 (m, 2H), 5.10-5.31 (m, 4H), 4.04-4.26 (m, 2H), 3.65-3.70 (m, 2H), 3.27-3.30 (m, 1H), 3.01-3.04 (m, 1H); $^{13}$C NMR (CDCl$_3$, 100 MHz, * denotes minor isomer): δ 136.98 (CH$_2$), 134.45 (CH$_2$), 117.38* (CH), 117.33 (CH), 116.57* (CH), 116.03 (CH), 81.34* (CH$_2$), 81.11 (CH$_2$), 72.45 (CH$_2$), 71.85* (CH), 71.07 (CH), 61.16 (CH); MS (m/z, relative intensity): 127 (M$^+$−31, 2), 101 (19), 83 (18), 57 (51); exact mass calculated for C$_8$H$_{14}$O$_3$ (M$^+$): 158.0943; found 158.0949.

Example 48

Preparation of cis- and trans-5-allyloxy-2,2-dimethyl-4-vinyl-[1,3]dioxane

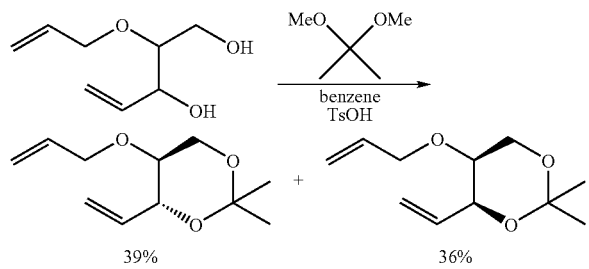

To a solution of 2-allyloxy-pentene-1,3-diol (100 mg, 0.63 mmol) In dry benzene (10 ml) was added 2,2-dimethoxypropane (0.39 ml, 3.15 mmol). The resulting solution was stirred for 5 min at ambient temperature, p-TsOH (12 mg, 0.06 mmol) was added and stirring was maintained for ca. 8 H. Aqueous NaHCO$_3$ (10 ml) was added and the mixture was diluted with EtOAc (50 mL), washed with brine (50 mL), dried over Na$_2$SO$_4$, concentrated in vacuo and purified by flash chromatography with 7% EtOAc-hexane.

trans-5-allyloxy-2,2-dimethyl-4-vinyl-[1,3]dioxane

Yield=48 mg, 39% yield; colorless liquid; $R_f$=0.83 in 15% EtOAc-hexane;

IR (neat): 2992, 1632, 1455, 1375, 1201, 1094 cm$^{-1}$;

$^1$H NMR (CDCl$_3$, 400 MHz) δ 5.71-5.92 (m, 2H), 5.34 (d, J=17.3 Hz, 1H), 5.12-5.23 (m, 3H), 4.06-4.10 (m, 1H), 3.95-3.97 (m, 2H), 3.90 (J=11.4, 5.4 Hz, 1H), 3.62 (dd, J=11.3, 9.1 Hz, 1H), 3.18-3.23 (m, 1H), 1.44 (s, 3H), 1.36 (s, 3H); $^{13}$C NMR (CDCl$_3$, 100 MHz) δ 136.62 (CH), 135.15 (CH), 118.03 (2×CH$_2$), 99.25 (C), 74.85 (CH), 74.43 (CH), 72.04 (CH$_2$), 63.34 (CH$_2$), 29.20 (CH$_3$), 20.04 (CH$_3$); MS (m/z, relative intensity): 198 (M$^+$, 2), 183 (15), 142 (19), 84 (90), 83 (38); exact mass calculated for C$_{11}$H$_{18}$O$_3$ (M$^+$): 198.1256; found 198.1255.

cis-5-allyloxy-2,2-dimethyl-4-vinyl-[1,3]dioxane

Yield=44 mg, 36% yield; colorless liquid; $R_f$=0.55 in 15% EtOAc-hexane; IR (neat): 2989, 1647, 1455, 1374, 1196, 1087, 993 cm$^{-1}$; $^1$H NMR (CDCl$_3$, 400 MHz) δ 5.94-6.03 (m, 1H), 5.81-5.88 (m, 1H), 5.11-5.33 (m, 4H), 4.37 (dd, J=5.4, 1.5 Hz, 1H), 3.90-4.15 (m, 4H), 3.18-3.20 (m, 1H), 1.43 (s, 3H), 1.42 (s, 3H); $^{13}$C NMR (CDCl$_3$, 100 MHz) δ 135.54 (CH), 134.97 (CH), 117.21 (CH$_2$), 116.98 (CH$_2$), 98.72 (C), 73.24 (CH), 72.22 (CH), 70.86 (CH$_2$), 62.09 (CH$_2$), 29.02 (CH$_3$), 19.16 (CH$_3$); MS (m/z, relative intensity): 183 (M$^+$−15, 8), 142 (5), 84 (100), 83 (38); exact mass calculated for C$_{11}$H$_{18}$O$_3$ (M$^+$): 198.1256; found 198.1254.

Example 49

Preparation of trans-2,2-dimethyl-4,4a,6,8a-tetrahydro-pyrano[3,2-d][1,3]dioxine

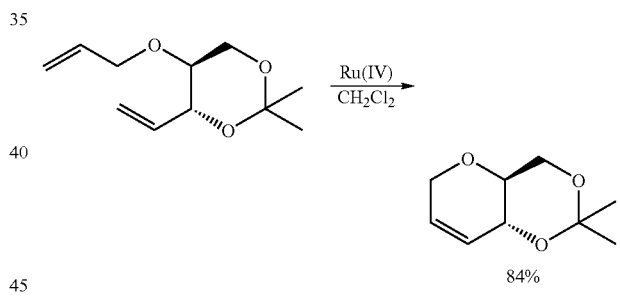

To a solution of trans-5-allyloxy-2,2-dimethyl-4-vinyl-[1,3]dioxane (300 mg, 1.52 mmol) in dry CH$_2$Cl$_2$ (10 mL) was added bis-(tricyclohexylphosphine)benzylidine ruthenium (IV) chloride (125 mg, 0.15 mmol). The mixture was stirred at ambient temperature for ca. 8H, filtered through filter paper and concentrated in vacuo to 1 mL. The residue was purified by flash chromatography with 5% EtOAc-hexane Yield=84% yield; colorless oil; $R_f$=0.48 in 10% EtOAc-hexane; 215 mg, IR (neat): 3200-3600, 2976, 1747, 1185, 1111, 1024 cm$^{-1}$;

$^1$H NMR (CDCl$_3$, 400 MHz) δ 5.70-5.79 (m, 1H), 5.66-5.69 (m, 1H), 4.14-4.28 (m, 3H), 3.88 (dd, J=11.0, 5.0 Hz, 1H), 3.72 (dd, J=10.4, 10.8 Hz, 1H), 3.28-3.34 (m, 1H), 1.49 (s, 3H), 1.39 (s, 3H);

$^{13}$C NMR (CDCl$_3$, 100 MHz) δ 127.19 (CH), 126.80 (CH), 99.65 (C), 71.37 (CH), 67.61 (CH), 66.39 (CH$_2$), 63.15 (CH$_2$), 29.24 (CH$_3$), 19.06 (CH$_3$);

MS (m/z, relative intensity): 170 (M+, 5), 169 (55), 97 (91), 83 (54), 70 (100); HRMS calculated for $C_9H_{14}O_3$ (M+): 170.0943; found 170.0944.

Example 50

Preparation of cis-2,2-dimethyl-4,4a,6,8a-tetrahydro-pyrano[3,2-d][1,3]dioxine

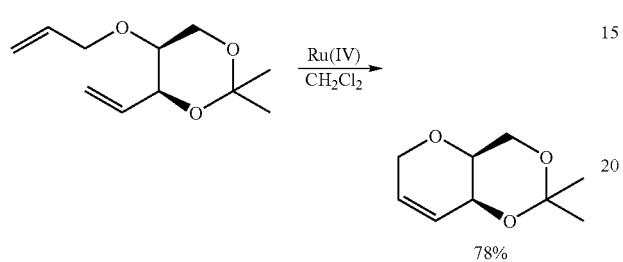

78%

To a solution of cis-5-allyloxy-2,2-dimethyl-4-vinyl-[1,3]dioxane (300 mg, 1.52 mmol) in dry $CH_2Cl_2$ (10 mL) was added bis-(tricyclohexylphosphine)benzylidine ruthenium (IV) chloride (120 mg, 0.14 mmol). The mixture was stirred at ambient temperature for ca. 8 H, filtered through filter paper and concentrated in vacuo to 1 mL. The residue was purified by flash chromatography with 15% EtOAc-hexane Yield=198 mg, 78%; colorless oil; $R_f$=0.15 in 10% EtOAc-hexane;

IR (neat): 3200-3600, 2976, 1747, 1185, 1111, 1024 cm$^{-1}$;

$^1$H NMR (CDCl$_3$, 400 MHz) δ 6.04-6.08 (m, 1H), 5.84-5.89 (m, 1H), 4.25-4.35 (m, 1H), 4.09-4.15 (m, 3H), 3.88 (dd, J=12.8, 2.8 Hz, 1H), 3.40 (dd, J=6.0, 2.8 Hz, 1H), 1.47 (s, 3H), 1.44 (s, 3H);

$^{13}$C NMR (CDCl$_3$, 100 MHz) δ 132.03 (CH), 123.20 (CH), 98.99 (C), 69.50 (CH), 65.29 (CH$_2$), 62.99 (CH$_2$), 61.57 (CH), 28.19 (CH$_3$), 19.82 (CH$_3$);

MS (m/z, relative intensity): 170 (M+, 5), 169 (55), 97 (91), 83 (54), 70 (100); HRMS calculated for $C_9H_{14}O_3$ (M+): 170.0943; found 170.0939.

Example 51

Preparation of cis-2-hydroxymethyl-3,6-dihydro-2H-pyran-3-ol

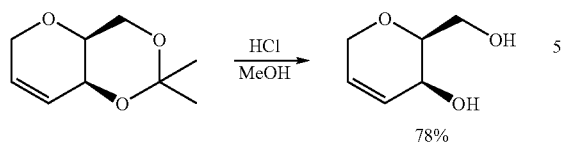

78%

To a solution of cis-5-allyloxy-2,2-dimethyl-4-vinyl-[1,3]dioxane (50 mg, 0.29 mmol) in MeOH (5 mL) was added a solution of methanolic HCl (0.5 mL, prepared from 0.5 mL conc. HCl in 30 mL of MeOH). The mixture was stirred for 30 min at ambient temperature. Aqueous saturated NaHCO$_3$ (5 mL) was added and the mixture was diluted with EtOAc (50 mL). The organic layer was washed with saturated NaHCO$_3$ (30 mL). The aqueous layer was washed with EtOAc (30 mL×2). The combined organic layers were dried over Na$_2$SO$_4$, concentrated in vacuo, and the residue was purified by flash chromatography with 100% EtOAc Yield=29 mg, 78% yield; colorless oil; $R_f$=0.25 in EtOAc;

Example 52

Preparation of trans-2-hydroxymethyl-3,6-dihydro-2H-pyran-3-ol

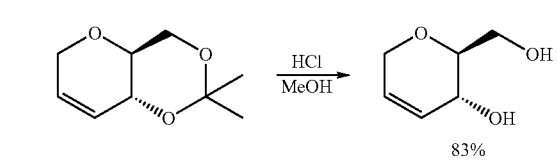

83%

To a solution of trans-5-allyloxy-2,2-dimethyl-4-vinyl-[1,3]dioxane (48 mg, 0.28 mmol) in MeOH (5 mL) was added a solution of methanolic HCl (0.5 mL, prepared from 0.5 mL conc. HCl in 30 mL of MeOH). The mixture was stirred for 30 min at ambient temperature. Aqueous saturated NaHCO$_3$ (5 mL) was added and the mixture was diluted with EtOAc (50 mL). The organic layer was washed with saturated NaHCO$_3$ (30 mL). The aqueous layer was washed with EtOAc (30 mL×2). The combined organic layers were washed with brine, dried over Na$_2$SO$_4$, concentrated in vacuo, and the residue was purified by flash chromatography with 100% EtOAc.

Yield=30 mg, 83% yield; colorless oil; $R_f$=0.20 in 100% EtOAc;

Example 53

Preparation of trans-2-hydroxymethyl-3,6-dihydro-2H-pyran-3-ol bis-(S)-Mosher ester

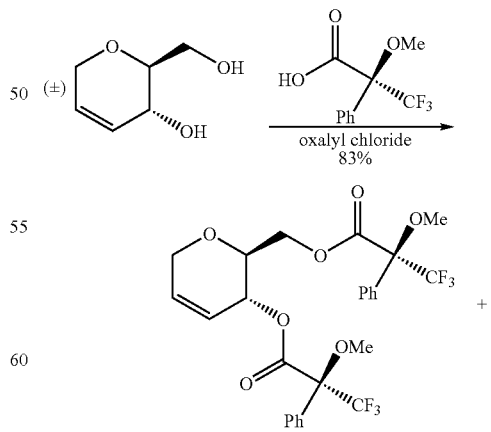

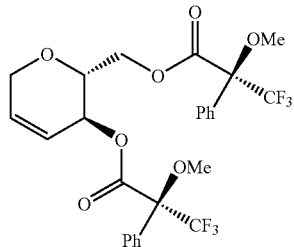

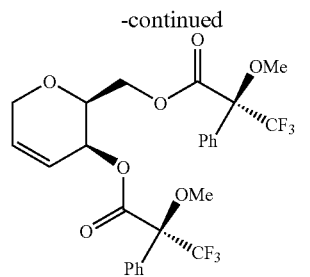

To a solution of (S)-Mosher acid (108 mg, 0.46 mmol) in dry benzene (1 mL) were added sequentially oxalyl chloride (0.5 mL) and DMF (1 drop). The solution was stirred for 5 min at ambient temperature, concentrated in vacuo and diluted with dry $CH_2Cl_2$ (3 mL). $Et_3N$ (0.13 mL, 0.92 mmol), DMAP (11 mg, 0.08 mmol) and a solution of racemic trans-2-hydroxymethyl-3,6-dihydro-2H-pyran-3-ol (22 mg, 0.17 mmol) in $CH_2Cl_2$ (2 mL) were added sequentially and the solution was stirred for 24 H. $H_2O$ (2 ml) was added and the mixture was diluted with $CH_2Cl_2$ (50 mL) and washed with brine (30 mL). The aqueous layer was washed with $CH_2Cl_2$ (50 mL×2). The combined organic layers were washed with brine, dried over $Na_2SO_4$, concentrated in vacuo, and the residue was purified by flash chromatography with 10% EtOAc-hexane Yield=79 mg, 83%; colorless oil; $R_f$=0.69 in 20% EtOAc-hexane.

IR (neat): 2952, 2849, 1752, 1650, 1495, 1271, 1170, 1122, 1023, 765 $cm^{-1}$;

$^1$H NMR (CDCl$_3$, 400 MHz, two isomers): δ 7.45-7.51 (m, 8H), 7.31-7.41 (m, 12H), 6.10-6.15 (m, 2H), 6.07-6.08 (m, 2H), 5.14-5.16 (m, 1H), 5.07-5.09 (m, 1H), 4.52-4.56 (m, 1H), 4.25-4.40 (m, 4H), 4.05-4.18 (m, 3H), 3.89-3.98 (m, 2H), 3.52-3.59 (m, 9H), 3.46-3.47 (s, 3H); $^{13}$C NMR (CDCl$_3$, 100 MHz, two isomers): δ 166.64 (C), 166.61 (C), 166.53 (C), 166.41 (C), 134.34 (CH), 134.14 (CH), 132.57 (C), 132.44 (C), 132.34 (C), 132.00 (C), 130.14 (2×CH), 130.10 (four of CH), 129.59 (C), 128.87 (six of CH and 2×C), 128.72 (two C), 127.97 (2×CH), 127.71 (four of CH), 127.68 (two C), 127.57 (2×CH), 126.96 (C), 121.02 (CH), 120.81 (CH), 73.44 (CH), 73.04 (CH), 67.03 (CH), 67.01 (CH), 65.91 (CH$_2$), 65.86 (CH$_2$), 64.71 (CH$_2$), 64.50 (CH$_2$), 55.86 (2×CH$_3$), 55.70 (2×CH$_3$); MS (m/z, relative intensity): 562 ($M^+$, 2), 342 (10), 128 (23), 91 (100);

Example 54

Preparation of cis-2-hydroxymethyl-3,6-dihydro-2H-pyran-3-ol bis-(S)-Mosher ester

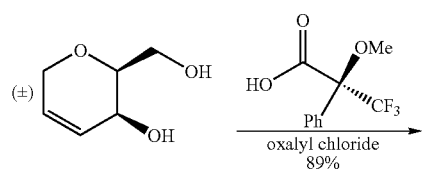

To a solution of (S)-Mosher acid (108 mg, 0.46 mmol) in dry benzene (1 mL) were added sequentially oxalyl chloride (0.5 mL) and DMF (1 drop). The solution was stirred for 5 min at ambient temperature, concentrated in vacuo and diluted with dry $CH_2Cl_2$ (3 mL). $Et_3N$ (0.13 mL, 0.92 mmol), DMAP (11 mg, 0.08 mmol), a solution of racemic cis-2-hydroxymethyl-3,6-dihydro-2H-pyran-3-ol (20 mg, 0.16 mmol) in $CH_2Cl_2$ (2 mL) were added sequentially and the solution was stirred for 24 H. $H_2O$ (2 ml) was added and the mixture was diluted with $CH_2Cl_2$ (50 mL) and washed with brine (30 mL). The aqueous layer was washed with $CH_2Cl_2$ (50 mL×2). The combined organic layers were washed with brine, dried over $Na_2SO_4$, concentrated in vacuo, and the residue was purified by flash chromatography with 10% EtOAc-hexane Yield=80 mg, 89%; colorless oil; $R_f$=0.49 in 20% EtOAc-hexane;

IR (neat): 2952, 2850, 1750, 1657, 1452, 1270, 1170, 1122, 1019, 721 $cm^{-1}$;

$^1$H NMR (CDCl$_3$, 400 MHz, two isomers): δ 7.58-7.45 (m, 8H), 7.40-7.30 (m, 12H), 6.00-5.90 (m, 2H), 5.85-5.80 (m, 1H), 5.78-5.70 (m, 1H), 5.48-5.38 (m, 2H), 4.44-4.35 (m, 2H), 4.20-4.03 (m, 6H), 3.82-3.72 (m, 1H), 3.70-3.65 (m, 1H), 3.555-3.45 (s, 12H); $^{13}$C NMR (CDCl$_3$, 100 MHz, two isomers): δ 166.35 (C), 166.20 (C), 166.14 (C), 165.81 (C), 132.11 (C), 132.07 (C), 132.01 (C), 131.66 (C), 130.64 (2×CH), 130.61 (2×CH), 129.81 (2×CH), 129.77 (2×CH), 129.65 (2×CH), 129.63 (2×CH), 128.59 (2×CH and one C), 128.53 (2×CH and one C), 128.19 (2×CH and 2×C), 127.41 (2×CH), 127.29 (2×C), 126.97 (2×C), 123.03 (two CH), 122.65 (2×CH), 73.09 (CH), 73.01 (CH), 67.40 (CH), 67.19 (CH), 65.36 (CH$_2$), 65.01 (CH$_2$), 64.40 (CH$_2$), 63.97 (CH$_2$), 55.48 (2×CH$_3$), 55.38 (2×CH$_3$); MS (m/z, relative intensity): 561 ($M^+$-1, 5), 345 (9), 128 (22), 105 (52), 95 (70), 91 (100);

Example 55

Preparation of racemic (4aS,7R,8R,8aS)-2,2-dimethyl-hexahydro-pyrano[3,2-d][1,3]dioxine-7,8-diol

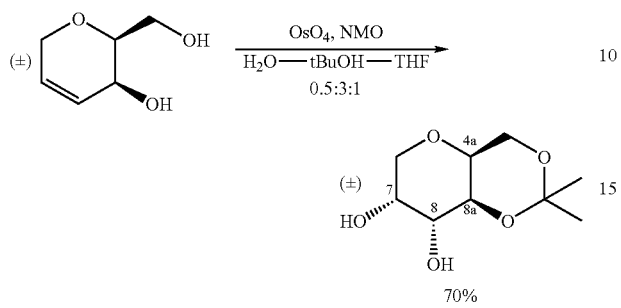

To a solution of 2,2-dimethyl-4,4a,6,8a-tetrahydro-pyrano[3,2-d][1,3]dioxine (50 mg, 0.29 mmol) in 4.5 mL of THF-tert-BuOH—H$_2$O (1:3:0.5) was added NMO (45 mg, 0.32 mmol) and the solution was stirred for 5 min at ambient temperature. OsO$_4$ (15 μL, 25 wt % in tert-BuOH) was added and the solution was stirred at ambient temperature for 4 days. Sodium hydrosulphite (0.2 g), Florisil (2.0 g) and H$_2$O (5 ml) were added and the mixture was stirred for 30 minutes, wash with acetone (100 mL), filtered through filter paper and extracted with EtOAc (80 mL×2). The combined organic layers were washed with brine (50 mL), dried over Na$_2$SO$_4$, concentrated in vacuo, and the residue was purified by flash chromatography with 60% EtOAc-hexane.

Yield=41 mg, 70%; colorless oil; R$_f$=0.13 in 70% EtOAc-hexane;

IR (neat) 3550-3100, 2929, 1392, 1081 cm$^{-1}$;

$^1$H NMR (C$_6$D$_6$, 400 MHz) δ 4.02-4.12 (m, 1H), 3.90-3.95 (m, 2H), 3.71-3.83 (m, 2H), 3.50-3.60 (m, 2H), 3.26 (br s, 1H), 1.48 (s, 3H), 1.15 (s, 3H);

$^{13}$C NMR (C$_6$D$_6$, 100 MHz) δ 99.02 (C), 70.55 (CH), 70.34 (CH), 67.05 (CH), 66.08 (CH$_2$), 65.61 (CH), 63.83 (CH$_2$), 30.27 (CH$_3$), 19.35 (CH$_3$);

MS (m/z, relative intensity): 204 (M$^+$, 5), 170 (18), 146 (12), 103 (42), 91 (91), 43 (100);

HRMS calculated for C$_9$H$_{16}$O$_5$ (M$^+$): 204.0998; found 204.0993.

Example 56

Preparation of the bis-(S)-Mosher ester of racemic (4aS,7R,8R,8aR)-2,2-dimethyl-hexahydro-pyrano[3,2-d][1,3]dioxine-7,8-diol

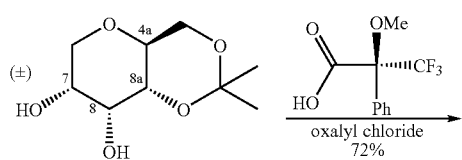

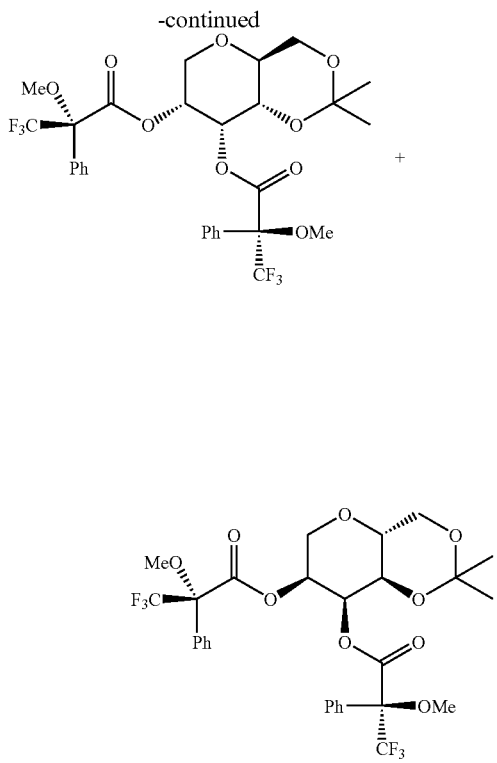

To a solution of (S)-Mosher acid (130 mg, 0.64 mmol) in dry benzene (1 mL) were sequentially added oxalyl chloride (0.5 mL) and DMF (1 drop). The solution was stirred for 5 min at ambient temperature, concentrated in vacuo and diluted with dry CH$_2$Cl$_2$ (3 mL). Et$_3$N (0.45 mL, 3.20 mmol), DMAP (40 mg, 0.32 mmol) and a solution of 2,2-dimethyl-hexahydro-pyrano[3,2-d][1,3]dioxine-7,8-diol (130 mg, 0.64 mmol) in CH$_2$C$_6$ (2 mL) were added sequentially and the solution was stirred for 24 H. H$_2$O (2 ml) was added, the mixture was diluted with CH$_2$Cl$_2$ (50 mL) and washed with brine (30 mL). The aqueous layer was washed with CH$_2$Cl$_2$ (50 mL×2). The combined organic layers were washed with brine, dried over Na$_2$SO$_4$, concentrated in vacuo, and the residue was purified by flash chromatography with 5% EtOAc-hexane Yield=314 mg, 72%; colorless oil; R$_f$=0.68 in 10% EtOAc-hexane; IR (neat): 3100-3650, 2926, 1377, 1321, 1156, 1108, 1062 cm$^{-1}$; $^1$H NMR (CDCl$_3$, 400 MHz, two isomers) δ 7.55-7.50 (m, 6H), 7.47-7.28 (m, 12H), 7.19-7.15 (m, 2H), 5.57-5.31 (m, 4H), 4.10-3.20 (m, 12H), 3.61 (s, 3H), 3.47 (s, 3H), 3.45 (s, 3H), 3.27 (s, 3H), 1.38 (s, 3H), 1.36 (s, 6H), 1.18 (s, 3H); $^{13}$C NMR (CDCl$_3$, 100 MHz, two isomers) δ 166.06 (C), 165.78 (C), 165.34 (C), 165.26 (C), 132.19 (C), 132.12 (C), 131.82 (C), 131.50 (C), 129.61 (CH), 129.52 (2×CH), 129.51 (C), 129.46 (CH), 128.29 (six of CH), 128.22 (3×CH), 128.13 (3×CH), 127.54 (2×C), 127.46 (2×CH), 127.36 (C), 127.09 (2×CH), 124.56 (C), 124.50 (C), 121.69 (C), 121.62 (C), 99.92 (2×C), 73.26 (2×CH), 72.53 (CH), 71.90 (CH), 71.81 (CH), 71.76 (CH), 69.13 (CH), 68.73 (CH), 68.32 (CH$_2$), 68.05 (CH$_2$), 61.88 (CH$_2$), 60.30 (CH$_2$), 55.55 (CH$_3$), 55.49 (CH$_3$), 55.26 (CH$_3$), 55.03 (CH$_3$), 28.96 (CH$_3$), 28.91 (CH$_3$), 18.77 (CH$_3$), 18.39 (CH$_3$); MS (m/z, relative intensity): 636 (M+, 2), 417 (3), 376 (15), 283 (39), 189 (100), 105 (22), 95 (51); HRMS calculated for $C_{29}H_{30}O_9F_6$ (M+): 636.1890; found 636.1900.

Example 57

Preparation of the (−)-(4aR,7R,8R,8aS)-2,2-dimethyl-hexahydro-pyrano[3,2-d][1,3]dioxine-7,8-diol and (+)-(4aS,7R,8R,8aR)-2,2-dimethyl-hexahydro-pyrano[3,2-d][1,3]dioxine-7,8-diol

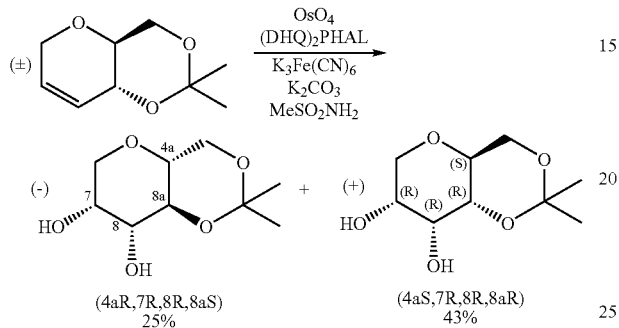

To a solution of racemic trans-2,2-dimethyl-4,4a,6,8a-tetrahydro-pyrano[3,2-d][1,3]dioxine (70 mg, 0.41 mmol) in $H_2O$-tert-BuOH (1:1, 4 mL), were added sequentially $K_3Fe(CN)_8$ (430 mg, 1.24 mmol), $K_2CO_3$ (180 mg, 1.24 mmol), $MeSO_2NH_2$ (75 mg, 0.82 mmol) and $(DHQ)_2PHAL$ (31 mg, 0.04 mmol) at 0° C. The solution was stirred for 5 min, $OsO_4$ (10 uL, 25 wt % in tert-BuOH) was added and the mixture was stirred for 64 H at ambient temperature. $Na_2SO_3$ (100 mg) was added and the mixture was stirred for 30 min, filtered through filter paper and extracted with EtOAc—$H_2O$ (4:1 v/v, 100 mL×2). The combined organic layers were washed with brine (50 mL), dried over $Na_2SO_4$, concentrated in vacuo, and the residue was purified by flash chromatography with 100% EtOAc.

(−)-(4aR,7R,8R,8aS)-2,2-dimethyl-hexahydro-pyrano[3,2-d][1,3]dioxine-7,8-diol

Yield=21 mg, 25%; colorless oil; $R_f$=0.30 in 100% EtOAc;
IR (neat): 3200-3600, 2976, 1747, 1185, 1111, 1024 cm$^{-1}$;
$^1$H NMR ($C_6D_6$, 500 MHz) δ 3.97 (dd, J=9.5 Hz, 1H), 3.90-3.82 (m, 2H), 3.74 (dd, J=10.5, 10.5 Hz, 1H), 3.56 (brs, 1H), 3.41 (dd, J=9.5, 3.5 Hz, 1H), 3.04-2.98 (m, 2H), 2.84 (br s, 2 OH), 1.45 (s, 3H), 1.27 (s, 3H); $^{13}$C NMR ($C_6D_8$, 125 MHz) δ 99.86 (C), 72.69 (CH), 72.15 (CH), 72.02 (CH), 70.36 ($CH_2$), 69.73 (CH), 62.30 ($CH_2$), 29.47 ($CH_3$), 19.12 ($CH_3$); MS (m/z, relative intensity): 204 (M+, 5), 186 (12), 98 (28), 73 (100); exact mass calculated for $C_9H_{16}O_5$ (M+): 204.0998; found 204.0991.

(+)-(4aS,7R,8R,8aR)-2,2-dimethyl-hexahydro-pyrano[3,2-d][1,3]dioxine-7,8-diol

Yield=36 mg, 43%; colorless oil; $R_f$=0.51 in 100% EtOAc;
IR (neat): 3200-3600, 2976, 1747, 1185, 1111, 1024 cm$^{-1}$;
$^1$H NMR ($C_6D_6$, 500 MHz) δ 3.88 (dd, J=10.0, 4.5 Hz, 1H), 3.85 (br s, 1H), 3.73 (dd, J=10.5, 5.5 Hz, 1H), 3.60-3.48 (m, 3H), 3.37 (dd, J=10.5, 10.5 Hz, 1H), 3.21 (d, J=10.5 Hz, 1H), 1.36 (s, 3H), 1.15 (3, 3H); $^{13}$C NMR (CeDe, 125 MHz) δ 99.32 (C), 72.24 (CH), 68.96 (CH), 67.40 (CH), 67.29 ($CH_2$), 66.62 (CH), 62.87 ($CH_2$), 29.19 ($CH_3$), 19.10 ($CH_3$); MS (m/z, relative intensity): 204 (M+, 3), 186 (8), 158 (4), 115 (10), 98 (26), 73 (100); exact mass calculated for $C_9H_{16}O_5$ (M+): 204.0998; found 204.0991.

Example 58

Preparation of (−)-(2R,3S,4R,5R)-2-hydroxymethyl-tetrahydro-pyran-3,4,5-triol

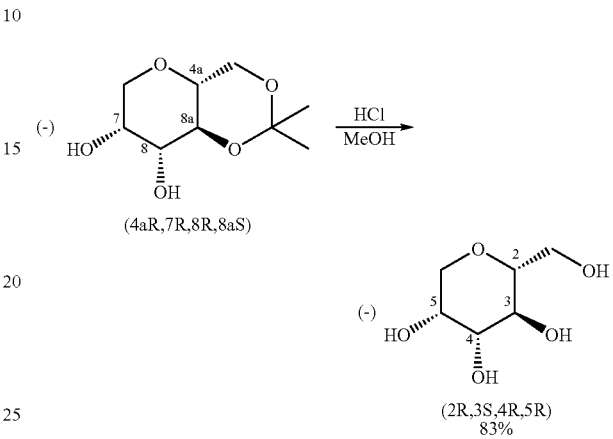

To a solution of (−)-(4aR,7R,8R,8aS)-2,2-dimethyl-hexahydro-pyrano[3,2-d][1,3]dioxine-7,8-diol (42 mg, 0.21 mmol) in MeOH (2 mL) was added a solution of methanolic HCl (0.6 mL, prepared from 0.5 mL conc. HCl in 30 mL of MeOH). The solution was stirred for 1H at ambient temperature and concentrated in vacuo.

Yield=28 mg, 83% yield;
IR (neat): 3000-4900, 2927, 1421, 1274, 1067 cm$^{-1}$; $^1$H NMR ($D_2O$, 500 MHz) δ 3.86 (br s, 1H), 3.80 (dd, J=12.5, 1.5 Hz, 1H), 3.77 (dd, J=12.5, 2.5 Hz, 1H), 3.58-3.44 (m, 4H), 3.20-3.16 (m, 1H); $^{13}$C NMR ($D_2O$, 125 MHz) a 80.68 (CH), 73.67 (CH), 70.00 ($CH_2$), 69.24 (CH), 67.45 (CH), 61.40 ($CH_2$); MS (m/z, relative intensity): 164 (M+, 5), 145 (32), 128 (10), 102 (71), 73 (100); exact mass calculated for $C_6H_{12}O_6$ (M+): 164.0685; found 164.0690.

Example 59

Preparation of (−)-(2S,3R,4R,5R)-2-hydroxymethyl-tetrahydro-pyran-3,4,5-triol

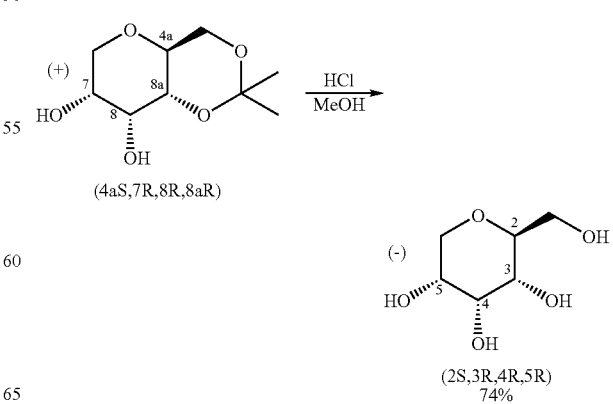

To a solution of (+)-(4aS,7R,8R,8aR)-2,2-dimethyl-hexahydro-pyrano[3,2-d][1,3]dioxine-7,8-diol (28 mg, 0.14 mmol) in MeOH (2 mL) was added a solution of methanolic HCl (0.4 mL, prepared from 0.5 mL conc. HCl in 30 mL of MeOH). The solution was stirred for 1H at ambient temperature and concentrated in vacuo.

Yield=17 mg, 74% yield;

IR (neat): 3000-3600, 2938, 1418, 1231, 1057, 911, 773 cm$^{-1}$;

$^1$H NMR (D$_2$O, 500 MHz) δ 4.04 (br s, 1H), 3.75 (d, J=12.0 Hz, 1H), 3.71-3.66 (m, 1H), 3.65-3.60 (m, 1H), 3.57-3.52 (m, 1H), 3.46-3.38 (m, 3H);

$^{13}$C NMR (D$_2$O, 125 MHz) δ 75.07 (CH), 70.56 (CH), 67.07 (CH), 66.78 (CH), 64.48 (CH$_2$), 61.34 (CH$_2$);

MS (m/z, relative intensity): 164 (M$^+$, 4), 146 (13), 128 (10), 103 (40), 102 (52), 98 (32), 73 (100); exact mass calculated for C$_6$H$_{12}$O$_5$ (M$^+$): 164.0685; found 164.0688.

Example 60

Preparation of (+)-(4aS,7R,8R,8aS)-2,2-dimethyl-hexahydro-pyrano[3,2-d][1,3]dioxine-7,8-diol

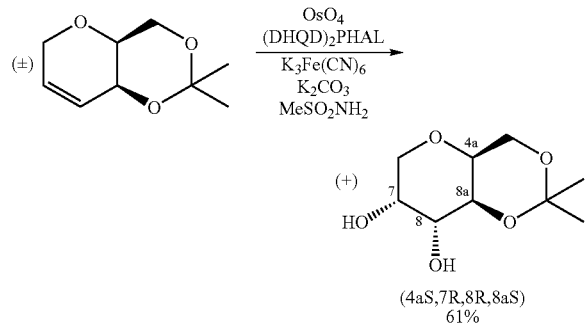

(4aS,7R,8R,8aS)
61%

To a solution of racemic cis-2,2-dimethyl-4,4a,6,8a-tetrahydro-pyrano[3,2-d][1,3]dioxine (100 mg. 0.58 mmol) in 4 mL of H$_2$O-tert-BuOH (1:1), were added sequentially K$_3$Fe(CN)$_6$ (580 mg, 1.76 mmol), K$_2$CO$_3$ (243 mg, 1.76 mmol), MeSO$_2$NH$_2$ (110 mg, 1.16 mmol) and (DHQD)$_2$PHAL (60 mg, 0.08 mmol) at 0° C. The solution was stirred for 5 min and OsO$_4$ (10 µL, 25 wt % in tert-BuOH) was added and stirring was maintained for 62 H at ambient temperature. Na$_2$SO$_3$ (100 mg) was added and the mixture was stirred for 30 min, filtered through filter paper and extracted with EtOAc—H$_2$O (4:1 v/v, 100 mL×2). The combined organic layer was washed with brine (50 mL), dried over Na$_2$SO$_4$ and concentrated in vacuo. The residue was purified by flash chromatography with 100% EtOAc.

Yield=72 mg, 61%; colorless oil; R$_f$=0.35 in 100% EtOAc;

IR (neat) 3600-3100, 2987, 2920, 1382, 1086 cm$^{-1}$; $^1$H NMR (C$_6$D$_6$, 400 MHz) δ 4.02-3.95 (m, 1H), 3.90-3.82 (m, 3H), 3.63 (dd, J=10.6, 5.4 Hz, 1H), 3.54 (dd, 12.7, 2.2 Hz, 1H), 3.47 (dd, J=10.6, 10.6 Hz, 1H), 3.18 (br s, 1H), 1.47 (s, 3H), 1.14 (s, 3H); $^{13}$C NMR (C$_6$D$_6$, 100 MHz) δ 98.29 (C), 69.70 (CH), 69.56 (CH), 66.30 (CH), 65.21 (CH$_2$), 64.80 (CH), 63.08 (CH$_2$), 29.57 (CH$_3$), 18.62 (CH$_3$); MS (m/z, relative intensity): 204 (M$^+$, 5), 170 (18), 146 (12), 103 (42), 91 (91), 59 (40), 57 (40), 43 (100); exact mass calculated for C$_9$H$_{16}$O$_5$ (M$^+$): 204.0998; found 204.0993.

Example 61

Preparation of (+)-(2S,3S,4R,5R)-2-hydroxymethyl-tetrahydro-pyran-3,4,5-triol

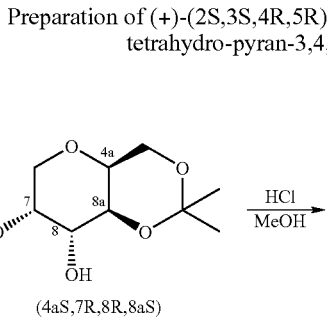

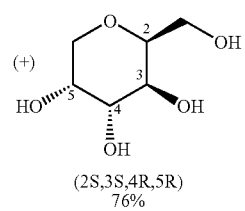

(2S,3S,4R,5R)
76%

To a solution of (+)-(4aS,7R,8R,8aS)-2,2-dimethyl-hexahydro-pyrano[3,2-d][1,3]dioxine-7,8-diol (36 mg, 0.18 mmol) in MeOH (2 mL) was added a solution of methanolic HCl (0.5 mL, prepared from 0.5 mL conc. HCl in 30 mL of MeOH). The solution was stirred for 1 H at ambient temperature and concentrated in vacuo.

Yield=15 mg, 76%;

IR (neat): 3000-3600, 2944, 2913, 2891, 1460, 1380, 1296, 1114, 1024 cm$^{-1}$; $^1$H NMR (D$_2$O, 400 MHz) δ 4.00-3.90 (m, 2H), 3.76-3.73 (m, 1H), 3.72-3.65 (m, 2H), 3.62-3.60 (m, 2H), 3.45 (dd, J=10.6 Hz, 1H); $^{13}$C NMR (D$_2$O, 100 MHz) 875.34 (CH), 69.86 (CH), 69.72 (CH), 65.36 (CH$_2$), 64.57 (CH), 61.40 (CH$_2$); MS (m/z, relative intensity): 164 (M$^+$, 2), 146 (13), 128 (11), 103 (33), 102 (26), 74 (31), 73 (72), 70 (100); exact mass calculated for C$_6$H$_{12}$O$_5$ (M$^+$): 164.0685; found 164.0680.

Example 62

Preparation of (+)-(4aS,7S,8S,8aR)-2,2-dimethyl-hexahydro-pyrano[3,2-d][1,3]dioxine-7,8-diol and (−)-(4aR,7S,8S,8aS)-2,2-dimethyl-hexahydro-pyrano[3,2-d][1,3]dioxine-7,8-diol

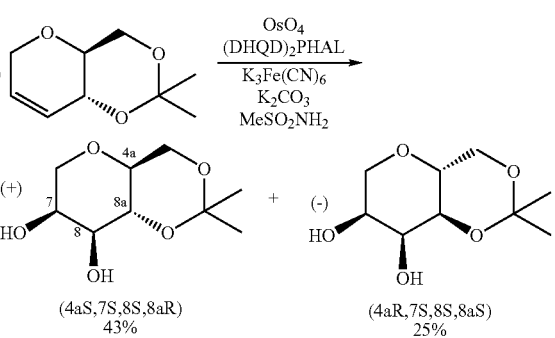

(4aS,7S,8S,8aR)
43%

(4aR,7S,8S,8aS)
25%

To a solution of racemic trans-2,2-dimethyl-4,4a,6,8a-tetrahydro-pyrano[3,2-d][1,3]dioxine (75 mg, 0.44 mmol) in 4 mL of H₂O-tert-BuOH (1:1), were added sequentially K₃Fe(CN)₆ (435 mg, 1.32 mmol), K₂CO₃ (182 mg, 1.32 mmol), MeSO₂NH₂ (76 mg, 0.88 mmol) and (DHQD)₂PHAL (31 mg, 0.04 mmol) at 0° C. The solution was stirred for 5 min, OsO₄ (10 μL, 25% wt in tert-BuOH) was added and the mixture was stirred for 56 H at ambient temperature. Na₂SO₃ (100 mg) was added and the mixture was stirred for 30 min, filtered through filter paper and extracted with EtOAc—H₂O (4:1 v/v, 100 mL×2). The combined organic layers were washed with brine (50 mL), dried over Na₂SO₄, concentrated in vacuo and the residue was purified by flash chromatography with 100% EtOAc.

(+)-(4aS,7S,8S,8aR)-2,2-dimethyl-hexahydro-pyrano[3,2-d][1,3]dioxine-7,8-diol

Yield=27 mg, 30%; colorless oil; $R_f$=0.29 in 100% EtOAc;
IR (neat): 3150-3600, 2965, 1749, 1901, 1124, 1096 cm⁻¹; ¹H NMR (C₆D₆, 500 MHz) δ 4.02 (dd, J=9.5, 9.5 Hz, 1H), 3.90-3.86 (m, 2H), 3.77 (dd, J=10.5, 10.5 Hz, 1H), 3.62 (br s, 1H), 3.46 (dd, J=9.5, 3.0 Hz, 1H), 3.19 (br. s, 2H), 3.20-3.00 (m, 2H), 1.47 (s, 3H), 1.31 (s, 3H); ° C. NMR (C₆D₆, 125 MHz) δ 99.92 (C), 72.77 (CH), 72.13 (CH), 72.02 (CH), 70.47(CH₂), 69.82 (CH), 62.28 (CH₂), 29.48 (CH₃), 19.15 (CH₃); MS (m/z, relative intensity): 204 (M⁺, 1), 186 (19), 170 (17), 128 (34), 105 (39), 97 (91), 84 (100); exact mass calculated for C₉H₁₆O₅ (M⁺): 204.0998; found 204.0999.

(−)-(4aR,7S,8S,8aS)-2,2-dimethyl-hexahydro-pyrano[3,2-d][1,3]dioxine-7,8-diol

Yield=39 mg, 43%; colorless oil; $R_f$=0.41 in 100% EtOAc;
IR (neat): 3200-3600, 2976, 1747, 1185, 1111, 1024 cm⁻¹; ¹H NMR (C₆D₆, 500 MHz) δ 3.88 (dd, J=11.5, 4.5 Hz, 1H), 3.85 (brs, 1H), 3.74 (dd, J=11.0, 6.0 Hz, 1H), 3.60-3.50 (m, 3H), 3.72 (dd, J=11.0, 11.0 Hz, 1H), 3.21 (dd, J=9.0, 2.0 Hz, 1H), 1.37 (s, 3H), 1.15 (s, 3H); ¹³C NMR (C₆D₆, 125 MHz) δ 99.32 (C), 72.24 (CH), 68.96 (CH), 67.40 (CH), 67.29 (CH₂), 66.62 (CH), 62.87 (CH₂), 29.20 (CH₃), 19.09 (CH₃); MS (m/z, relative intensity): 186 (M⁺−18, 5), 170 (6), 128 (39), 105 (42), 97 (91), 84 (100); exact mass calculated for C₉H₁₆O₅ (M⁺): 204.0998; found 204.0989

Example 63

Preparation of (+)-(2S,3R,4S,5S)-2-hydroxymethyl-tetrahydro-pyran-3,4,5-triol

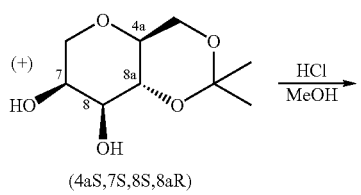

(4aS,7S,8S,8aR)

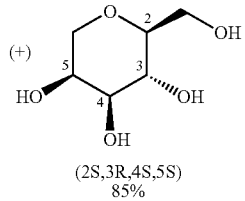

(2S,3R,4S,5S)
85%

To a solution of (+)-(4aS,7S,8S,8aR)-2,2-dimethyl-hexahydro-pyrano[3,2-d][1,3]dioxine-7,8-diol (24 mg, 0.12 mmol) in MeOH (2 mL) was added a solution of methanolic HCl (0.4 mL, prepared from 0.5 mL conc. HCl in 30 mL of MeOH). The solution was stirred for 1 H at ambient temperature and concentrated in vacuo.

Yield=17 mg, 85%; IR (neat): 3000-4900, 2927, 1421, 1274, 1067 cm⁻¹; ¹H NMR (D₂O, 500 MHz) δ 3.86 (br s, 1H), 3.81 (dd, J=12.5, 1.5 Hz, 1H), 3.78 (dd, J=12.5, 2.5 Hz, 1H), 3.57 (dd, J=12.5, 6.5 Hz, 1H), 3.55-3.49 (m, 2H), 3.46 (d, J=9.5 Hz, 1H), 3.18 (ddd, J=9.5, 6.5, 2.5 Hz, 1H); ¹³C NMR (H₂O₁ 125 MHz) δ 80.67 (CH), 73.99 (CH), 69.99 (CH₂), 69.22 (CH), 67.45 (CH), 61.39 (CH₂); MS (m/z, relative intensity): 164 (M⁺, 3), 146 (12), 128 (7), 102 (34), 98 (16), 73 (100); exact mass calculated for C₆H₁₂O₅ (M⁺): 164.0685; found 164.0692.

Example 64

Preparation of (+)-(2R,3S,4S,5S)-2-hydroxymethyl-tetrahydro-pyran-3,4,5-triol

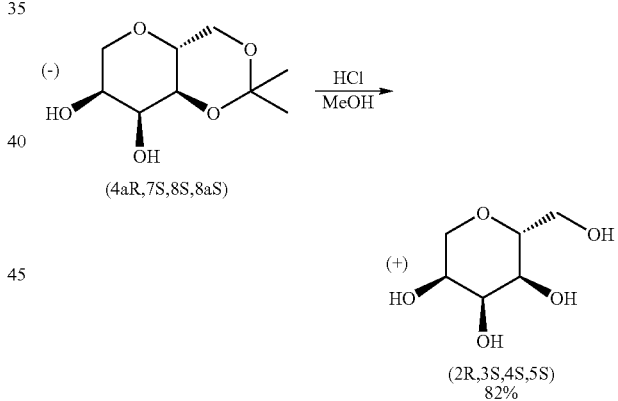

(4aR,7S,8S,8aS)

(2R,3S,4S,5S)
82%

To a solution of (−)-(4aR,7S,8S,8aS)-2,2-dimethyl-hexahydropyrano[3,2-d][1,3]dioxine-7,8-diol (20 mg, 0.09 mmol) in MeOH (2 mL) was added a solution of methanolic HCl (0.5 mL, prepared from 0.5 mL conc. HCl in 30 mL of MeOH). The solution was stirred for 1H at ambient temperature and concentrated in vacuo.

Yield=12 mg, 74%;
IR (neat): 3000-3600, 2938, 1418, 1231, 1057, 911, 773 cm⁻¹; ¹H NMR (D₂O, 500 MHz) δ 4.03 (br s, 1H), 3.74 (dd, J=12.0, 1.2 Hz, 1H), 3.69-3.64 (m, 1H), 3.61 (dd, J=10.5, 5.5 Hz, 1H), 3.56-3.50 (m, 1H), 3.45-3.43 (m, 2H), 3.40 (dd, J=10.5, 10.5 Hz, 1H); ¹³C NMR (D₂O, 125 MHz) δ 75.03 (CH), 70.55 (CH), 67.03 (CH), 66.75 (CH), 64.46 (CH₂), 61.31 (CH₂); MS (m/z, relative intensity): 164 (M⁺, 5), 146 (13), 128 (9), 103 (38), 102 (50), 73 (100); exact mass calculated for C₆H₁₂O₅ (M⁺): 164.0685; found 164.0685.

Example 65

Preparation of (−)-(4aR,7S,8S,8aR)-2,2-dimethyl-hexahydro-pyrano[3,2-d][1,3]dioxine-7,8-diol

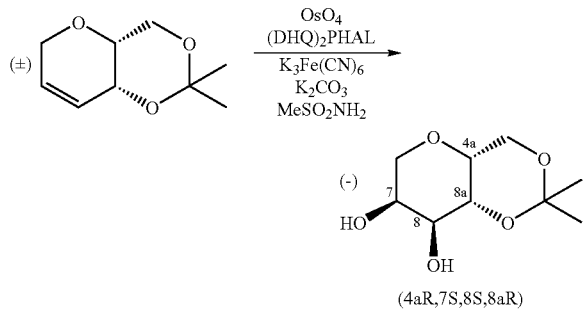

(4aR,7S,8S,8aR)
36%

To a solution of racemic cis-2,2-dimethyl-4,4a,6,8a-tetrahydro-pyrano[3,2-d][1,3]dioxine (52 mg. 0.30 mmol) in 4 mL of H$_2$O-tert-BuOH (1:1), were added sequentially K$_3$Fe(CN)$_6$ (312 mg, 0.90 mmol), K$_2$CO$_3$ (131 mg, 0.90 mmol), MeSO$_2$NH$_2$ (55 mg, 0.60 mmol) and (DHQ)$_2$PHAL (23 mg, 0.03 mmol) at 0° C. The mixture was stirred for 5 min., OsO$_4$ (10 μL, 25 wt % in tert-BuOH) was added and the mixture was stirred for 64 H at ambient temperature. Na$_2$SO$_3$ (100 mg) was added and the mixture was stirred for 30 min, filtered through filter paper and extracted with EtOAc—H$_2$O (4:1 v/v, 100 mL×2). The combined organic layers were washed with brine (50 mL), dried over Na$_2$SO$_4$, and concentrated in vacuo. The residue was purified by flash chromatography with 100% EtOAc.

Yield=22 mg, 36%; colorless oil; R$_f$=0.46 in EtOAc;

IR (neat): 3200-3600, 2976, 1747, 1185, 1111, 1024 cm$^{-1}$;

$^1$H NMR (C$_6$D$_6$, 400 MHz) δ 4.00-3.95 (m, 1H), 3.90-3.80 (m, 3H), 3.63 (dd, J=10.6, 5.5 Hz, 1H), 3.56 (d, J=2.0 Hz, 1H), 3.53-3.47 (m, 1H), 3.18 (brs, 1H), 1.47 (s, 3H), 1.14 (s, 3H);

$^{13}$C NMR (C$_6$D$_6$, 100 MHz) δ 98.28 (C), 69.70 (CH), 69.56 (CH), 66.31 (CH), 65.21 (CH$_2$), 64.80 (CH), 63.08 (CH$_2$), 29.57 (CH$_3$), 18.62 (CH$_3$);

MS (m/z, relative intensity): 204 (M$^+$, 6), 170 (19), 146 (12), 103 (42), 91 (92), 43 (100);

HRMS calculated for C$_9$H$_{16}$O$_5$ (M$^+$): 204.0998; found 204.0989.

Example 66

Preparation of (−)-(2R,3R,4S,5S)-2-hydroxymethyl-tetrahydro-pyran-3,4,5-triol

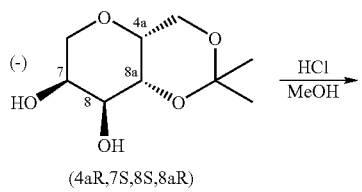

(4aR,7S,8S,8aR)

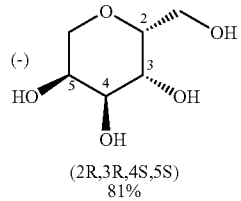

(2R,3R,4S,5S)
81%

To a solution of (−)-(4aR,7S,8S,8aR)-2,2-dimethyl-hexahydro-pyrano[3,2-d][1,3]dioxine-7,8-diol (22 mg, 0.10 mmol) in MeOH (2 mL) was added a solution of methanolic HCl (0.5 mL, prepared from 0.5 mL conc. HCl in 30 mL of MeOH). The solution was stirred for 1H at ambient temperature. Aqueous saturated NaHCO$_3$ (5 mL) was added and the mixture was diluted with EtOAc (50 mL). The mixture was washed with saturated NaHCO$_3$ (30 mL). The aqueous layer was washed with EtOAc (30 mL×2). The combined organic layers were dried over Na$_2$SO$_4$, and concentrated in vacuo Yield=13 mg, 82%;

IR (neat): 3000-3600, 2944, 2913, 2891, 1460, 1380, 1296, 1114, 1024 cm$^{-1}$; $^1$H NMR (D$_2$O, 500 MHz) δ 3.92-3.83 (m, 2H), 3.72-3.70 (m, 1H), 3.69-3.60 (m, 2H), 3.58-3.55 (m, 2H), 3.42 (dd, J=10.5, 10.5 Hz, 1H); $^{13}$C NMR (D$_2$O, 125 MHz) δ 77.67 (CH), 72.15 (CH), 72.03 (CH), 67.67 (CH$_2$), 66.86 (CH), 63.73 (CH$_2$); MS (m/z, relative intensity): 164 (M$^+$, 2), 146 (13), 128 (9), 103 (33), 102 (26), 74 (33), 73 (81), 43 (100); exact mass calculated for C$_6$H$_{12}$O$_5$ (M$^+$): 164.0685; found in 164.0689.

Example 67

Preparation of (+)-(4aS,7S,8S,8aR)-2,2-dimethyl-hexahydro-pyrano[3,2-d][1,3]dioxine-7,8-diol

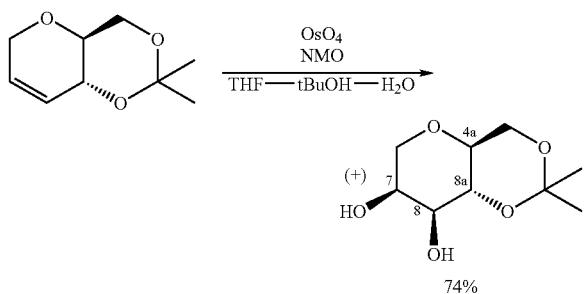

74%

To a solution of optically pure (4aS,8aR-2,2-dimethyl-4,4a,6,8a-tetrahydro-pyrano[3,2-d][1,3]dioxine (50 mg, 0.29 mmol) in 4.5 mL of THF-tert-BuOH-H$_2$O (1:3:0.5) was added NMO (45 mg, 0.32 mmol) and the solution was stirred for 5 min. at ambient temperature. OsO$_4$ (15 μL, 25 wt % In tert-BuOH) was added and the solution was stirred at ambient temperature for 4 days. Sodium hydrosulphite (0.2 g), Florisil (2.0 g) and H$_2$O (5 ml) were added and the mixture was stirred for 30 min, wash with acetone (100 mL), filtered through filter paper and extracted with EtOAc (80 mL×2). The combined organic layers were washed with brine (50 mL), dried over Na$_2$SO$_4$, and concentrated in vacuo. The residue was purified by flash chromatography with 100% EtOAc.

Yield=44 mg, 74%; optical purity=99.0%;

Example 68

Preparation of (+)-(4aR,7S,8S,8aS)-2,2-dimethyl-hexahydro-pyrano[3,2-d][1,3]dioxine-7,8-diol

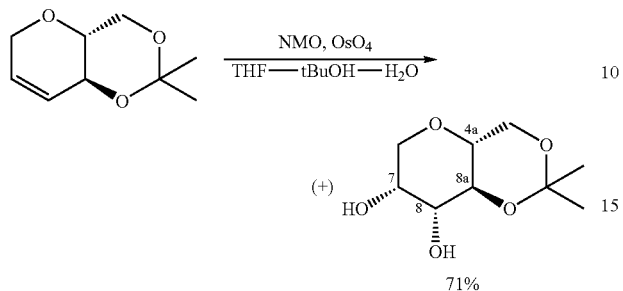

To a solution of optically pure (4aR,8aS-2,2-dimethyl-4,4a,6,8a-tetrahydro-pyrano[3,2-d][1,3]dioxine (50 mg, 0.29 mmol) in 4.5 mL of THF-tert-BuOH—H$_2$O (1:3:0.5) was added NMO (45 mg, 0.32 mmol) and the solution was stirred for 5 min. at ambient temperature. OsO$_4$ (15 μL, 25 wt % in tert-BuOH) was added and the solution was stirred at ambient temperature for 4 days. Sodiumhydrosulphite (0.2 g), Florisil (2.0 g) and H$_2$O (5 ml) were added and the mixture was stirred for 30 min, wash with acetone (100 mL), filtered through filter paper and extracted with EtOAc (80 mL×2). The combined organic layers were washed with brine (50 mL), dried over Na$_2$SO$_4$, and concentrated in vacuo. The residue was purified by flash chromatography with 100% EtOAc.

Yield=42 mg, 71%; optical purity=99%

Example 69

Preparation of (+)-(4aS,7R,8R,8aS)-2,2-dimethyl-hexahydro-pyrano[3,2-d][1,3]dioxine-7,8-diol

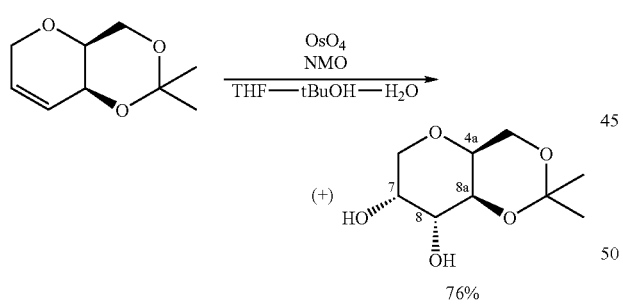

To a solution of optically pure (4aS,8aS)-2,2-dimethyl-4,4a,6,8a-tetrahydro-pyrano[3,2-d][1,3]dioxine (48 mg, 0.28 mmol) in 4.5 mL of THF-tert-BuOH—H$_2$O (1:3:0.5) was added NMO (45 mg, 0.32 mmol) and the solution was stirred for 5 min. at ambient temperature. OsO$_4$ (15 μL, 25 wt % in tert-BuOH) was added and the solution was stirred at ambient temperature for 4 days. Sodiumhydrosulphite (0.2 g), Florisil (2.0 g) and H$_2$O (5 ml) were added and the mixture was stirred for 30 min, wash with acetone (100 mL), filtered through filter paper and extracted with EtOAc (80 mL×2). The combined organic layers were washed with brine (50 mL), dried over Na$_2$SO$_4$, and concentrated in vacuo. The residue was purified by flash chromatography with 100% EtOAc Yield=43 mg, 76%; optical purity=99% .

Example 70

Preparation of (−)-(4aR,7S,8S,8aR)-2,2-dimethyl-hexahydro-pyrano[3,2-d][1,3]dioxine-7,8-diol

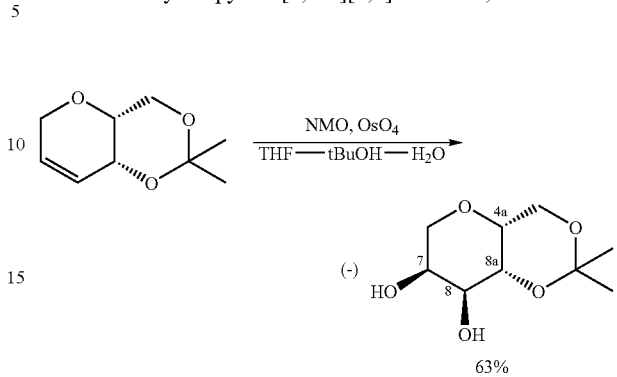

To a solution of optically pure (4aR,8aR)-2,2-dimethyl-4,4a,6,8a-tetrahydro-pyrano[3,2-d][1,3]dioxine (50 mg, 0.29 mmol) in 4.5 mL of THF-tert-BuOH—H$_2$O (1:3:0.5) was added NMO (45 mg, 0.32 mmol) and the solution was stirred for 5 min. at ambient temperature. OsO$_4$ (15 μL, 25 wt % in tert-BuOH) was added and the solution was stirred at ambient temperature for 4 days. Sodiumhydrosulphite (0.2 g), Florisil (2.0 g) and H$_2$O (5 ml) were added and the mixture was stirred for 30 min, wash with acetone (100 mL), filtered through filter paper and extracted with EtOAc (80 mL×2). The combined organic layers were washed with brine (50 mL), dried over Na$_2$SO$_4$, and concentrated in vacuo. The residue was purified by flash chromatography with 100% EtOAc.

Yield=37 mg, 63%; optical purity=99%

Example 71

Preparation of 2,2-dimethyl-hexahydro-pyrano[3,2-d][1,3]dioxine-7,8-diol

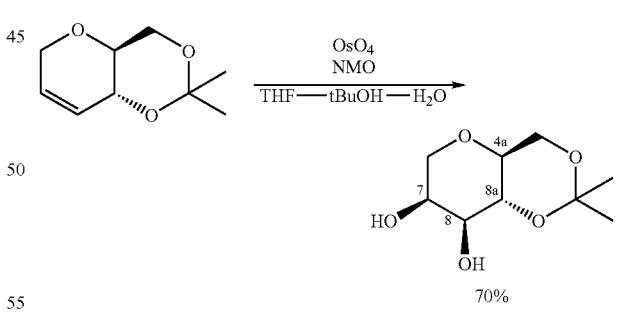

To a solution of 2,2-dimethyl-4,4a,6,8a-tetrahydro-pyrano[3,2-d][1,3]dioxine (50 mg, 0.29 mmol) in 4.5 mL of THF-tert-BuOH—H$_2$O (1:3:0.5) was added NMO (45 mg, 0.32 mmol) and the solution was stirred for 5 min. at ambient temperature. OsO$_4$ (15 μL, 25 wt % in tert-BuOH) was added and the solution was stirred at ambient temperature for 4 days. Sodiumhydrosulphite (0.2 g), Florisil (2.0 g) and H$_2$O (5 ml) were added and the mixture was stirred for 30 min, wash with acetone (100 mL), filtered through filter paper and extracted with EtOAc (80 mL×2). The combined organic layers were washed with brine (50 mL), dried over $Na_2SO_4$, and concentrated in vacuo. The residue was purified by flash chromatography with 100% EtOAc.

Yield=41 mg, 70%.

IR (neat): 3000-3600, 2952, 1473, 1268, 1161, 1087, 1021 $cm^{-1}$;

$^1$H NMR ($C_8D_6$, 400 MHz) δ 3.80-4.00 (m, 3H), 3.75 (dd, J=13.2, 13.2 Hz, 1H), 3.53 (br s, 1H), 3.35-3.42 (m, 1H), 2.90-3.00 (m, 2H), 2.50 (br s, 1H), 1.44 (s, 3H), 1.24 (s, 3H);

$^{13}$C NMR ($C_6D_6$, 100 MHz) δ 99.86 (C), 72.65 (CH), 72.14 (CH), 72.03 (CH), 70.29 ($CH_2$), 69.68 (CH), 62.30 ($CH_2$), 29.47 ($CH_3$), 19.12 ($CH_3$); MS (m/z, relative intensity): 186 ($M^+$–18, 6), 170 (7), 141 (3), 128 (36), 115 (42), 95 (91), 84 (100).

Although the invention has been described with reference to the above examples, it will be understood that modifications and variations are encompassed within the spirit and scope of the invention. Accordingly, the invention is limited only by the following claims.

The invention claimed is:

1. A process for preparing compound of formula H comprising contacting compound of formula G under conditions suitable to produce compound of formula H,

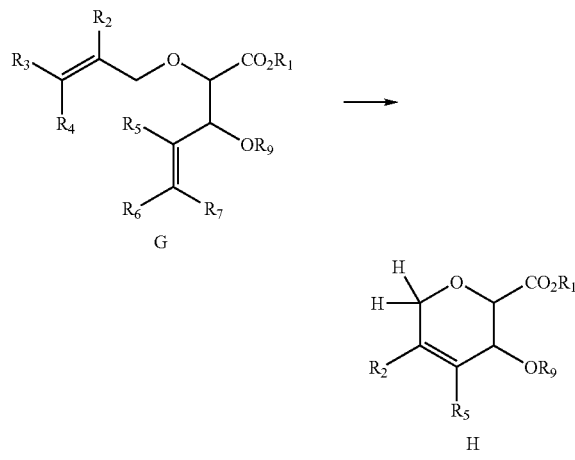

wherein:
- a) $R_1$ is selected from the group consisting of alkyl, substituted alkyl and aryl;
- b) $R_2$ and $R_5$ are independently selected from the group consisting of hydrogen, alkyl, substituted alkyl and aryl;
- c) $R_3=R_4=R_6=R_7$=hydrogen, or $R_3$, $R_4$, $R_6$, $R_7$ are selected such that three out of four are hydrogen and the fourth is selected from the group consisting of alkyl, substituted alkyl and aryl; and
- d) $R_9$ is selected from the group consisting of hydrogen, alkyl, substituted alkyl, aryl and hydroxyl protecting group.

2. A process according to claim 1, wherein carboxylic ester of formula G is contacted with a ring-closing metathesis catalyst selected from the group consisting of 2,6-diisopropylphenylimidoneophylidene molybdenum (IV) bis-(tert-butoxide), 2,6-diisopropylphenylimidoneophylidene molybdenum (IV) bis-(hexafluoro-tert-butoxide), 2,6-diisopropylphenylimidoneophylidene[racemic-BIPHEN] molybdenum (IV), 2,6-diisopropylphenylimidoneophylidene[(R)-(+)-BIPHEN] molybdenum (IV), 2,6-diisopropylphenylimidoneophylidene[(S)-(−)-BIPHEN] molybdenum (IV), bis-(tricyclohexylphosphine)benzylidine ruthenium (IV) dichloride, bis-(tricyclohexylphosphine)-3-methyl-2-butenylidene ruthenium (IV) dichloride, bis-(tricyclopentylphosphine)benzylidine ruthenium (IV) dichloride, bis-(tricyclopentylphosphine)-3-methyl-2-butenylidene ruthenium (IV) dichloride, tricyclohexylphosphine-(1,3-bis(2,4,6-trimethylphenyl)-4,5-dihydroimidazol-2-ylidene)-benzylidine ruthenium (IV) dichloride, tricyclohexylphosphine-(1,3-bis(2,6-diisopropylphenyl)-4,5-dihydroimidazol-2-ylidene)-benzylidine ruthenium (IV) dichloride, (1,3-bis(2,4,6-trimethylphenyl)-4,5-dihydroimidazol-2-ylidene)-2-isopropoxyphenylmethylene ruthenium (IV) dichloride, (tricyclopentylphosphine)-2-isopropoxyphenylmethylene ruthenium (IV) dichloride, and (tricyclopentylphosphine)-2-methoxy-3-naphthylmethylene ruthenium (IV) dichloride under conditions suitable to produce compound of formula H.

3. A process according to claim 1, wherein $R_1$=ethyl, and $R_2=R_3=R_4=R_5=R_6=R_7=R_9$=hydrogen, or $R_1$=ethyl, and $R_6$=methyl, and $R_2=R_3=R_4=R_5=R_7=R_9$=hydrogen, or $R_1$=ethyl, and $R_6$=phenyl, and $R_2=R_3=R_4=R_5=R_7=R_9$=hydrogen.

4. A compounds of formula H,

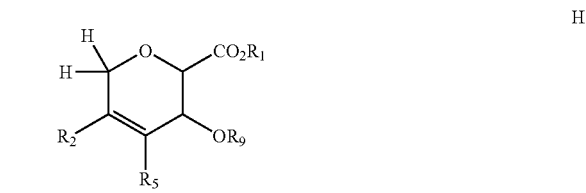

wherein:
- a) $R_1$ is selected from the group consisting of alkyl, substituted alkyl and aryl;
- b) $R_2$ and $R_5$ are independently selected from the group consisting of hydrogen, alkyl, substituted alkyl and aryl; and
- c) $R_9$ is selected from the group consisting of hydrogen, alkylcarbonyl, substituted alkylcarbonyl, arylcarbonyl and hydroxyl protecting group.

5. The compound of claim 4, wherein the compound includes all stereoisomers of a compound of formula H, wherein $R_1$=ethyl and $R_2=R_5=R_9$=hydrogen, or $R_1$=ethyl and $R_2=R_5$=hydrogen and $R_9$=acetyl, including (2R,3R)-3-hydroxy-3,6-dihydro-2H-pyran-2-carboxylic acid ethyl ester, (2S,3S)-3-hydroxy-3,6-dihydro-2H-pyran-2-carboxylic acid ethyl ester, (2S,3R)-3-hydroxy-3,6-dihydro-2H-pyran-2-carboxylic acid ethyl ester, (2R,3S)-3-hydroxy-3,6-dihydro-2H-pyran-2-carboxylic acid ethyl ester, (2R,3R)-3-acetoxy-3,6-dihydro-2H-pyran-2-carboxylic acid ethyl ester, (2S,3S)-3-acetoxy-3,6-dihydro-2H-pyran-2-carboxylic acid ethyl ester, (2R,3S)-3-acetoxy-3,6-dihydro-2H-pyran-2-carboxylic acid ethyl ester, (2S,3R)-3-acetoxy-3,6-dihydro-2H-pyran-2-carboxylic acid ethyl ester.

6. A process for preparing compound of formula H comprising contacting compound of formula I with a resolving enzyme and an acylating agent under suitable conditions to produce optically pure 3,6-dihydro-2H-pyran of formula H,

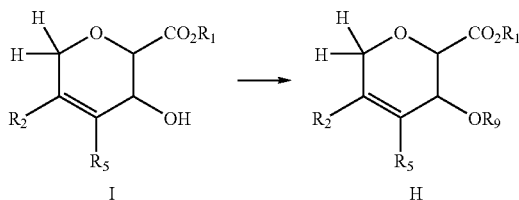

wherein:
a) $R_1$ is selected from the group consisting of alkyl, substituted alkyl and aryl;
b) $R_2$ and $R_5$ are independently selected from the group consisting of hydrogen, alkyl, substituted alkyl and aryl; and
c) $R_9$ is selected from the group consisting of hydrogen, alkylcarbonyl, substituted alkylcarbonyl and arylcarbonyl.

7. A The process according to claim 6, wherein the enzymatic resolution comprises an enzyme-catalyzed transesterification of a compound of formula I, wherein the enzymatic resolution includes the use of a lipase, esterase, peptidase, acylase or protease enzyme of mammalian, plant, fungal or bacterial origin is selected from the group consisting of Lipase Amano lipase PS-D (immobilized lipase from *Pseudomonas cepacia*), Amano Lipase PS-C (immobilized lipase from *Pseudomonas cepacia*), Roche Chirazyme L-3 (lipase, lyophilizate, from *Candida Rugosa*), Roche Chirazyme L-3 (purified lipase, lyophilizate, from *Candida Rugosa*), Roche Chirazyme L-3 (purified lipase, carrier-fixed, carrier 2, lyophilizate, from *Candida rugosa*), Roche Chirazyme L-5 (lipase, solution, from *Candida antartica*, type A), Roche Chirazyme L-5 (lipase, lyophilizate, from *Candida antartica*, type A), Roche Chirazyme L-5 (lipase, carrier-fixed, carrier 1, lyophilizate, from *Candida antartica*, type A), Roche Chirazyme L-10 (lipase, lyophilizate, from *Alcaligines* sp.), Altus Biologics 8 (lipase from *Mucor meihei*) and Altus Biologics 27 (lipase from *Alcaligenes* sp.), and wherein the acylating agent is selected from the group consisting of ethyl acetate, vinyl acetate, vinyl propionate, vinyl butyrate, isopropenyl acetate, 1-ethoxyvinyl acetate, trichloroethyl butyrate, trifluoroethyl butyrate, trifluoroethyl laureate, S-ethyl thiooctanoate, biacetyl monooxime acetate, acetic anhydride, succinic anhydride, amino acid and diketene, and where the reaction is carried out between 0° C. and 40° C. in a solvent or in mixtures of solvents selected from the group consisting of acetonitrile, dichloromethane, dichloroethane, diethyl ether, dioxane, tetrahydrofuran, dimethyl formamide, dimethyl acetamide, N-methylpyrrolidine, dimethyl sulfoxide, benzene, toluene, dichlorobenzene, xylene, methanol, ethanol, isopropanol and water and wherein the optically pure 3,6-dihydro-2H-pyran H is isolated by the use of at least one method selected from the group consisting of chromatography, crystallization, re-crystallization and distillation.

8. The process according to claim 6, wherein $R_1$ is ethyl, $R_2$ and $R_5$ are hydrogen, and $R_9$ is selected from the group consisting of hydrogen and acetyl, and wherein the substituted 3,6-dihydro-2H-pyran H selected from the group consisting of (2R,3R) 3-acetoxy-3,6-dihydro-2H-pyran-2-carboxylic acid ethyl ester, (2S,3S) 3-hydroxy-3,6-dihydro-2H-pyran-2-carboxylic acid ethyl ester, (2S,3R) 3-acetoxy-3,6-dihydro-2H-pyran-2-carboxylic acid ethyl ester, and (2R,3S) 3-hydroxy-3,6-dihydro-2H-pyran-2-carboxylic acid ethyl ester.

9. A process for preparing compound of formula J, comprising contacting compound of formula H under conditions suitable to produce a substituted tetrahydropyran of formula J,

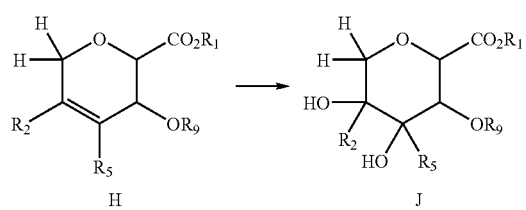

wherein:
a) $R_1$ is selected from the group consisting of alkyl, substituted alkyl and aryl;
b) $R_2$ and $R_5$ are independently selected from the group consisting of hydrogen, alkyl, substituted alkyl and aryl; and
c) $R_9$ is selected from the group consisting of hydrogen, alkyl, substituted alkyl, alkylcarbonyl, substituted alkylcarbonyl, aryl, arylcarbonyl and hydroxyl protecting group.

10. The process according to claim 9, wherein the compound of formula H is contacted with any suitable mixtures of compounds selected from the group consisting of osmium tetroxide, potassium permanganate, thallium acetate, potassium periodate, silver acetate, N-methylmorpholine oxide, trimethylamine oxide, tert-butyl peroxide, iodine, potassium ferricyanide, pyridine, quinuclidine, dihydroquinine acetate, dihydroquinidine acetate, dihydroquinine anthraquinone-1,4-diyl diether (($DHQ)_2AQN$), dihydroquinine phthalazine-1,4-diyl diether (($DHQ)_2PHAL$), dihydroquinine 2,5-diphenyl-4,6-pyrimidinediyl diether (($DHQ)_2PYR$), dihydroquinidine anthraquinone-1,4-diyl diether (($DHQD)_2AQN$), dihydroquinidine phthalazine-1,4-diyl diether (($DHQD)_2PHAL$), dihydroquinidine 2,5-diphenyl-4,6-pyrimidinediyl diether (($DHQD)_2PYR$), tetraethyl ammonium hydroxide, tetraethyl ammonium acetate, and N,N,N'N'-tetramethylethylene diamine under conditions suitable to produce compound of formula J.

11. The process according to claim 9, wherein $R_1$=ethyl, and $R_2$=$R_5$=hydrogen and $R_9$=acetyl, or $R_1$=ethyl, and $R_2$=$R_5$=$R_9$=hydrogen.

* * * * *